US009795619B2

(12) United States Patent
Cai et al.

(10) Patent No.: US 9,795,619 B2
(45) Date of Patent: *Oct. 24, 2017

(54) PHARMACEUTICAL COMPOSITIONS

(71) Applicant: GlaxoSmithKline LLC, Wilmington, DE (US)

(72) Inventors: Shenshen Cai, Collegeville, PA (US); Brian Alvin Johns, Research Triangle Park, NC (US); Andrew Spaltenstein, Research Triangle Park, NC (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,673

(22) PCT Filed: Dec. 14, 2013

(86) PCT No.: PCT/US2013/075196
§ 371 (c)(1),
(2) Date: Jun. 12, 2015

(87) PCT Pub. No.: WO2014/093941
PCT Pub. Date: Jun. 19, 2014

(65) Prior Publication Data
US 2015/0313917 A1   Nov. 5, 2015

Related U.S. Application Data

(60) Provisional application No. 61/737,177, filed on Dec. 14, 2012.

(51) Int. Cl.
A61K 31/57    (2006.01)
A61K 45/06    (2006.01)
A61K 31/56    (2006.01)
C07J 63/00    (2006.01)
A61K 31/575   (2006.01)
A61K 31/568   (2006.01)

(52) U.S. Cl.
CPC .......... A61K 31/575 (2013.01); A61K 31/568 (2013.01); A61K 45/06 (2013.01); C07J 63/008 (2013.01)

(58) Field of Classification Search
CPC .... A61K 31/568; A61K 31/575; A61K 45/06; C07J 63/008
See application file for complete search history.

(56) References Cited

U.S. PATENT DOCUMENTS

| 5,034,394 | A  |   | 7/1991  | Daluge |
|---|---|---|---|---|
| 5,358,721 | A  | * | 10/1994 | Guittard ............... A61K 9/0004 424/468 |
| 9,102,685 | B2 | * | 8/2015  | Johns .................... C07C 219/24 |
| 2003/0026843 | A1 | * | 2/2003  | Bogue ..................... A61K 9/14 424/490 |
| 2005/0142205 | A1 | * | 6/2005  | Rashba-Step ........ A61K 9/0019 424/490 |
| 2006/0205697 | A1 |   | 9/2006  | Robinson et al. ............. 514/170 |
| 2007/0197646 | A1 |   | 2/2007  | Bradbury et al. ............. 514/170 |
| 2008/0206161 | A1 | * | 8/2008  | Tamarkin ............... A61K 9/0014 424/45 |
| 2009/0023698 | A1 |   | 1/2009  | Krasutsky et al. ........... 514/169 |
| 2009/0275583 | A1 |   | 4/2009  | Yager et al. .................... 514/76 |
| 2010/0190795 | A1 |   | 7/2010  | Yli-Kauhaluoma et al. . 514/176 |
| 2011/0218204 | A1 |   | 1/2011  | Parthasaradhi Reddy et al. ............................. 552/510 |
| 2011/0144071 | A1 | * | 6/2011  | Grawe ................. A61K 9/1652 514/173 |
| 2011/0282055 | A1 | * | 11/2011 | Yoshida ............... A61K 31/351 544/95 |
| 2012/0046291 | A1 |   | 2/2012  | Nitz et al. |
| 2012/0302534 | A1 | * | 11/2012 | Gao ....................... A61K 31/50 514/176 |
| 2016/0120878 | A1 |   | 5/2016  | Hatcher et al. |

FOREIGN PATENT DOCUMENTS

| WO | WO 2001090046 | 11/2001 | |
|---|---|---|---|
| WO | WO 2005/112929 | 12/2005 | |
| WO | 2006106103 A2 | 10/2006 | |
| WO | WO 2006117666 A2 * | 11/2006 | ........... A61K 9/0048 |
| WO | 2007147882 A2 | 12/2007 | |
| WO | WO 2007/141390 | 12/2007 | |
| WO | WO 2007141389 | 12/2007 | |
| WO | WO 2007141391 | 12/2007 | |
| WO | WO 2007141392 | 12/2007 | |
| WO | WO 2008057420 | 5/2008 | |
| WO | WO 2009082818 | 7/2009 | |
| WO | WO 2009082819 | 7/2009 | |
| WO | WO 2010053817 | 5/2010 | |
| WO | WO 2010054606 | 5/2010 | |
| WO | WO 2011007230 | 1/2011 | |
| WO | WO 2011100308 | 8/2011 | |
| WO | WO 2012/037320 | 3/2012 | |
| WO | WO 2013020245 | 2/2013 | |
| WO | WO 2013020246 | 2/2013 | |
| WO | WO 2013/090664 | 6/2013 | |
| WO | WO 2013090683 | 6/2013 | |
| WO | WO 2014/035945 | 3/2014 | |
| WO | 2016046786 A1 | 3/2016 | |

OTHER PUBLICATIONS

Aiken et al. (Trends in Molecular Medicine, Jan. 2005, vol. 11, pp. 31-36).*

(Continued)

Primary Examiner — Mark V Stevens
(74) Attorney, Agent, or Firm — James P. Riek; R. Steve Thomas; William R. Majarian

(57) ABSTRACT

The present invention relates to long acting pharmaceutical compositions of betulin derivatives or pharmaceutically acceptable salts thereof, useful in the treatment or prevention of Human Immunodeficiency Virus (HIV) infections.

41 Claims, 3 Drawing Sheets

(56) References Cited

OTHER PUBLICATIONS

Lan et al (Medicinal Chemistry Research, 2011, vol. 20, pp. 1247-1259).*
U.S. Appl. No. 13/714,627, filed Dec. 14, 2012 Derivatives of Betulin.
U.S. Appl. No. 14/461,731, filed Aug. 18, 2014 Compounds and Compositions for Treating Hiv with Derivatives of Betulin.
Azijn, et al., "TMC278, a Next-Generation Nonnucleoside Reverse Transcriptase Inhibitor (NNRTI), Active against Wild-Type and NNRTI-Resistant HIV-1"; Antimicrobial Agents and Chemotherapy; Feb. 2010; pp. 718-727; vol. 54, No. 2.; American Society for Microbiology.
Highleyman, "ICAAC 2012: Long-acting Integrase Inhibitor S/GSK1265744 Active Against HIV Subtypes"; Retrieved from Internet: http://WwW.hivhepatitis.com/hiv-aids/hiv-aids-topics/hiv-tretmen . . . ; Sep. 14, 2010; pp. 1-2.
Knapp, D., et al., "In Vitro Selection of Clinically Relevant Bevirimat Resistance Mutations Revealed by "Deep" Sequencing of Serially Passaged Quasispecies-Containing Recombinant HIV-1" J. Clin. Microbial., (2011) 49(1) pp. 201-208.
PCT International Written Opinion for PCT/US2012/069637.
Yoshinaga, et al., "Antiviral characteristics of S/GSK1265744, an HIV integrase inhibitor dosed by oral or long-actin{1 3 parenteral injection"; 52nd Interscience Conference on Antimicrobial Agents and Chemotherapy; Sep. 9-12, 1;1012; pp. 1-13.
Andrews et al., Long-acting integrase inhibitor protects macaques from intrarectal simian/human immunodeficiency virus. Science. Mar. 7, 2014;343(6175):1151-4.
Dolgin, Long-acting HIV drugs advanced to overcome adherence challenge. Nat Med. Apr. 2014;20(4):323-4.
Lansdon et al., Crystal structures of HIV-1 reverse transcriptase with etravirine (TMC125)and rilpivirine (TMC278): implications for drug design. J Med Chem. May 27, 2010;53(10):4295-9.
The Merck Index. Abacavir. 14th Edition, p. 9 (2013).
U.S. Appl. No. 13/714,627, filed Dec. 14, 2012 (now U.S. Pat. No. 9,102,685).
U.S. Appl. No. 13/714627, Non Final dated Jul. 1, 2014.
U.S. Appl. No. 13/714,627 Notice of allowance filed Dec. 2, 2014.
U.S. Appl. No. 13/714,627 Notice of allowance dated Mar. 31, 2015.
U.S. Appl. No. 13/714,627 preliminary amendment filed May 27, 2014.
U.S. Appl. No. 13/714,627 RCE amendment filed Mar. 2, 2015.
U.S. Appl. No. 13/714,627 Response filed Sep. 25, 2014.
U.S. Appl. No. 14/365,802, filed Jun. 16, 2014 Derivatives of Betulin.
U.S. Appl. No. 14/365,802 Non Final dated Jun. 26, 2015.
U.S. Appl. No. 14/365,802 preliminary amendment filed Jun. 16, 2014.
U.S. Appl. No. 14/365,802 Response to Office Action dated Dec. 23, 2015.
U.S. Appl. No. 14/461,731, filed Aug. 18, 2014 Derivatives of Betulin.
U.S. Appl. No. 14/461,731 Final dated May 10, 2016.
U.S. Appl. No. 14/461,731 Issue Fee Payment dated Feb. 28, 2017.
U.S. Appl. No. 14/461,731 Non Final dated Nov. 19, 2015.
U.S. Appl. No. 14/461,731 Notice of allowance dated Dec. 9, 2016.
U.S. Appl. No. 14/461,731 Petition to Withdraw dated Mar. 21, 2017.
U.S. Appl. No. 14/461,731 RCE amendment filed Nov. 10, 2016.
U.S. Appl. No. 14/461,731 Response filed Feb. 19, 2016.
U.S. Appl. No. 15/464,553, filed Mar. 21, 2017 Derivatives of Betulin.
U.S. Appl. No. 15/464,553 Preliminary Amendment filed Apr. 28, 2017.
U.S. Appl. No. 15/514,564, filed Mar. 27, 2017 Derivatives of Betulin.
U.S. Appl. No. 15/514,564 Preliminary Amendment filed Mar. 27, 2017.
U.S. Appl. No. 14/757,754, filed Dec. 23, 2015 Derivatives of Betulin.
U.S. Appl. No. 14/757,754 Preliminary Amendment filed Dec. 23, 2015.
U.S. Appl. No. 14/757,754 Non Final Office Action dated Feb. 1, 2017.
U.S. Appl. No. 14/757,754 Response filed May 1, 2017.

* cited by examiner

PHARMACEUTICAL COMPOSITIONS

CROSS-REFERENCE TO RELATED APPLICATIONS

This application is filed pursuant to 35 USC 371 as a United States National Phase Application of International Patent Application Serial No. PCT/US2013/075196 filed on Dec. 14, 2013, which claims priority from 61/737,177 filed on Dec. 14, 2012 in the United States.

FIELD OF THE INVENTION

The present invention relates to long acting parenteral (LAP) formulations of betulin derivatives as well as methods of treating Human Immunodeficiency Virus (HIV) infection and acquired immunodeficiency syndrome (AIDS) using the same.

BACKGROUND OF THE INVENTION

Presently, long-term suppression of viral replication with antiretroviral drugs is the only option for treating HIV-1 infection. To date, a number of approved drugs have been shown to greatly increase patient survival. However, therapeutic regimens known as highly active antiretroviral therapy (HAART) are often complex because a combination of different drugs must be administered to the patient to avoid the rapid emergence of drug-resistant HIV-1 variants. Such regimens typically entail frequent administration of multiple drugs at high doses to maintain efficacious drug plasma levels. Consequently, a prescribed treatment may require ingestion of multiple and/or large dosage forms which can lead to reduced patient compliance resulting in reduced drug efficacy and development of multiple drug resistant strains of HIV. Therefore, despite the positive impact of HAART on patient survival, drug effectiveness and resistance issues can still occur with sometimes fatal consequence.

The emergence of multidrug-resistant (MDR) HIV-1 isolates has serious clinical consequences and must be suppressed with a new drug regimen, known as salvage therapy. Current guidelines recommend that salvage therapy includes at least two, and preferably three, fully active drugs. Typically, first-line therapies combine three to four drugs targeting the viral enzymes reverse transcriptase (RT) and protease (PR). One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase (IN) inhibitors. However, resistance to all three new drug classes has already been reported both in vitro and in vivo.

Accordingly, successful treatments of HIV-1-infected patients which alleviate compliance issues and are effective against resistant strains are a continual need.

PCT Published Application No. WO2013090664 deriving from U.S. Provisional Application 61/576,448, filed Dec. 16, 2011, discloses maturation inhibitors which are betulin derivatives useful in the treatment of HIV infection and AIDS. Such betulin derivatives include 4-(((3aR,5aR,5bR,7aR,9S,11aR,11bR,13aS)-3a-((R)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid which is the compound of Formula I,

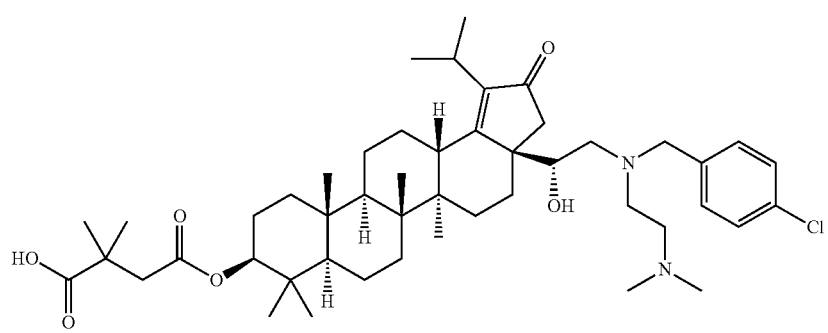

I

SUMMARY OF THE INVENTION

The present invention addresses the issue of non-compliance as well as treatment of resistant strains of HIV by formulating betulin derivatives, including the compound of Formula I, as a LAP composition suitable for administration, for example, once per month, once every 2 months, once every 3 months, once every 6 months or once every 12 months.

In a first aspect of the present invention, there is provided a LAP pharmaceutical composition including at least one betulin derivative or a pharmaceutically acceptable salt thereof.

In a second aspect of the present invention, there is provided a LAP pharmaceutical composition including the compound of Formula I

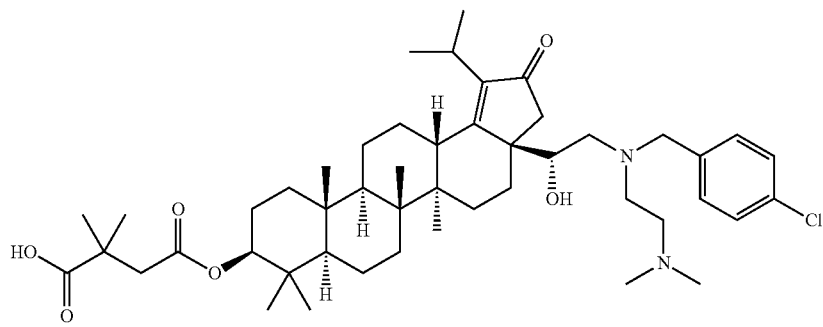

or a pharmaceutically acceptable salt thereof.

In a third aspect of the present invention, there is provided a method for the treatment of an HIV infection in a human having an HIV infection including administering to the human a LAP pharmaceutical composition including at least one betulin derivative or a pharmaceutically acceptable salt thereof.

In a fourth aspect of the present invention, there is provided a method for the treatment of an HIV infection in a human having an HIV infection including administering to the human a LAP pharmaceutical composition including the compound of Formula I

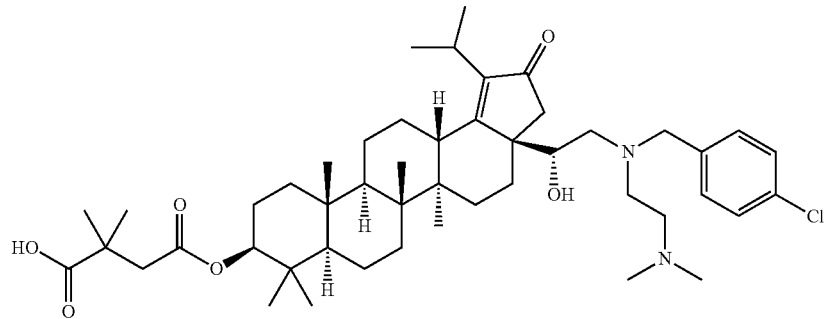

or a pharmaceutically acceptable salt thereof.

In a fifth aspect of the present invention, there is provided use of a LAP pharmaceutical composition including at least one betulin derivative or a pharmaceutically acceptable salt thereof in medical therapy.

In a sixth aspect of the present invention, there is provided use a LAP pharmaceutical composition including the compound of Formula I

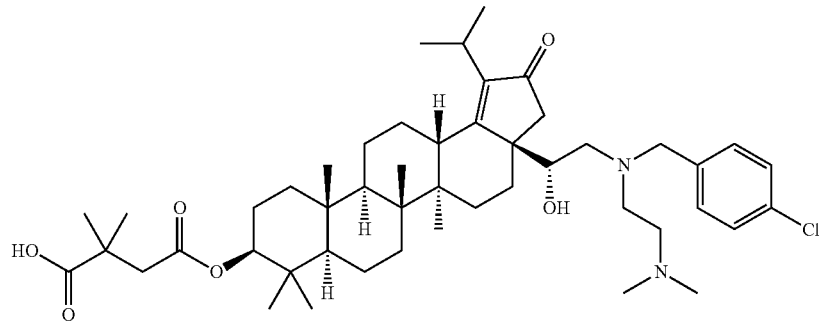

or a pharmaceutically acceptable salt thereof in medical therapy.

In a seventh aspect of the present invention, there is provided the use of at least one betulin derivative or a pharmaceutically acceptable salt thereof in the preparation of a long acting parenteral medicament for use in the treatment of HIV infection in a human.

In an eighth aspect of the present invention, there is provided the use of a compound of Formula I

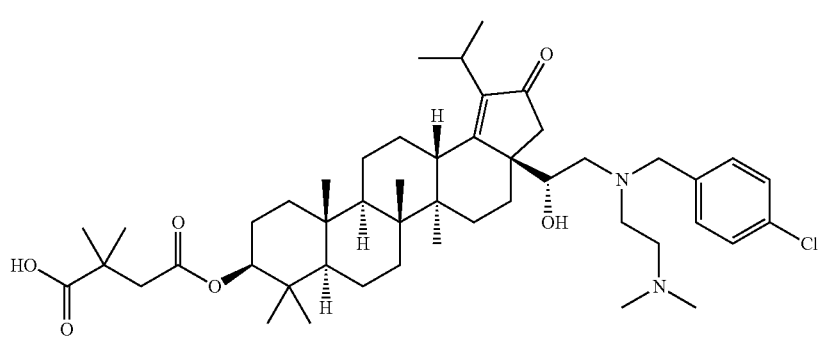

I or a pharmaceutically acceptable salt thereof in the preparation of a long acting parenteral medicament for use in the treatment of HIV infection in a human.

DETAILED DESCRIPTION OF THE INVENTION

Figure 1:
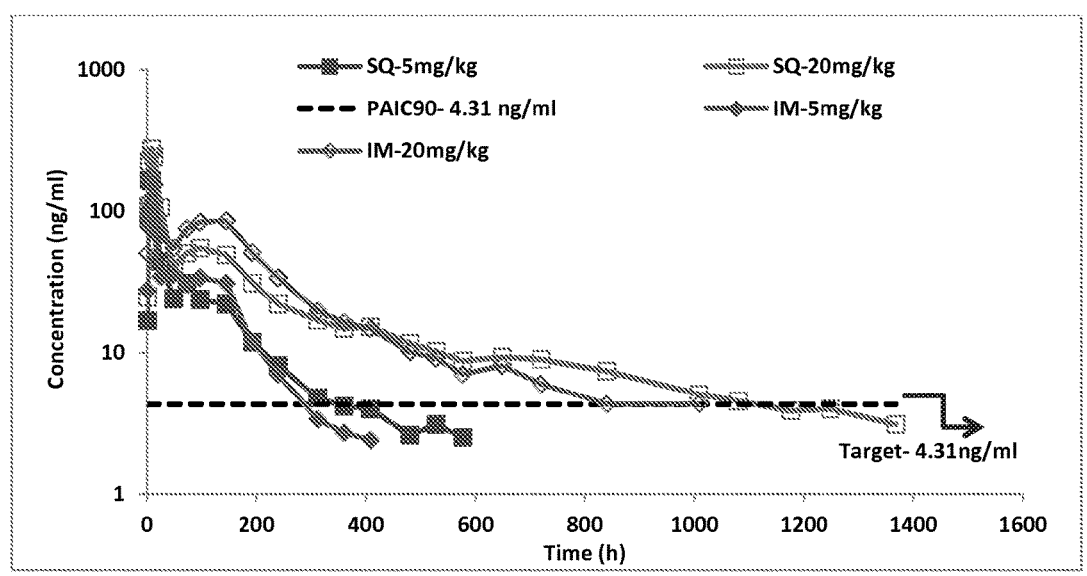
FIG. 1 depicts a plot of LAP Mean Concentration of a compound of Formula I versus time in hours of a LAP Rat PK study at 5 mg/kg and 20 mg/kg doses.

The HIV Gag polyprotein precursor (Pr55Gag), which is composed of four protein domains matrix (MA), capsid (CA), nucleocapsid (NC) and p6 and two spacer peptides, SP1 and SP2, represents a new therapeutic target. Although the cleavage of the Gag polyprotein plays a central role in the progression of infectious virus particle production, to date, no antiretroviral drug has been approved for this mechanism.

In most cell types, assembly occurs at the plasma membrane, and the MA domain of Gag mediates membrane binding. Assembly is completed by budding of the immature particle from the cell. Concomitant with particle release, the virally encoded PR cleaves Gag into the four mature protein domains, MA, CA, NC and p6, and the two spacer peptides, SP1 and SP2. Gag-Pol is also cleaved by PR, liberating the viral enzymes PR, RT and IN. Gag proteolytic processing induces a morphological rearrangement within the particle, known as maturation. Maturation converts the immature, donut-shaped particle to the mature virion, which contains a condensed conical core composed of a CA shell surrounding the viral RNA genome in a complex with NC and the viral enzymes RT and IN. Maturation prepares the virus for infection of a new cell and is absolutely essential for particle infectivity.

Bevirimat (PA-457) is a maturation inhibitor that inhibits the final step in the processing of Gag, the conversion of capsid-SP1 (p25) to capsid, which is required for the formation of infectious viral particles. Bevirimat has activity against ART-resistant and wild-type HIV, and has shown synergy with antiretrovirals from all classes. Bevirimat reduced HIV viral load by a mean of 1.3 $\log_{10}$/mL in patients who achieved trough levels of >=20 µg/mL and who did not have any of the key baseline Gag polymorphisms at Q369, V370 or T371. However, Bevirimat users with Gag polymorphisms at Q369, V370 or T371 demonstrated significantly lower load reductions than patients without Gag polymorphisms at these sites.

Other examples of maturation inhibitors can be found in PCT Patent Application No. WO2011/100308, "Derivatives of Betulin"; PCT Patent Application No. PCT/US2012/024288, "Novel Anti-HIV Compounds and Methods of Use Thereof"; Chinese PCT Application No. PCT/CN2011/001302, "Carbonyl Derivatives of Betulin"; Chinese PCT Application No. PCT/CN2011/001303, "Methylene Derivatives of Betulin"; Chinese PCT Application Nos. PCT/CN2011/002105 and PCT/CN2011/002159, "Propenoate Derivatives of Betulin"; and U.S. Provisional Application No. 61/576,448, "Derivatives of Betulin". With each iteration of maturation inhibitor a need exists to optimize the polymorphism isolate coverage and achieve maximum potency while minimizing the protein shift. To date, no maturation inhibitor has achieved an optimal balance of these three properties.

4-(((3aR,5aR,5bR,7aR,9S,11aR,11bR,13aS)-3a-((R)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid which is the compound of Formula I,

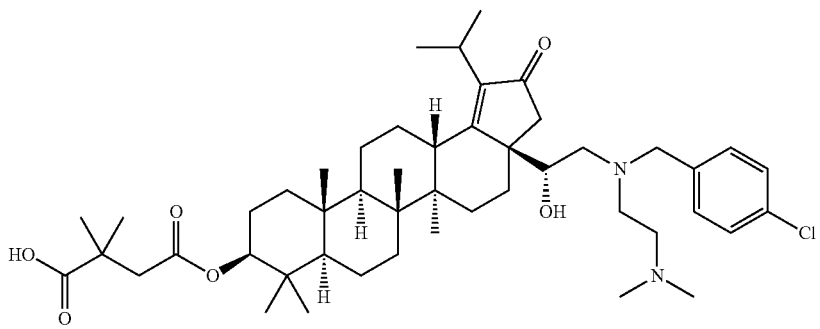

I is a maturation inhibitor believed to provide optimization of the polymorphism isolate coverage which achieves maximum potency while minimizing the protein shift. This compound is currently being developed for the treatment of HIV infection and associated disease states. In addition, for purposes of the present invention, a suitable compound other than the compound of Formula I may also be selected from any compound described in Table 1 below.

In spite of major progress made in the past decade to inhibit the replication of HIV-1, thereby preventing the clinical presentation of AIDS, none of the currently available treatments for HIV infection can cure the infection. Also HAART, or highly active antiretroviral therapy consisting of at least three antiretroviral drugs, may fail following the development of viral resistance. Factors contributing to the incomplete suppression of HIV and to the development of resistance include insufficient drug potency, non-compliance, restricted tissue penetration, drug resistance and several host factors, such as host genetics. Thus, compliance during a life-long treatment is crucial, as establishing minimal inhibitory drug concentrations in the blood inhibits viral growth and the development of resistant strains.

The present invention addresses such problematic issues in the treatment of HIV by formulating a betulin derivative, including -(((3aR,5aR,5bR,7aR,9S,11aR,11bR,13aS)-3a-((R)-2-((4-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid (the compound of Formula I) as a long-acting parenteral (LAP) composition or depot formulation suitable for administration, for example, once per week, once every two weeks, once per month, once every 2 months, once every 3 months, once every 6 months or once every 12 months.

Long-acting parenteral formulations of "betulin derivatives" (meaning the compound of Formula I and the compounds of Table 1) could generate sustained effective inhibitory concentrations with infrequent dosing and may improve adherence to therapy. Next to facilitating maintenance of viral suppression following traditional anti-HIV therapy, a long-acting formulation, may also serve as a practical opportunity for pre-exposure prophylaxis.

The present invention features pharmaceutical compositions comprising an active ingredient which is the compound of Formula I, or a pharmaceutically acceptable salt thereof, suitable for administration once monthly or longer.

Further features of the present invention are methods of using these pharmaceutical compositions.

In one embodiment, the present invention features pharmaceutical compositions, comprising a compound of Formula I, or a pharmaceutically acceptable salt thereof, and a surfactant system.

In other embodiments, the present invention features a pharmaceutical composition, comprising a therapeutically effective amount of hexadecyloxypropyl-9-R-[2-(phosphonomethoxy)propyl]-adenine, or a pharmaceutically acceptable salt thereof, and a surfactant system.

Pharmaceutically acceptable salts include, but are not limited to those described in PCT Published Application No. WO2013090664 deriving from U.S. Provisional Application 61/576,448, filed Dec. 16, 2011.

The term "therapeutically effective amount," as used herein, means a sufficient amount of a drug, compound, composition, product or pharmaceutical agent to abate or reverse or treat a malady in a human or other mammal.

The present invention features parenteral pharmaceutical compositions for administration to a subject, for example a human.

In another embodiment, the present invention features long-acting parenteral pharmaceutical compositions comprising a compound of formula (I) or a pharmaceutically acceptable salt thereof, and a surfactant system for weekly (once every week) administration.

In another embodiment, the present invention features long-acting parenteral pharmaceutical compositions comprising a compound of formula (I) or a pharmaceutically acceptable salt thereof, and a surfactant system for bi-weekly (once every two weeks) administration.

In another embodiment, the present invention features long-acting parenteral pharmaceutical compositions comprising a compound of formula (I) or a pharmaceutically acceptable salt thereof, and a surfactant system for once monthly administration.

In another embodiment, the present invention features long-acting parenteral pharmaceutical compositions comprising a compound of formula (I) or a pharmaceutically acceptable salt thereof, and a surfactant system for bi-monthly (once every two months) administration.

In another embodiment, the present invention features long-acting parenteral pharmaceutical compositions comprising a compound of formula (I) or a pharmaceutically acceptable salt thereof, and a surfactant system for tri-monthly (once every three months) administration.

In another embodiment, the present invention features long-acting parenteral pharmaceutical compositions comprising a compound of formula (I) or a pharmaceutically acceptable salt thereof, and a surfactant system administration once every six or twelve months, or any time point within this range.

The compositions of the present invention provide for the slow release of a compound of formula (I) over an extended period of time within the body of a subject. Therefore, in order to achieve therapeutic levels of drug, a compound of formula (I) advantageously is released from the composition within approximately one to three months, or any time point within this range.

An embodiment of the present invention is a pharmaceutical composition suitable for parenteral administration comprising a compound of formula (I) and a surfactant system comprising a combination of polymers providing for the release of a compound of formula (I) over a period of one week to three months. A suitable combination of polymers is, for example, polysorbate 80 and polyvinylpyrrolidone (PVP).

The compositions of the present invention may be administered to the subject by various routes, including intramuscular (IM), intravenous (IV), or subcutaneous (SQ). Therefore, in one embodiment, the compositions of the present invention are administered to a subject by an intramuscular route. In another embodiment, the compositions of the present invention are administered to a subject by an intravenous route. In another embodiment, the compositions of the present invention are administered to a subject by a subcutaneous route.

For purposes of the present invention, a "surfactant system" means any formulation suitable for pharmaceutical purposes that includes at least one surfactant. For example, a surfactant system that can be used with the present invention may include, in addition to a surfactant, additional components such as buffers, polymers (for drug particles), wetting agents, stabilizers, tonicity modifiers, and solvents such as water.

The surfactant system may include any surfactant as long as it is compatible with pharmaceutical applications. For example, suitable surfactants include, but are not limited to, polyoxyethylene sorbitan fatty acid esters (polysorbates such as polysorbate 20 or 80), poloxamers (such as LUTROL™ F68, F108 and F127 which are block copolymers of ethylene oxide and propylene oxide, sodium dodecylsulfate and/or sodium lauryl sulphate), sorbitan esters of fatty acids (SPAN), polyethoxylated castor oil and its derivatives, tocopheryl polyethylene glycol succinate, and polyvinyl alcohols. In certain embodiments, the surfactant system comprises an amount of surfactant that ranges from about 0.01% (w/v) to about 5% (w/v) surfactant. In other embodiments, the surfactant system comprises an amount of surfactant that ranges from about 0.1% (w/v) to about 3% (w/v) surfactant. In still other embodiments, the surfactant system comprises about 0.2% (w/v) surfactant. In still other embodiments, the surfactant system comprises about 0.4% (w/v) surfactant. In other embodiments, the surfactant system comprises polysorbate-80 (e.g., Tween-80). In still other embodiments, the surfactant system comprises 0.4% (w/v) polysorbate-80.

Representative stabilizers include, but are not limited to, polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyarluronic acid, polyvinyl alcohol (PVA) and polyvinylpyrrolidone (PVP). In certain embodiments, the surfactant system comprises an amount of stabilizer that ranges from about 0.01% (w/v) to about 5% (w/v) stabilizer. In other embodiments, the surfactant system comprises an amount of stabilizer that ranges from about 1% (w/v) to about 5% (w/v) stabilizer. In other embodiments, the surfactant system comprises an amount of stabilizer that ranges from about 1% (w/v) to about 3% (w/v) stabilizer. In still other embodiments, the surfactant system comprises about 2% (w/v) stabilizer. In other embodiments, the surfactant system comprises polyethylene glycols. In other embodiments, the surfactant system comprises PEG-3350. In still other embodiments, the surfactant system comprises 2% (w/v) PEG-3350.

Suitable buffer salts include, but are not limited to, buffer salts selected from phosphate salts, citrate salts, acetate salts, and tartrate salts, etc. In certain embodiments, the surfactant system comprises an amount of buffer salts that ranges from about 1 mM to about 100 mM buffer salt. In other embodiments, the surfactant system comprises an amount of buffer salts that ranges from about 2 mM to about 50 mM buffer salt. In other embodiments, the surfactant system comprises an amount of buffer salts that ranges from about 3 mM to about 25 mM buffer salt. In other embodiments, the surfactant system comprises an amount of buffer salts that ranges from about 5 mM to about 15 mM buffer salt. In still other embodiments, the surfactant system comprises about 10 mM buffer salt. In certain embodiments, the pH of the buffer salt is adjusted to range from about pH 6.0 to about pH 8.0. In other embodiments, the pH of the buffer salt is adjusted to range from about pH 6.5 to about pH 7.5. In other embodiments, the pH of the buffer salt is adjusted to range from about pH 6.7 to about pH 7.3. In one embodiment, the buffer salt comprises phosphate buffered saline (PBS). In another embodiment, the buffer salt comprises phosphate buffered saline at a concentration of about 10 mM. In another embodiment, the buffer salt comprises phosphate buffered saline at a concentration of about 10 mM and a pH of about 6.9.

Suitable tonicity modifiers include, but are not limited to, sodium chloride, mannitol, sucrose, maltose, and dextrose, etc. In one embodiment, the tonicity modifier comprises sodium chloride. In another embodiment, the tonicity modifier is sodium chloride. In certain embodiments, the surfactant system comprises a concentration of tonicity modifier that ranges from about 0 to about 350 mM. In certain embodiments, the surfactant system comprises a concentration of tonicity modifier that ranges from about 0 to about 175 mM. In certain embodiments, the surfactant system has a tonicity that ranges from about 250 to about 350 mOsmol/kg.

In one embodiment, the compound of Formula I (or any compound in Table 1) can be suspended as microparticles in a surfactant system and aqueous buffer. In some embodiments, the compound of Formula I can be in an amorphous form or in a crystalline form. Typically, the drug particle size ($D_{50}$) will range from about 0.05 µm to about 100 µm. In other embodiments, the drug particle size will range from about 0.1 µm to about 50 µm. In other embodiments, the drug particle size will range from about 0.1 µm to about 20 µm. In other embodiments, the drug particle size ($D_{50}$) will range from about 0.1 µm to about 10 µm. In other embodiments, the drug particle size ($D_{50}$) will range from about 0.1 µm to about 5 µm. In other embodiments, the drug particle size ($D_{50}$) will range from about 1 µm to about 5 µm. In other embodiments, the drug particle size ($D_{50}$) will range from about 0.05 µm to about 0.05 µm. In other embodiments, the drug particle size ($D_{50}$) will range from about 0.5 µm to about 5 µm. In other embodiments, the drug particle size ($D_{50}$) will range from about 5 µm to about 25 µm. In other embodiments, the drug particle size ($D_{50}$) will range from about 25 µm to about 100 µm.

In still other embodiments, the drug particle size in the surfactant system can be mixed sizes. For example, having substantially different particle sizes from relatively large to relatively small, can achieve acceptable pharmacokinetic parameters for the formulation because the small particles are absorbed and metabolized quicker than the larger particles. This type of mixed particle size formulation could enhance the long acting nature of the present invention by providing a quicker release of drug to the subject early after administration while still maintaining a long acting release of the drug at distant times after administration. Therefore, in one embodiment, the present LAP invention could comprise two or more substantially different particle sizes that would allow for earlier and later release of the compound of Formula I (or compound of Table 1) and such differing absorption kinetics would be a means of enhancing a durable long acting drug exposure. In one embodiment, the compound of Formula I is in a microparticle form, wherein the microparticles of the compound of Formula I range in size from about 0.05 μm to about 100 μm, wherein said microparticles comprise two or more substantially different particle sizes.

In still other embodiments, the drug particles of the compound of Formula I (or any compound in Table 1) are encapsulated into polymer based microparticles that can, optionally, be subsequently freeze dried for extended storage. When the term "encapsulated" is used with regards to the present invention, it is meant that the compound of Formula I (or any compound in Table 1) is substantially surrounded by a polymer even though some compound may still be present on the surface of the encapsulated compound/polymer structure. Immediately before use, the dry microparticles can optionally suspended in an aqueous buffer solution. The polymers used to prepare such microparticles can be selected from a series of biodegradable polymers including poly(lactic-co-glycolic) acid ($M_w$ 5-200 kD) and its derivatives, such as polyethylene glycol based amphiphilic polymers, etc. The microparticle size ($D_{50}$) could range from about 1 μm to about 100 μm and the drug encapsulation could range from about 10% to about 70% (w/w). In one embodiment, the drug particles of the compound of Formula I (or any compound in Table 1) are encapsulated into polymer based microparticles such as those containing Resomer™. In another embodiment, the drug particles of the compound of Formula I (or any compound in Table 1) are encapsulated into polymer based microparticles such as those containing Resomer™ 752 S.

In other embodiments, in-situ gels could be used to encapsulate the compound of Formula I. This could be a water-miscible organic solvent-based solution that contains both the compound of Formula I and a gel-forming polymer that is water-insoluble. Once administrated (IM or SC), the organic solvent dissipates away and the water-insoluble polymer precipitates out to form the gel containing the compound of Formula I. The compound of Formula I would then slowly diffuse out as the polymer-based gel degrades in body. The polymers used to prepare in-situ gels are selected from a series biodegradable polymers including poly(lactic-co-glycolic) acid ($M_w$ 5-200 kD) and its derivatives, polyethylene glycol based amphiphilic polymers, etc. The organic solvents are selected from N-methyl pyrrolidone (NMP), dimethylsulfoxide (DMSO), dimethylformamide (DMF), dimethylacetamie (DMA), etc. The concentration of the polymer in the organic solvent could be between 1-50% (w/w) and the compound of Formula I concentration could be between 1-50% (w/w).

Alternatively, the microparticle formulation can be made through spray-drying process. Similarly, the organic solution containing both the compound of Formula I and the selected polymer prepared as described herein is subjected to a spray-drying process where the organic solvent is rapidly evaporated under nitrogen gas flow to form the compound of Formula I encapsulated microparticles. The drying temperature is no less than 35 C and the solution spray rate is no less than 0.1 ml/min. For the in-situ gel microparticles, the compound of Formula I and the selected polymer could be co-dissolved into the suitable organic solvent wherein the organic solvent must meet the following criteria: a) has a good solubility for the selected polymer; b) has a good miscibility with aqueous solution; and c) has a low toxicity and demonstrated safety when use in human; for example N-methyl pyrrolidone (NMP), dimethylsulfoxide (DMSO), dimethylformamide (DMF), dimethylacetamie (DMA), etc. The resulted solution containing both the compound of Formula I and selected polymer can be formulated by varying the polymer concentration, the polymer to the compound of Formula I ratio in the solvent so as to control the gel forming rate after administration and the subsequent drug diffusion rate. The solution finally is subjected to a terminal sterilization by γ-irradiation on dry ice at a minimum dose of 25 kGy.

An example of a combination of polymers includes a polysorbate, for example, polysorbate 80 as wetting agent and a polyvinylpyrrolidone (PVP), for example, Plasdone K29/32 as a stabilizer. Therefore, in one embodiment, the present invention features a parenteral pharmaceutical composition comprising a compound of formula (I), or a pharmaceutically acceptable salt thereof, and polysorbate 80 and the polyvinylpyrrolidone: Plasdone K29/32.

An embodiment of the present invention is a pharmaceutical composition for parenteral administration comprising a compound of formula (I) and a surfactant system suitable for commonly known sterilization technologies such as gamma irradiation, electron beam irradiation and autoclave sterilization.

An embodiment of the present invention is a pharmaceutical composition for parenteral administration comprising a compound of formula (I) and a surfactant system that can be manufactured using aseptic technique.

An embodiment of the present invention is a pharmaceutical composition for parenteral administration comprising a compound of formula (I) and a surfactant system suitable for gamma radiation sterilization.

An embodiment of the present invention is a pharmaceutical composition for parenteral administration comprising a compound of formula (I) and a surfactant system suitable for sterilization technologies by electron beam irradiation or autoclave sterilization.

An embodiment of the present invention is a pharmaceutical composition for parenteral administration that can be presented as a "ready to use" sterile suspension or lyophile for reconstitution.

The compositions of the present invention may be administered by subcutaneous or intramuscular injection. The compositions of the present invention may also be administered by intradermal or intravitreal injection or implant. The compositions of the present invention may also be administered by other parenteral routes of administration.

The preparation of the compositions of the present invention may be performed by milling using a wet bead mill and sterilized by gamma irradiation.

Another feature of the present invention is to simplify treatment regimens for HIV with the goal of enhancing patient compliance by providing a simplified dosage form containing therapeutically effective amounts of a compound of formula (I) or a pharmaceutically acceptable salt thereof.

The present invention also features a method for treating HIV infections in a human, which method comprises administering to said human a composition according to the invention. The present invention features the use of a pharmaceutical composition according to the invention in the treatment of HIV infections. The present invention features the manufacture of a medicament according to the invention for use in medical therapy. The present invention features the manufacture of a medicament according to the invention for use in the treatment of HIV infection.

The present invention also features a method for treating HIV infections in a human which method comprises administering to said human a composition according to the invention before, during, or after therapy with a compound of formula (I) in tablet or solution form.

It will be appreciated by those skilled in the art that reference herein to "treatment" extends to treatment of an established malady, infection or symptoms thereof.

The present invention also features a method for preventing HIV infections in a human, which method comprises administering to said human a composition according to the invention. The present invention features the use of a pharmaceutical composition according to the invention in the prevention of HIV infections. The present invention features the manufacture of a medicament according to the invention for use in prophylactic medical therapy. The present invention features the manufacture of a medicament according to the invention for use in preventing HIV infection.

The present invention also features a method for treating or preventing HIV infections in a human which method comprises administering to said human a composition according to the invention before, during, or after therapy with a compound of formula (I) in tablet or solution form.

Therefore, in certain embodiments of the present invention, there is provided a single treatment pharmaceutical composition comprising a therapeutically effective amount of a long acting formulation comprising a compound of formula (I):

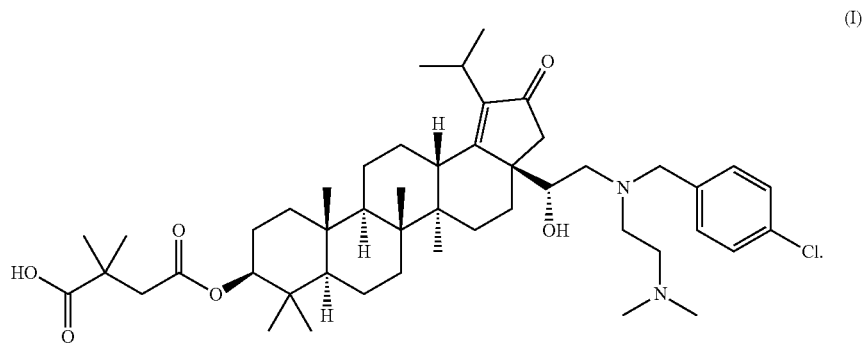

or a pharmaceutically acceptable salt thereof, in a pharmaceutically acceptable carrier for parenteral administration.

In other embodiments, there is provided a parenteral pharmaceutical composition comprising a compound of formula (I):

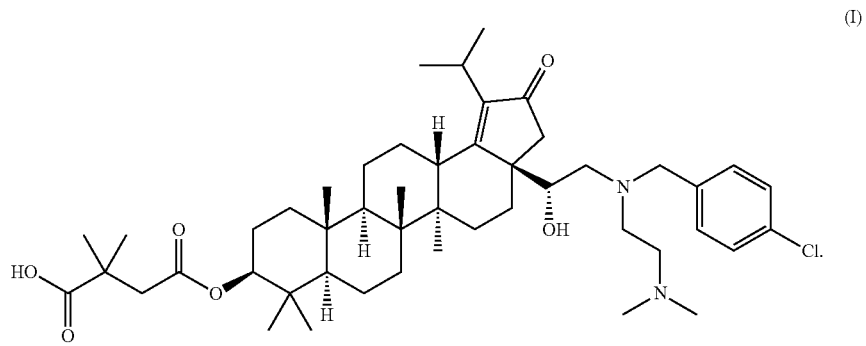

or a pharmaceutically acceptable salt thereof.

In other embodiments, there is provided a pharmaceutical composition comprising a compound of formula (I) that is formulated for subcutaneous administration.

In other embodiments, there is provided a pharmaceutical composition comprising a compound of formula (I) that is formulated for intramuscular administration.

In other embodiments, there is provided a pharmaceutical composition comprising a compound of formula (I) that is formulated for administration once weekly or longer.

In other embodiments, there is provided a pharmaceutical composition comprising a compound of formula (I) that is formulated for administration once weekly.

In other embodiments, there is provided a pharmaceutical composition comprising a compound of formula (I) that is formulated for administration once per month.

In other embodiments, there is provided a pharmaceutical composition comprising a compound of formula (I) that is formulated for administration once every two months. In other embodiments, there is provided a pharmaceutical composition comprising a compound of formula (I) that is formulated for administration once every three months. In other embodiments, there is provided a pharmaceutical composition comprising a compound of formula (I) that is formulated for administration at any interval between 30 and 365 days.

In other embodiments, there is provided a pharmaceutical composition comprising a compound of formula (I), wherein the compound of formula (I) is present in the composition in the form of crystalline nanoparticles.

In other embodiments, there is provided a pharmaceutical composition comprising a compound of formula (I), wherein the compound of formula (I) is present in the composition in the form of matrix release particles.

In other embodiments, there is provided a pharmaceutical composition comprising a compound of formula (I), wherein the composition can be terminally sterilized by gamma irradiation.

In other embodiments, there is provided a method for the treatment of an HIV infection in a human having an HIV infection comprising administering to the human a single treatment pharmaceutical composition comprising a therapeutically effective amount of a long acting formulation comprising a compound of formula (I):

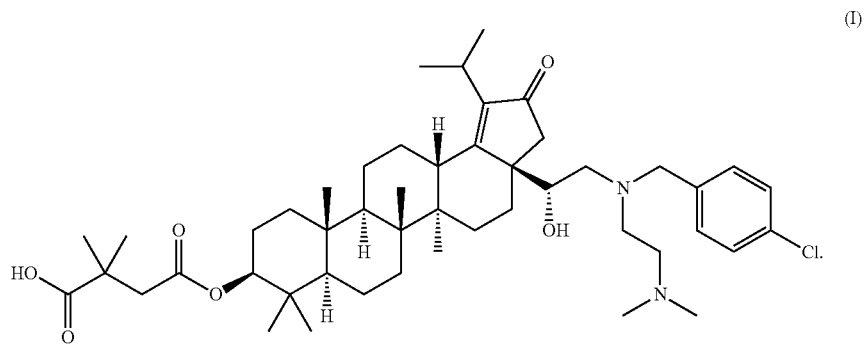

(I)

or a pharmaceutically acceptable salt thereof, in a pharmaceutically acceptable carrier for parenteral administration.

In other embodiments, there is provided a method for the prevention of an HIV infection in a human comprising administering to a human at risk of acquiring an HIV infection, a single treatment pharmaceutical composition comprising a therapeutically effective amount of a long acting formulation comprising a compound of formula (I):

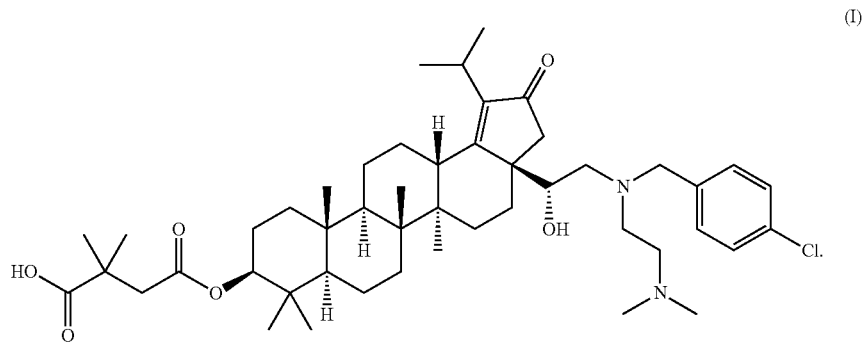

(I)

or a pharmaceutically acceptable salt thereof, in a pharmaceutically acceptable carrier for parenteral administration.

In other embodiments, there is provided a LAP pharmaceutical composition, comprising: at least one betulin derivative or a pharmaceutically acceptable salt thereof.

In other embodiments, there is provided a LAP pharmaceutical composition, comprising: the compound of Formula I

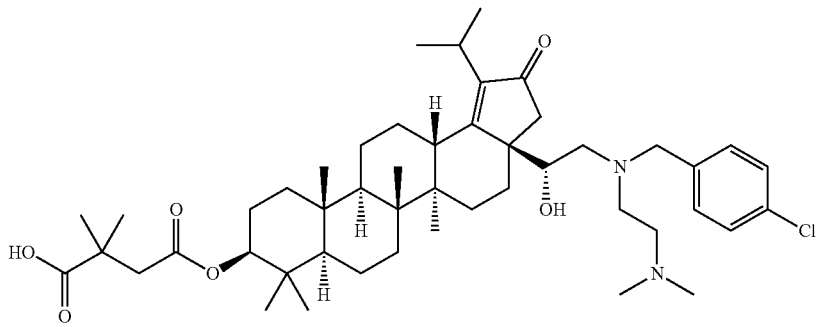

I or a pharmaceutically acceptable salt thereof.

In other embodiments, there is provided a method for the treatment of an HIV infection in a human having an HIV infection, comprising: administering to the human a LAP pharmaceutical composition including at least one betulin derivative or a pharmaceutically acceptable salt thereof.

In other embodiments, there is provided a method for the treatment of an HIV infection in a human having an HIV infection, comprising: administering to the human a LAP pharmaceutical composition including the compound of Formula I

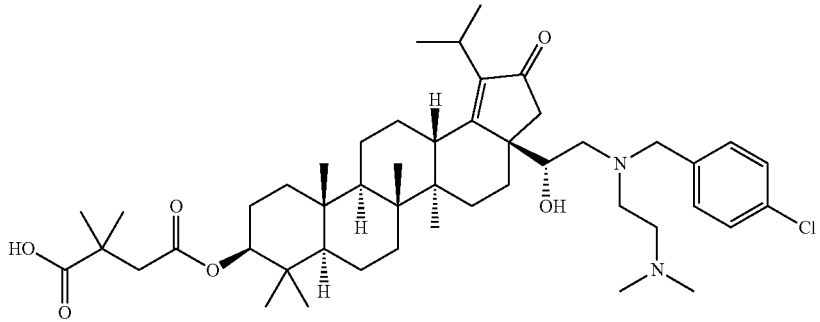

I or a pharmaceutically acceptable salt thereof.

In other embodiments, there is provided a method for the prevention of an HIV infection in a human having an HIV infection, comprising: administering to the human a LAP pharmaceutical composition including at least one betulin derivative or a pharmaceutically acceptable salt thereof.

In other embodiments, there is provided a method for the prevention of an HIV infection in a human having an HIV infection, comprising: administering to the human a LAP pharmaceutical composition including the compound of Formula I

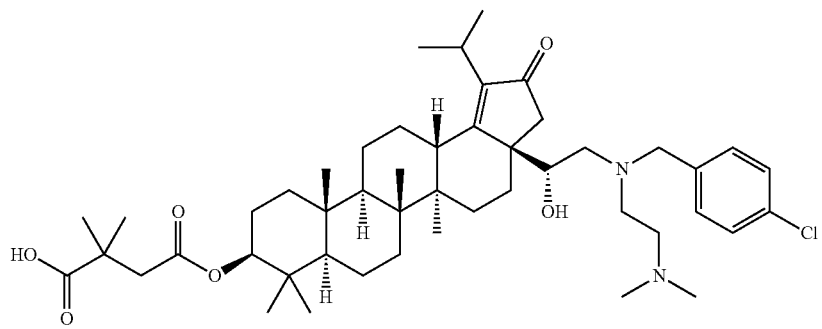

or a pharmaceutically acceptable salt thereof.

In other embodiments, there is provided a LAP pharmaceutical composition, comprising: the compound of Formula I

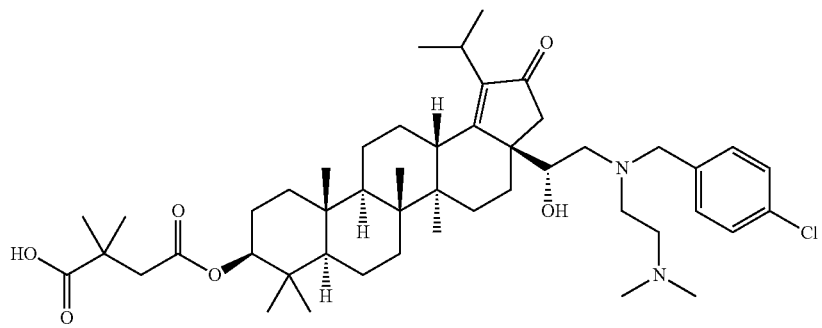

or a pharmaceutically acceptable salt thereof, further comprising a surfactant system.

In other embodiments, there is provided a LAP pharmaceutical composition, comprising: the compound of Formula I

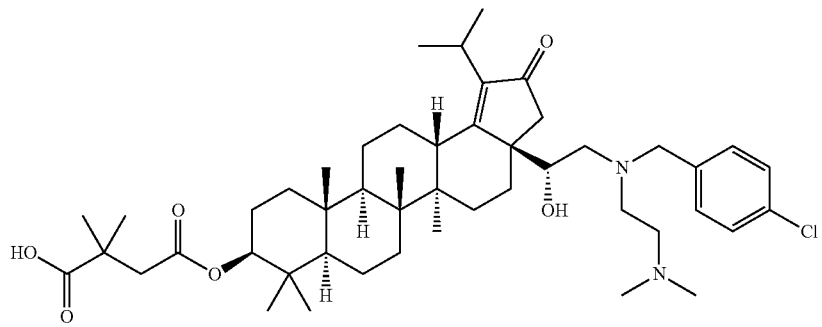

or a pharmaceutically acceptable salt thereof, further comprising a surfactant system, wherein the surfactant system comprises a surfactant in an amount ranging from about 0.1% (w/v) to about 3% (w/v) surfactant, or an amount ranging from 0.2% (w/v) to about 0.4% (w/v) surfactant, or the surfactant system comprises about 0.4% (w/v) surfactant.

In other embodiments, there is provided a LAP pharmaceutical composition, comprising: the compound of Formula I

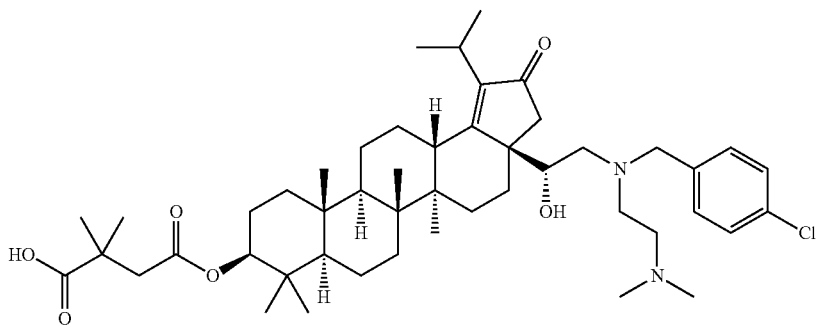

or a pharmaceutically acceptable salt thereof,
in combination with one or more additional compounds selected from the group consisting of dolutegravir, ritonavir, rilpivirine, and a compound having the following structure:

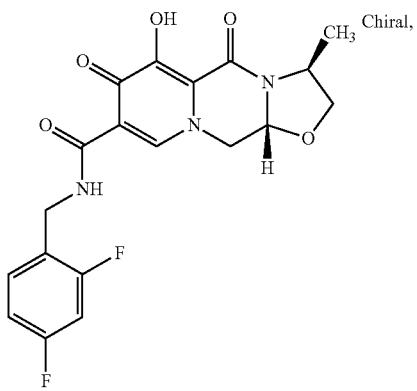 [SMILES: C[C@H]1CO[C@@H]2Cn3cc(C(=O)NCc4ccc(F)cc4F)c(=O)c(O)c3C(=O)N12]

or a pharmaceutically acceptable salt thereof.

In other embodiments, there is provided a method for the treatment of an HIV infection in a human having an HIV infection, comprising: administering to the human a LAP pharmaceutical composition including the compound of Formula I in combination with one or more additional compounds selected from the group consisting of dolutegravir, ritonavir, rilpivirine, and a compound having the following structure:

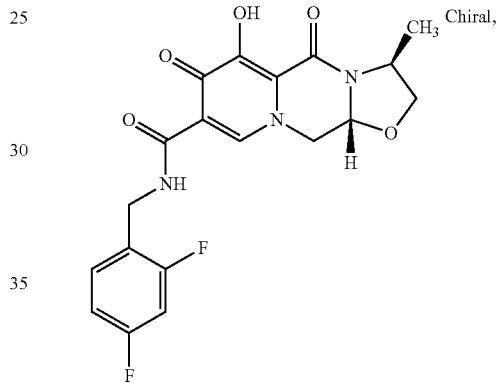

or a pharmaceutically acceptable salt thereof.

In other embodiments, there is provided a LAP pharmaceutical composition, comprising: the compound of Formula I

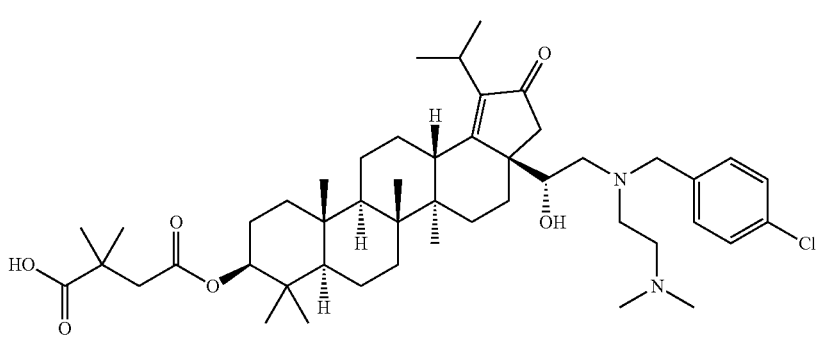

or a pharmaceutically acceptable salt thereof,

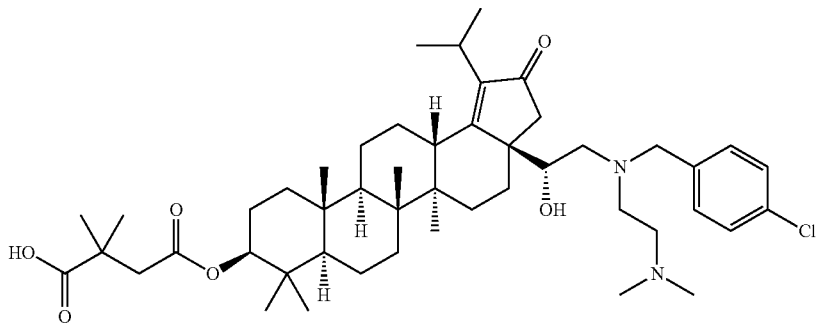

I or a pharmaceutically acceptable salt thereof, in combination with any boosting agent, such as, ritonavir. The boosting agent could be dosed simultaneously as the compound of Formula I in the same IV or SC syringe, or it could be dosed separately as an oral tablet or capsule.

In other embodiments, the LAP composition comprising the compound of Formula I is administered to the subject only after the subject has been administered treatment comprising a generally accepted antiretroviral (ARV) regimen. An initial ARV regimen generally consists of two NRTIs in combination with an NNRTI, a PI (preferably boosted with ritonavir [RTV]), an INSTI, or a CCR5 antagonist (namely maraviroc [MVC]). In clinical trials, NNRTI-, PI-, INSTI-, or CCR5 antagonist-based regimens have all resulted in HIV RNA decreases and CD4 cell increases in a large majority of patients. For example, one generally accepted ARV regimen comprises could be selected from any of the following for antiretroviral (ARV)-naive patients:

efavirenz/tenofovir disoproxil fumarate/emtricitabine (EFV/TDF/FTC)

ritonavir-boosted atazanavir+tenofovir disoproxil fumarate/emtricitabine (ATV/r+TDF/FTC)

ritonavir-boosted darunavir+tenofovir disoproxil fumarate/emtricitabine (DRV/r+TDF/FTC)

raltegravir+tenofovir disoproxil fumarate/emtricitabine (RAL+TDF/FTC)

While the present invention has been described in terms of the compound of Formula (I), it is contemplated that other betulin derivatives may be utilized in lieu of or with the compound of Formula I in the LAP formulations of the present invention. Such betulin derivatives may be chosen from those shown in Table 1 below:

TABLE 1

| Parent Structure | Chemical Name |
|---|---|
|  | 4-[(1R)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl]amino}ethoxy]-2,2-dimethyl-4-oxobutanoic acid |

TABLE 1-continued

| Parent Structure | Chemical Name |
|---|---|
| | 4-[(1R)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl][2-(dimethylamino)ethyl]amino}ethoxy}-2,2-dimethyl-4-oxobutanoic acid |
| | 4-[(1S)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl]amino}ethoxy]-2,2-dimethyl-4-oxobutanoic acid |
| | 4-[(1S)-1-[(1R,2R,5R,10S,13R,14R,17S,19R)-17-[(3-carboxy-3,3-dimethylpropanoyl)oxy]-1,2,14,18,18-pentamethyl-7-oxo-8-(propan-2-yl)pentacyclo[11.8.0.0^{2,10}.0^{5,9}.0^{14,19}]henicos-8-en-5-yl]-2-{[(4-chlorophenyl)methyl][2-(dimethylamino)ethyl]amino}ethoxy]-2,2-dimethyl-4-oxobutanoic acid |
| | 4-{[(1R,2R,5R,10S,13R,14R,17S,19R)-5-(2-{[(4-chlorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
| --- | --- |
|  | 4-{[(1R,2R,5R,10S,13R,14R,17S,19R)-5-[2-(benzylamino)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-(2-{[(3-chlorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-(2-{[(3-chloro-2-fluorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-(2-{[1-(4-chlorophenyl)cyclopropyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| | 4-{[(1R,2R,5R,10S,13R,14R,17S,19R)-5-(2-{[(4-chlorophenyl)methyl][2-(dimethylamino)ethyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-(2-{[1-(4-chlorophenyl)cyclopropyl][2-(dimethylamino)ethyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-(2-{[(4-chlorophenyl)methyl](methyl)amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-(2-{N-[(4-chlorophenyl)methyl]acetamido}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
|  | 4-{[(1R,2R,5R,10S,13R,14R,17S,19R)-5-[(1R)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-[(1S)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-[(1S)-2-{[(4-chlorophenyl)methyl]yl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-[(1R)-1-(acetyloxy)-2-{[(4-chlorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| | 4-{[(1R,2R,5R,10S,13R,14R,17S,19R)-5-[(1S)-2-{[(4-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1S)-1-(acetyloxy)-2-{[(4-chlorophenyl)methyl][2-(dimethylamino)ethyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1R)-1-(acetyloxy)-2-{[(4-chlorophenyl)methyl][2-(dimethylamino)ethyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 5-{[(1R,2R,5R,10S,13R,14R,17S,19R)-5-[(1R)-2-{[(4-chlorophenyl)methyl][2-(dimethylamino)ethyl]amino}-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |

TABLE 1-continued

| Parent Structure | Chemical Name |
|---|---|
| 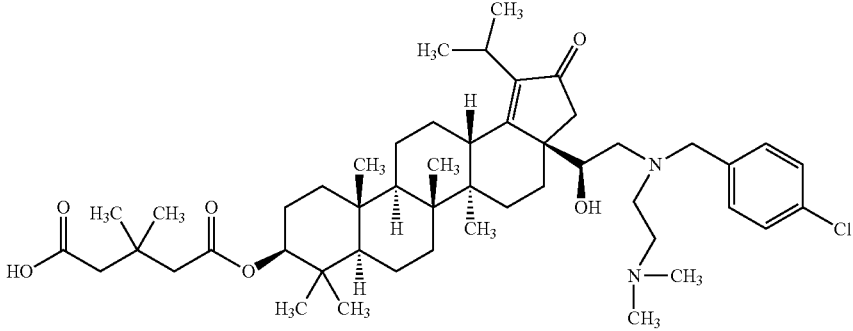 | 5-{[(1R,2R,5R,10S,13R,14R,17S,19R)-5-[(1S)-2-{[(4-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |
| 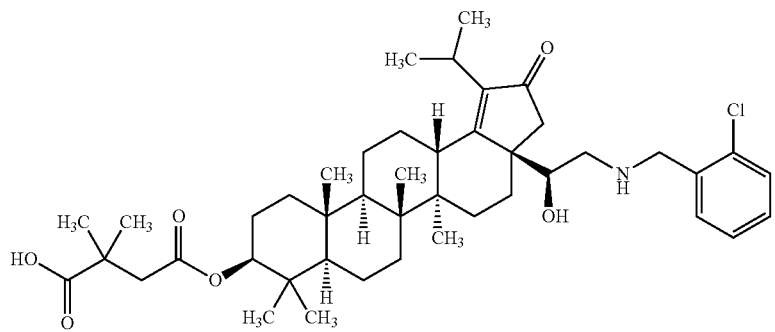 | 4-{[(1R,2R,5R,10S,13R,14R,17S,19R)-5-[(1S)-2-{[(2-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 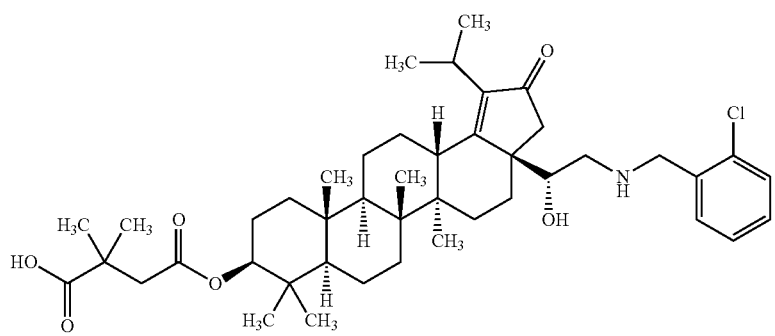 | 4-{[(1R,2R,5R,10S,13R,14R,17S,19R)-5-[(1R)-2-{[(2-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 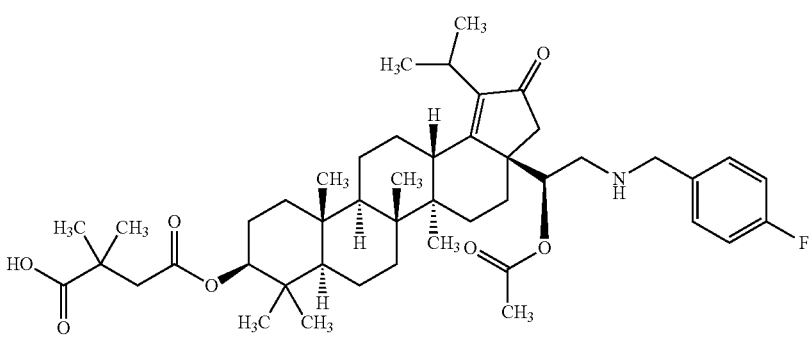 | 4-{[(1R,2R,5R,10S,13R,14R,17S,19R)-5-[(1S)-1-(acetyloxy)-2-{[(4-fluorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| 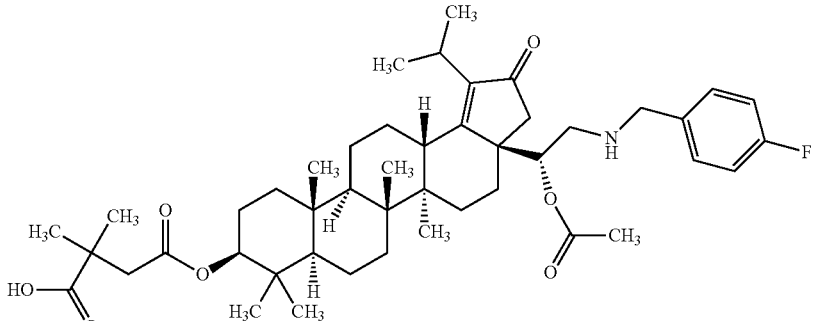 | 4-{[(1R,2R,5R,10S,13R,14R,17S,19R)-5-[(1R)-1-(acetyloxy)-2-{[(4-fluorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 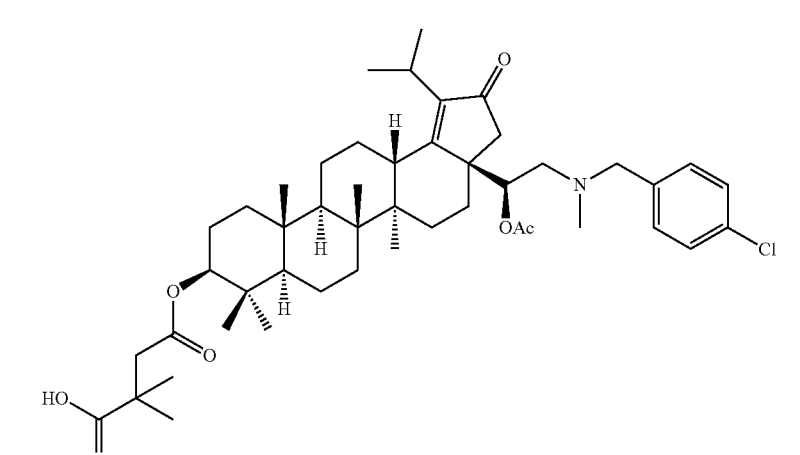 | 4-(((3aR,5aR,5bR,7aR,9S,11aR,11bR,13aS)-3a-((S)-1-acetoxy-2-((4-fluorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 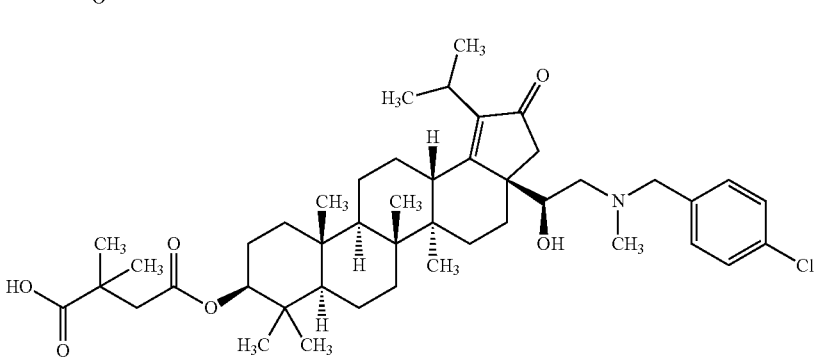 | 4-{[(1R,2R,5R,10S,13R,14R,17S,19R)-5-[(1S)-2-{[(4-chlorophenyl)methyl](methyl)amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 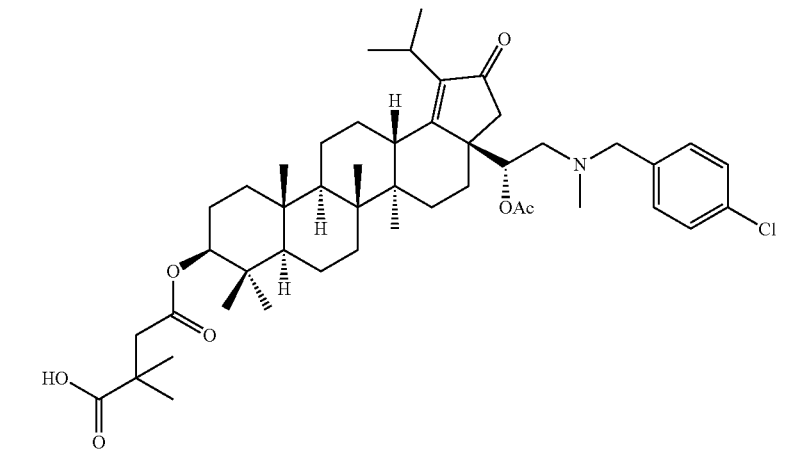 | 4-(((3aR,5aR,5bR,7aR,9S,11aR,11bR,13aS)-3a-((R)-1-Acetoxy-2-((4-chlorobenzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Parent Structure | Chemical Name |
|---|---|
| | 4-{[(1R,2R,5R,10S,13R,14R,17S,19R)-5-[(1R)-2-{[(4-chlorophenyl)methyl](methyl)amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-(((3aR,5aR,5bR,7aR,9S,11aR,11bR,13aS)-3a-((S)-1-Acetoxy-2-(N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-{[(1R,2R,5R,10S,13R,14R,17S,19R)-5-[(1S)-2-{N-[(4-chlorophenyl)methyl]acetamido}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-(((3aR,5aR,5bR,7aR,9S,11aR,11bR,13aS)-3a-((S)-2-(N-(4-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Parent Structure | Chemical Name |
|---|---|
| | 4-(((3aR,5aR,5bR,7aR,9S,11aR,11bR,13aS)-3a-((R)-2-(N-(4-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-(((3aR,5aR,5bR,7aR,9S,11aR,11bR,13aS)-3a-((S)-2-(N-(2-Chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-{[(1R,2R,5R,10S,13R,14R,17S,19R)-5-[(1S)-1-(acetoxy)-2-{[(2-chlorophenyl)methyl][2-(dimethylamino)ethyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1S)-1-{[(3-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| 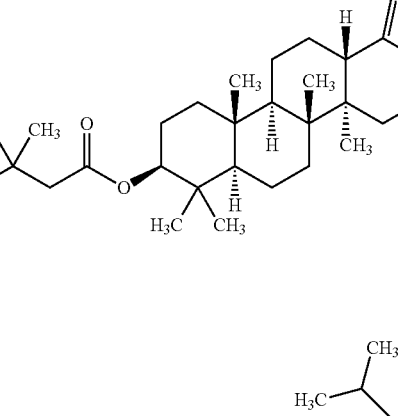 | 4-{[(1R,2R,5R,10S,13R,14R,17S,19R)-5-[(1R)-2-{[(3-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 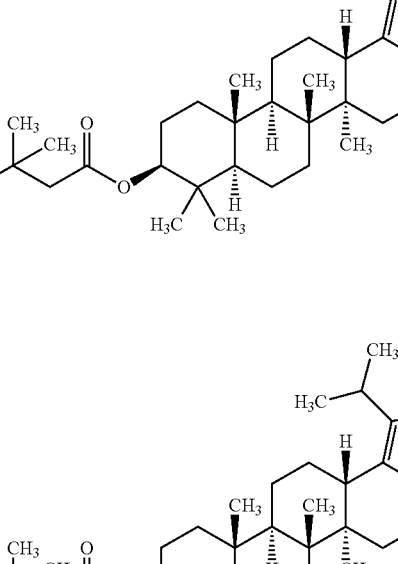 | 4-{[(1R,2R,5R,10S,13R,14R,17S,19R)-5-[(1S)-2-{[(3-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1R)-2-{[(3-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 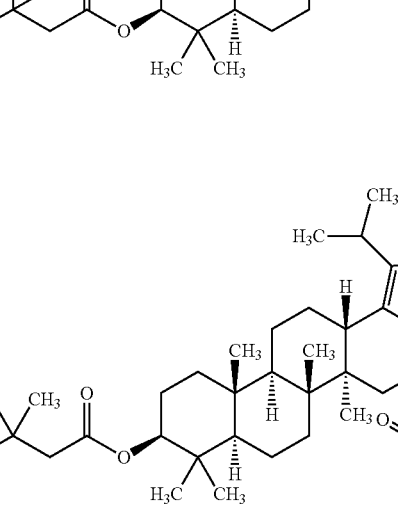 | 4-{[(1R,2R,5R,10S,13R,14R,17S,19R)-5-[(1S)-1-(acetyloxy)-2-{[(3-chlorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| 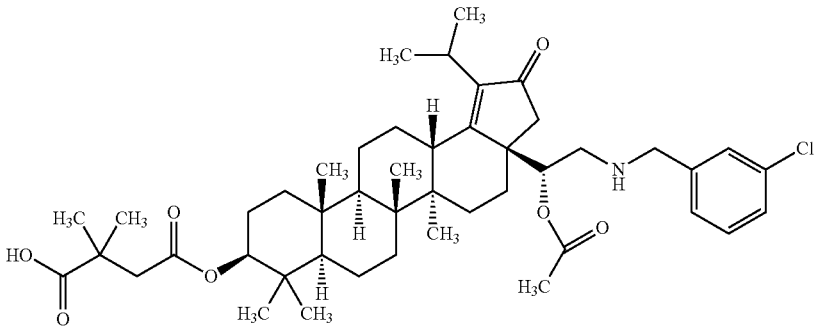 | 4-{[(1R,2R,5R,10S,13R,14R,17S,19R)-5-[(1R)-1-(acetyloxy)-2-{[(3-chlorophenyl)methyl]amino}ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 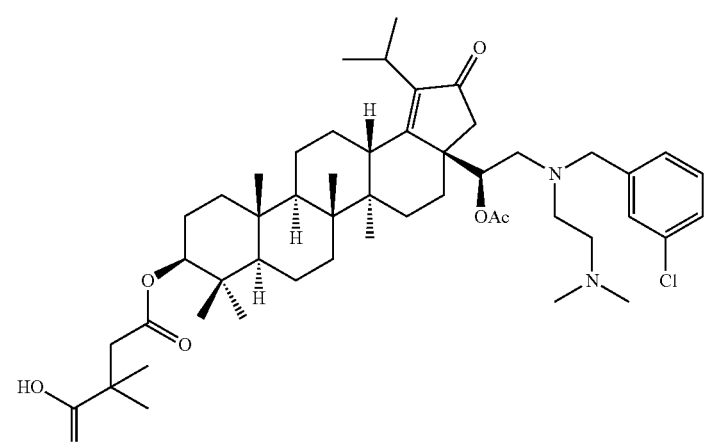 | 4-(((3aR,5aR,5bR,7aR,9S,11aR,11bR,13aS)-3a-((S)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 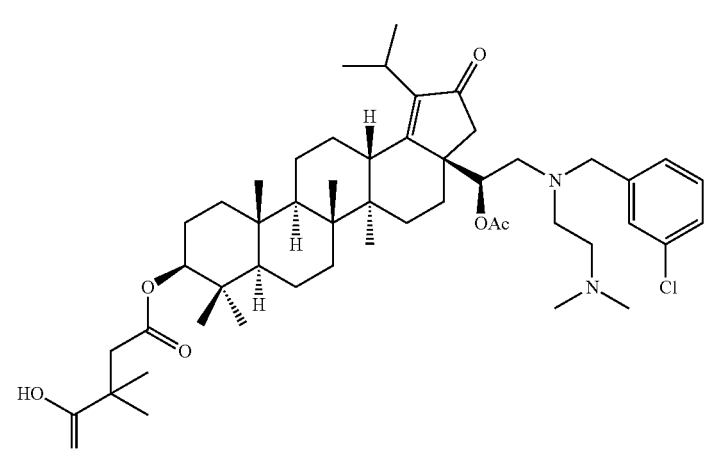 | 4-(((3aR,5aR,5bR,7aR,9S,11aR,11bR,13aS)-3a-((R)-1-acetoxy-2-((3-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Parent Structure | Chemical Name |
|---|---|
| 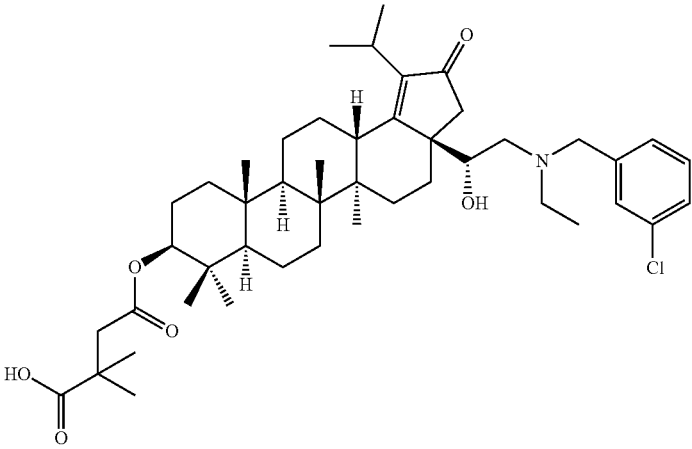 | 4-(((3aR,5aR,5bR,7aR,9S,11aR,11bR,13aS)-3a-((R)-2-((3-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 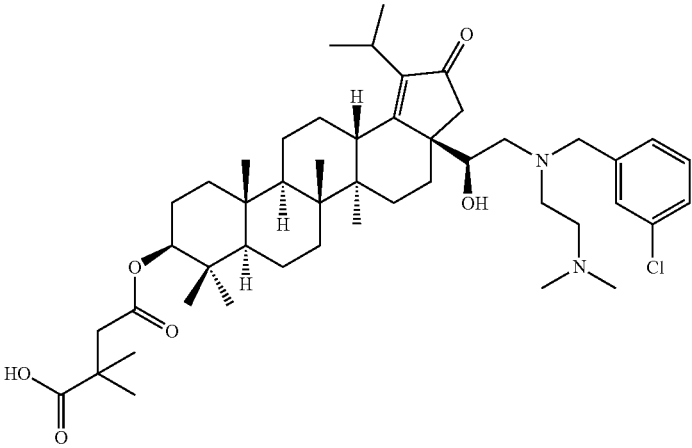 | 4-(((3aR,5aR,5bR,7aR,9S,11aR,11bR,13aS)-3a-((S)-2-((3-Chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 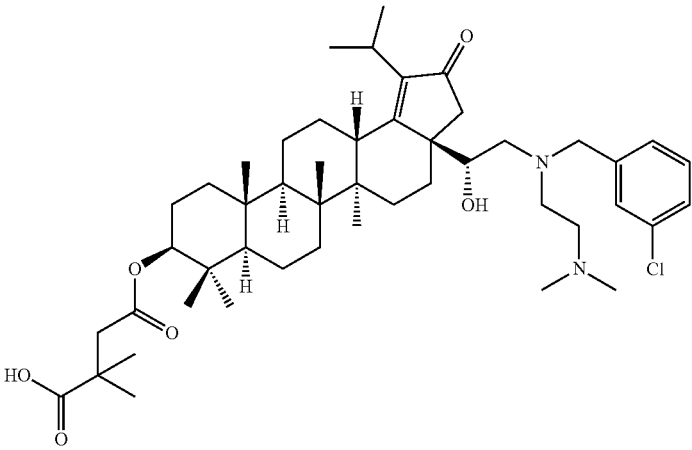 | 4-(((3aR,5aR,5bR,7aR,9S,11aR,11bR,13aS)-3a-((R)-2-((3-Chlorobenzyl)(2-(dimethylamino)ethyl)amino)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid. |

TABLE 1-continued

| Parent Structure | Chemical Name |
|---|---|
| 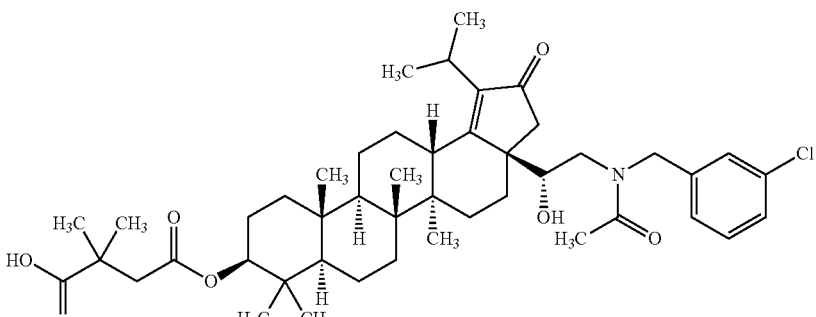 | 4-{[(1R,2R,5R,10S,13R,14R,17S,19R)-5-[(1R)-2-{N-[(3-chlorophenyl)methyl]acetamido}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 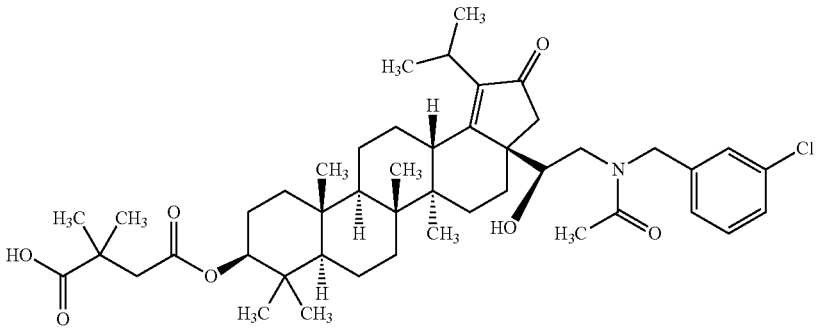 | 4-{[(1R,2R,5R,10S,13R,14R,17S,19R)-5-[(1S)-2-{N-[(3-chlorophenyl)methyl]acetamido}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 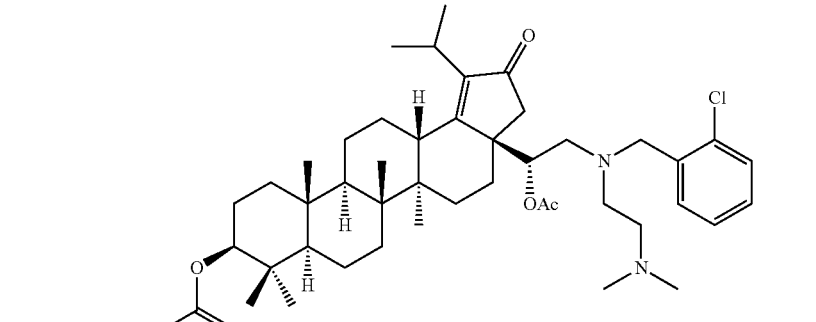 | 4-(((3aR,5aR,5bR,7aR,9S,11aR,11bR,13aS)-3a-((R)-1-acetoxy-2-((2-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 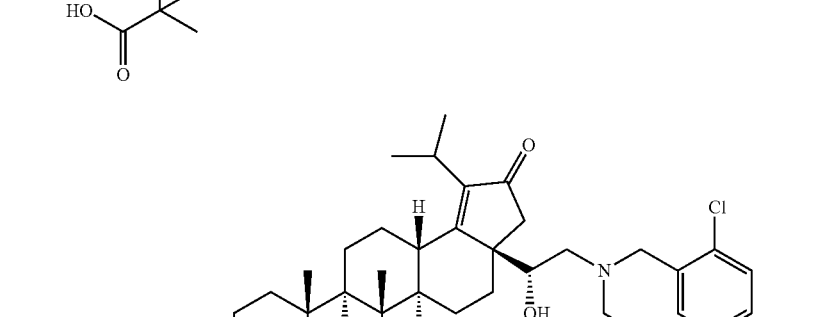 | 4-(((3aR,5aR,5bR,7aR,9S,11aR,11bR,13aS)-3a-((R)-2-((2-chlorobenzyl)(ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |

TABLE 1-continued

| Parent Structure | Chemical Name |
|---|---|
| 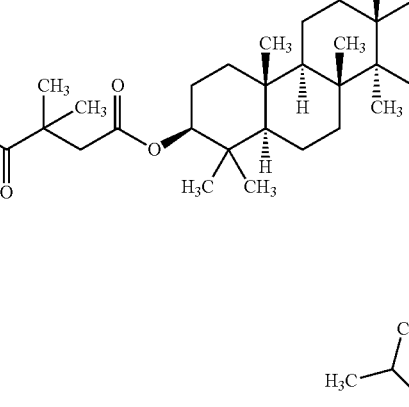 | 4-{[(1R,2R,5R,10S,13R,14R,17S,19R)-5-[(1R)-2-{[(2-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 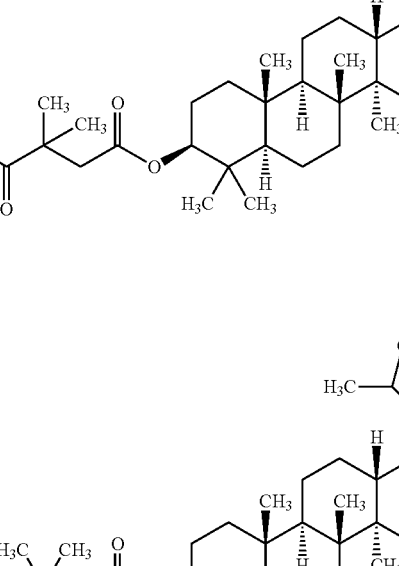 | 4-{[(1R,2R,5R,10S,13R,14R,17S,19R)-5-[(1S)-2-{[(2-chlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 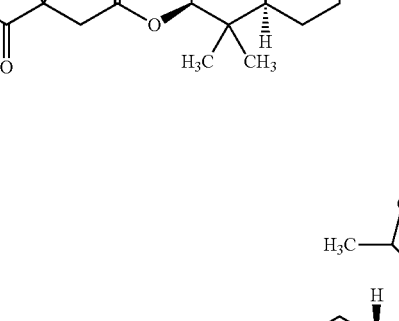 | 4-{[(1R,2R,5R,10S,13R,14R,17S,19R)-5-[(1R)-1-(acetyloxy)-2-(benzylamino)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 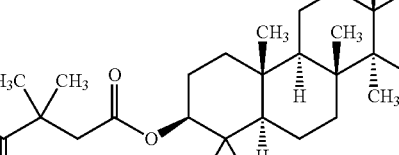 | 4-{[(1R,2R,5R,10S,13R,14R,17S,19R)-5-[(1S)-1-(acetyloxy)-2-(benzylamino)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| 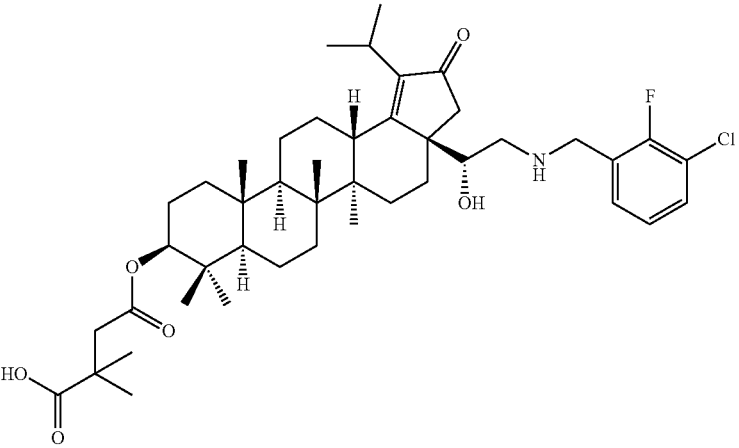 | 4-(((3aR,5aR,5bR,7aR,9S,11aR,11bR,13aS)-3a-((R)-2-((3-Chloro-2-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 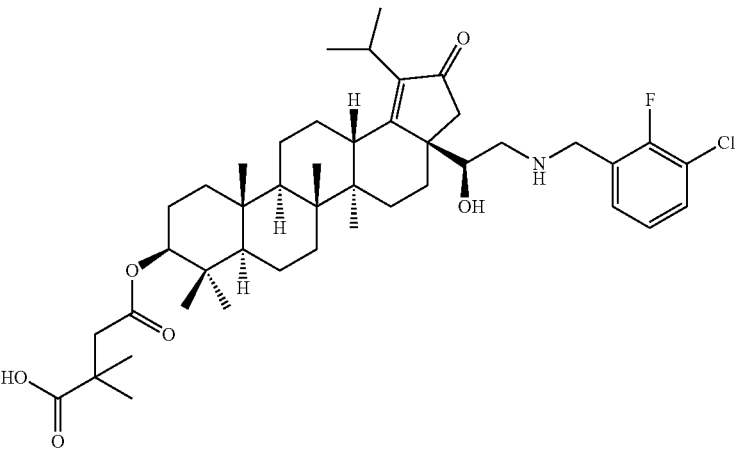 | 4-(((3aR,5aR,5bR,7aR,9S,11aR,11bR,13aS)-3a-((S)-2-((3-chloro-2-fluorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| 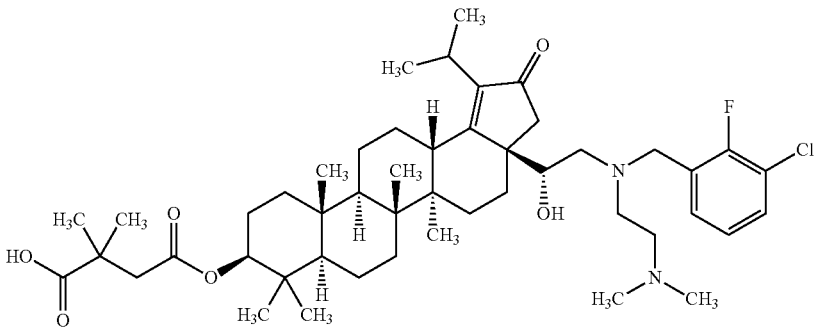 | 4-{[(1R,2R,5R,10S,13R,14R,17S,19R)-5-[(1R)-2-{[(3-chloro-2-fluorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 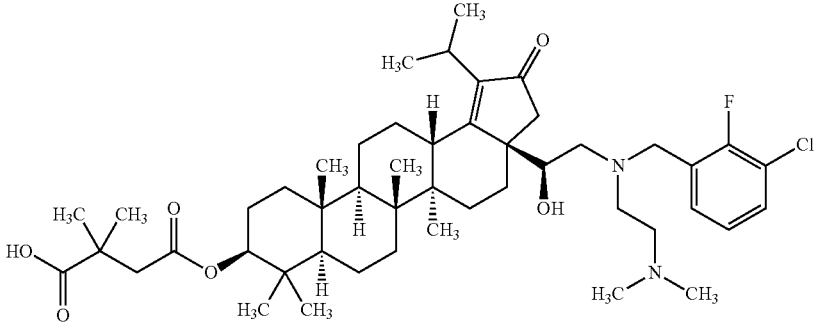 | 4-{[(1R,2R,5R,10S,13R,14R,17S,19R)-5-[(1S)-2-{[(3-chloro-2-fluorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| | 4-{[(1R,2R,5R,10S,13R,14R,17S,19R)-5-[(1R)-1-hydroxy-2-[(propan-2-yl)amino]ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1R)-2-(cyclohexylamino)-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5S,10S,13R,14R,17S,19R)-5-[1-hydroxy-2-(4-methylpiperazin-1-yl)ethyl]-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-(2-{[(4-chlorophenyl)methyl]amino}ethyl)-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| | 4-{[(1R,2R,5S,10S,13R,14R,17S,19R)-5-[(1S)-2-{[(4-chlorophenyl)methyl]amino}-1-hydroxyethyl]-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5S,10S,13R,14R,17S,19R)-5-[(1S)-2-[(cyclohexylmethyl)amino]-1-hydroxyethyl]-1,2,14,18,18-pentamethyl-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1S)-2-(cyclohexylamino)-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1R)-1-hydroxy-2-(1,2,3,4-tetrahydroisoquinolin-2-yl)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| 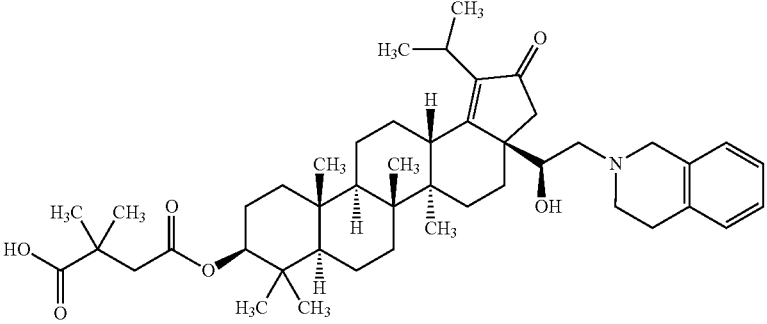 | 4-{[(1R,2R,5R,10S,13R,14R,17S,19R)-5-[(1S)-1-hydroxy-2-(1,2,3,4-tetrahydroiso-quinolin-2-yl)ethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 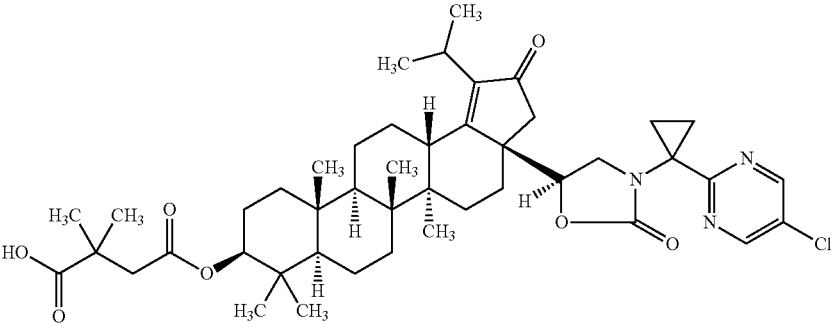 | 4-{[(1R,2R,10S,13R,14R,17S,19R)-5-[(5S)-3-[1-(5-chloropyrimidin-2-yl)cyclopropyl]-2-oxo-1,3-oxazolidin-5-yl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 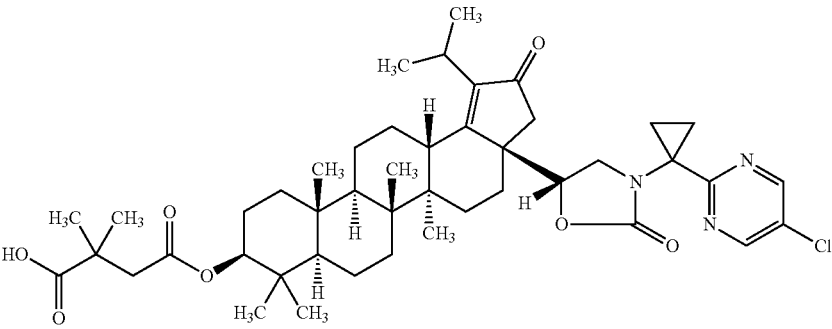 | 4-{[(1R,2R,10S,13R,14R,17S,19R)-5-[(5R)-3-[1-(5-chloropyrimidin-2-yl)cyclopropyl]-2-oxo-1,3-oxazolidin-5-yl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 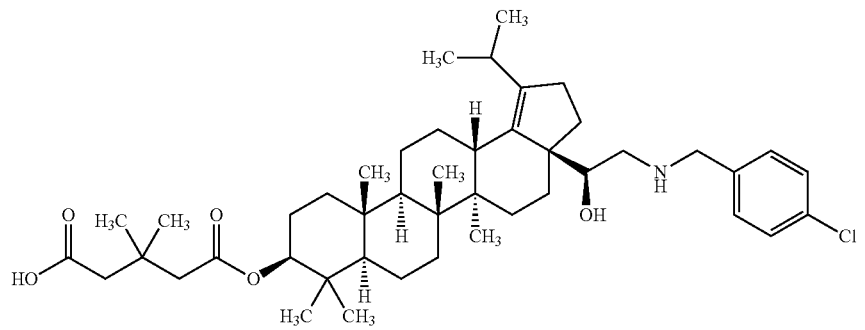 | 5-{[(1R,2R,5R,10S,13R,14R,17S,19R)-5-[(1S)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |

TABLE 1-continued

| Parent Structure | Chemical Name |
|---|---|
| | 4-(((3aR,5aR,5bR,7aR,9S,11aR,11bR,13aS)-3a-((R)-2-(3,4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-(((3aR,5aR,5bR,7aR,9S,11aR,11bR,13aS)-3a-((S)-2-(3,4-dihydroisoquinolin-2(1H)-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-(((3aS,5aR,5bR,7aR,9S,11aR,11bR,13aS)-3a-((R)-1-hydroxy-2-(4-methylpiperazin-1-yl)ethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-(((3aR,5aR,5bR,7aR,9S,11aR,11bR,13aS)-3a-(2-((4-chlorobenzyl)amino)ethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid |
| | 4-(((3aS,5aR,5bR,7aR,9S,11aR,11bR,13aS)-3a-((S)-2-((cyclohexylmethyl)amino)-1-hydroxyethyl)-1-isopropyl-5a,5b,8,8,11a-pentamethyl-3,3a,4,5,5a,5b,6,7,7a,9,10,11,11a,11b,12,13,13a-octadecahydro-2H-cyclopenta[a]chrysen-9-yl)oxy)-2,2-dimethyl-4-oxobutanoic acid |

TABLE 1-continued

| Parent Structure | Chemical Name |
|---|---|
| 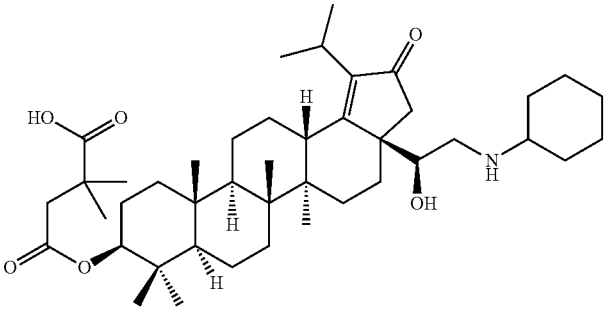 | 4-(((3aR,5aR,5bR,7aR,9S,11aR, 11bR,13aS)-3a-((S)-2-(cyclohexylamino)-1-hydroxyethyl)-1-isopropyl-5a, 5b,8,8,11a-pentamethyl-2-oxo-3,3a,4,5,5a,5b,6,7,7a,8,9,10,11, 11a,11b,12,13,13a-octadeca-hydro-2H-cyclopenta[a]chrysen-9-yl)oxy)-2,2-dimethyl-4-oxobutanoic acid |
| 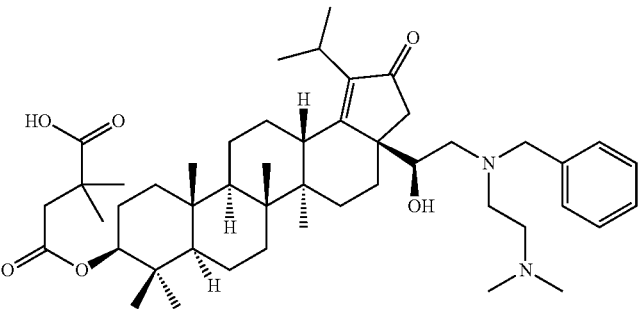 | 4-(((3aR,5aR,5bR,7aR,9S,11aR, 11bR,13aS)-3a-((S)-2-(benzyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)-2,2-dimethyl-4-oxobutanoic acid |
| 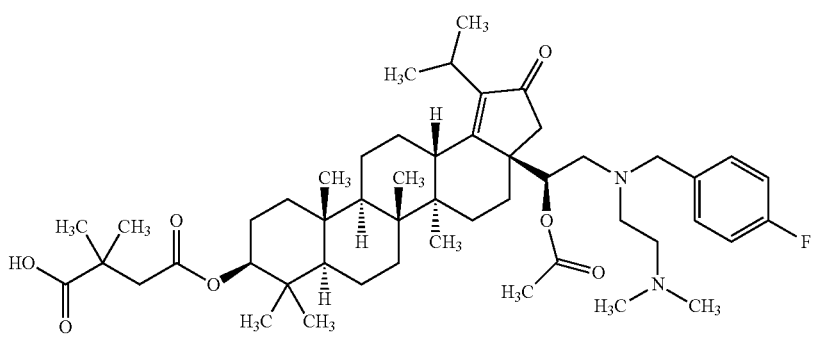 | 4-{[(1R,2R,5R,10S,13R,14R, 17S,19R)-5-[(1S)-1-(acetyloxy)-2-{[2-(dimethyl-amino)ethyl][(4-fluorophenyl)methyl]amino}ethyl]-1,2,14,18, 18-pentamethyl-7-oxo-8-(propan-2-yl)pentacyclo [11.8.0.0^{2,10}.0^{5,9}.0^{14,19}]henicos-8-en-17-yl]oxy}-2,2-dimethyl-4-oxobutanoic acid |
| 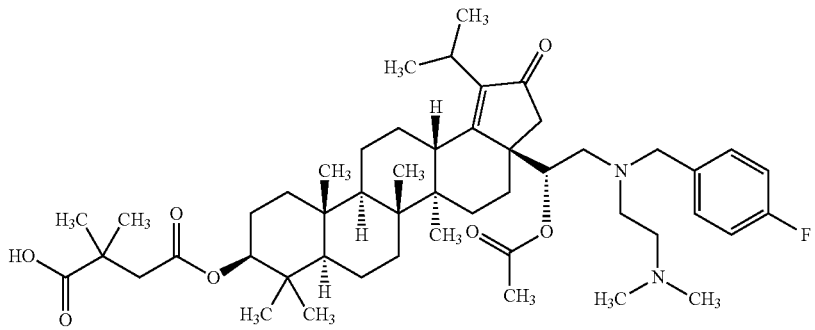 | 4-{[(1R,2R,5R,10S,13R,14R, 17S,19R)-5-[(1R)-1-(acetyloxy)-2-{[2-(dimethyl-amino)ethyl][(4-fluorophenyl)methyl]amino}ethyl]-1,2,14,18 18-pentamethyl-7-oxo-8-(propan-2-yl)pentacyclo [11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
|  | 5-{[(1R,2R,5R,10S,13R,14R,17S,19R)-5-[(1R)-2-{[(4-chlorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-3,3-dimethyl-5-oxopentanoic acid |
|  | 5-(((3aR,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid |
|  | 4-{[(1R,2R,5R,10S,13R,14R,17S,19R)-5-[(1S)-2-{[(2,4-dichlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
|  | 4-{[(1R,2R,5R,10S,13R,14R,17S,19R)-5-[(1R)-2-{benzyl[2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| | 4-{[(1R,2R,5R,10S,13R,14R,17S,19R)-5-[(1R)-2-{[2-(dimethylamino)ethyl][(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1R)-2-{[(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1S)-2-{[2-(dimethylamino)ethyl][4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| | 4-{[(1R,2R,5R,10S,13R,14R,17S,19R)-5-[(1S)-2-{[(4-fluorophenyl)methyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |

TABLE 1-continued

| Parent Structure | Chemical Name |
|---|---|
| 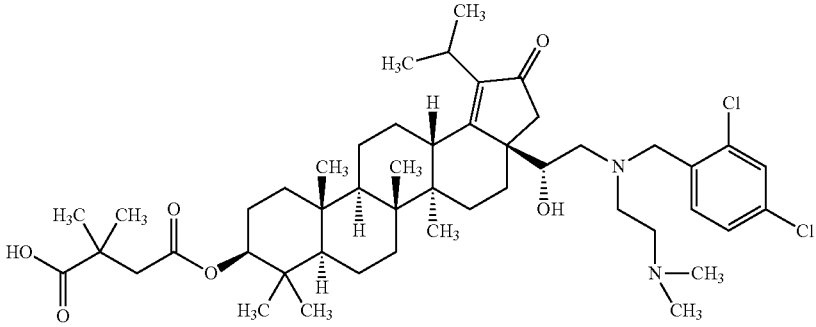 | 4-{[(1R,2R,5R,10S,13R,14R,17S,19R)-5-[(1R)-2-{[(2,4-dichlorophenyl)methyl][2-(dimethylamino)ethyl]amino}-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 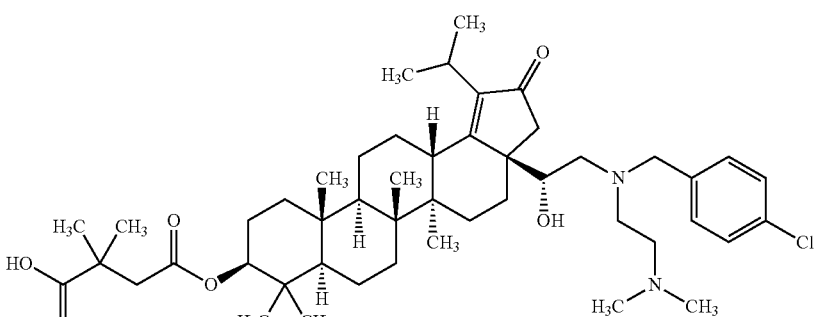 | 4-{[(1R,2R,5R,10S,13R,14R,17S,19R)-5-[(1R)-2-[1-(4-chlorophenyl)-N-[2-(dimethylamino)ethyl]formamido]-1-hydroxyethyl]-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 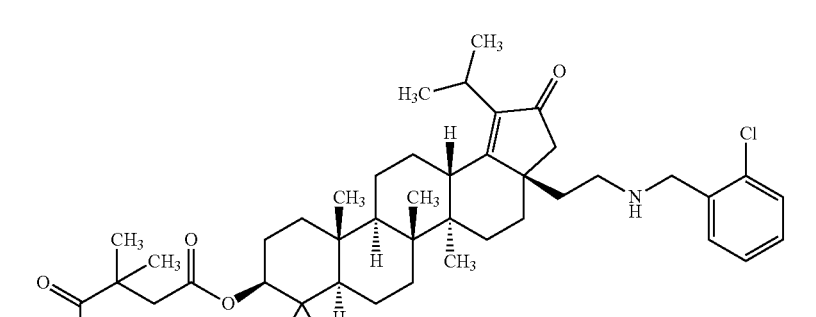 | 4-{[(1R,2R,5R,10S,13R,14R,17S,19R)-5-(2-{[(2-chlorophenyl)methyl]amino}ethyl)-1,2,14,18,18-pentamethyl-7-oxo-8-(propan-2-yl)pentacyclo[11.8.0.0^{2,10}.0^{5,9}.0^{14,19}]henicos-8-en-17-yl]oxy}-2,2-dimethyl-4-oxobutanoic acid |
| 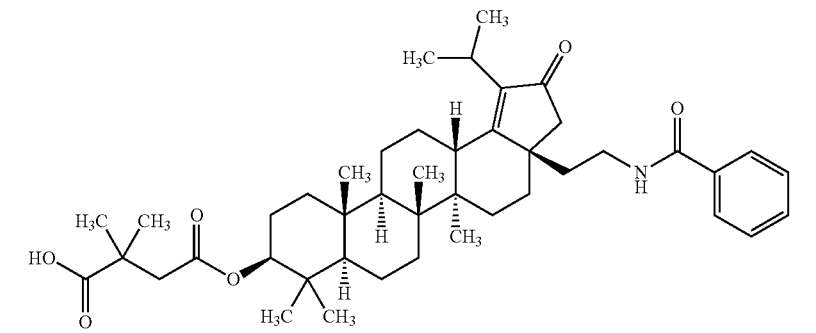 | 2,2-dimethyl-4-oxo-4-{[(1R,2R,5R,10S,13R,14R,17S,19R)-1,2,14,18,18-pentamethyl-7-oxo-5-[2-(phenylformamido)ethyl]-8-(propan-2-yl)pentacyclo[11.8.0.0^{2,10}.0^{5,9}.0^{14,19}]henicos-8-en-17-yl]oxy}butanoic acid | or pharmaceutically acceptable salts thereof.

In one embodiment, the betulin derivative is a compound of formula II:

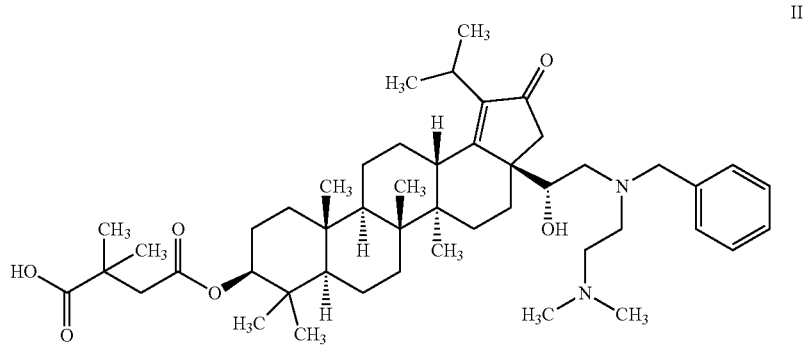

II or a pharmaceutically acceptable salt thereof.

Below are additional betulin derivatives that are suitable for the LAP formulations described herein.

Example 84

Compound 153

4-(((3aR,5aR,5bR,7aR,9S,11aR,11bR,13aS)-3a-(((((R)-1-(4-Chlorophenyl)ethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

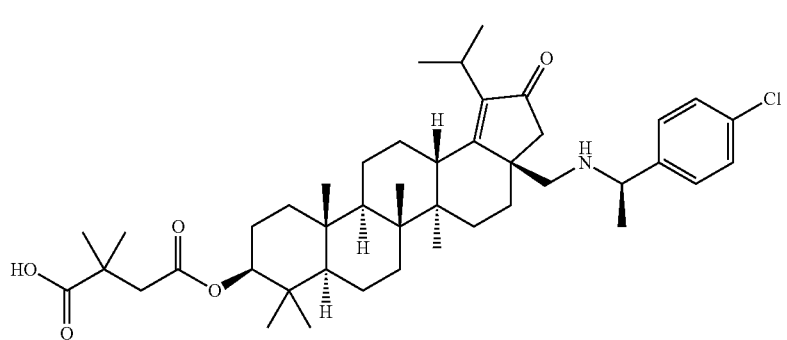

153

LC/MS: m/z calculated 721.5. found 722.3 (M+1)$^+$.

Example 85

Compound 154

4-(((3aR,5aR,5bR,7aR,9S,11aR,11bR,13aS)-3a-((N-(4-chlorobenzyl)acetamido)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

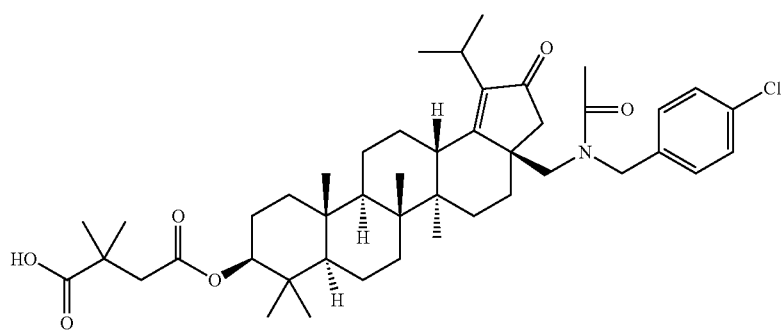

154

LC/MS: m/z calculated 749.4. found 750.3 (M+1)$^+$.

Example 86

Compound 155

4-(((3aR,5aR,5bR,7aR,9S,11aR,11bR,13aS)-3a-(((4-chlorobenzyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

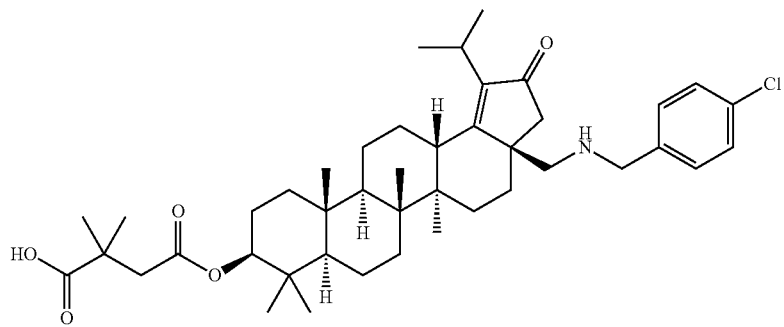

155

LC/MS: m/z calculated 707.4. found 708.3 (M+1)$^+$.

Example 87

Compound 156

4-(((3aR,5aR,5bR,7aR,9S,11aR,11bR,13aS)-3a-((N-(4-chlorophenethyl)acetamido)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

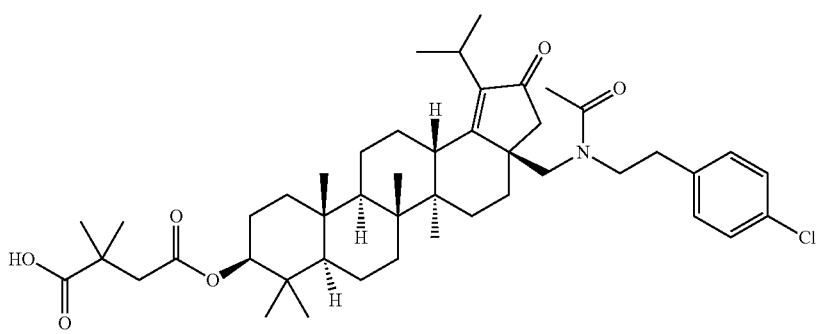

156

LC/MS: m/z calculated 763.5. found 764.3 (M+1)$^+$.

Example 88

Compound 157

4-(((3aR,5aR,5bR,7aR,9S,11aR,11bR,13aS)-3a-(((4-chlorophenethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

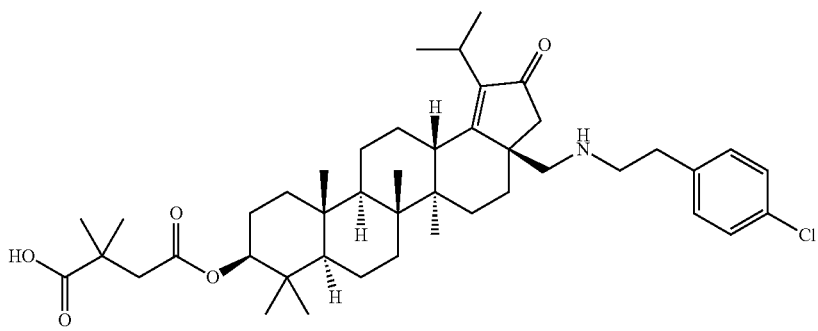

157

LC/MS: m/z calculated 721.5. found 722.3 (M+1)$^+$.

Example 89

Compound 158

4-(((3aR,5aR,5bR,7aR,9S,11aR,11bR,13aS)-3a-((R)-2-((4-chlorobenzyl)(3-methoxypropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

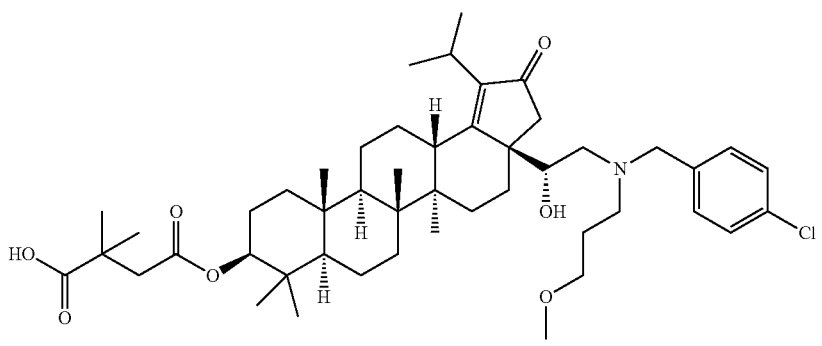

158

LC/MS: m/z calculated 809.50. found 810.7 (M+1)$^+$.

Example 90

Compound 159

4-(((3aR,5aR,5bR,7aR,9S,11aR,11bR,13aS)-3a-((S)-2-((4-chlorobenzyl)(3-methoxypropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

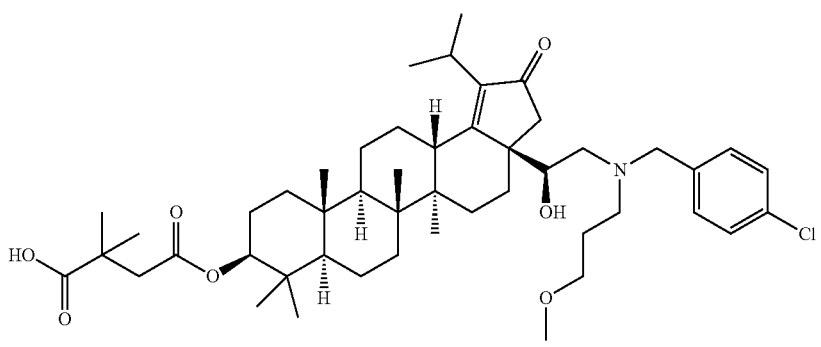

159

LC/MS: m/z calculated 809.5. found 810.4 (M+1)$^+$.

Example 91

Compound 160

4-(((3aR,5aR,5bR,7aR,9S,11aR,11bR,13aS)-3a-((R)-2-((4-chlorobenzyl)(2-methoxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

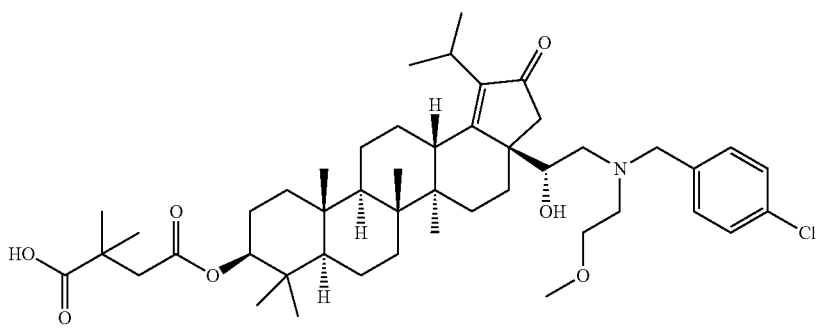

160

LC/MS: m/z calculated 795.5. found 796.3 (M+1)⁺.

Example 92

Compound 161

4-(((3aR,5aR,5bR,7aR,9S,11aR,11bR,13aS)-3a-((S)-2-((4-chlorobenzyl)(2-methoxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

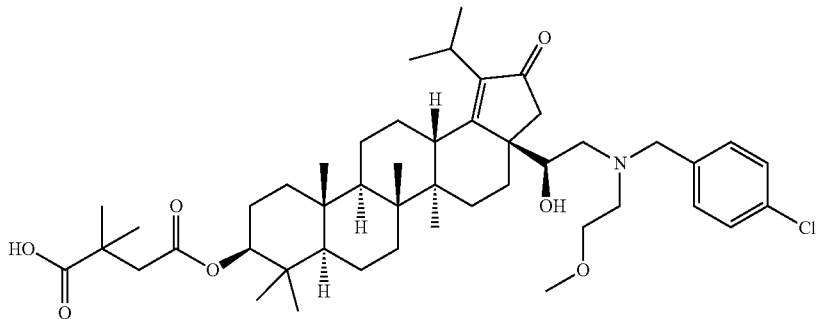

161

LC/MS: m/z calculated 795.5. found 796.3 (M+1)⁺.

Example 93

Compound 162

4-(((3aR,5aR,5bR,7aR,9S,11aR,11bR,13aS)-3a-((S)-2-(4-chloro-N-(2-(dimethylamino)ethyl)benzamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

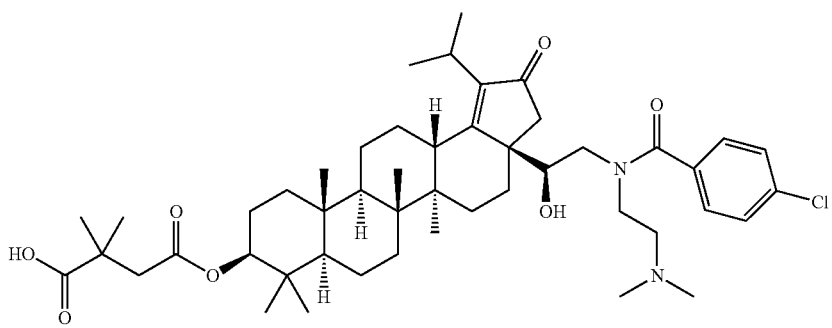

162

LC/MS: m/z calculated 822.5. found 823.5 (M+1)$^+$.

Example 94

Compound 163

4-(((3aS,5aR,5bR,7aR,9S,11aR,11bR,13aS)-3a-((R)-2-((4-chlorobenzyl)(2-(dimethylamino)ethyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

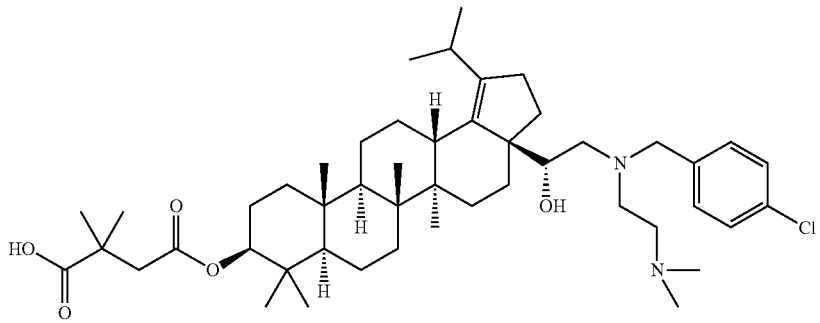

163

LC/MS: m/z calculated 794.5. found 795.5 (M+1)$^+$.

Example 95

Compound 164

4-(((3aR,5aR,5bR,7aR,9S,11aR,11bR,13aS)-3a-((R)-2-((4-chlorobenzyl)((R)-pyrrolidin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

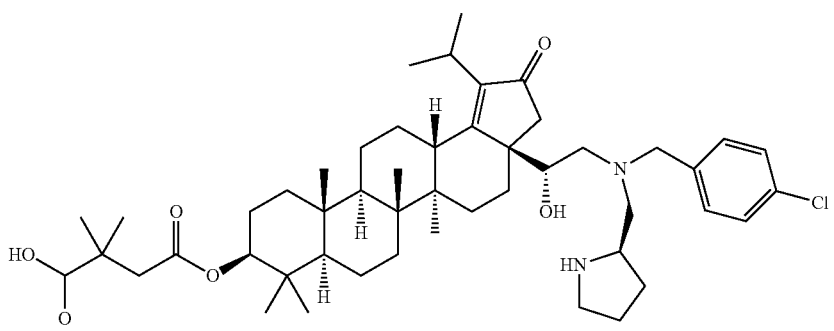

164

LC/MS: m/z calculated 820.5. found 821.5 (M+1)$^+$.

Example 96

Compound 165

4-(((3aR,5aR,5bR,7aR,9S,11aR,11bR,13aS)-3a-((S)-2-((4-chlorobenzyl)((R)-pyrrolidin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

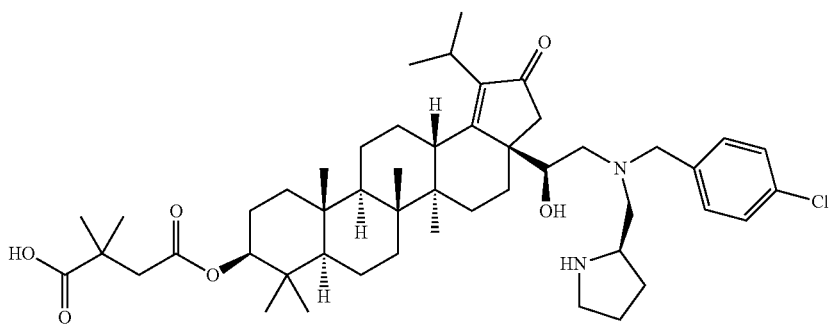

165

LC/MS: m/z calculated 820.5. found 821.5 (M+1)$^+$.

Example 97

Compound 166

4-(((3aR,5aR,5bR,7aR,9S,11aR,11bR,13aS)-3a-((R)-2-((4-chlorobenzyl)(2-hydroxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

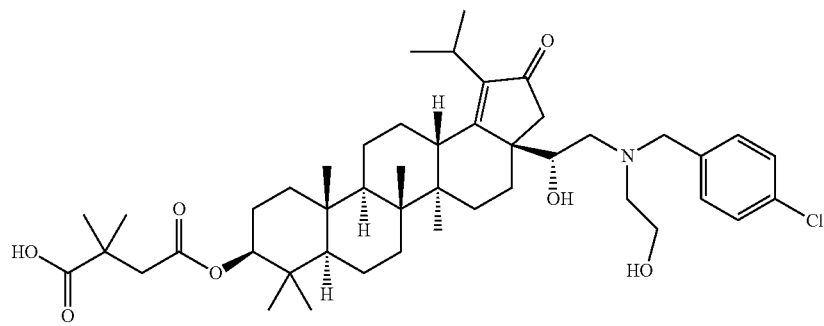

LC/MS: m/z calculated 781.5. found 782.5 (M+1)$^+$.

Example 98

Compound 167

4-(((3aR,5aR,5bR,7aR,9S,11aR,11bR,13aS)-3a-((R)-4-(4-chlorobenzyl)-5,6-dioxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

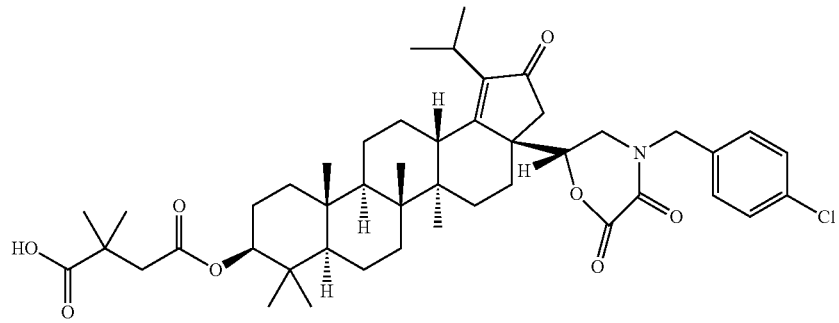

LC/MS: m/z calculated 791.4. found 792.5 (M+1)$^+$.

Example 99

Compound 168

4-(((3aR,5aR,5bR,7aR,9S,11aR,11bR,13aS)-3a-((S)-2-(((5-chloropyridin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

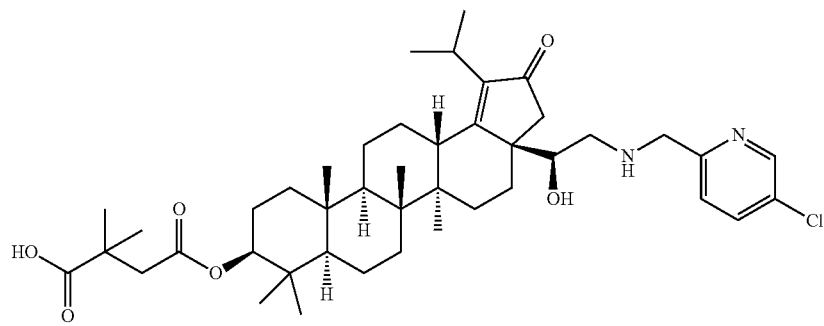

168

LC/MS: m/z calculated 738.4. found 739.5 (M+1)$^+$.

Example 100

Compound 169

4-(((3aR,5aR,5bR,7aR,9S,11aR,11bR,13aS)-3a-((R)-4-(4-chlorobenzyl)-5-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

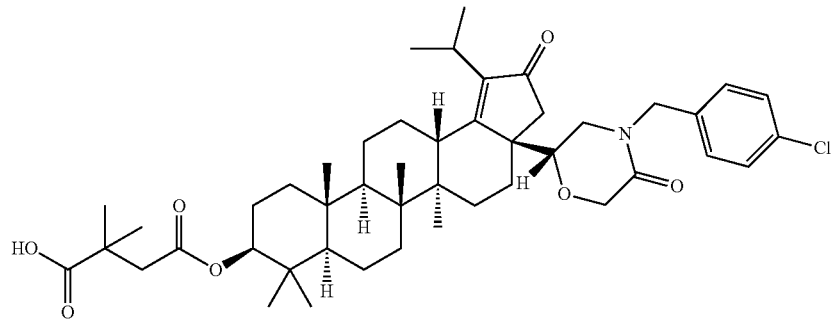

169

LC/MS: m/z calculated 777.4. found 778.6 (M+1)$^+$.

Example 101

Compound 170

4-(((3aR,5aR,5bR,7aR,9S,11aR,11bR,13aS)-3a-((R)-4-(4-chlorobenzyl)-6-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

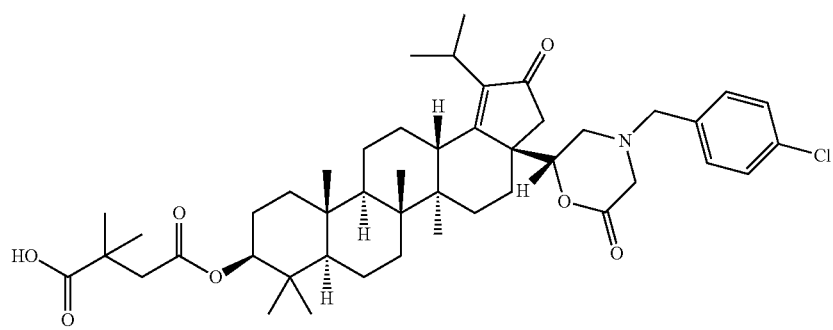

170

LC/MS: m/z calculated 777.4. found 777.9 (M+1)$^+$.

Example 102

Compound 171

4-(((3aR,5aR,5bR,7aR,9S,11aR,11bR,13aS)-3a-((S)-4-(4-chlorobenzyl)-5-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

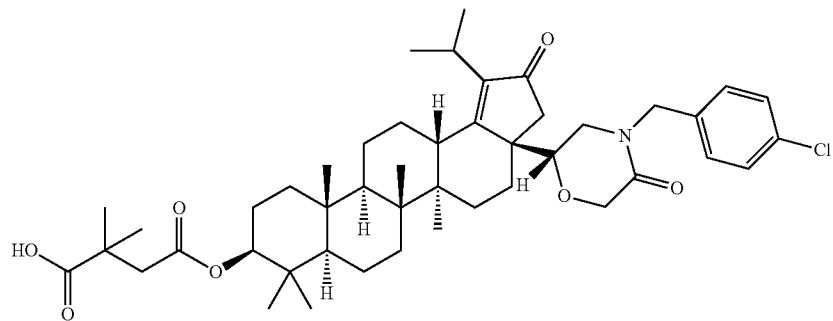

171

LC/MS: m/z calculated 777.4. found 777.9 (M+1)$^+$.

Example 103

Compound 172

4-(((3aR,5aR,5bR,7aR,9S,11aR,11bR,13aS)-3a-((R)-2-(((5-chloropyridin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

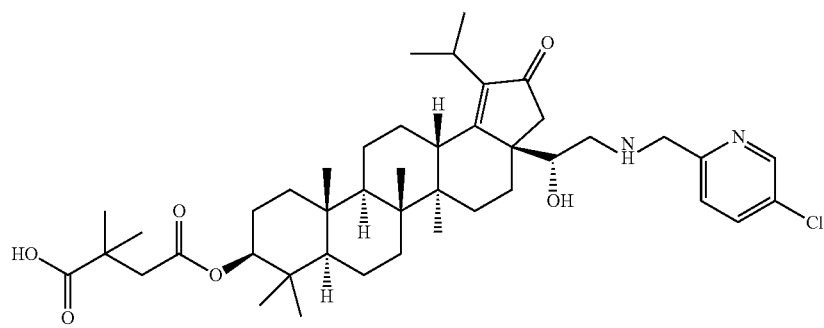

172

LC/MS: m/z calculated 737.4. found 739.4 (M+1)$^+$.

Example 104

Compound 173

4-(((3aR,5aR,5bR,7aR,9S,11aR,11bR,13aS)-3a-((S)-2-((4-chlorobenzyl)(2-hydroxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

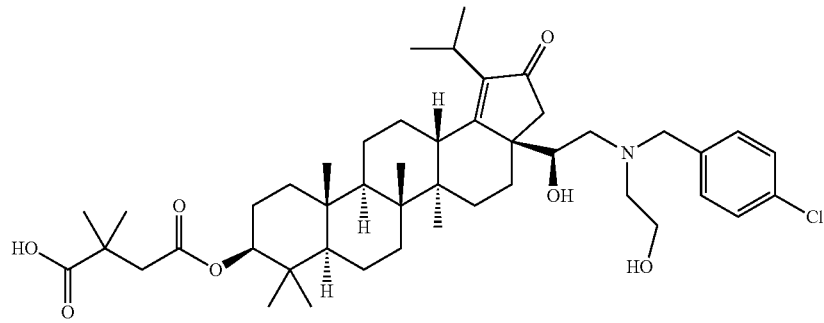

173

LC/MS: m/z calculated 781.5. found 782.3 (M+1)$^+$.

Example 105

Compound 174

4-(((3aR,5aR,5bR,7aR,9S,11aR,11bR,13aS)-3a-(((4-chlorobenzyl)(2-(dimethylamino)ethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

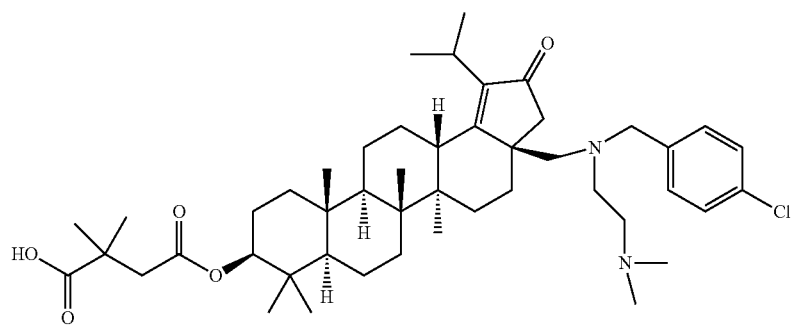

174

LC/MS: m/z calculated 778.5. found 779.5 (M+1)$^+$.

Example 106

Compound 175

4-(((3aR,5aR,5bR,7aR,9S,11aR,11bR,13aS)-3a-((4-chlorophenethyl)(2-(dimethylamino)ethyl)amino)methyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

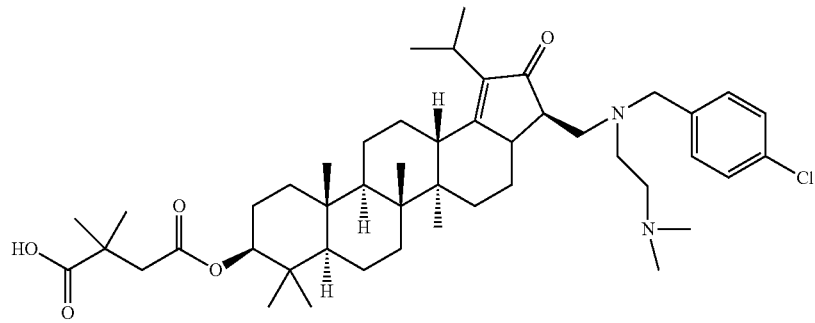

175

LC/MS: m/z calculated 792.5. found 793.5 (M+1)$^+$.

Example 107

Compound 176

4-(((3aR,5aR,5bR,7aR,9S,11aR,11bR,13aS)-3a-((S)-2-(N-(4-chlorobenzyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

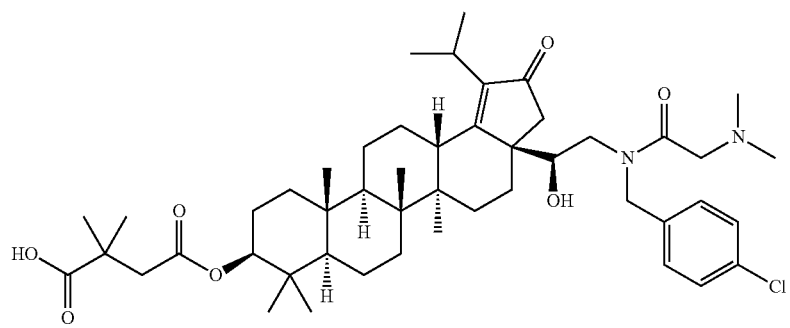

176

LC/MS: m/z calculated 822.5. found 823.5 (M+1)$^+$.

Example 108

Compound 177

4-(((3aR,5aR,5bR,7aR,9S,11aR,11bR,13aS)-3a-((R)-2-(N-(4-chlorobenzyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

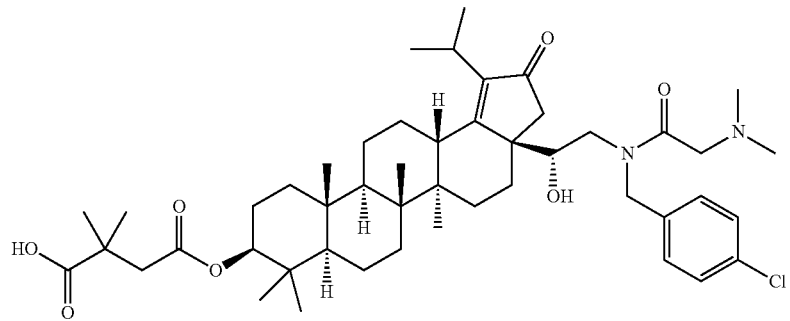

177

LC/MS: m/z calculated 822.5. found 823.5 (M+1)$^+$.

Example 109

Compound 178

4-(((3aR,5aR,5bR,7aR,9S,11aR,11bR,13aS)-3a-((R)-2-((4-chlorobenzyl)(2-(pyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

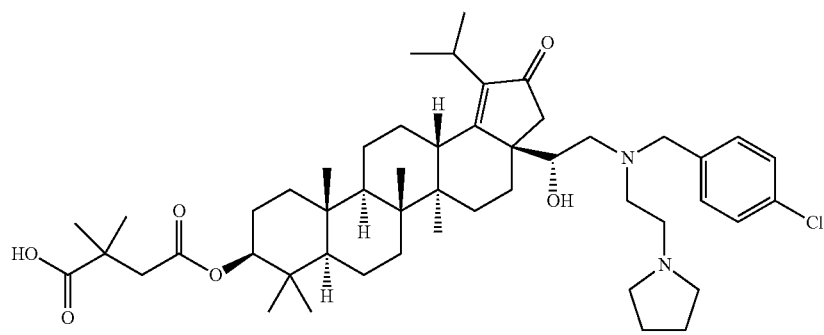

178

LC/MS: m/z calculated 834.5. found 835.5 (M+1)$^+$.

Example 110

Compound 179

4-(((3aR,5aR,5bR,7aR,9S,11aR,11bR,13aS)-3a-((S)-2-((4-chlorobenzyl)(2-(pyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

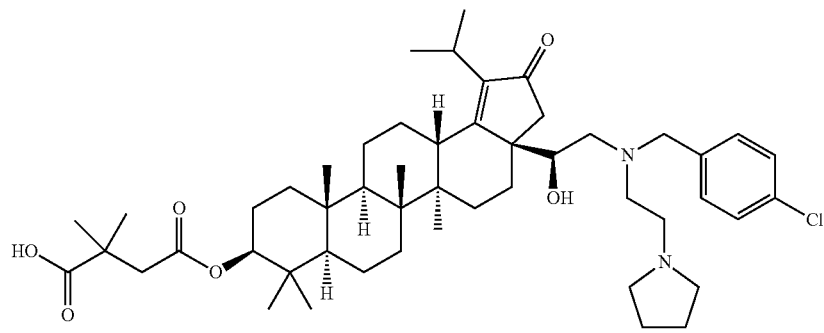

179

LC/MS: m/z calculated 834.5. found 835.5 (M+1)$^+$.

Example 111

Compound 180

4-(((3aR,5aR,5bR,7aR,9S,11aR,11bR,13aS)-3a-((R)-2-((4-chlorobenzyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

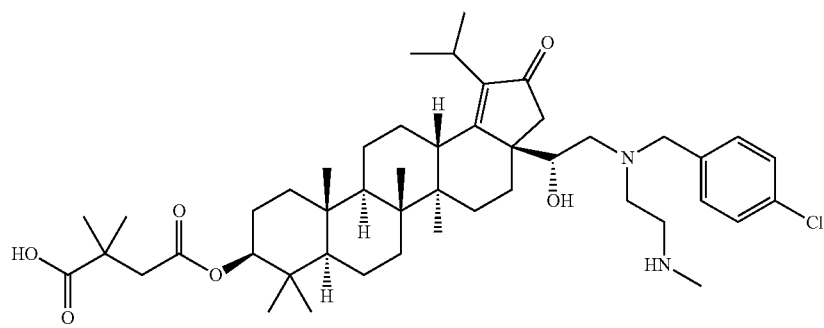

180

LC/MS: m/z calculated 794.5. found 795.4 (M+1)$^+$.

Example 112

Compound 181

4-(((3aR,5aR,5bR,7aR,9S,11aR,11bR,13aS)-3a-((S)-2-((2-aminoethyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

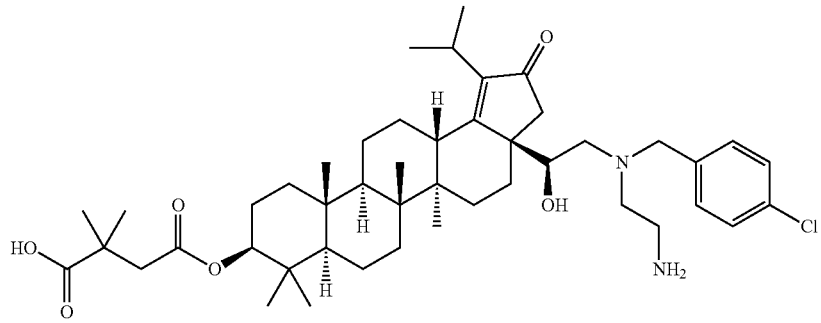

181

LC/MS: m/z calculated 780.5. found 781.4 (M+1)$^+$.

Example 113

Compound 182

4-(((3aR,5aR,5bR,7aR,9S,11aR,11bR,13aS)-3a-((R)-2-((2-aminoethyl)(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

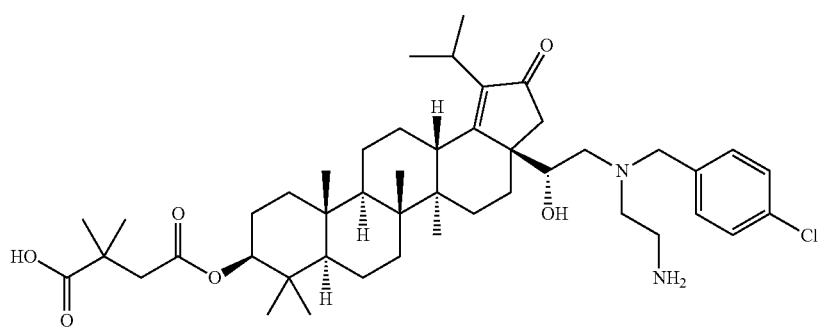

182

LC/MS: m/z calculated 780.5. found 781.4 (M+1)$^+$.

Example 114

Compound 183

4-(((3aR,5aR,5bR,7aR,9S,11aR,11bR,13aS)-3a-((S)-2-((4-chlorobenzyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

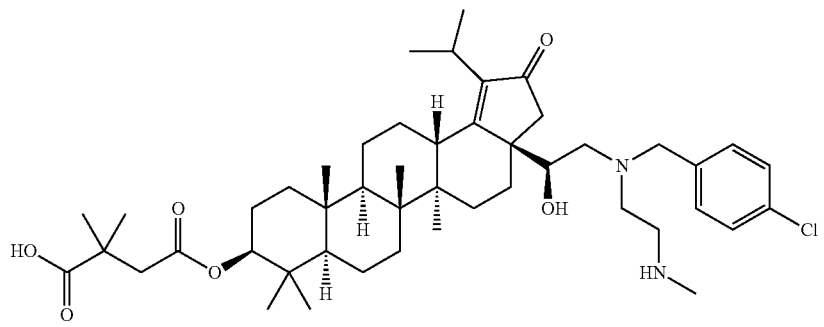

183

LC/MS: m/z calculated 794.5. found 795.5 (M+1)$^+$.

Example 115

Compound 184

4-(((3aR,5aR,5bR,7aR,9S,11aR,11bR,13aS)-3a-((R)-2-((4-chlorobenzyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

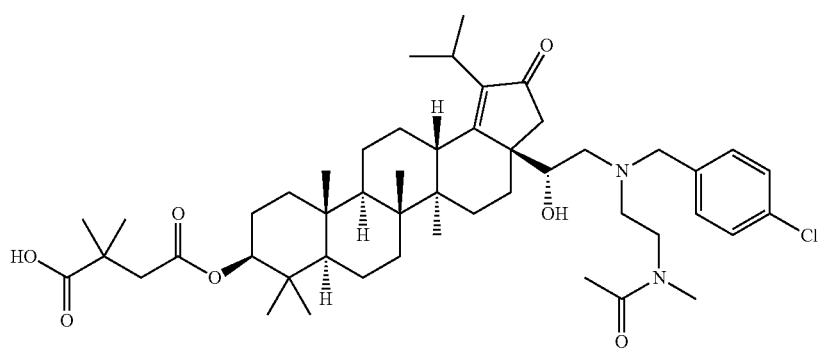

184

LC/MS: m/z calculated 836.5. found 837.5 (M+1)$^+$.

Example 116

Compound 185

4-(((3aR,5aR,5bR,7aR,9S,11aR,11bR,13aS)-3a-((S)-2-((4-chlorobenzyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

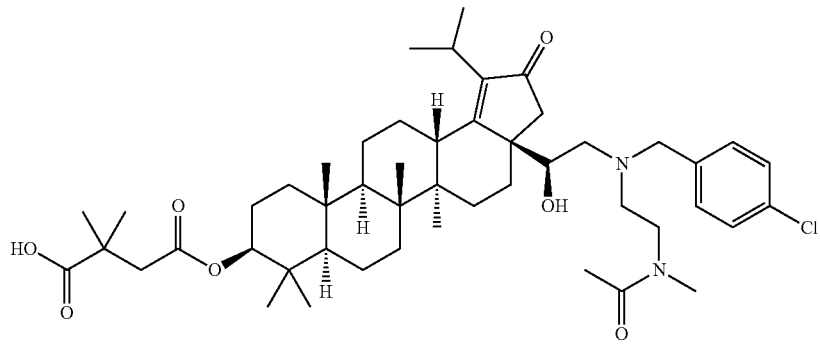

185

LC/MS: m/z calculated 836.5. found 837.5 (M+1)$^+$.

Example 117

Compound 186

4-(((3aR,5aR,5bR,7aR,9S,11aR,11bR,13aS)-3a-((S)-2-(((S)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

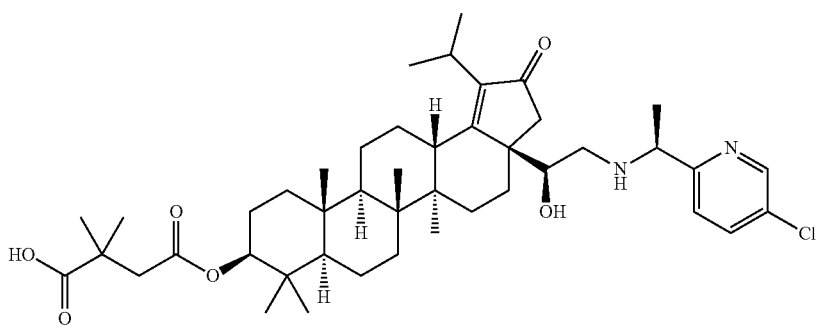

186

LC/MS: m/z calculated 752.5. found 753.4 (M+1)$^+$.

Example 118

Compound 187

4-(((3aR,5aR,5bR,7aR,9S,11aR,11bR,13aS)-3a-((R)-2-(((S)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

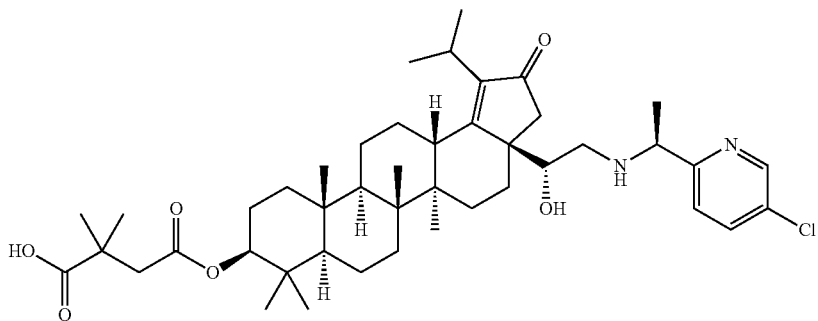

187

LC/MS: m/z calculated 752.5. found 753.4 (M+1)$^+$.

Example 119

Compound 188

4-(((3aR,5aR,5bR,7aR,9S,11aR,11bR,13aS)-3a-((R)-2-((2-(dimethylamino)ethyl)(phenethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

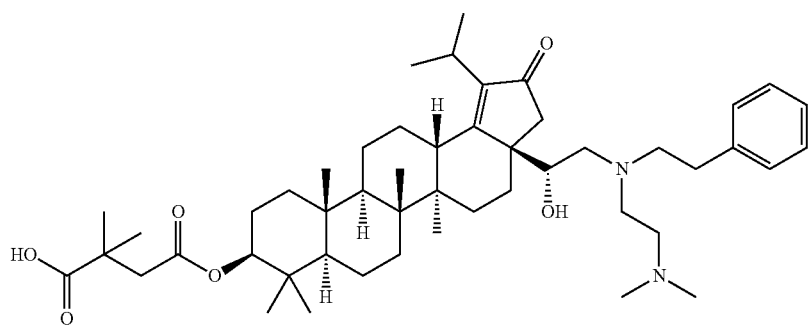

188

LC/MS: m/z calculated 788.6. found 789.5 (M+1)$^+$.

Example 120

Compound 189

4-(((3aR,5aR,5bR,7aR,9S,11aR,11bR,13aS)-3a-((S)-2-(cyclohexyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

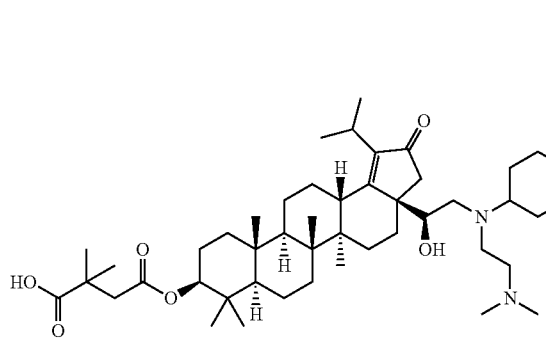

189

LC/MS: m/z calculated 766.6. found 767.6 (M+1)$^+$.

Example 121

Compound 190

4-(((3aR,5aR,5bR,7aR,9S,11aR,11bR,13aS)-3a-((R)-2-(cyclohexyl(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

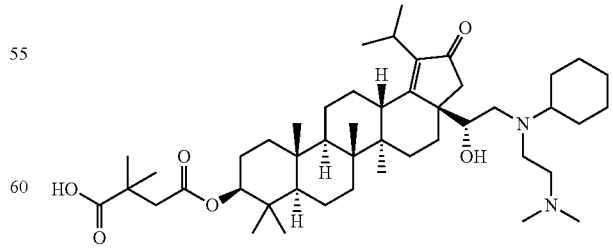

190

LC/MS: m/z calculated 766.6. found 767.6 (M+1)$^+$.

Example 122

Compound 191

4-(((3aR,5aR,5bR,7aR,9S,11aR,11bR,13aS)-3a-((S)-2-(((5-chloropyridin-2-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

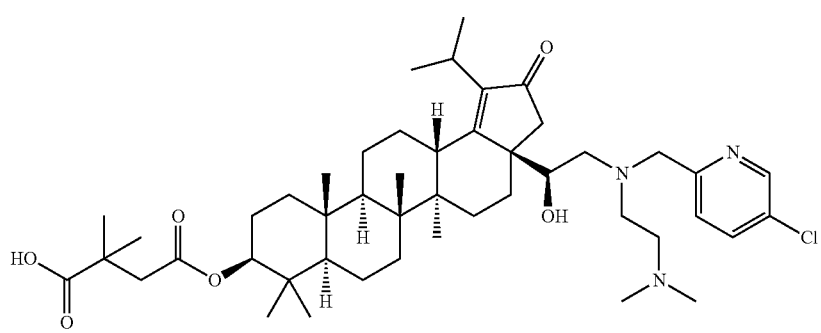

191

LC/MS: m/z calculated 809.5. found 810.5 $(M+1)^+$.

Example 123

Compound 192

4-(((3aR,5aR,5bR,7aR,9S,11aR,11bR,13aS)-3a-(2-(N-(4-chlorobenzyl)-2-(dimethylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

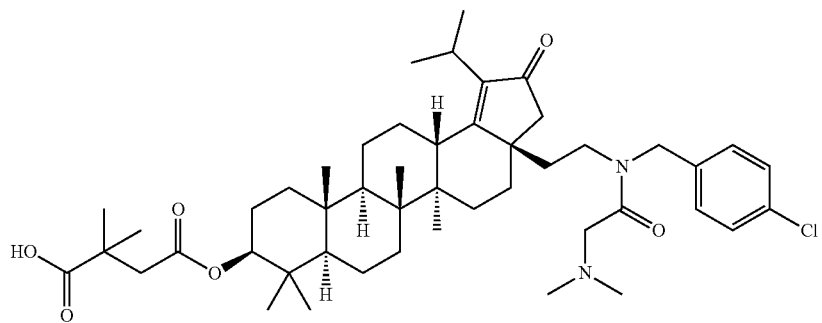

192

LC/MS: m/z calculated 806.5. found 807.4 $(M+1)^+$.

Example 124

Compound 193

4-(((3aR,5aR,5bR,7aR,9S,11aR,11bR,13aS)-3a-(2-(2-amino-N-(4-chlorobenzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

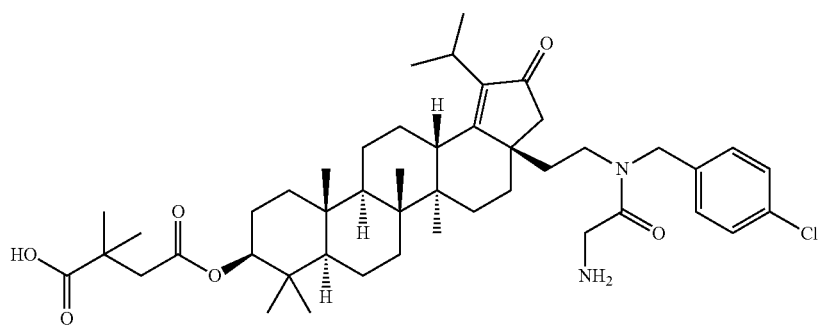

193

LC/MS: m/z calculated 778.5. found 779.4 (M+1)$^+$.

Example 125

Compound 194

4-(((3aR,5aR,5bR,7aR,9S,11aR,11bR,13aS)-3a-(2-(N-(4-chlorobenzyl)-2-(methylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

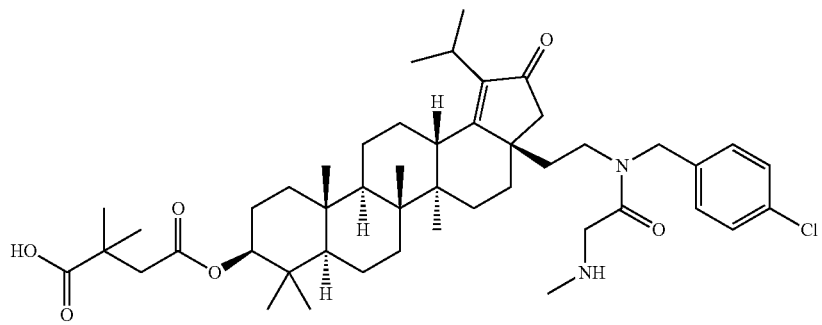

194

LC/MS: m/z calculated 792.5. found 793.4 (M+1)$^+$.

Example 126

Compound 195

4-(((3aR,5aR,5bR,7aR,9S,11aR,11bR,13aS)-3a-((S)-2-(((S)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid ![Compound 195 structure]

195

LC/MS: m/z calculated 760.5. found 761.5 (M+1)$^+$.

Example 127

Compound 196

4-(((3aR,5aR,5bR,7aR,9S,11aR,11bR,13aS)-3a-((R)-2-(((R)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

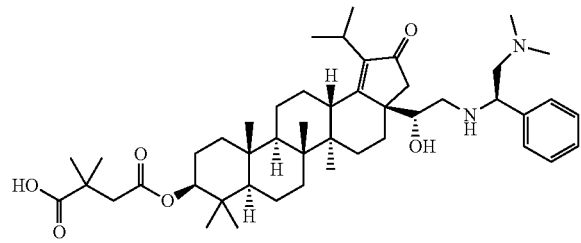

196

LC/MS: m/z calculated 760.5. found 761.5 (M+1)$^+$.

Example 128

Compound 197

4-(((3aR,5aR,5bR,7aR,9S,11aR,11bR,13aS)-3a-((R)-2-(((R)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

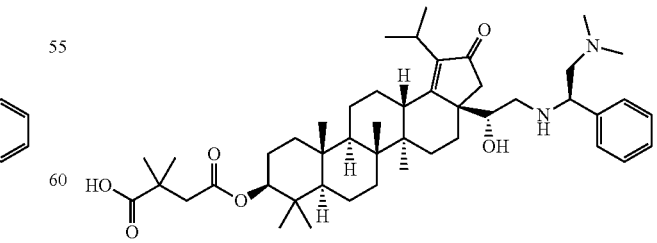

197

LC/MS: m/z calculated 760.5. found 761.5 (M+1)$^+$.

Example 129

Compound 198

4-(((3aR,5aR,5bR,7aR,9S,11aR,11bR,13aS)-3a-((R)-2-((4-chlorobenzyl)(3-(dimethylamino)propyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

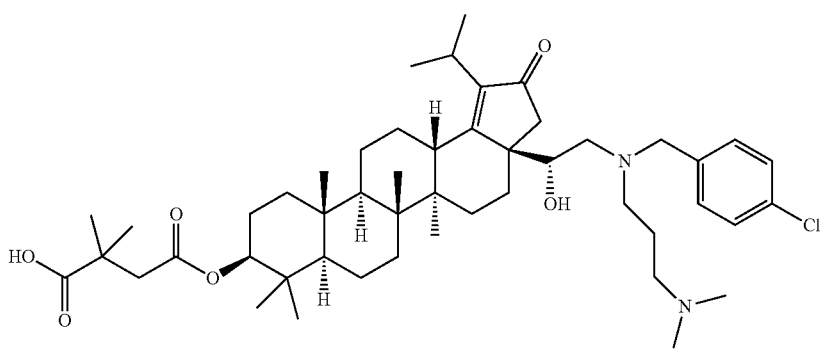

198

LC/MS: m/z calculated 822.5. found 823.5 $(M+1)^+$.

Example 130

Compound 199

4-(((3aR,5aR,5bR,7aR,9S,11aR,11bR,13aS)-3a-(((S)-2-((4-chlorobenzyl)(3-(dimethylamino)propyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

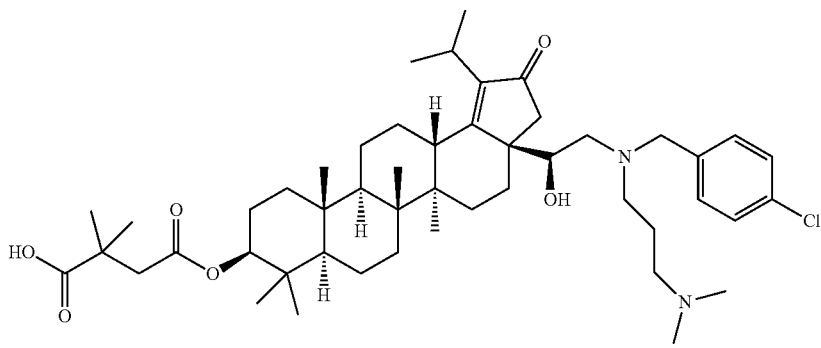

199

LC/MS: m/z calculated 822.5. found 823.5 $(M+1)^+$.

Example 131

Compound 200

4-(((3aR,5aR,5bR,7aR,9S,11aR,11bR,13aS)-1-isopropyl-5a,5b,8,8,11a-pentamethyl-2-oxo-3a-(2-(phenethylamino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

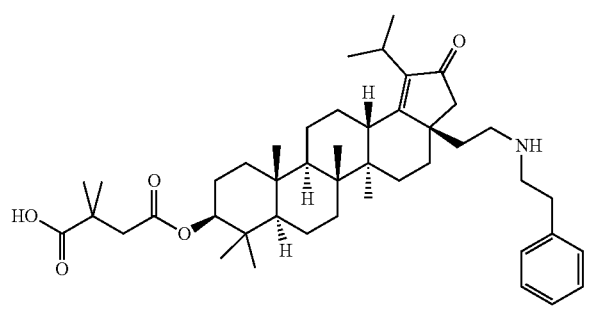

LC/MS: m/z calculated 701.5. found 702.5 (M+1)⁺.

Example 132

Compound 201

4-(((3aR,5aR,5bR,7aR,9S,11aR,11bR,13aS)-3a-((R)-2-((2-(dimethylamino)ethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

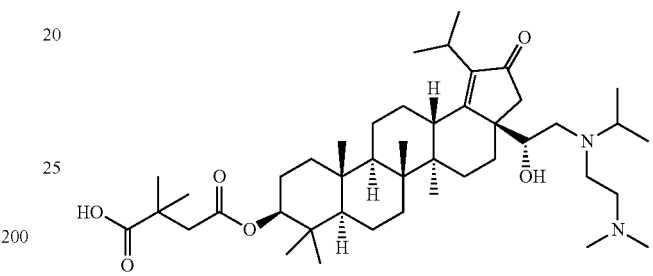

LC/MS: m/z calculated 726.5. found 727.5 (M+1)⁺.

Example 133

Compound 202

2-(((R)-2-((3aR,5aR,5bR,7aR,9S,11aR,11bR,13aS)-9-((3-carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-hydroxyethyl)(4-chlorobenzyl)amino)-N,N,N-trimethylethanaminium trifluoroacetate

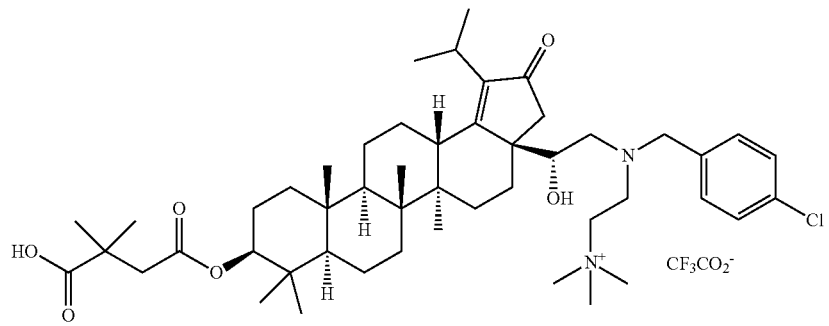

LC/MS: m/z calculated 823.5. found 823.5 (M)⁺.

Example 134

Compound 203

4-(((3aR,5aR,5bR,7aR,9S,11aR,11bR,13aS)-3a-((S)-4-(4-chlorobenzyl)-6-oxomorpholin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

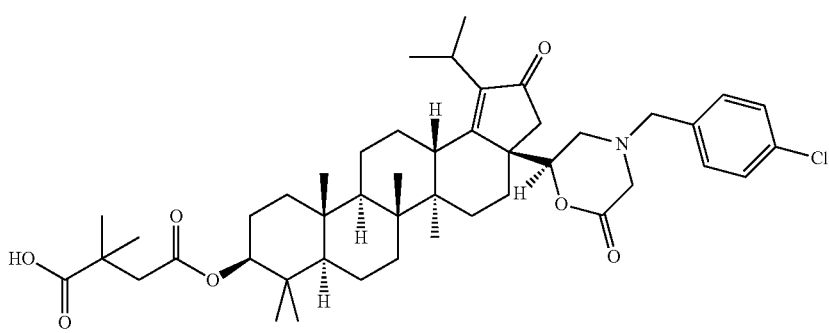

LC/MS: m/z calculated 777.4. found 778.4 $(M+1)^+$.

Example 135

Compound 204

4-(((3aR,5aR,5bR,7aR,9S,11aR,11bR,13aS)-3a-((R)-2-(((S)-2-(dimethylamino)-1-phenylethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

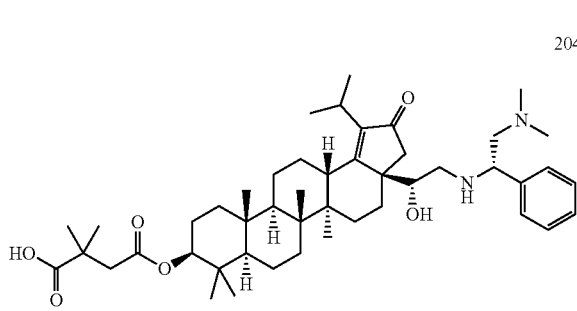

LC/MS: m/z calculated 760.5. found 761.4 $(M+1)^+$.

Example 136

Compound 205

4-(((3aR,5aR,5bR,7aR,9S,11aR,11bR,13aS)-3a-((S)-2-((2-(dimethylamino)ethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

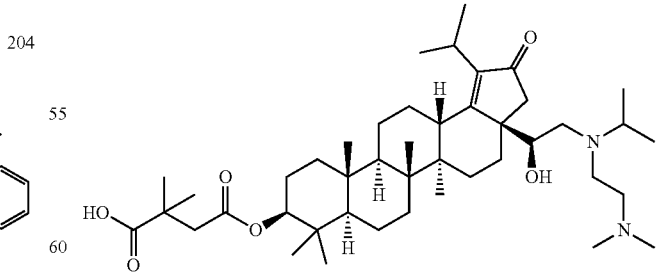

LC/MS: m/z calculated 726.6. found 727.5 $(M+1)^+$.

Example 137

Compound 206

4-(((3aR,5aR,5bR,7aR,9S,11aR,11bR,13aS)-3a-((R)-2-(((5-chloropyridin-2-yl)methyl)(2-(dimethyl-amino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

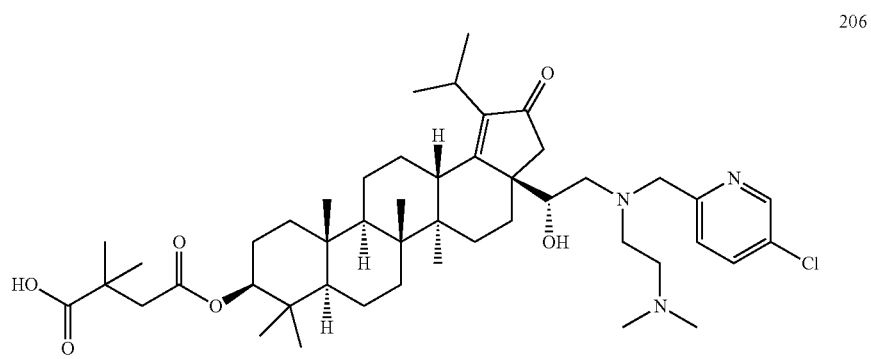

206

LC/MS: m/z calculated 809.5. found 810.5 (M+1)$^+$.

Example 138

Compound 207

4-(((3aR,5aR,5bR,7aR,9S,11aR,11bR,13aS)-3a-((S)-1-hydroxy-2-(isopropylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 139

Compound 208

4-(((3aR,5aR,5bR,7aR,9S,11aR,11bR,13aS)-3a-(2-(((R)-2-(dimethylamino)-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

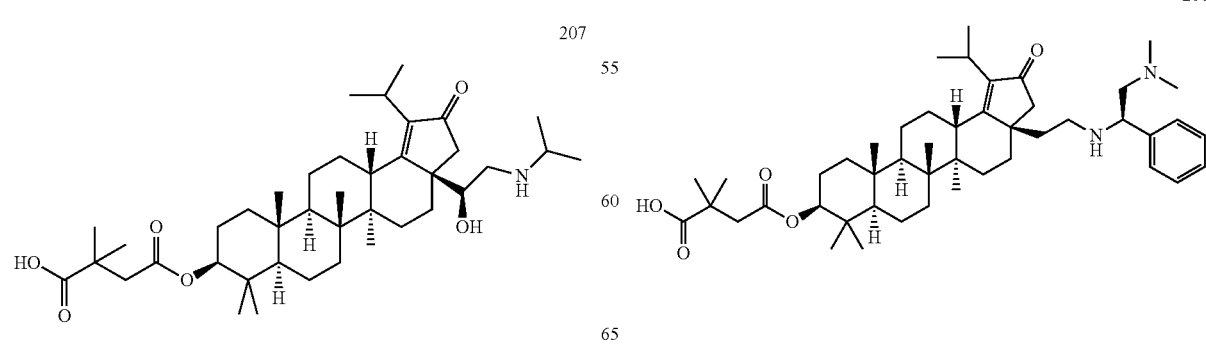

LC/MS: m/z calculated 655.5. found 656.4 (M+1)$^+$.

LC/MS: m/z calculated 744.5. found 745.5 (M+1)$^+$.

Example 140

Compound 209

4-(((3aR,5aR,5bR,7aR,9S,11aR,11bR,13aS)-3a-(2-(((S)-2-(dimethylamino)-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

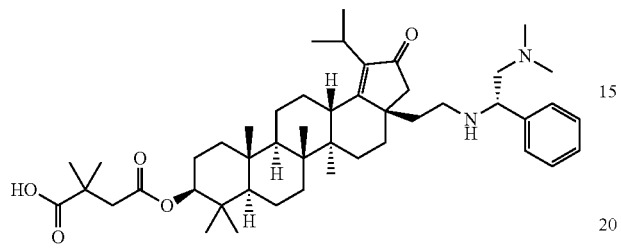

LC/MS: m/z calculated 744.5. found 745.5 $(M+1)^+$.

Example 141

Compound 210

2-(((S)-2-((3aR,5aR,5bR,7aR,9S,11aR,11bR,13aS)-9-((3-carboxy-3-methylbutanoyl)oxy)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)-2-hydroxyethyl)(4-chlorobenzyl)amino)-N,N,N-trimethylethanaminium trifluoroacetate

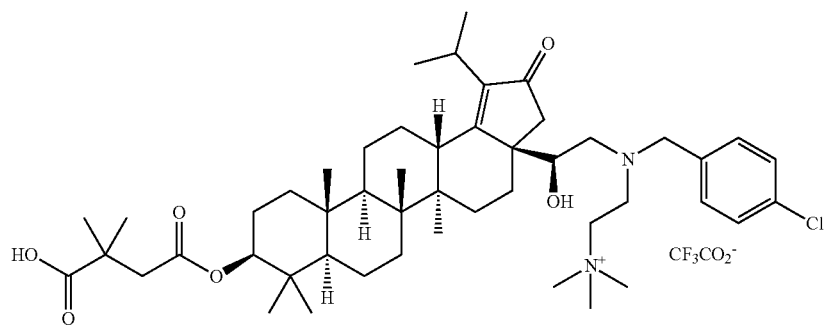

LC/MS: m/z calculated 823.5. found 823.5 $(M)^+$.

Example 142

Compound 211

4-(((3aR,5aR,5bR,7aR,9S,11aR,11bR,13aS)-3a-((R)-4-(4-chlorobenzyl)-6-oxopiperazin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

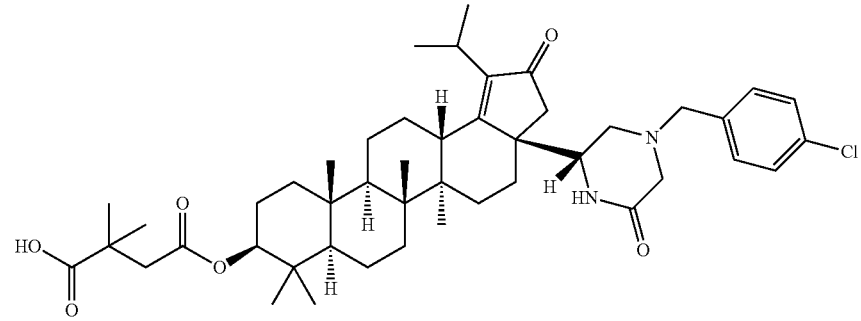

LC/MS: m/z calculated 776.5. found 777.4 $(M+1)^+$.

Example 143

Compound 212

4-(((3aR,5aR,5bR,7aR,9S,11aR,11bR,13aS)-3a-((S)-4-(4-chlorobenzyl)-1-methyl-6-oxopiperazin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

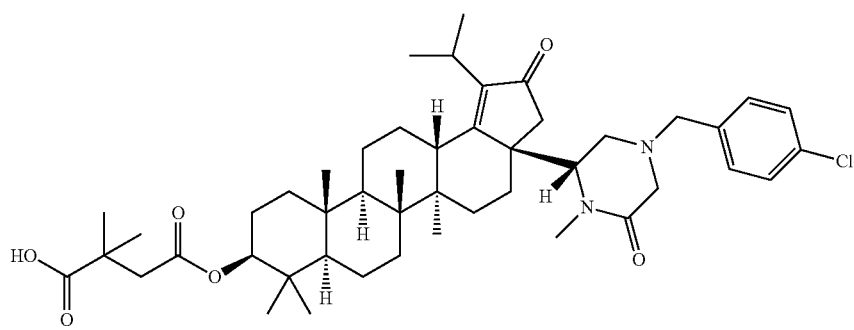

212

LC/MS: m/z calculated 790.5. found 791.4 (M+1)$^+$.

Example 144

Compound 213

4-(((3aR,5aR,5bR,7aR,9S,11aR,11bR,13aS)-3a-((R)-2-((4-chlorobenzyl)(2-(dimethylamino)ethyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

213

LC/MS: m/z calculated 822.5. found 823.5 (M+1)$^+$.

Example 145

Compound 214

4-(((3aR,5aR,5bR,7aR,9S,11aR,11bR,13aS)-3a-((S)-1-hydroxy-2-(piperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

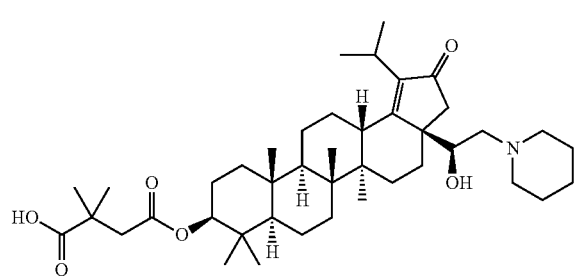

LC/MS: m/z calculated 681.5. found 682.5 (M+1)$^+$.

Example 146

Compound 215

4-(((3aR,5aR,5bR,7aR,9S,11aR,11bR,13aS)-3a-((R)-1-hydroxy-2-(piperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

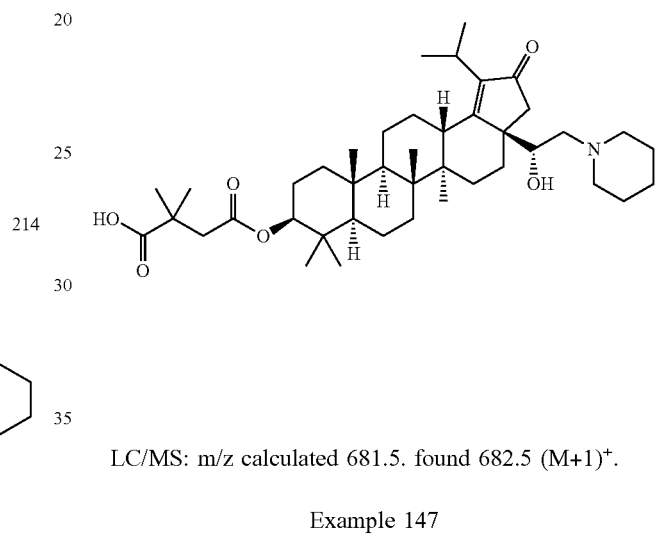

LC/MS: m/z calculated 681.5. found 682.5 (M+1)$^+$.

Example 147

Compound 216

4-(((3aS,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

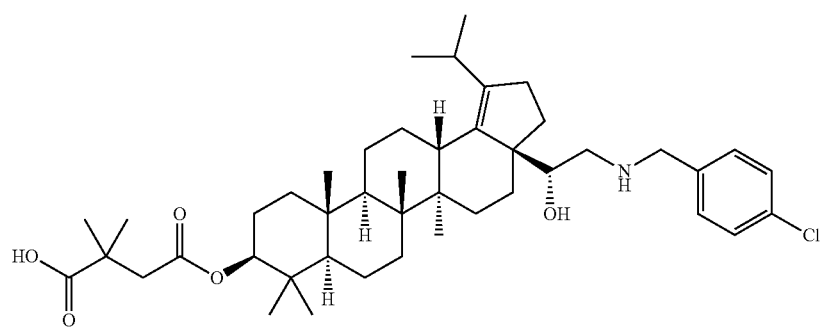

LC/MS: m/z calculated 723.5. found 724.4 (M+1)$^+$.

Example 148

Compound 217

4-(((3aS,5aR,5bR,7aR,9S,11aR,11bR,13aS)-3a-((R)-2-((4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 149

Compound 218

4-(((3aS,5aR,5bR,7aR,9S,11aR,11bR,13aS)-3a-((S)-2-((4-chlorobenzyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

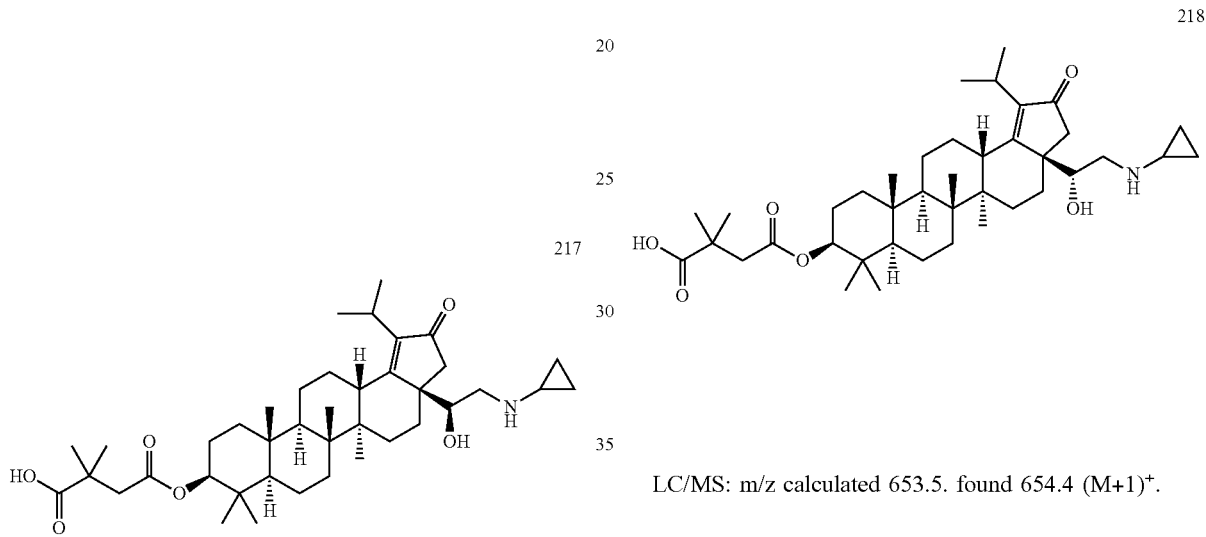

LC/MS: m/z calculated 653.5. found 654.4 (M+1)$^+$.

LC/MS: m/z calculated 653.5. found 654.4 (M+1)$^+$.

Example 150

Compound 219

4-(((3aR,5aR,5bR,7aR,9S,11aR,11bR,13aS)-3a-((S)-2-((4-chlorobenzyl)(2-(dimethylamino)ethyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

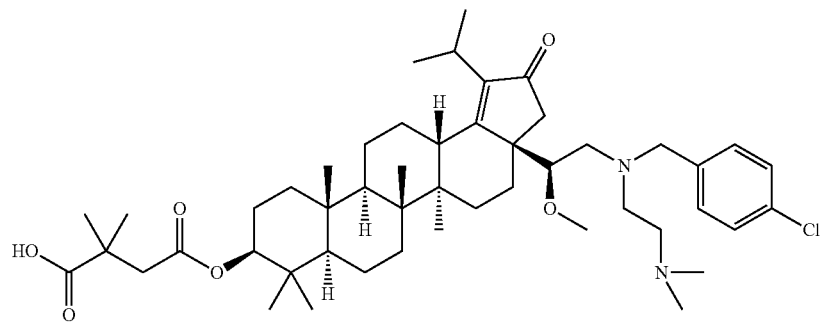

LC/MS: m/z calculated 822.5. found 823.5 (M+1)$^+$.

Example 151

Compound 220

5-(((3aR,5aR,5bR,7aR,9S,11aR,11bR,13aS)-3a-((R)-2-(benzylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid

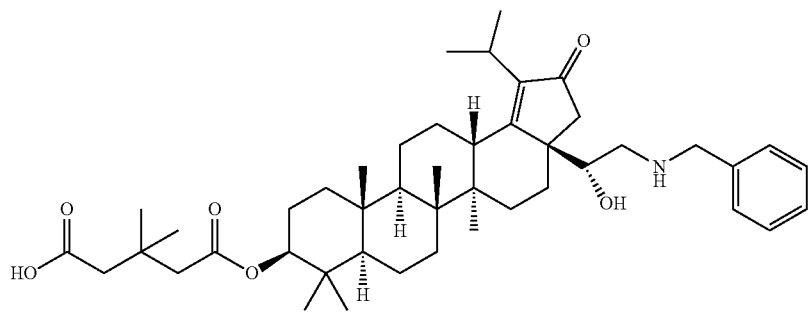

220

LC/MS: m/z calculated 717.5. found 718.5 (M+1)$^+$.

Example 152

Compound 221

4-(((3aR,5aR,5bR,7aR,9S,11aR,11bR,13aS)-3a-((R)-2-((4-chlorobenzyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

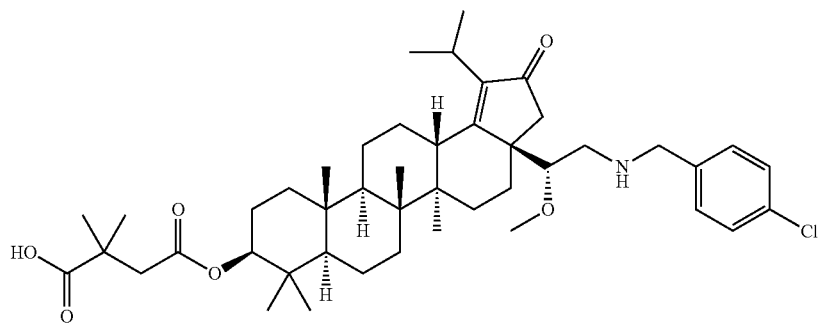

221

LC/MS: m/z calculated 751.5. found 752.5 (M+1)$^+$.

Example 153

Compound 222

4-(((3aR,5aR,5bR,7aR,9S,11aR,11bR,13aS)-3a-((S)-2-((4-chlorobenzyl)amino)-1-methoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

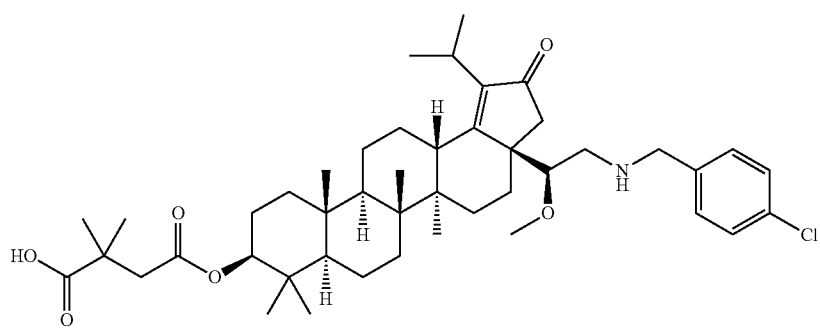

222

LC/MS: m/z calculated 751.5. found 752.5 (M+1)+.

Example 154

Compound 223

5-(((3aR,5aR,5bR,7aR,9S,11aR,11bR,13aS)-3a-((R)-2-(2-(dimethylamino)-N-(4-fluorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid

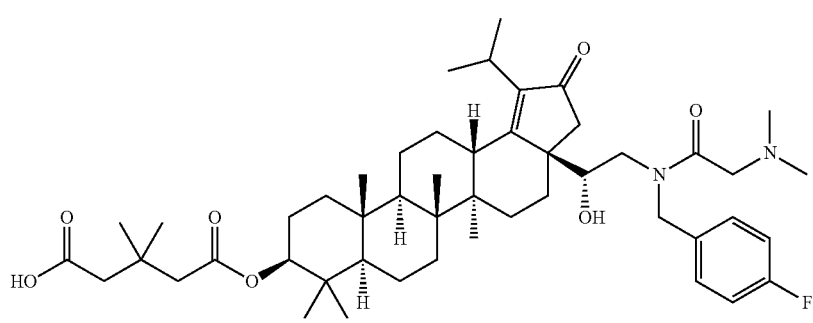

223

LC/MS: m/z calculated 820.5. found 821.5 (M+1)+.

Example 155

Compound 224

4-(((3aR,5aR,5bR,7aR,9S,11aR,11bR,13aS)-3a-((R)-2-((cyclohexylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

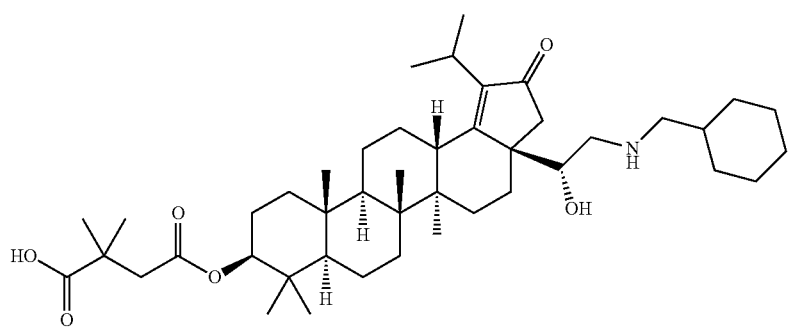

224

LC/MS: m/z calculated 709.5. found 710.6 (M+1)$^+$.

Example 156

Compound 225

4-(((3aR,5aR,5bR,7aR,9S,11aR,11bR,13aS)-3a-((S)-4-(4-chlorobenzyl)-1-methyl-5-oxopiperazin-2-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

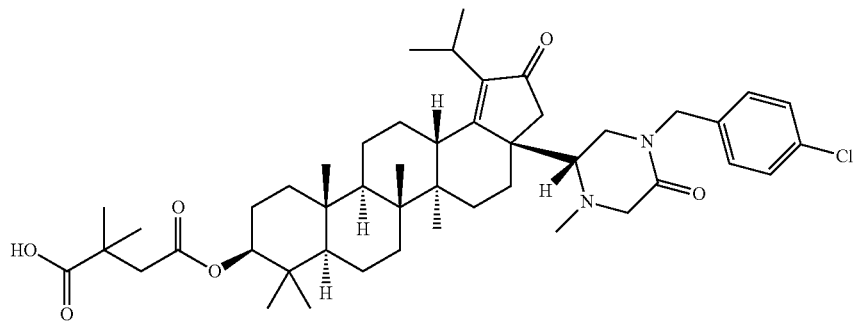

211

LC/MS: m/z calculated 790.5. found 791.5 (M+1)$^+$.

Example 157

Compound 226

4-(((3aR,5aR,5bR,7aR,9S,11aR,11bR,13aS)-3a-((R)-2-((cyclohexylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

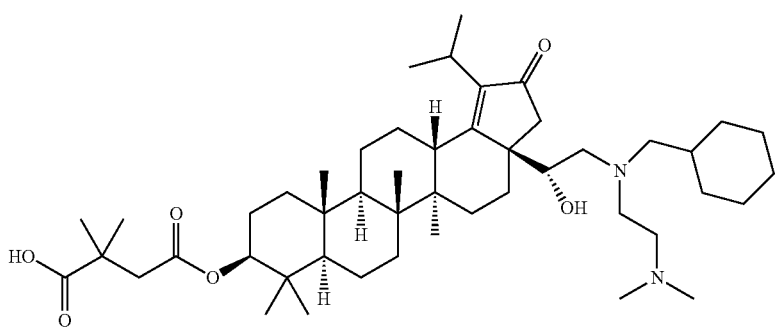

226

LC/MS: m/z calculated 780.6. found 781.5 (M+1)$^+$.

Example 158

Compound 227

4-(((3aR,5aR,5bR,7aR,9S,11aR,11bR,13aS)-3a-((R)-2-((cyclopropylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

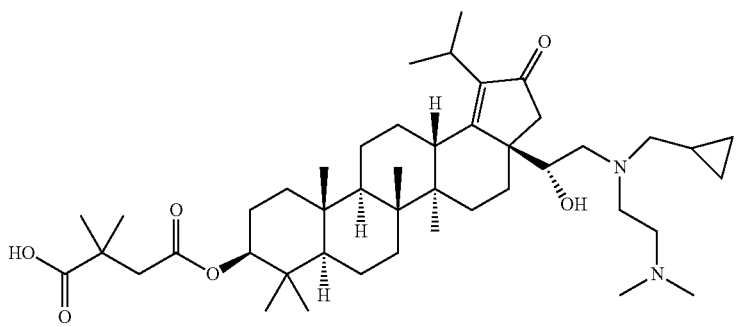

227

LC/MS: m/z calculated 738.6. found 739.8 (M+1)$^+$.

Example 159

Compound 228

2-(2-(((3aR,5aR,5bR,7aR,9S,11aR,11bR,13aS)-3a-((R)-2-(benzylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2-oxoethoxy)acetic acid

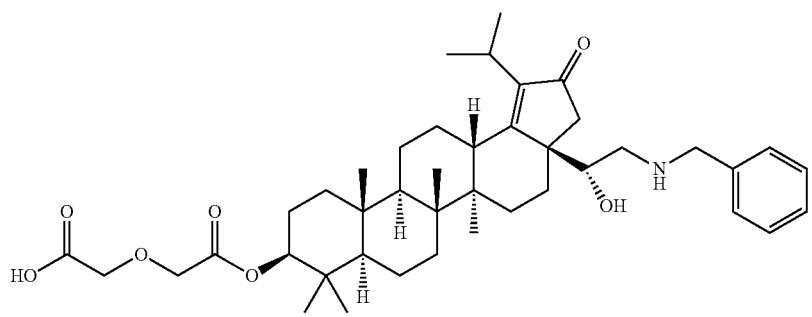

228

LC/MS: m/z calculated 691.4. found 692.5 (M+1)$^+$.

Example 160

Compound 229

4-(((3aR,5aR,5bR,7aR,9S,11aR,11bR,13aS)-3a-(2-((4-chloro-2-((dimethylamino)methyl)benzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

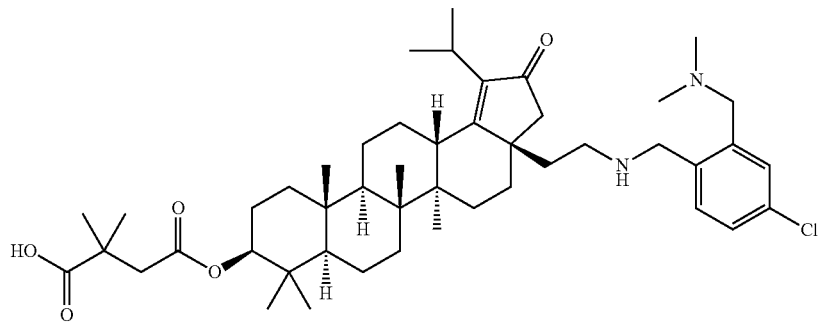

229

LC/MS: m/z calculated 778.5. found 779.5 (M+1)$^+$.

Example 161

Compound 230

4-(((3aR,5aR,5bR,7aR,9S,11aR,11bR,13aS)-3a-(2-(N-(4-chloro-2-((dimethylamino)methyl)benzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

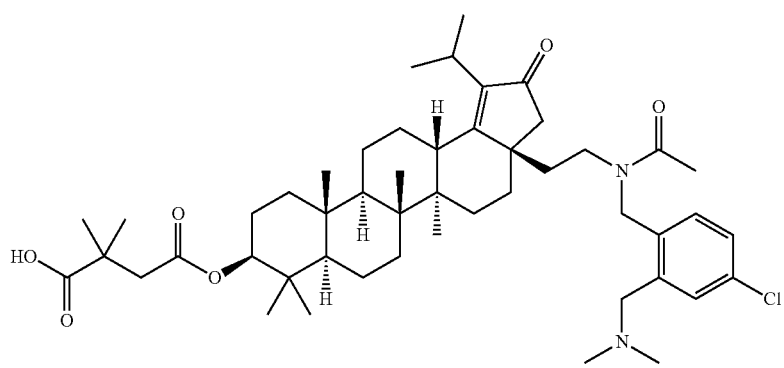

230

LC/MS: m/z calculated 820.5. found 821.7 (M+1)$^+$.

Example 162

Compound 231

4-(((3aR,5aR,5bR,7aR,9S,11aR,11bR,13aS)-3a-(2-(N-(4-chloro-2-((dimethylamino)methyl)benzyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

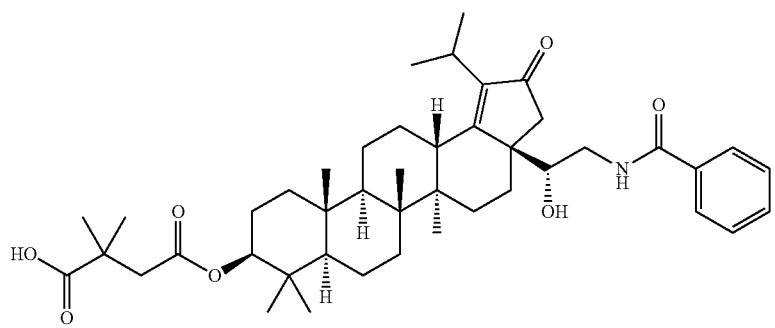

231

LC/MS: m/z calculated 717.5. found 718.5 (M+1)$^+$.

Example 163

Compound 232

4-(((3aR,5aR,5bR,7aR,9S,11aR,11bR,13aS)-3a-((S)-2-benzamido-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

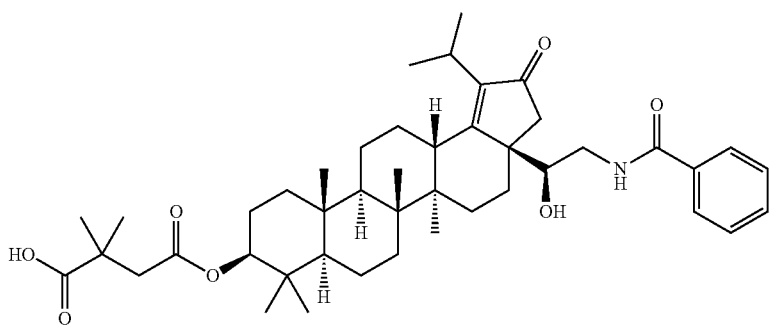

232

LC/MS: m/z calculated 717.5. found 718.5 (M+1)$^+$.

Example 164

Compound 233

4-(((3aR,5aR,5bR,7aR,9S,11aR,11bR,13aS)-3a-((R)-1-hydroxy-2-(N-methylbenzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

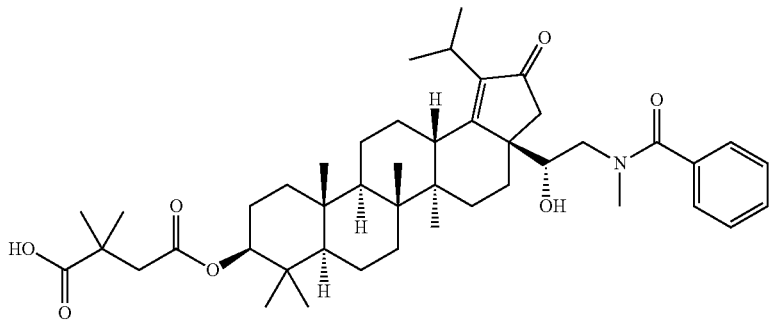

233

LC/MS: m/z calculated 731.5. found 732.3 (M+1)$^+$.

Example 165

Compound 234

4-(((3aR,5aR,5bR,7aR,9S,11aR,11bR,13aS)-3a-((S)-1-hydroxy-2-(N-methylbenzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

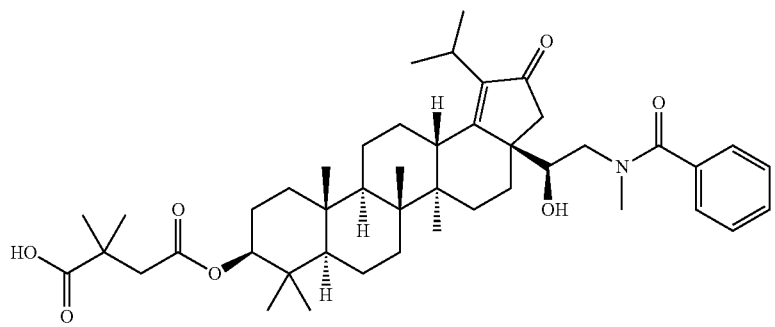

234

LC/MS: m/z calculated 731.5. found 732.5 (M+1)$^+$.

Example 166

Compound 235

4-(((3aS,5aR,5bR,7aR,9S,11aR,11bR,13aS)-3a-((S)-2-((4-chlorobenzyl)(2-(dimethylamino)ethyl)amino)-1-hydroxyethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

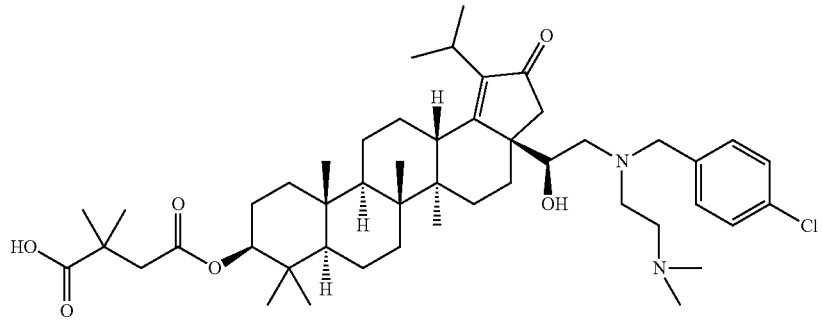

235

LC/MS: m/z calculated 794.5. found 795.7 (M+1)$^+$.

Example 167

Compound 236

4-(((3aR,5aR,5bR,7aR,9S,11aR,11bR,13aS)-3a-((R)-2-(2-(dimethylamino)-N-(pyridin-2-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

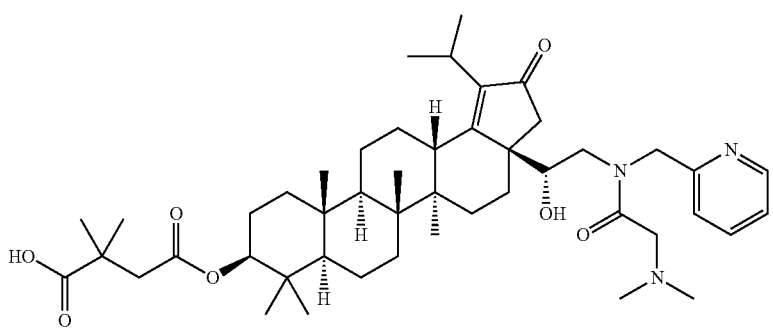

236

LC/MS: m/z calculated 789.5. found 790.5 (M+1)$^+$.

Example 168

Compound 237

4-(((3aR,5aR,5bR,7aR,9S,11aR,11bR,13aS)-3a-((R)-1-hydroxy-2-(2-(methylamino)-N-(pyridin-2-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

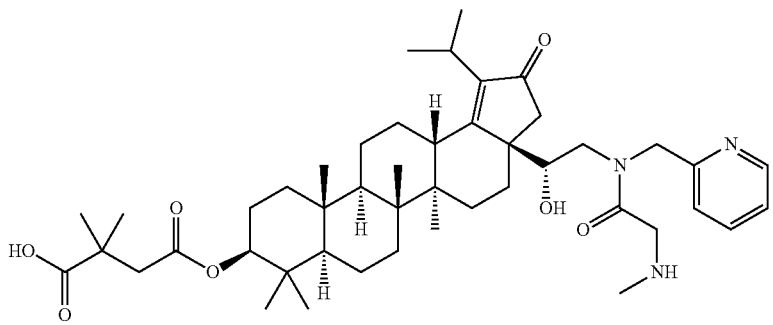

237

LC/MS: m/z calculated 775.5. found 776.5 (M+1)$^+$.

Example 169

Compound 238

4-(((3aR,5aR,5bR,7aR,9S,11aR,11bR,13aS)-3a-(2-((4-chloro-2-((dimethylamino)methyl)benzyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

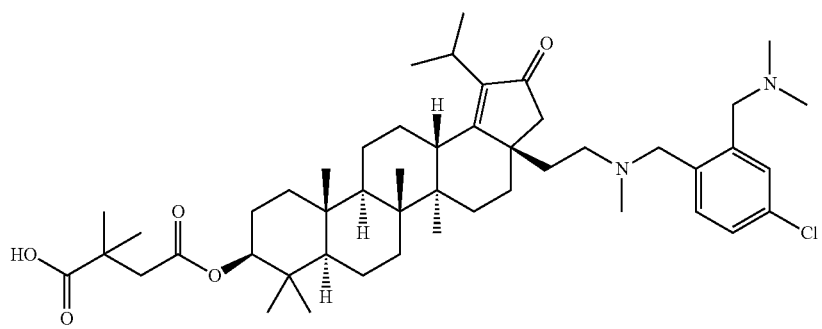

238

LC/MS: m/z calculated 792.5. found 793.5 (M+1)$^+$.

Example 170

Compound 239

4-(((3aR,5aR,5bR,7aR,9S,11aR,11bR,13aS)-3a-((R)-1-acetoxy-2-((2-chlorobenzyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

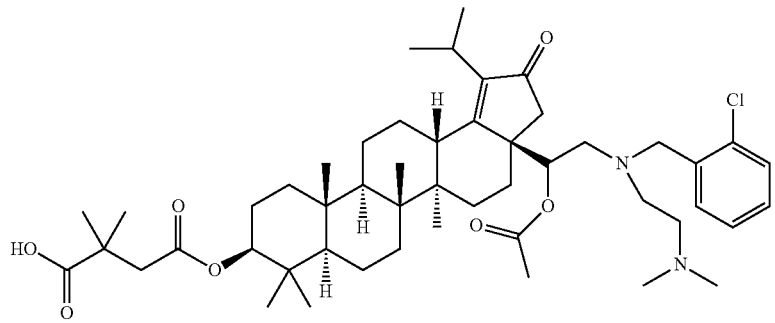

239

LC/MS: m/z calculated 850.5. found 851.5 (M+1)$^+$.

Example 171

Compound 240

4-(((3aR,5aR,5bR,7aR,9S,11aR,11bR,13aS)-3a-((R)-2-(2-amino-N-benzylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

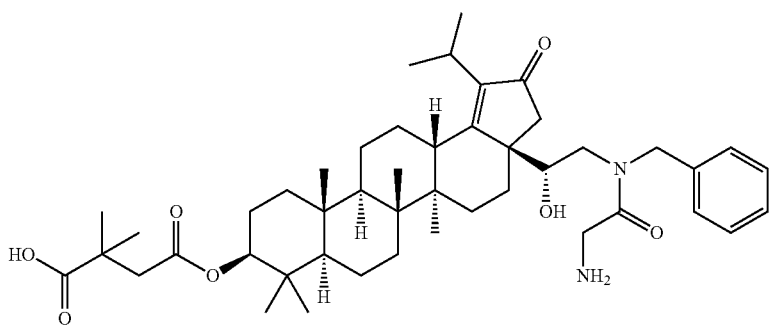

240

LC/MS: m/z calculated 760.5. found 761.5 (M+1)⁺.

Example 172

Compound 241

4-(((3aR,5aR,5bR,7aR,9S,11aR,11bR,13aS)-3a-((R)-2-(N-benzyl-2-(methylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

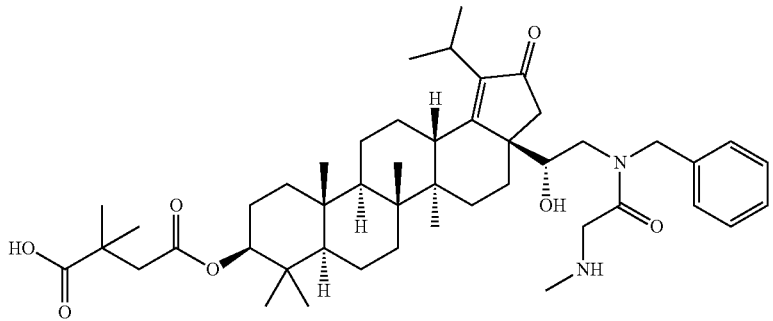

241

LC/MS: m/z calculated 774.5. found 775.5 (M+1)⁺.

Example 173

Compound 242

4-(((3aR,5aR,5bR,7aR,9S,11aR,11bR,13aS)-3a-((R)-2-(N-benzyl-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

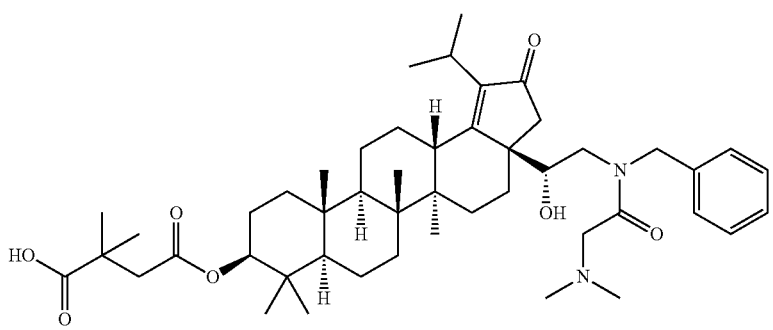

242

LC/MS: m/z calculated 788.5. found 789.5 (M+1)$^+$.

Example 174

Compound 243

4-(((3aR,5aR,5bR,7aR,9S,11aR,11bR,13aS)-3a-((R)-2-(2-amino-N-(pyridin-2-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

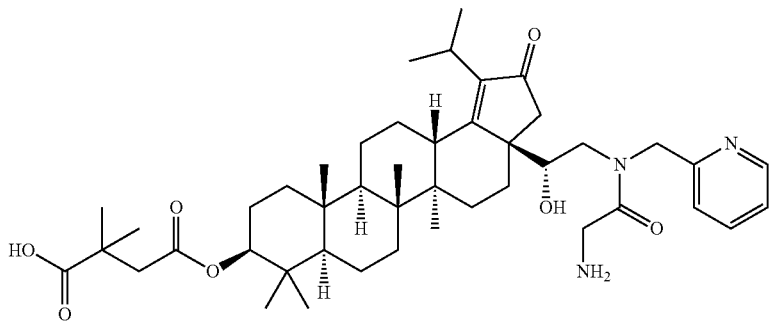

243

LC/MS: m/z calculated 761.5. found 762.5 (M+1)$^+$.

Example 175

Compound 244

4-(((3aR,5aR,5bR,7aR,9S,11aR,11bR,13aS)-3a-((S)-2-(((R)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

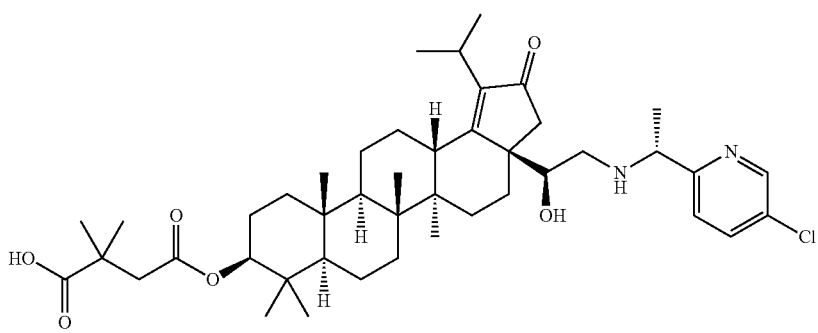

244

LC/MS: m/z calculated 752.5. found 753.5 (M+1)$^+$.

Example 176

Compound 245

4-(((3aR,5aR,5bR,7aR,9S,11aR,11bR,13aS)-3a-((R)-2-(((R)-1-(5-chloropyridin-2-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

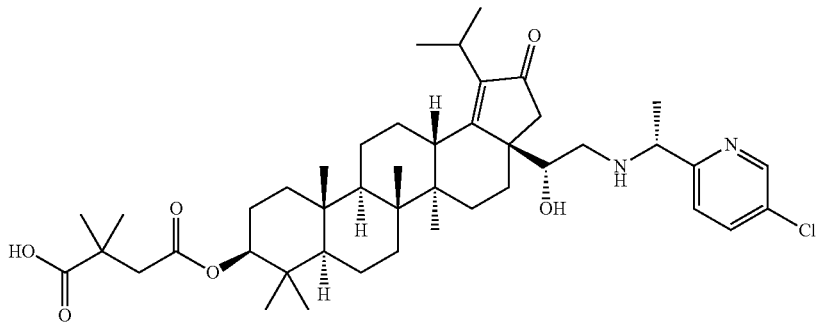

245

LC/MS: m/z calculated 752.5. found 753.4 (M+1)$^+$.

Example 177

Compound 246

4-(((3aR,5aR,5bR,7aR,9S,11aR,11bR,13aS)-3a-((R)-2-(N—((R)-1-(5-chloropyridin-2-yl)ethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

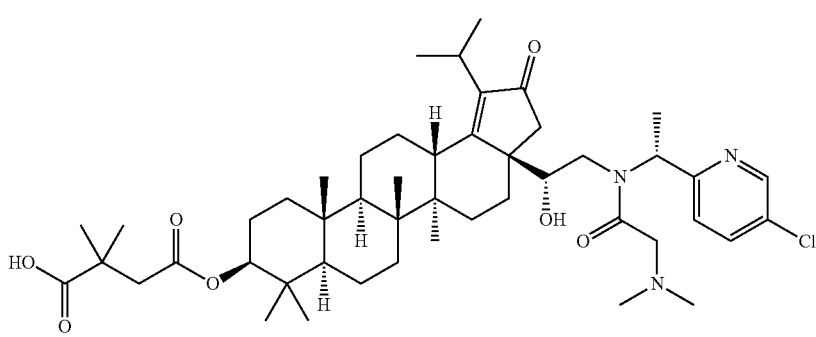

246

LC/MS: m/z calculated 837.5. found 838.5 (M+1)$^+$.

Example 178

Compound 247

4-(((3aR,5aR,5bR,7aR,9S,11aR,11bR,13aS)-3a-((S)-2-((2-(dimethylamino)ethyl)(phenethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

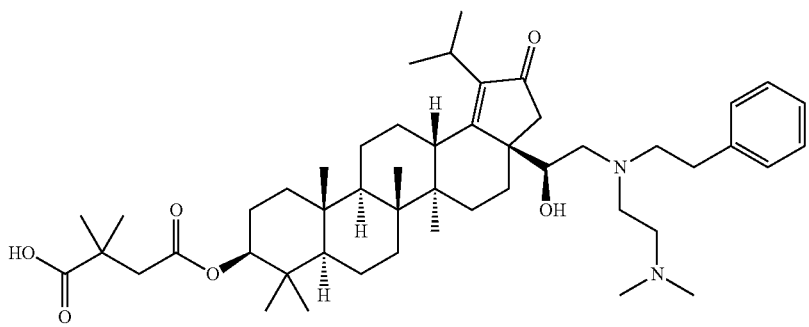

247

LC/MS: m/z calculated 788.6. found 789.5 (M+1)$^+$.

Example 179

Compound 248

5-(((3aR,5aR,5bR,7aR,9S,11aR,11bR,13aS)-3a-((R)-2-(N-benzyl-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-3,3-dimethyl-5-oxopentanoic acid

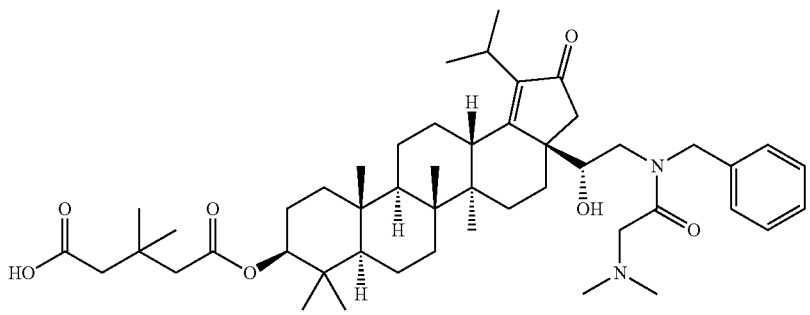

248

LC/MS: m/z calculated 802.6. found 803.5 (M+1)$^+$.

Example 180

Compound 249

4-(((3aR,5aR,5bR,7aR,9S,11aR,11bR,13aS)-3a-((R)-2-(N-(2-(dimethylamino)ethyl)cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

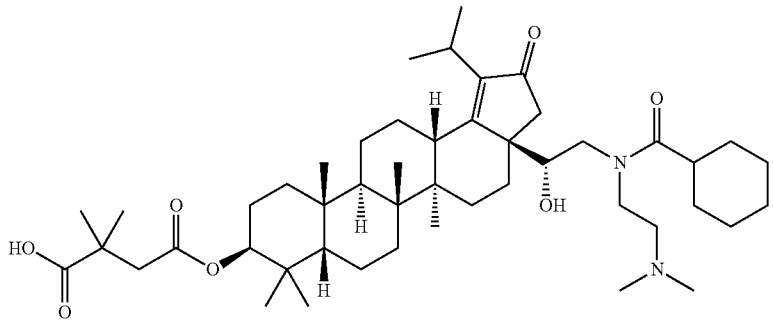

249

LC/MS: m/z calculated 794.6. found 795.5 (M+1)$^+$.

Example 181

Compound 250

4-(((3aR,5aR,5bR,7aR,9S,11aR,11bR,13aS)-3a-((R)-2-(cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

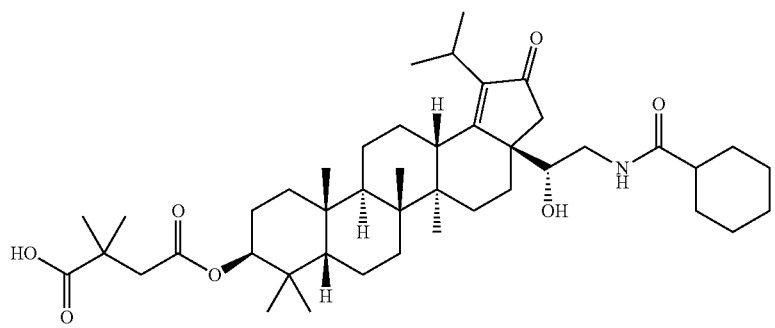

250

LC/MS: m/z calculated 723.5. found 724.5 (M+1)$^+$.

Example 182

Compound 251

4-(((3aR,5aR,5bR,7aR,9S,11aR,11bR,13aS)-3a-((R)-2-(2-amino-N—((S)-1-(5-chloropyridin-2-yl)ethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

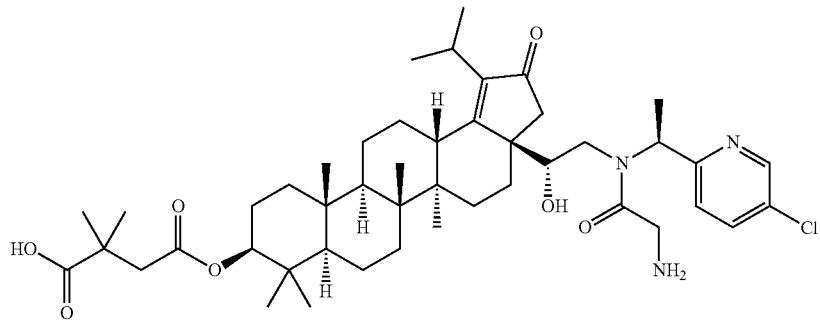

251

LC/MS: m/z calculated 809.5. found 810.4 (M+1)$^+$.

Example 183

Compound 252

4-(((3aR,5aR,5bR,7aR,9S,11aR,11bR,13aS)-3a-((R)-2-(N—((S)-1-(5-chloropyridin-2-yl)ethyl)-2-(methylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

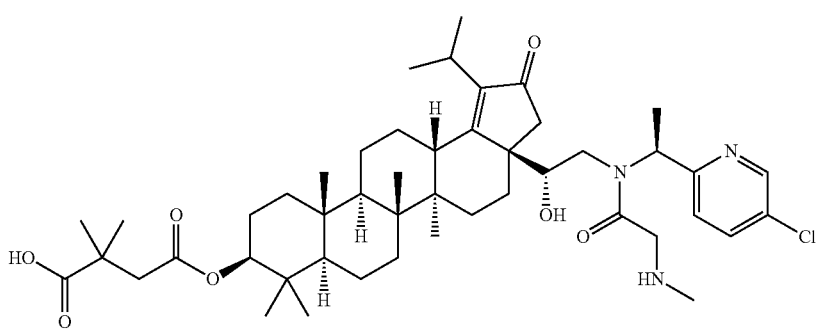

252

LC/MS: m/z calculated 823.5. found 824.5 (M+1)$^+$.

Example 184

Compound 253

4-(((3aR,5aR,5bR,7aR,9S,11aR,11bR,13aS)-3a-((R)-2-(N—((S)-1-(5-chloropyridin-2-yl)ethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

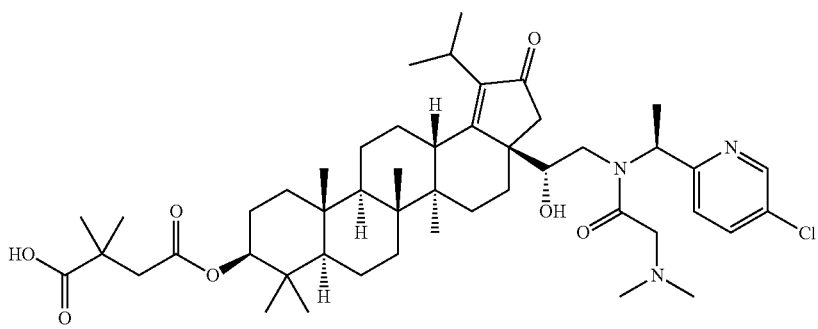

253

LC/MS: m/z calculated 837.5. found 838.5 (M+1)$^+$.

Example 185

Compound 254

4-(((3aR,5aR,5bR,7aR,9S,11aR,11bR,13aS)-3a-((R)-2-((2-aminoethyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

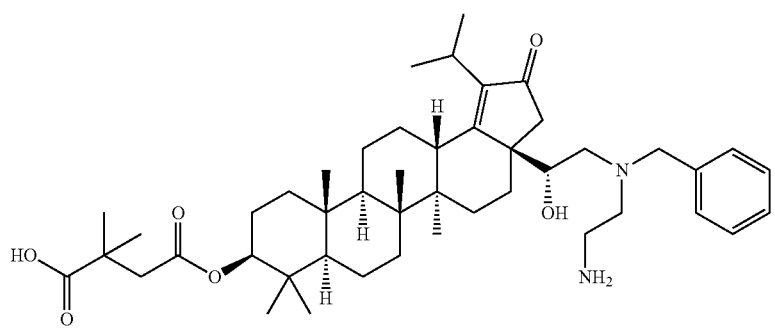

254

LC/MS: m/z calculated 746.5. found 747.5 (M+1)$^+$.

Example 186

Compound 255

4-(((3aR,5aR,5bR,7aR,9S,11aR,11bR,13aS)-3a-((R)-2-((cyclobutylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

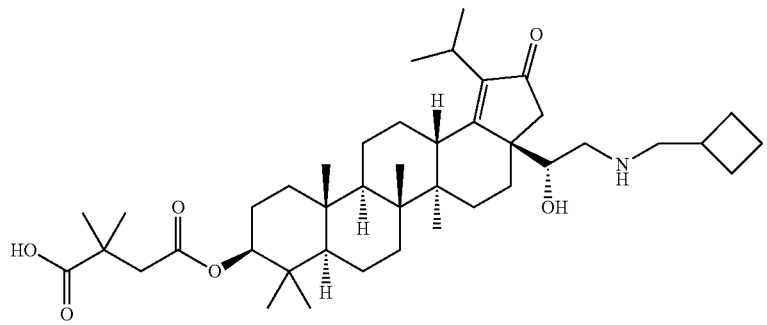

255

LC/MS: m/z calculated 681.5. found 682.5 (M+1)$^+$.

Example 187

Compound 256

4-(((3aR,5aR,5bR,7aR,9S,11aR,11bR,13aS)-3a-((R)-1-acetoxy-2-(benzyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

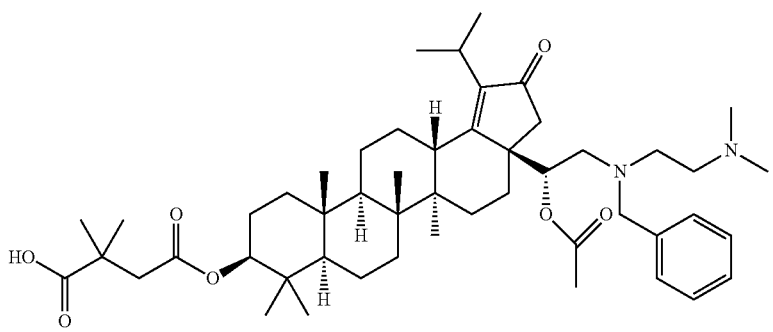

256

LC/MS: m/z calculated 816.6. found 817.5 (M+1)$^+$.

Example 188

Compound 257

4-(((3aR,5aR,5bR,7aR,9S,11aR,11bR,13aS)-3a-((S)-1-acetoxy-2-(benzyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

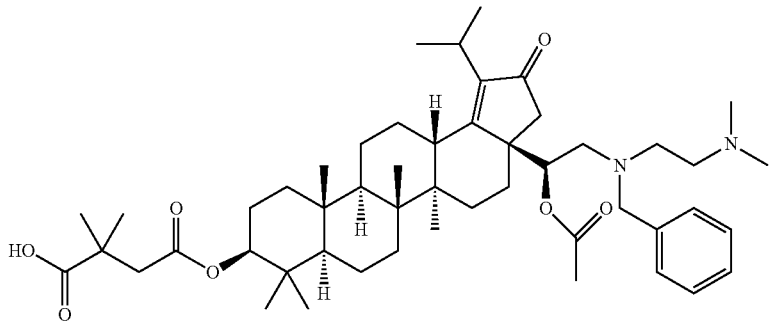

257

LC/MS: m/z calculated 816.6. found 817.5 (M+1)$^+$.

Example 189

Compound 258

4-(((3aR,5aR,5bR,7aR,9S,11aR,11bR,13aS)-3a-((S)-2-(cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

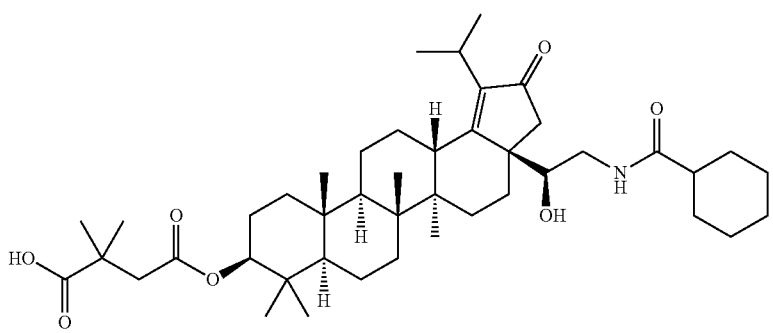

258

LC/MS: m/z calculated 723.5. found 724.5 (M+1)$^+$.

Example 190

Compound 259

4-(((3aR,5aR,5bR,7aR,9S,11aR,11bR,13aS)-3a-((S)-2-((cyclobutylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

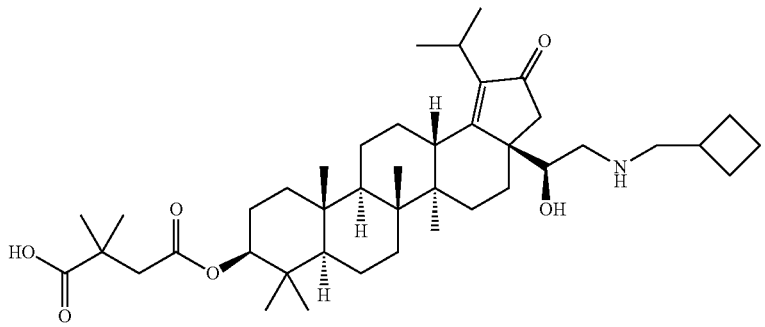

259

LC/MS: m/z calculated 681.5. found 682.5 (M+1)$^+$.

Example 191

Compound 260

4-(((3aR,5aR,5bR,7aR,9S,11aR,11bR,13aS)-3a-((S)-2-(N-(2-(dimethylamino)ethyl)cyclohexanecarboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

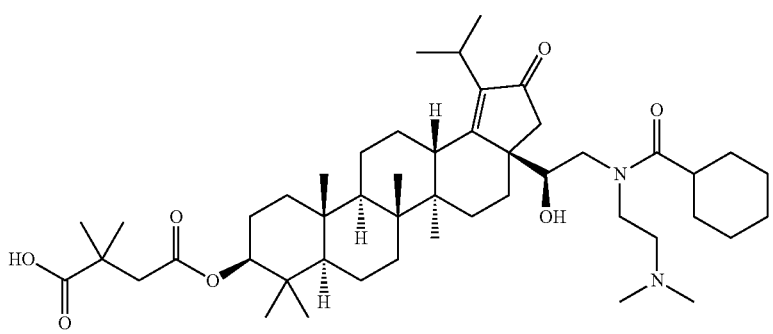

260

LC/MS: m/z calculated 794.6. found 795.6 (M+1)$^+$.

Example 192

Compound 261

4-(((3aR,5aR,5bR,7aR,9S,11aR,11bR,13aS)-3a-((S)-2-((cyclobutylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

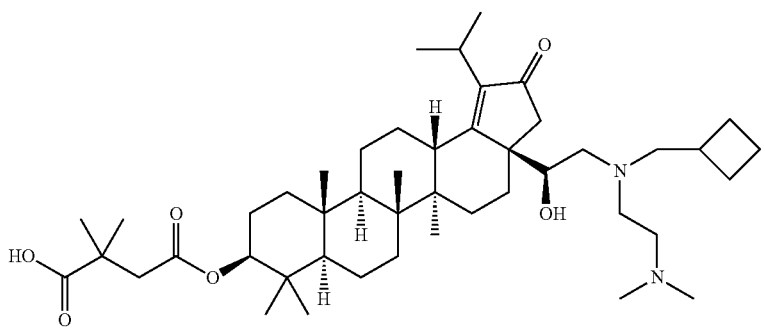

261

LC/MS: m/z calculated 752.6. found 753.6 (M+1)$^+$.

Example 193

Compound 262

4-(((3aR,5aR,5bR,7aR,9S,11aR,11bR,13aS)-3a-((R)-2-(((1H-pyrazol-3-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

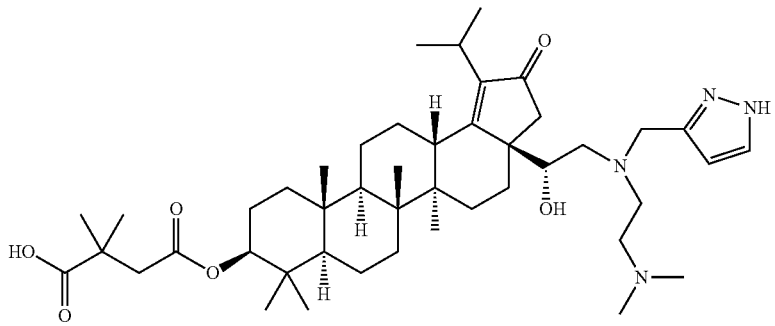

262

LC/MS: m/z calculated 764.6. found 765.5 (M+1)$^+$.

Example 194

Compound 263

4-(((3aR,5aR,5bR,7aR,9S,11aR,11bR,13aS)-3a-((R)-2-((cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

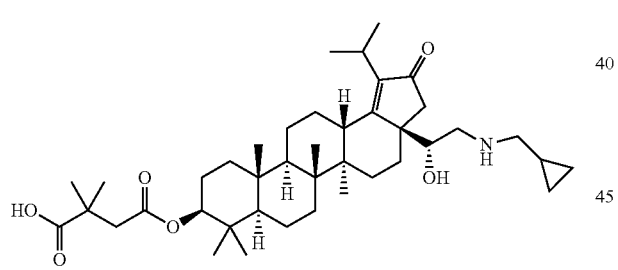

263

LC/MS: m/z calculated 667.5. found 668.5 (M+1)$^+$.

Example 195

Compound 264

4-(((3aR,5aR,5bR,7aR,9S,11aR,11bR,13aS)-3a-((1S)-1-hydroxy-2-((2-hydroxy-2-phenylethyl)(methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

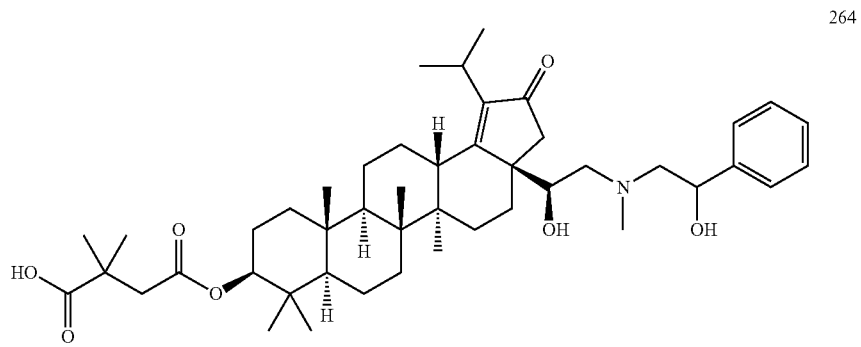

264

LC/MS: m/z calculated 747.5. found 748.5 (M+1)$^+$.

Example 196

Compound 265

4-(((3aR,5aR,5bR,7aR,9S,11aR,11bR,13aS)-3a-((S)-1-hydroxy-2-((2-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

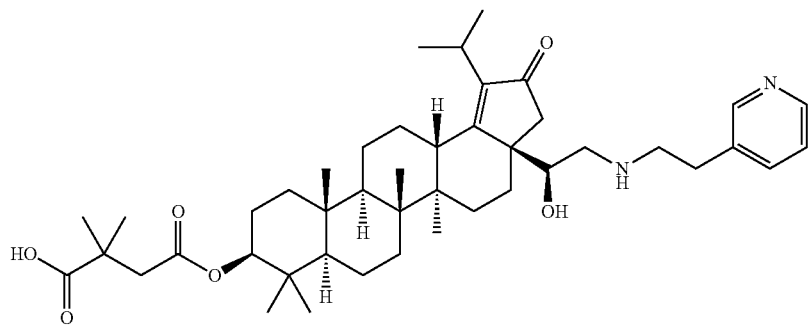

LC/MS: m/z calculated 718.5. found 719.5 (M+1)$^+$.

Example 197

Compound 266

4-(((3aR,5aR,5bR,7aR,9S,11aR,11bR,13aS)-3a-((S)-1-hydroxy-2-((R)-3-hydroxypiperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

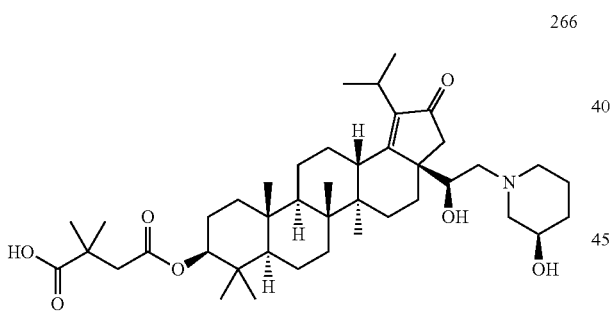

LC/MS: m/z calculated 697.5. found 698.5 (M+1)$^+$.

Example 198

Compound 267

4-(((3aR,5aR,5bR,7aR,9S,11aR,11bR,13aS)-3a-((S)-1-hydroxy-2-((3-(2-oxopyrrolidin-1-yl)propyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

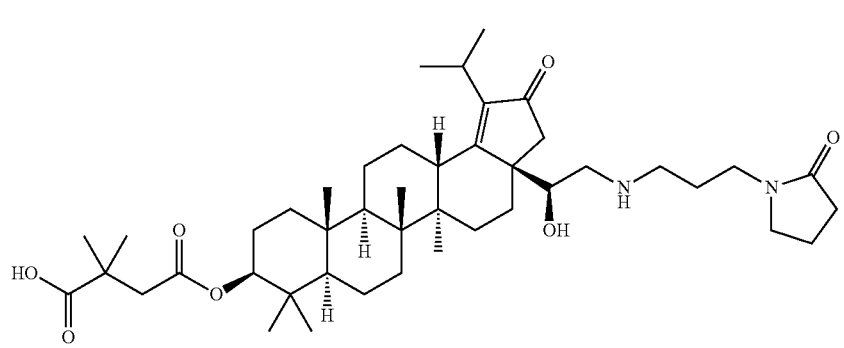

LC/MS: m/z calculated 738.5. found 739.5 (M+1)$^+$.

Example 199

Compound 268

4-(((3aR,5aR,5bR,7aR,9S,11aR,11bR,13aS)-3a-((S)-1-hydroxy-2-((2-phenoxyethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

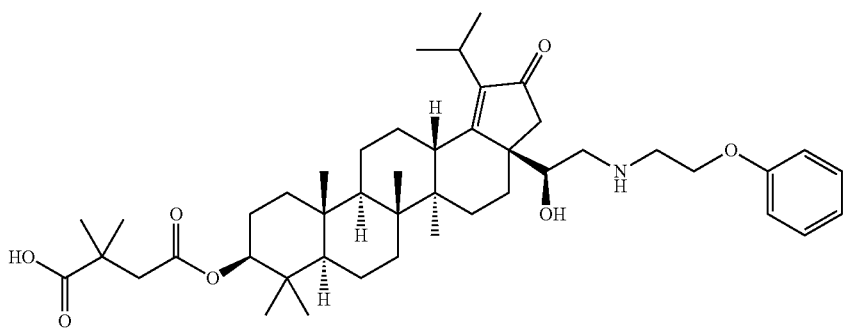

268

LC/MS: m/z calculated 733.5. found 734.5 (M+1)$^+$.

Example 200

Compound 269

4-(((3aR,5aR,5bR,7aR,9S,11aR,11bR,13aS)-3a-((S)-1-hydroxy-2-(4-(2-hydroxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

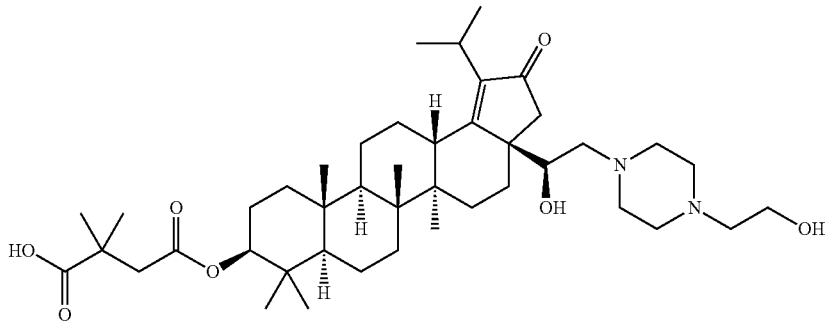

269

LC/MS: m/z calculated 726.5. found 727.5 (M+1)$^+$.

Example 201

Compound 270

4-(((3aR,5aR,5bR,7aR,9S,11aR,11bR,13aS)-3a-((1S)-2-(2,6-dimethylmorpholino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

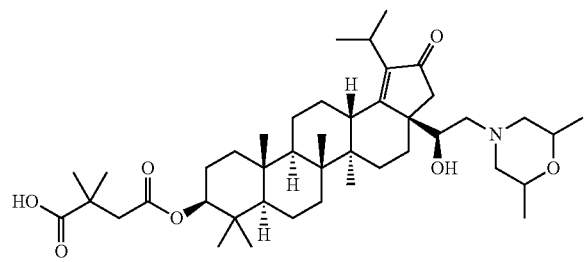

LC/MS: m/z calculated 711.5. found 712.5 (M+1)$^+$.

Example 202

Compound 271

4-(((3aR,5aR,5bR,7aR,9S,11aR,11bR,13aS)-3a-((S)-1-hydroxy-2-thiomorpholinoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

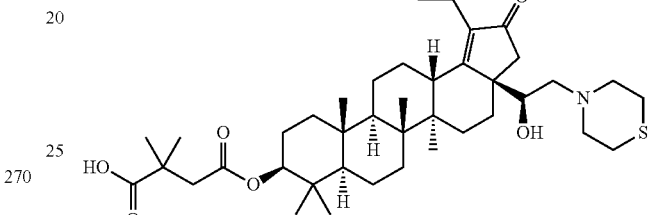

LC/MS: m/z calculated 699.5. found 700.4 (M+1)$^+$.

Example 203

Compound 272

4-(((3aR,5aR,5bR,7aR,9S,11aR,11bR,13aS)-3a-((S)-1-hydroxy-2-((3-morpholinopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

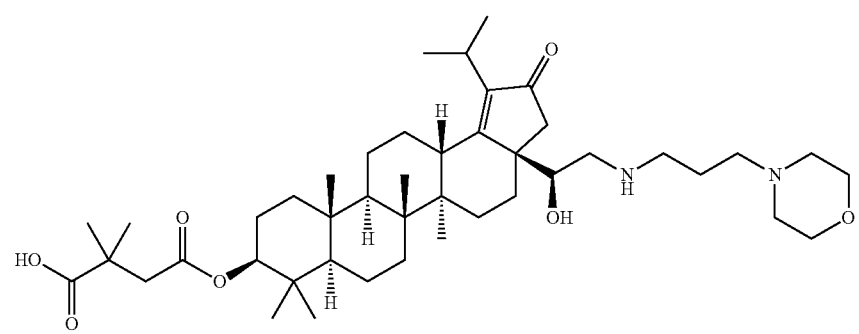

LC/MS: m/z calculated 740.5. found 741.5 (M+1)$^+$.

Example 204

Compound 273

4-(((3aR,5aR,5bR,7aR,9S,11aR,11bR,13aS)-3a-((S)-2-((3-(1H-imidazol-1-yl)propyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

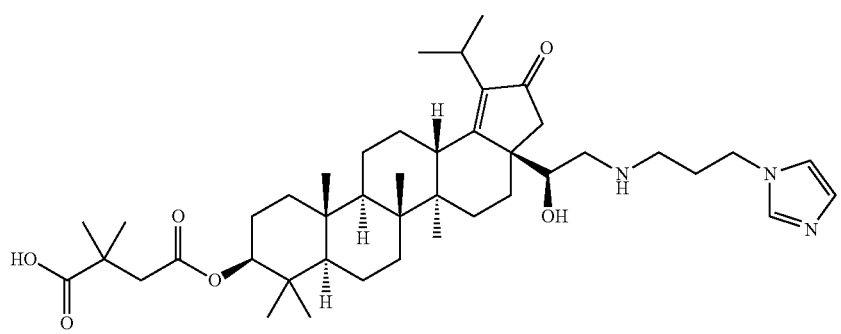

273

LC/MS: m/z calculated 721.5. found 722.5 (M+1)$^+$.

Example 205

Compound 274

4-(((3aR,5aR,5bR,7aR,9S,11aR,11bR,13aS)-3a-((S)-1-hydroxy-2-((4-hydroxyphenethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

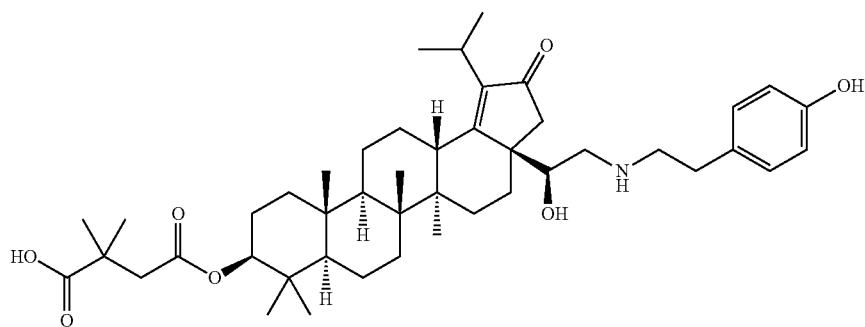

274

LC/MS: m/z calculated 733.5. found 734.5 (M+1)$^+$.

Example 206

Compound 275

4-(((3aR,5aR,5bR,7aR,9S,11aR,11bR,13aS)-3a-((R)-2-(cyclopentylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

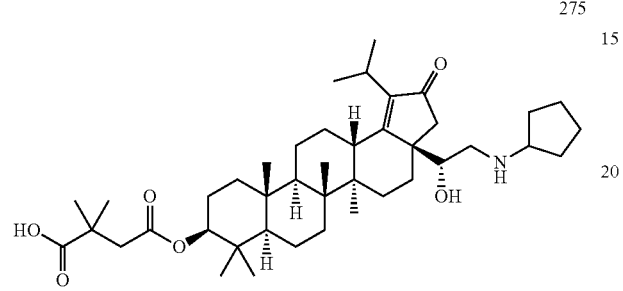

LC/MS: m/z calculated 681.5. found 682.5 (M+1)$^+$.

Example 207

Compound 276

4-(((3aR,5aR,5bR,7aR,9S,11aR,11bR,13aS)-3a-((S)-2-((cyclohexylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

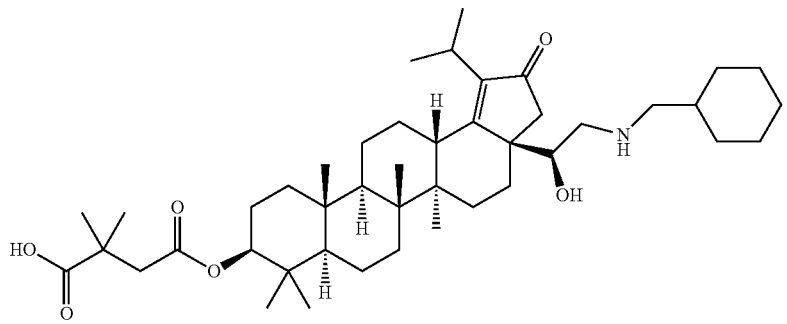

LC/MS: m/z calculated 709.5. found 710.5 (M+1)$^+$.

Example 208

Compound 277

4-(((3aR,5aR,5bR,7aR,9S,11aR,11bR,13aS)-3a-((R)-2-((cyclobutylmethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

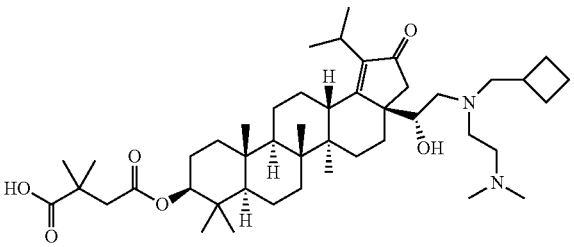

LC/MS: m/z calculated 752.6. found 753.6 (M+1)$^+$.

Example 209

Compound 278

4-(((3aR,5aR,5bR,7aR,9S,11aR,11bR,13aS)-3a-((R)-2-(((1H-pyrazol-4-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

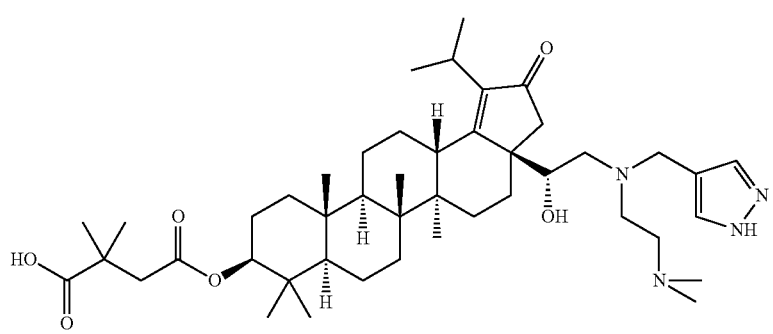

278

LC/MS: m/z calculated 764.6. found 765.5 (M+1)$^+$.

Example 210

Compound 279

4-(((3aR,5aR,5bR,7aR,9S,11aR,11bR,13aS)-3a-((S)-2-((cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

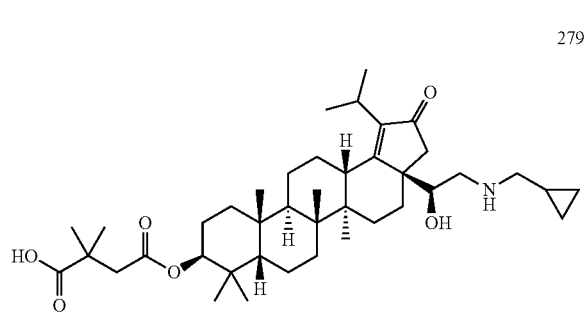

279

LC/MS: m/z calculated 667.5. found 668.5 (M+1)$^+$.

Example 211

Compound 280

4-(((3aR,5aR,5bR,7aR,9S,11aR,11bR,13aS)-3a-((S)-2-(cyclobutylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

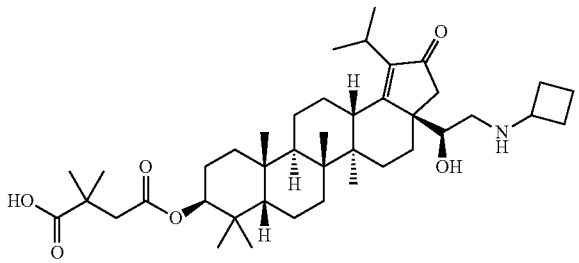

280

LC/MS: m/z calculated 667.5. found 668.5 (M+1)$^+$.

Example 212

Compound 281

4-(((3aR,5aR,5bR,7aR,9S,11aR,11bR,13aS)-3a-((R)-2-(cyclobutylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

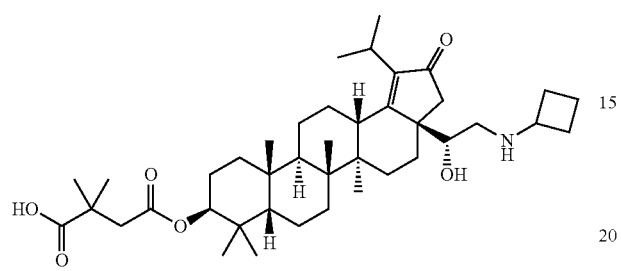

LC/MS: m/z calculated 667.5. found 668.5 (M+1)$^+$.

Example 213

Compound 282

4-(((3aR,5aR,5bR,7aR,9S,11aR,11bR,13aS)-3a-((S)-1-hydroxy-2-((3-(pyrrolidin-1-yl)propyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

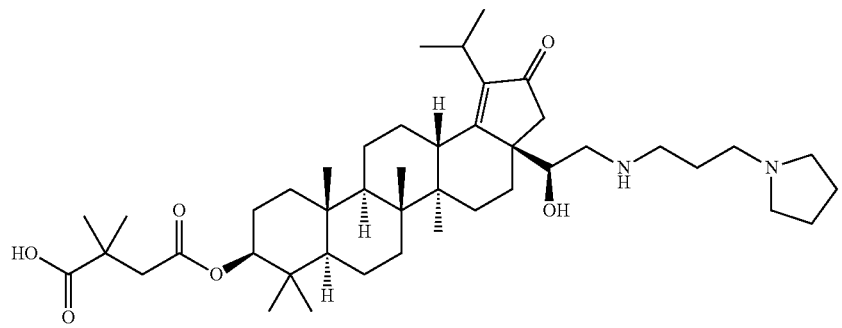

LC/MS: m/z calculated 724.5. found 725.5 (M+1)$^+$.

Example 214

Compound 283

4-(((3aR,5aR,5bR,7aR,9S,11aR,11bR,13aS)-3a-((S)-1-hydroxy-2-(4-(pyridin-2-yl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

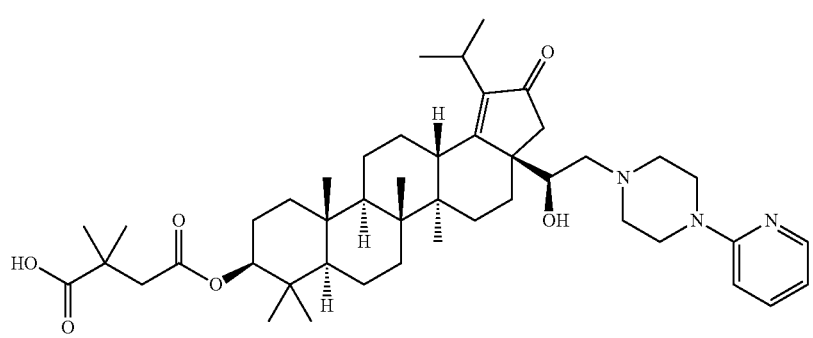

LC/MS: m/z calculated 759.5. found 760.5 (M+1)$^+$.

Example 215

Compound 284

4-(((3aR,5aR,5bR,7aR,9S,11aR,11bR,13aS)-3a-((S)-1-hydroxy-2-(4-methyl-1,4-diazepan-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

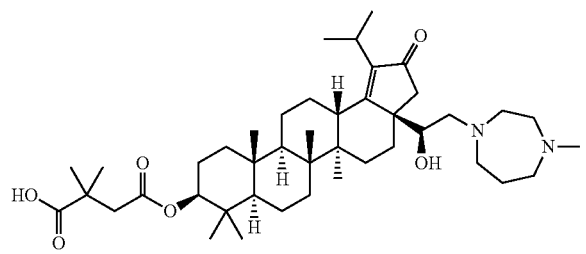

LC/MS: m/z calculated 710.5. found 711.5 (M+1)$^+$.

Example 216

Compound 285

4-(((3aR,5aR,5bR,7aR,9S,11aR,11bR,13aS)-3a-((S)-1-hydroxy-2-((4-sulfamoylphenethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

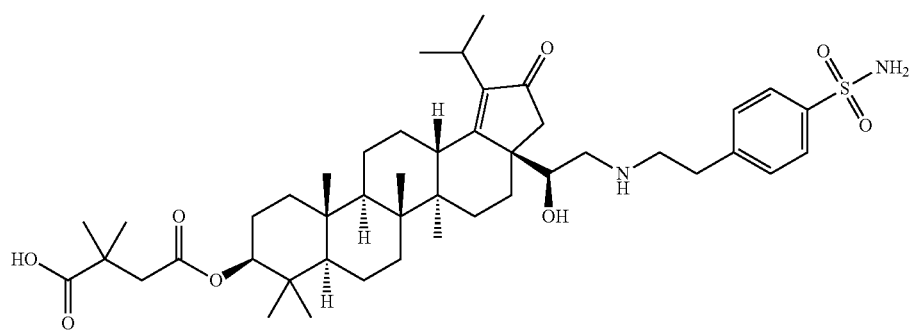

LC/MS: m/z calculated 796.5. found 797.5 (M+1)$^+$.

Example 217

Compound 286

4-(((3aR,5aR,5bR,7aR,9S,11aR,11bR,13aS)-3a-((S)-2-(4-carbamoylpiperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

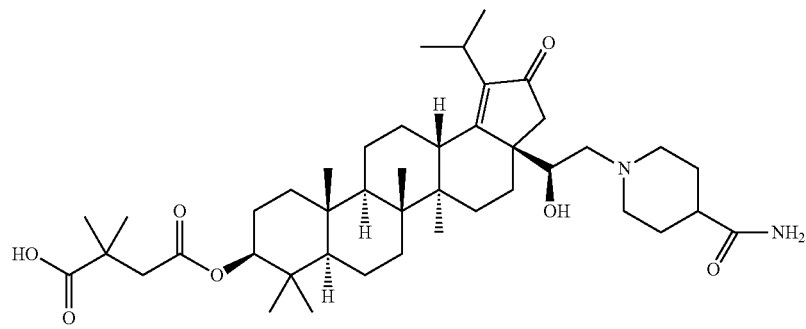

LC/MS: m/z calculated 724.5. found 725.5 (M+1)$^+$.

Example 218

Compound 287

4-(((3aR,5aR,5bR,7aR,9S,11aR,11bR,13aS)-3a-((S)-1-hydroxy-2-(4-(2-methoxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

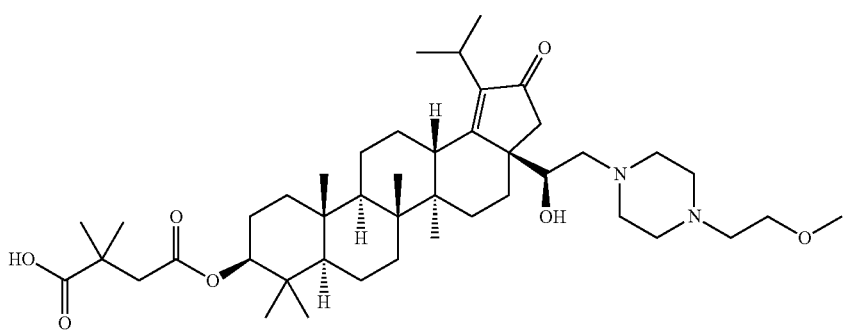

287

LC/MS: m/z calculated 740.5. found 741.5 (M+1)$^+$.

Example 219

Compound 288

4-(((3aR,5aR,5bR,7aR,9S,11aR,11bR,13aS)-3a-((S)-1-hydroxy-2-(((R)-2-hydroxy-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

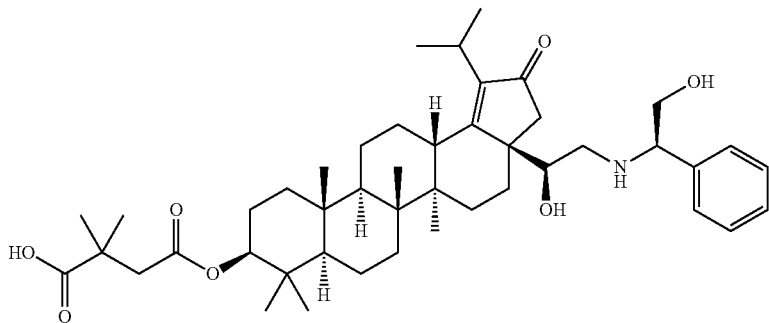

288

LC/MS: m/z calculated 733.5. found 734.5 (M+1)$^+$.

Example 220

Compound 289

4-(((3aR,5aR,5bR,7aR,9S,11aR,11bR,13aS)-3a-((1S)-1-hydroxy-2-(octahydroisoquinolin-2(1H)-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

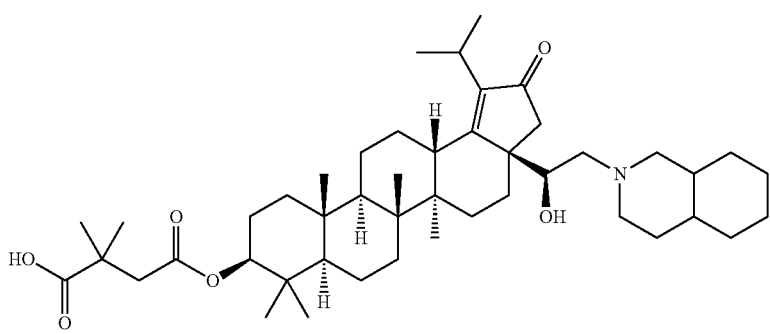

289

LC/MS: m/z calculated 735.5. found 736.5 $(M+1)^+$.

Example 221

Compound 290

4-(((3aR,5aR,5bR,7aR,9S,11aR,11bR,13aS)-3a-((S)-1-hydroxy-2-((3-(piperidin-1-yl)propyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

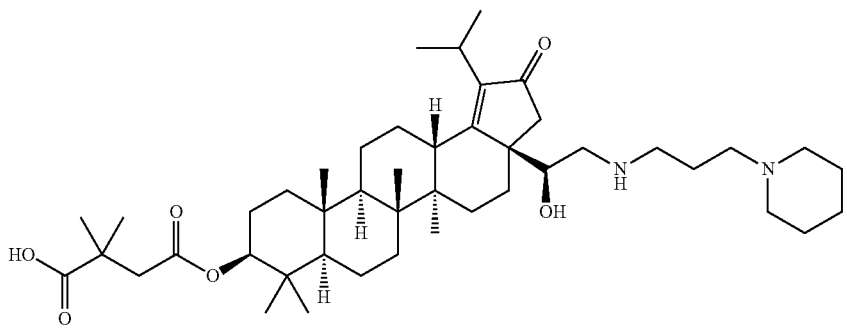

290

LC/MS: m/z calculated 738.5. found 739.5 $(M+1)^+$.

Example 222

Compound 291

4-(((3aR,5aR,5bR,7aR,9S,11aR,11bR,13aS)-3a-((R)-2-(2-(dimethylamino)-N4S)-1-(pyridin-2-yl)ethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

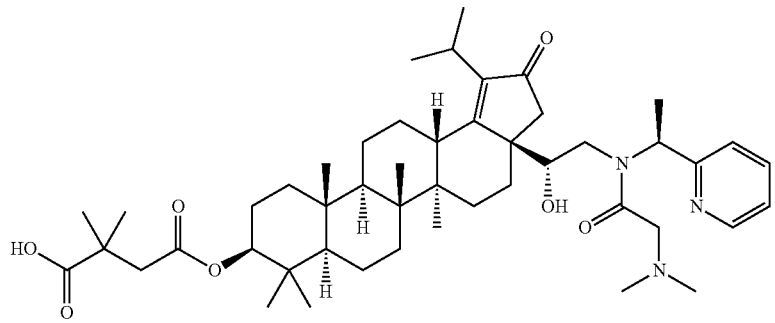

291

LC/MS: m/z calculated 803.5. found 804.5 (M+1)$^+$.

Example 223

Compound 292

4-(((3aR,5aR,5bR,7aR,9S,11aR,11bR,13aS)-3a-((S)-2-(cyclopentylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

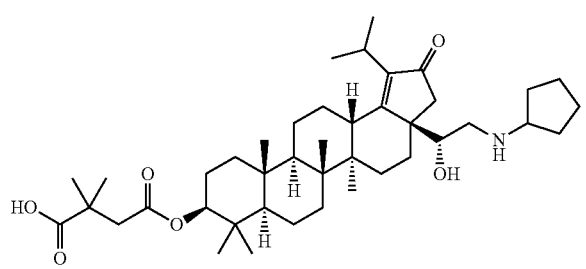

292

LC/MS: m/z calculated 681.5. found 682.5 (M+1)$^+$.

Example 224

Compound 293

4-(((3aR,5aR,5bR,7aR,9S,11aR,11bR,13aS)-3a-((S)-2-(benzo[d][1,3]dioxol-5-ylamino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

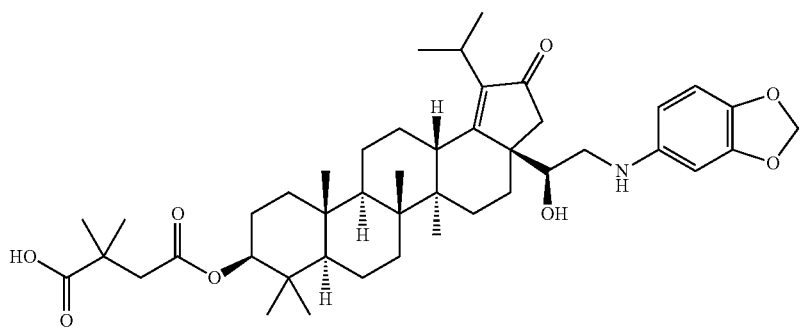

293

LC/MS: m/z calculated 733.5. found 734.5 (M+1)$^+$.

Example 225

Compound 294

4-(((3aR,5aR,5bR,7aR,9S,11aR,11bR,13aS)-3a-((S)-1-hydroxy-2-((2-(thiophen-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

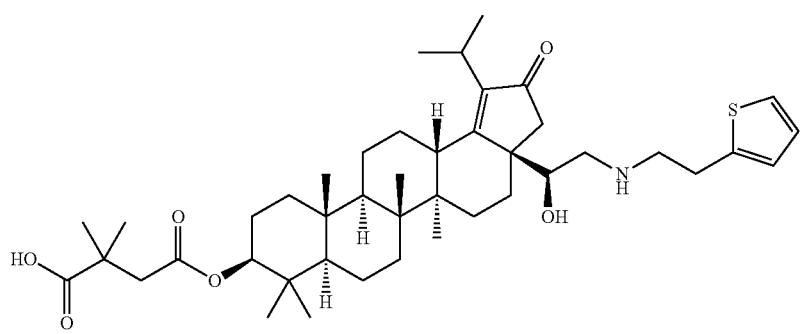

294

LC/MS: m/z calculated 723.5. found 724.4 $(M+1)^+$.

Example 226

Compound 295

4-(((3aR,5aR,5bR,7aR,9S,11aR,11bR,13aS)-3a-((S)-1-hydroxy-2-(4-(4-methylbenzyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

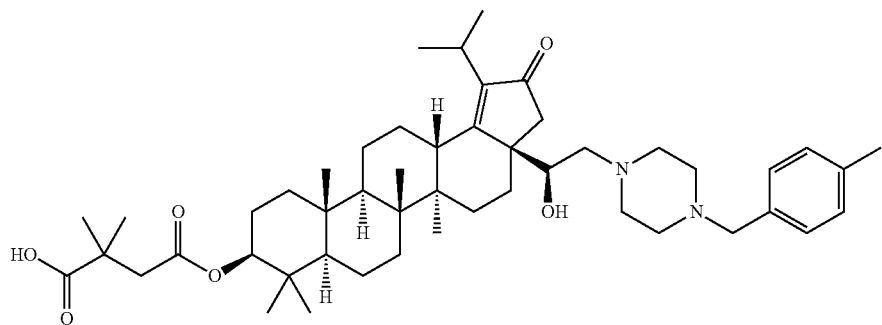

295

LC/MS: m/z calculated 786.5. found 787.5 $(M+1)^+$.

Example 227

Compound 296

4-(((3aR,5aR,5bR,7aR,9S,11aR,11bR,13aS)-3a-((S)-2-(bis(2-methoxyethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

296

LC/MS: m/z calculated 729.5. found 730.5 (M+1)+.

Example 228

Compound 297

4-(((3aR,5aR,5bR,7aR,9S,11aR,11bR,13aS)-3a-((1S)-1-hydroxy-2-((2-methylcyclohexyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

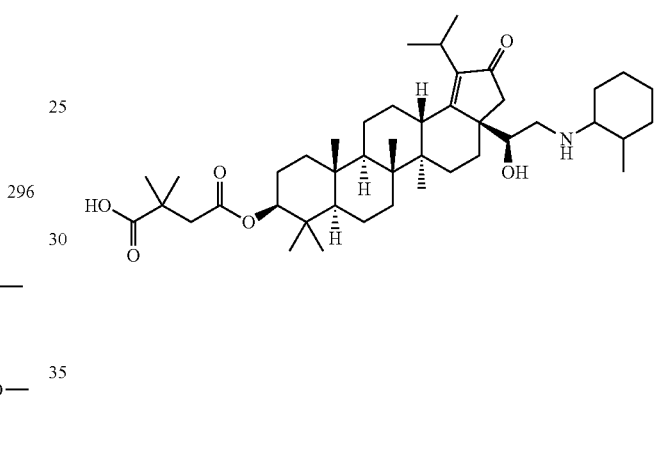

297

LC/MS: m/z calculated 709.5. found 710.5 (M+1)+.

Example 229

Compound 298

4-(((3aR,5aR,5bR,7aR,9S,11aR,11bR,13aS)-3a-((1S)-1-hydroxy-2-((2-(1-methylpyrrolidin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

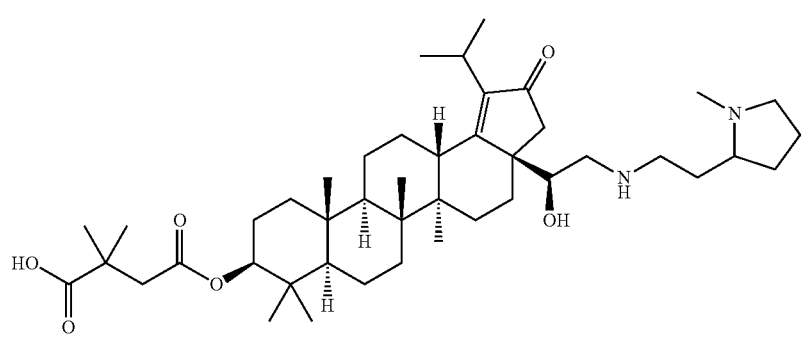

298

LC/MS: m/z calculated 724.5. found 725.5 (M+1)+.

Example 230

Compound 299

4-(((3aR,5aR,5bR,7aR,9S,11aR,11bR,13aS)-3a-((S)-1-hydroxy-2-(((1r,4S)-4-hydroxycyclohexyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

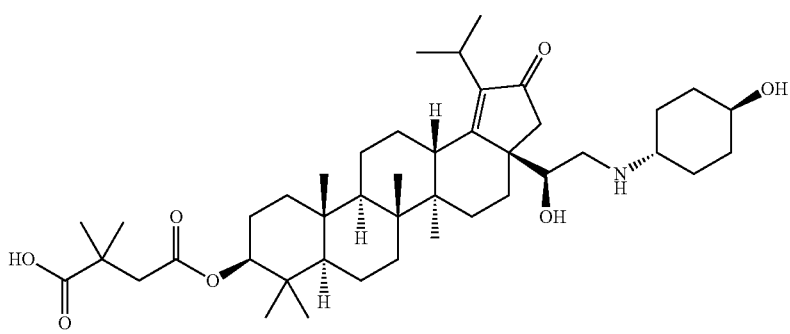

299

LC/MS: m/z calculated 711.5. found 712.4 (M+1)$^+$.

Example 231

Compound 300

4-(((3aR,5aR,5bR,7aR,9S,11aR,11bR,13aS)-3a-((S)-2-(4-ethylpiperazin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

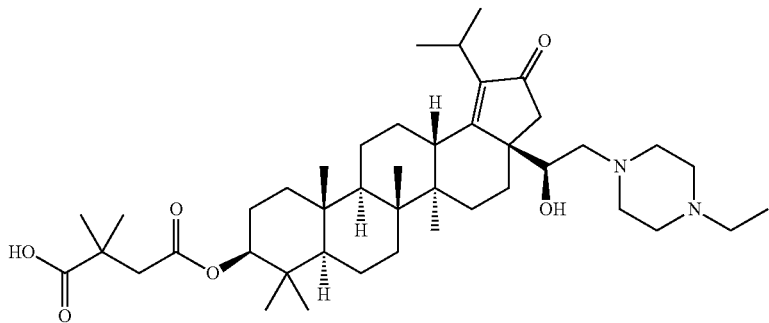

300

LC/MS: m/z calculated 710.5. found 711.5 (M+1)$^+$.

Example 232

Compound 301

4-(((3aR,5aR,5bR,7aR,9S,11aR,11bR,13aS)-3a-((S)-1-hydroxy-2-(((S)-2-hydroxypropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

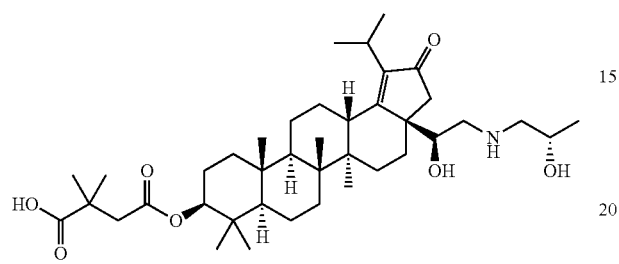

LC/MS: m/z calculated 671.5. found 672.4 (M+1)$^+$.

Example 233

Compound 302

4-(((3aR,5aR,5bR,7aR,9S,11aR,11bR,13aS)-3a-((S)-2-((4-chlorophenyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

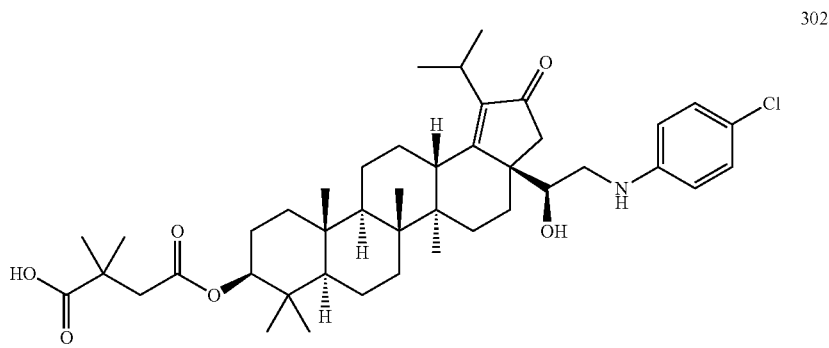

LC/MS: m/z calculated 723.4. found 724.4 (M+1)$^+$.

Example 234

Compound 303

4-(((3aR,5aR,5bR,7aR,9S,11aR,11bR,13aS)-3a-((S)-1-hydroxy-2-(isoindolin-2-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

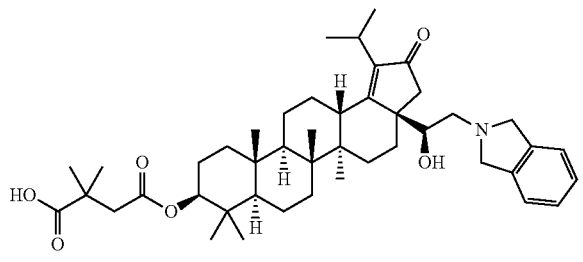

LC/MS: m/z calculated 715.5. found 716.5 (M+1)$^+$.

Example 235

Compound 304

4-(((3aR,5aR,5bR,7aR,9S,11aR,11bR,13aS)-3a-((R)-2-(((S)-1-(5-chloropyridin-2-yl)ethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

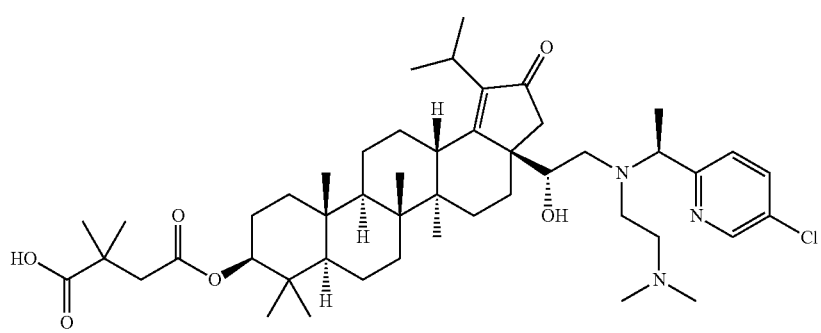

304

LC/MS: m/z calculated 823.5. found 824.5 (M+1)$^+$.

Example 236

Compound 305

4-(((3aR,5aR,5bR,7aR,9S,11aR,11bR,13aS)-3a-((S)-2-(((S)-1-(5-chloropyridin-2-yl)ethyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

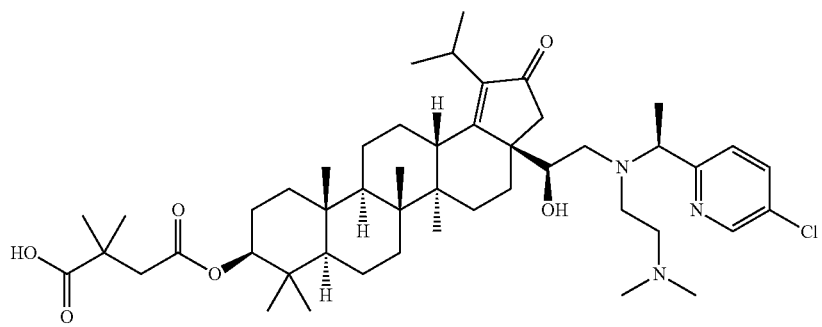

305

LC/MS: m/z calculated 823.5. found 824.5 (M+1)$^+$.

Example 237

Compound 306

4-(((3aR,5aR,5bR,7aR,9S,11aR,11bR,13aS)-3a-((R)-1-hydroxy-2-(isoindolin-2-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

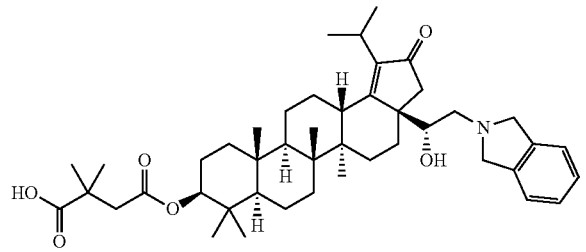

306

LC/MS: m/z calculated 715.5. found 716.5 (M+1)⁺.

Example 238

Compound 307

4-(((3aR,5aR,5bR,7aR,9S,11aR,11bR,13aS)-3a-((S)-2-((2-(5-chloropyridin-2-yl)propan-2-yl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

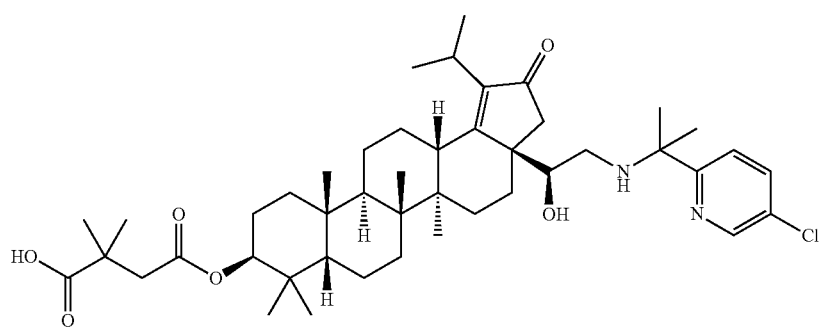

307

LC/MS: m/z calculated 766.5. found 767.5 (M+1)⁺.

Example 239

Compound 308

4-(((3aR,5aR,5bR,7aR,9S,11aR,11bR,13aS)-3a-((R)-2-((2-(5-chloropyridin-2-yl)propan-2-yl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

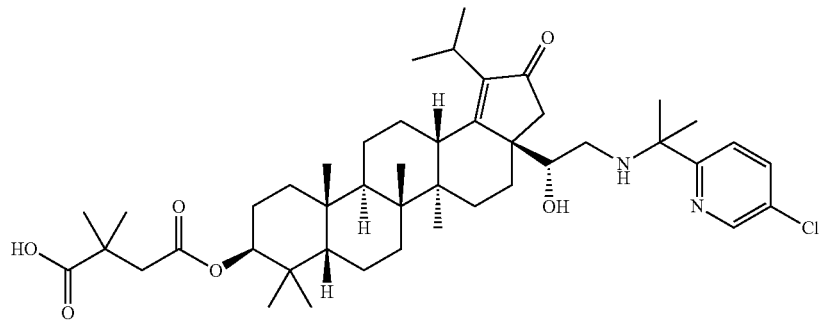

308

LC/MS: m/z calculated 766.5. found 767.6 (M+1)⁺.

Example 240

Compound 309

4-(((3aR,5aR,5bR,7aR,9S,11aR,11bR,13aS)-3a-((R)-1-hydroxy-2-(((S)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

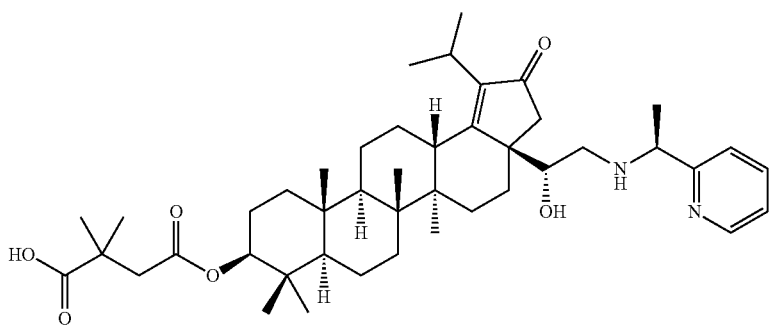

309

LC/MS: m/z calculated 718.5. found 719.5 $(M+1)^+$.

Example 241

Compound 310

4-(((3aR,5aR,5bR,7aR,9S,11aR,11bR,13aS)-3a-((S)-1-hydroxy-2-((pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

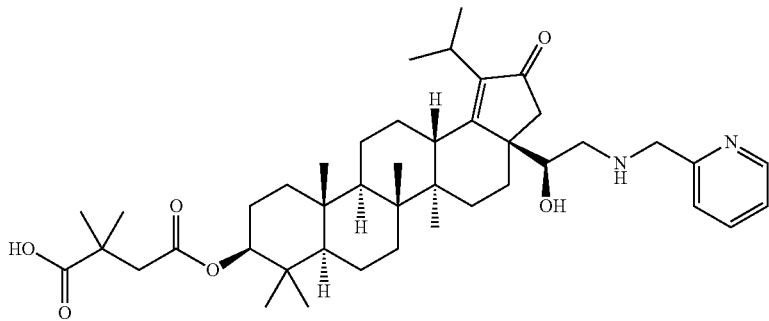

310

LC/MS: m/z calculated 704.5. found 705.5 $(M+1)^+$.

Example 242

Compound 311

4-(((3aR,5aR,5bR,7aR,9S,11aR,11bR,13aS)-3a-((R)-1-hydroxy-2-((pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

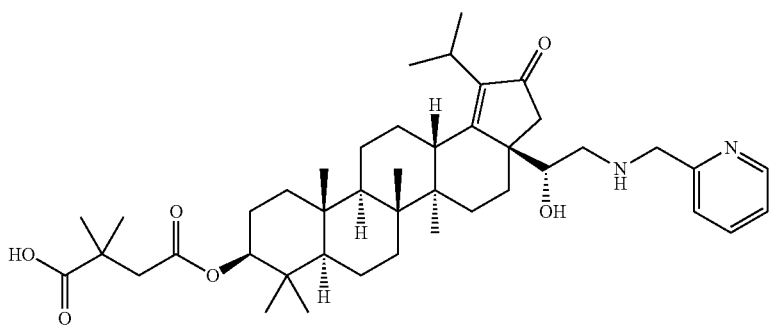

311

LC/MS: m/z calculated 704.5. found 705.5 (M+1)$^+$.

Example 243

Compound 312

4-(((3aR,5aR,5bR,7aR,9S,11aR,11bR,13aS)-3a-((R)-2-((2-(dimethylamino)ethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

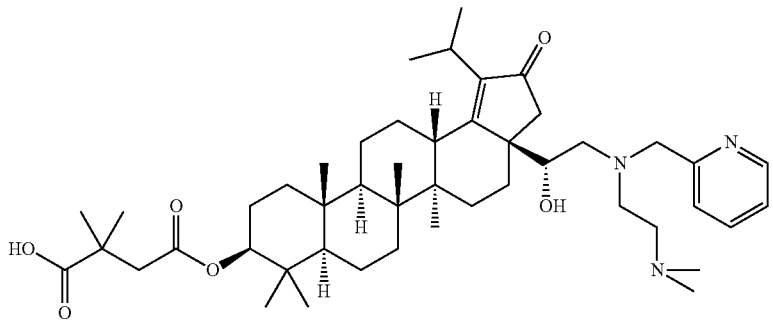

312

LC/MS: m/z calculated 775.5. found 776.5 (M+1)$^+$.

Example 244

Compound 313

4-(((3aR,5aR,5bR,7aR,9S,11aR,11bR,13aS)-3a-((S)-1-hydroxy-2-(phenylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

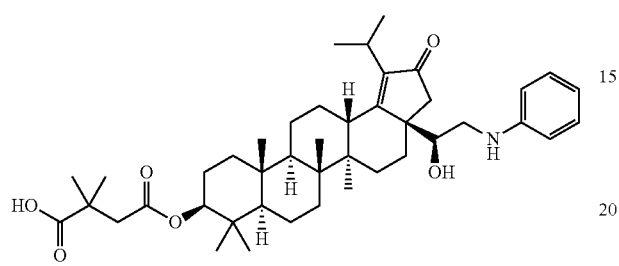

313

LC/MS: m/z calculated 689.5. found 690.5 (M+1)$^+$.

Example 245

Compound 314

4-(((3aR,5aR,5bR,7aR,9S,11aR,11bR,13aS)-3a-((S)-1-hydroxy-2-((4-methoxyphenyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

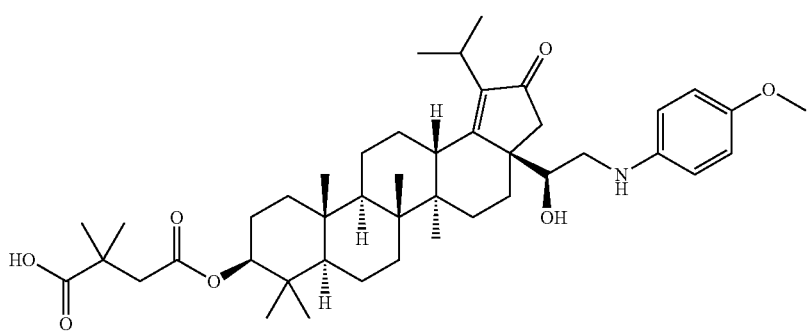

314

LC/MS: m/z calculated 719.5. found 720.5 (M+1)$^+$.

Example 246

Compound 315

4-(((3aR,5aR,5bR,7aR,9S,11aR,11bR,13aS)-3a-((S)-1-hydroxy-2-((S)-2-(hydroxymethyl)pyrrolidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

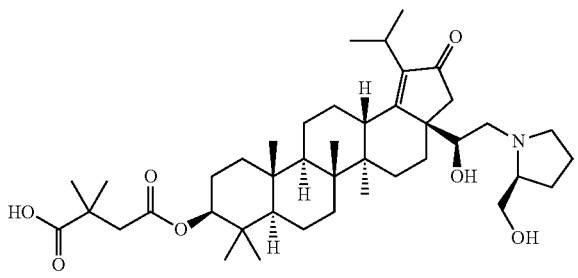

315

LC/MS: m/z calculated 697.5. found 698.5 (M+1)$^+$.

Example 247

Compound 316

4-(((3aR,5aR,5bR,7aR,9S,11aR,11bR,13aS)-3a-((S)-2-((R)-3-(ethoxycarbonyl)piperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

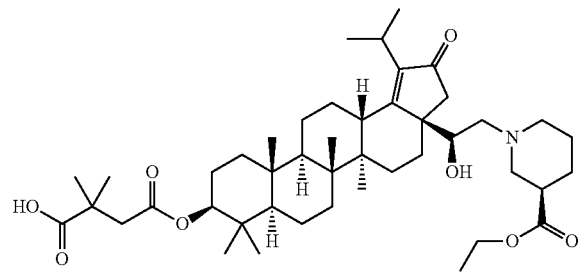

316

LC/MS: m/z calculated 753.5. found 754.5 (M+1)⁺.

Example 248

Compound 317

4-(((3aR,5aR,5bR,7aR,9S,11aR,11bR,13aS)-3a-((S)-2-(4-formylpiperazin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

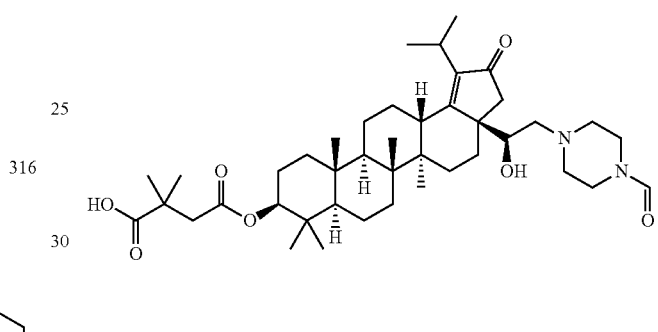

317

LC/MS: m/z calculated 710.5. found 711.5 (M+1)⁺.

Example 249

Compound 318

4-(((3aR,5aR,5bR,7aR,9S,11aR,11bR,13aS)-3a-((S)-2-(4-benzylpiperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

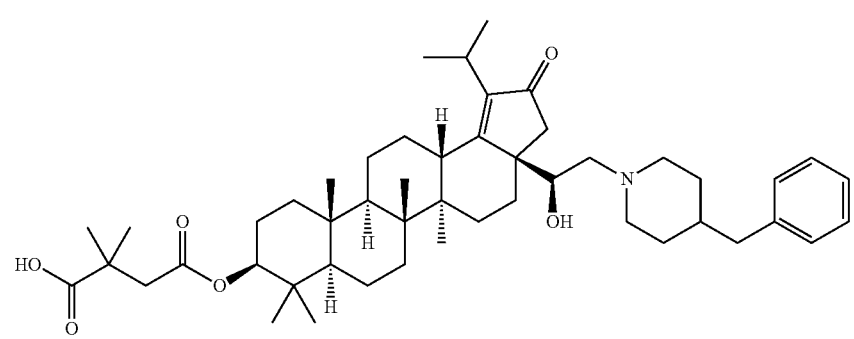

318

LC/MS: m/z calculated 771.5. found 772.5 (M+1)⁺.

Example 250

Compound 319

4-(((3aR,5aR,5bR,7aR,9S,11aR,11bR,13aS)-3a-((S)-2-(4-acetylpiperazin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

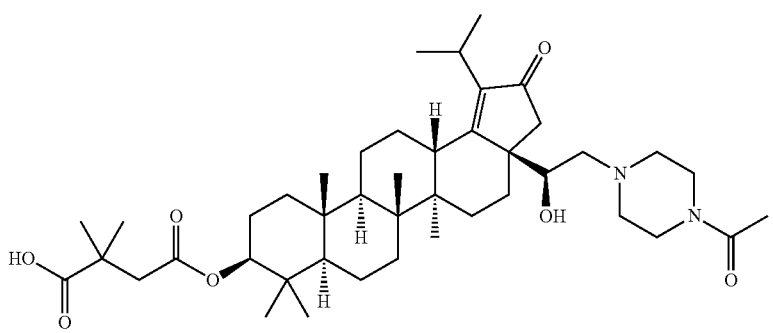

319

LC/MS: m/z calculated 724.5. found 725.5 (M+1)$^+$.

Example 251

Compound 320

4-(((3aR,5aR,5bR,7aR,9S,11aR,11bR,13aS)-3a-((S)-1-hydroxy-2-(4-(2-morpholinoethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

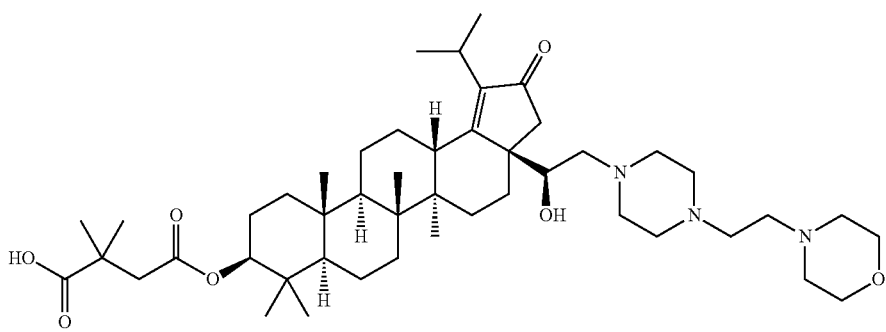

320

LC/MS: m/z calculated 795.6. found 796.5 (M+1)$^+$.

Example 252

Compound 321

4-(((3aR,5aR,5bR,7aR,9S,11aR,11bR,13aS)-3a-((R)-2-(benzyl(carboxymethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

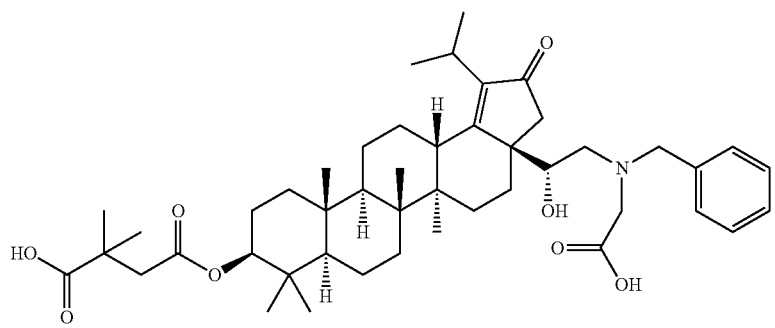

321

LC/MS: m/z calculated 761.5. found 762.5 (M+1)$^+$.

Example 253

Compound 322

4-(((3aR,5aR,5bR,7aR,9S,11aR,11bR,13aS)-3a-((S)-1-hydroxy-2-(((S)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

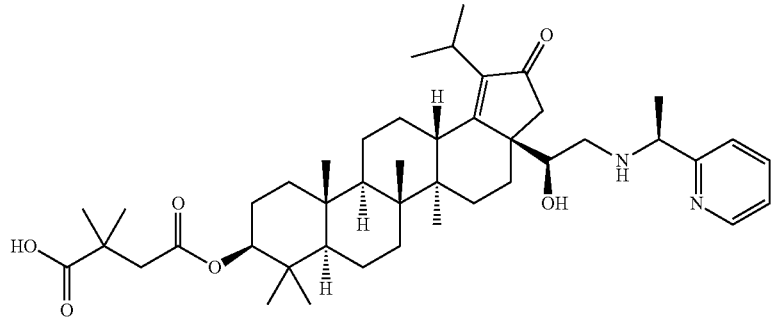

322

LC/MS: m/z calculated 718.5. found 719.5 (M+1)$^+$.

Example 254

Compound 323

4-(((3aR,5aR,5bR,7aR,9S,11aR,11bR,13aS)-3a-((R)-2-(2-(dimethylamino)-N—((R)-1-(pyridin-2-yl)ethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

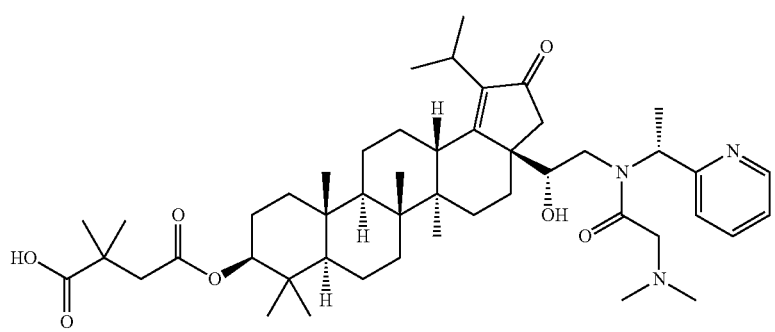

323

LC/MS: m/z calculated 803.5. found 804.5 (M+1)$^+$.

Example 255

Compound 324

4-(((3aR,5aR,5bR,7aR,9S,11aR,11bR,13aS)-3a-((R)-1-hydroxy-2-((2-(methylamino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

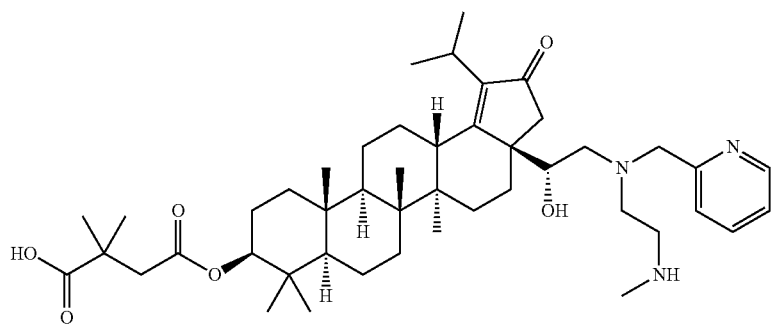

324

LC/MS: m/z calculated 761.5. found 762.5 (M+1)$^+$.

Example 256

Compound 325

4-((3aR,5aR,5bR,7aR,9S,11aR,11bR,13aS)-3a-((R)-2-(bis(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 1-tert-butyl 2,2-dimethylsuccinate

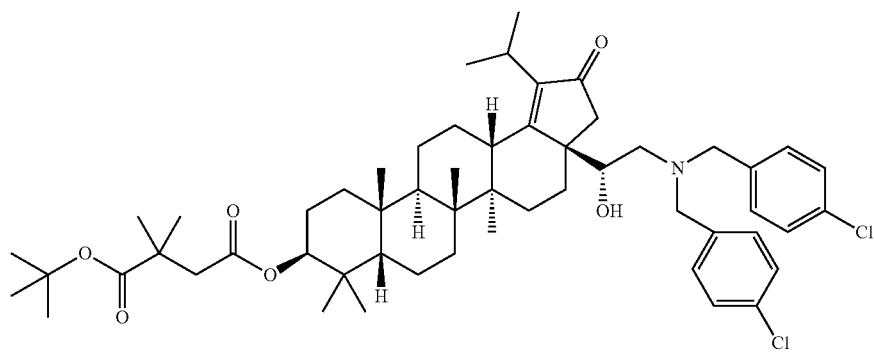

325

LC/MS: m/z calculated 917.5. found 918.5 (M+1)$^+$.

Example 257

Compound 326

4-(((3aR,5aR,5bR,7aR,9S,11aR,11bR,13aS)-3a-((R)-2-(bis(4-chlorobenzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

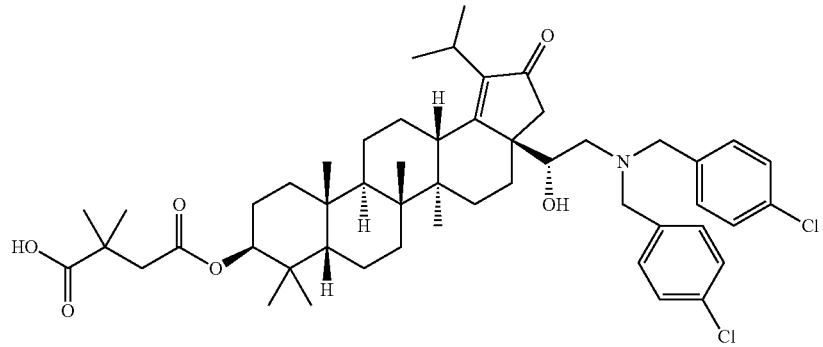

326

LC/MS: m/z calculated 861.4. found 862.4 (M+1)$^+$.

Example 258

Compound 327

4-(((3aR,5aR,5bR,7aR,9S,11aR,11bR,13aS)-3a-((R)-1-hydroxy-2-((2-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

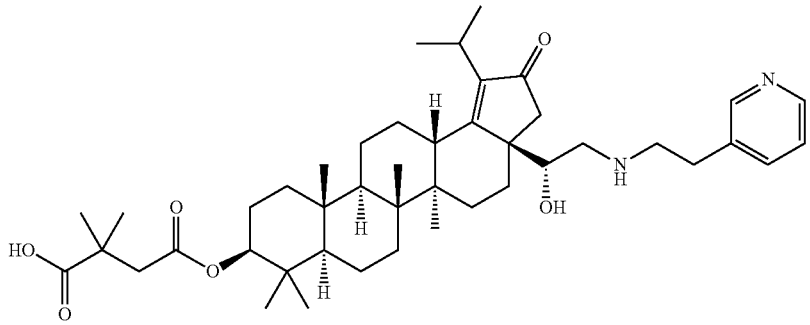

327

LC/MS: m/z calculated 718.5. found 719.5 (M+1)$^+$.

Example 259

Compound 328

4-(((3aR,5aR,5bR,7aR,9S,11aR,11bR,13aS)-3a-((R)-1-hydroxy-2-((R)-3-hydroxypiperidin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

328

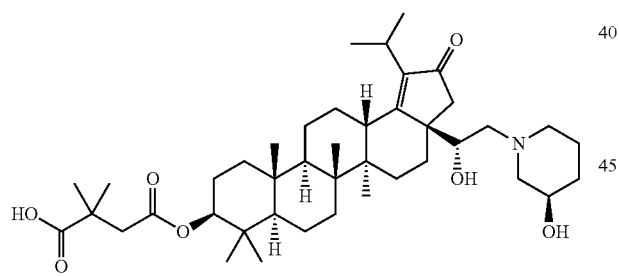

LC/MS: m/z calculated 697.5. found 698.5 (M+1)$^+$.

Example 260

Compound 329

4-(((3aR,5aR,5bR,7aR,9S,11aR,11bR,13aS)-3a-((R)-1-hydroxy-2-((4-hydroxyphenethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

329

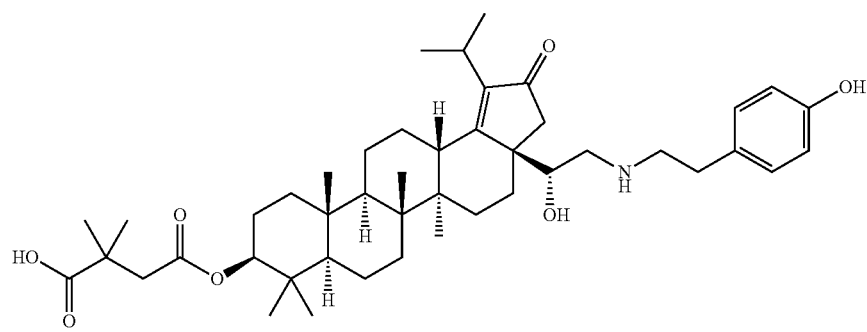

LC/MS: m/z calculated 733.5. found 734.4 (M+1)$^+$.

Example 261

Compound 330

4-(((3aR,5aR,5bR,7aR,9S,11aR,11bR,13aS)-3a-((R)-1-hydroxy-2-(4-(2-hydroxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

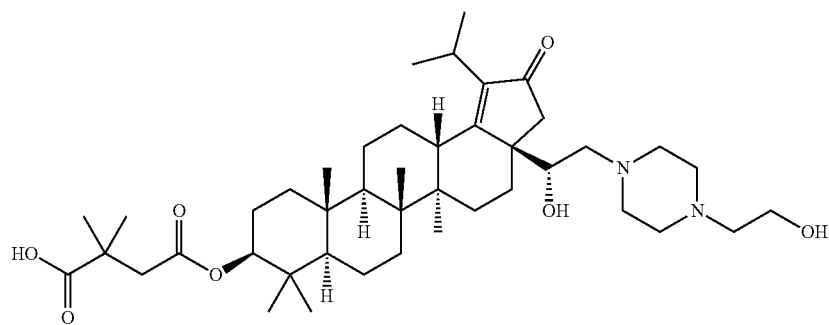

330

LC/MS: m/z calculated 726.5. found 727.5 (M+1)$^+$.

Example 262

Compound 331

4-(((3aR,5aR,5bR,7aR,9S,11aR,11bR,13aS)-3a-((R)-1-hydroxy-2-thiomorpholinoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

331

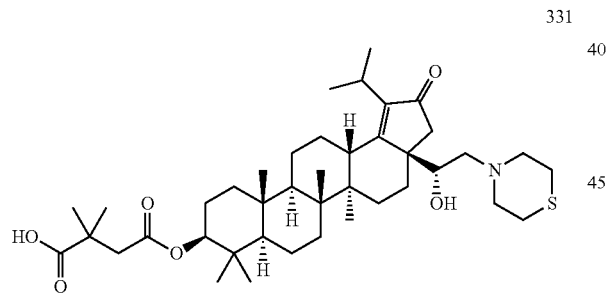

LC/MS: m/z calculated 699.4. found 700.4 (M+1)$^+$.

Example 263

Compound 332

4-(((3aR,5aR,5bR,7aR,9S,11aR,11bR,13aS)-3a-((R)-1-hydroxy-2-(4-(pyridin-2-yl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

332

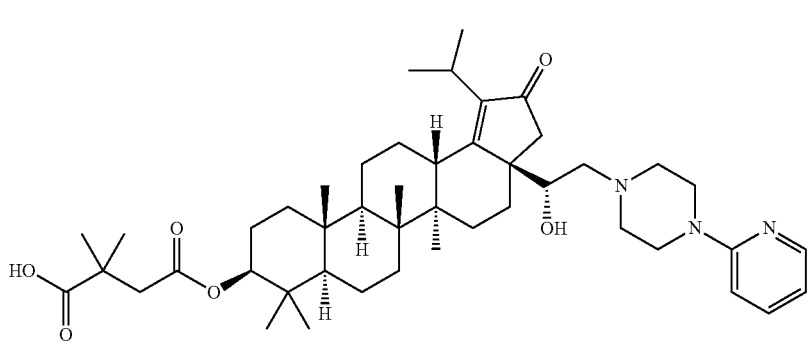

LC/MS: m/z calculated 759.5. found 760.5 (M+1)$^+$.

Example 264

Compound 333

4-(((3aR,5aR,5bR,7aR,9S,11aR,11bR,13aS)-3a-((R)-1-hydroxy-2-(4-methyl-1,4-diazepan-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

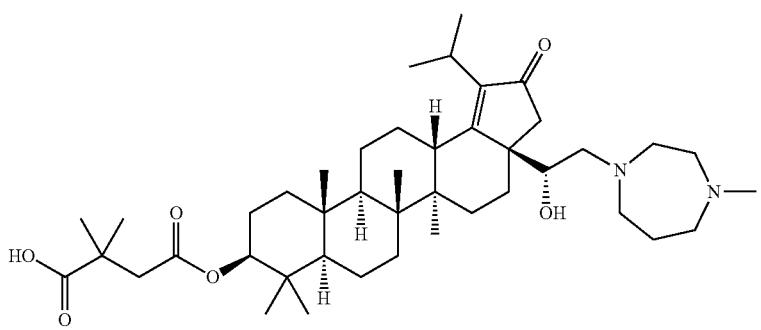

333

LC/MS: m/z calculated 710.5. found 711.5 (M+1)⁺.

Example 265

Compound 334

4-(((3aR,5aR,5bR,7aR,9S,11aR,11bR,13aS)-3a-((R)-2-(4-carbamoylpiperidin-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

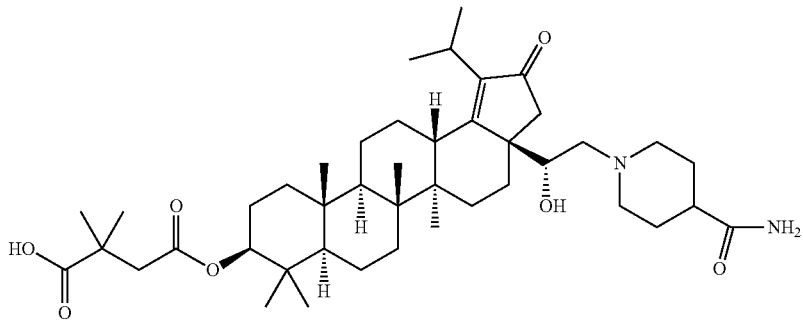

334

LC/MS: m/z calculated 724.5. found 725.5 (M+1)⁺.

Example 266

Compound 335

4-(((3aR,5aR,5bR,7aR,9S,11aR,11bR,13aS)-3a-((R)-1-hydroxy-2-(4-(2-methoxyethyl)piperazin-1-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

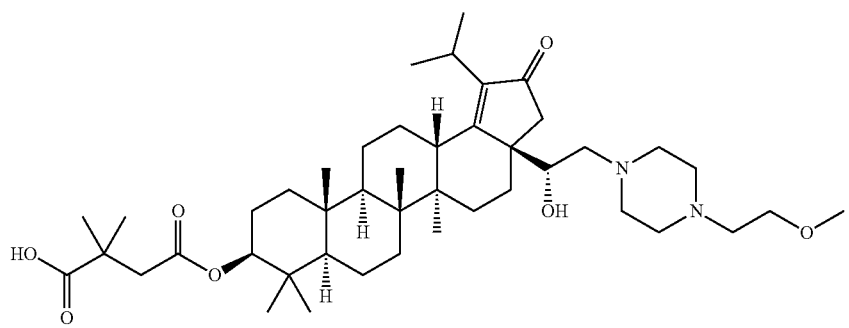

335

LC/MS: m/z calculated 740.5. found 741.5 (M+1)$^+$.

Example 267

Compound 336

4-(((3aR,5aR,5bR,7aR,9S,11aR,11bR,13aS)-3a-((R)-1-hydroxy-2-(((R)-2-hydroxy-1-phenylethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

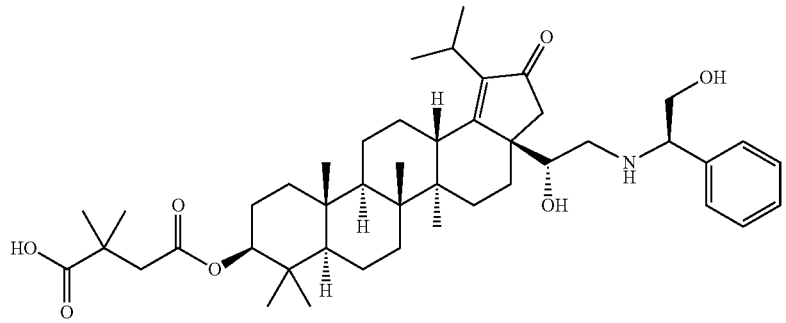

336

LC/MS: m/z calculated 733.5. found 734.5 (M+1)$^+$.

Example 268

Compound 337

4-(((3aR,5aR,5bR,7aR,9S,11aR,11bR,13aS)-3a-((S)-1-hydroxy-2-((pyrimidin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

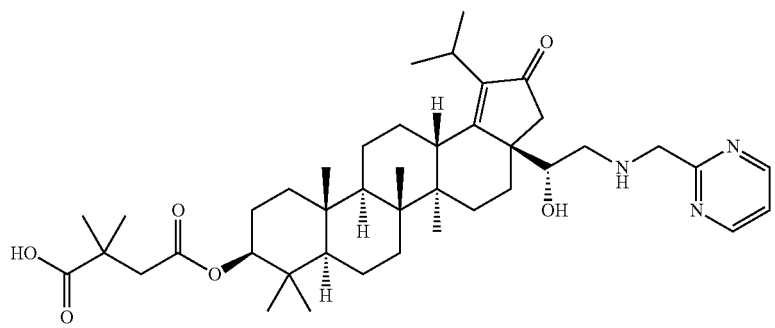

337

LC/MS: m/z calculated 705.5. found 706.4 (M+1)$^+$.

Example 269

Compound 338

4-(((3aR,5aR,5bR,7aR,9S,11aR,11bR,13aS)-3a-((R)-1-hydroxy-2-((pyrimidin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

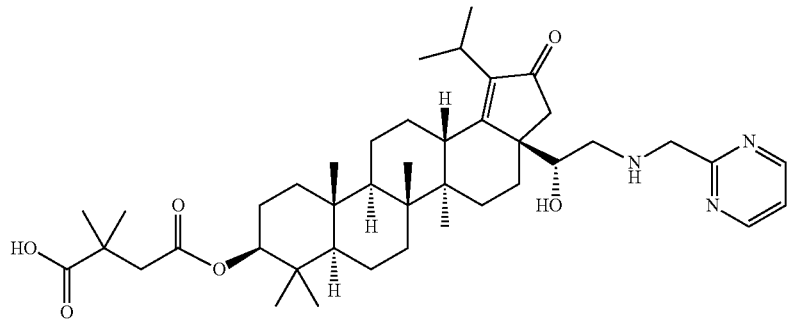

338

LC/MS: m/z calculated 705.5. found 706.4 (M+1)$^+$.

Example 270

Compound 339

4-(((3aR,5aR,5bR,7aR,9S,11aR,11bR,13aS)-3a-((R)-2-(N-benzyl-2-(dimethylamino)-2-oxoacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

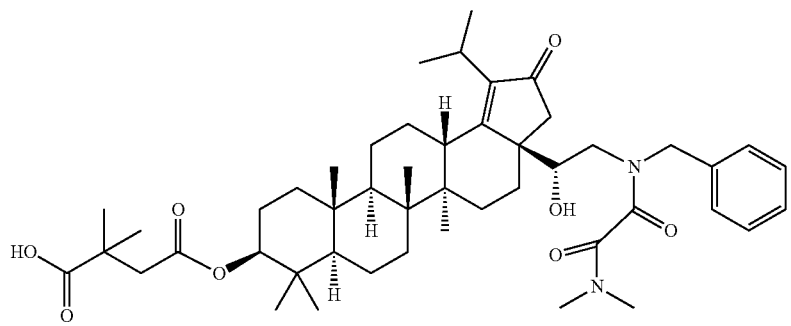

339

LC/MS: m/z calculated 802.5. found 803.5 (M+1)$^+$.

Example 271

Compound 340

4-(((3aR,5aR,5bR,7aR,9S,11aR,11bR,13aS)-3a-((S)-2-((4-chloro-2-((dimethylamino)methyl)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

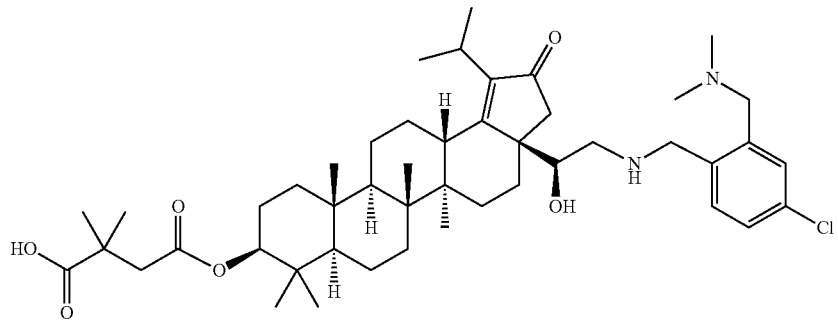

340

LC/MS: m/z calculated 794.5. found 795.5 (M+1)$^+$.

Example 272

Compound 341

4-(((3aR,5aR,5bR,7aR,9S,11aR,11bR,13aS)-3a-((R)-2-((4-chloro-2-((dimethylamino)methyl)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

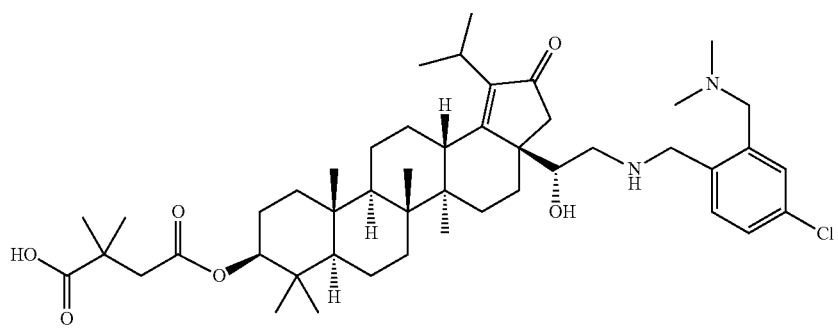

341

LC/MS: m/z calculated 794.5. found 795.5 (M+1)$^+$.

Example 273

Compound 342

4-(((3aR,5aR,5bR,7aR,9S,11aR,11bR,13aS)-3a-((S)-2-((4-chloro-2-((dimethylamino)methyl)benzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

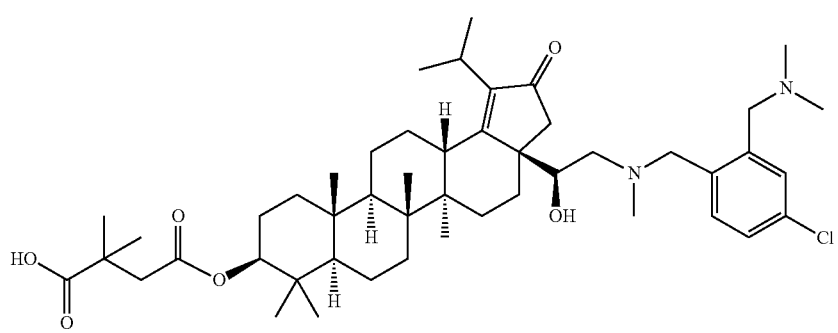

342

LC/MS: m/z calculated 808.5. found 809.5 (M+1)$^+$.

Example 274

Compound 343

4-(((3aR,5aR,5bR,7aR,9S,11aR,11bR,13aS)-3a-((R)-2-(N-(4-chloro-2-((dimethylamino)methyl)benzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

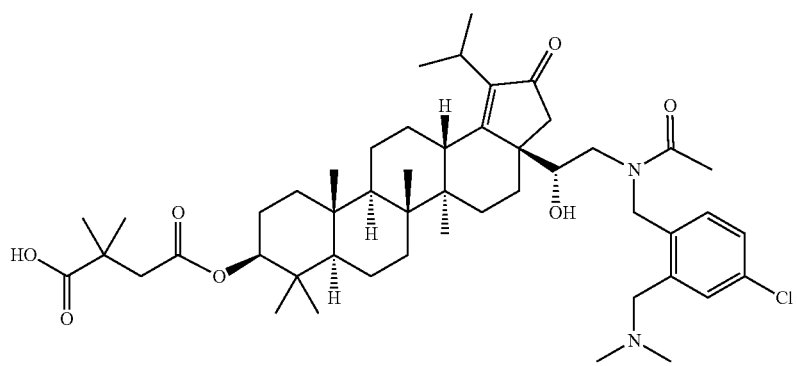

343

LC/MS: m/z calculated 836.5. found 837.5 (M+1)$^+$.

Example 275

Compound 344

4-(((3aR,5aR,5bR,7aR,9S,11aR,11bR,13aS)-3a-((R)-2-((4-chloro-2-((dimethylamino)methyl)benzyl)(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

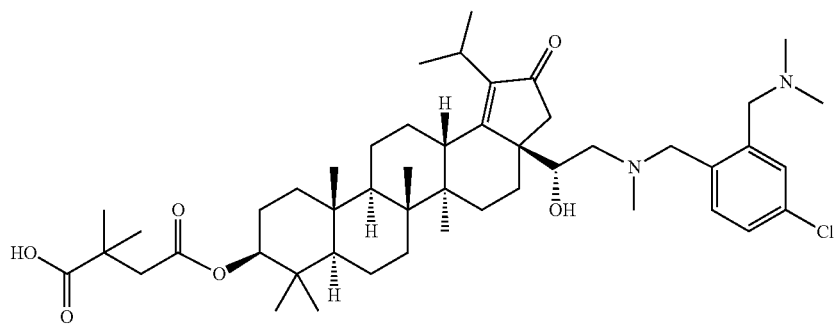

344

LC/MS: m/z calculated 808.5. found 809.5 (M+1)$^+$.

Example 276

Compound 345

4-(((3aR,5aR,5bR,7aR,9S,11aR,11bR,13aS)-3a-((R)-2-(N-(cyclopropylmethyl)-2-(dimethylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

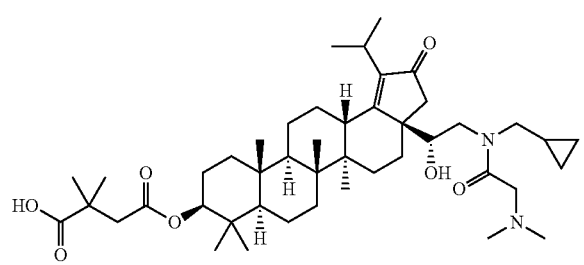

345

LC/MS: m/z calculated 752.5. found 753.5 (M+1)⁺.

Example 277

Compound 346

4-(((3aR,5aR,5bR,7aR,9S,11aR,11bR,13aS)-3a-((R)-2-(benzyl(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

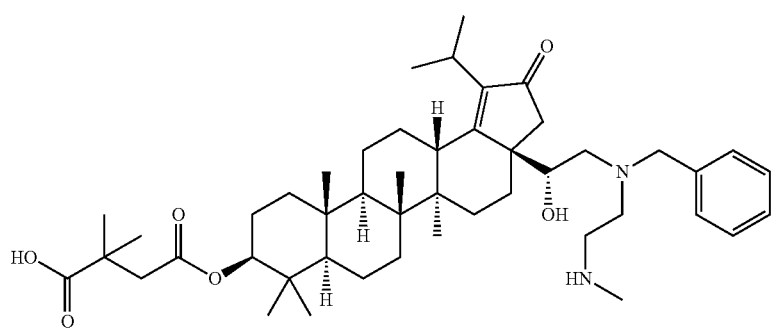

346

LC/MS: m/z calculated 760.5. found 761.5 (M+1)⁺.

Example 278

Compound 347

4-(((3aR,5aR,5bR,7aR,9S,11aR,11bR,13aS)-3a-((R)-2-((cyclopropylmethyl)(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

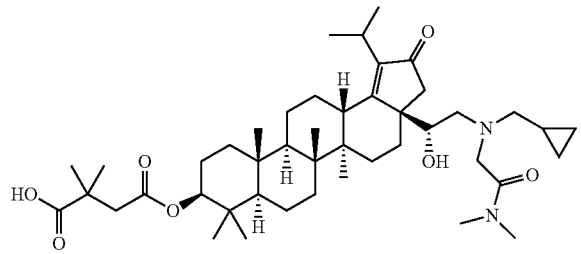

347

LC/MS: m/z calculated 752.5. found 753.5 (M+1)⁺.

Example 279

Compound 348

4-(((3aR,5aR,5bR,7aR,9S,11aR,11bR,13aS)-3a-((R)-2-((2-acetamidoethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 280

Compound 349

4-(((3aR,5aR,5bR,7aR,9S,11aR,11bR,13aS)-3a-((R)-2-((cyclopropylmethyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

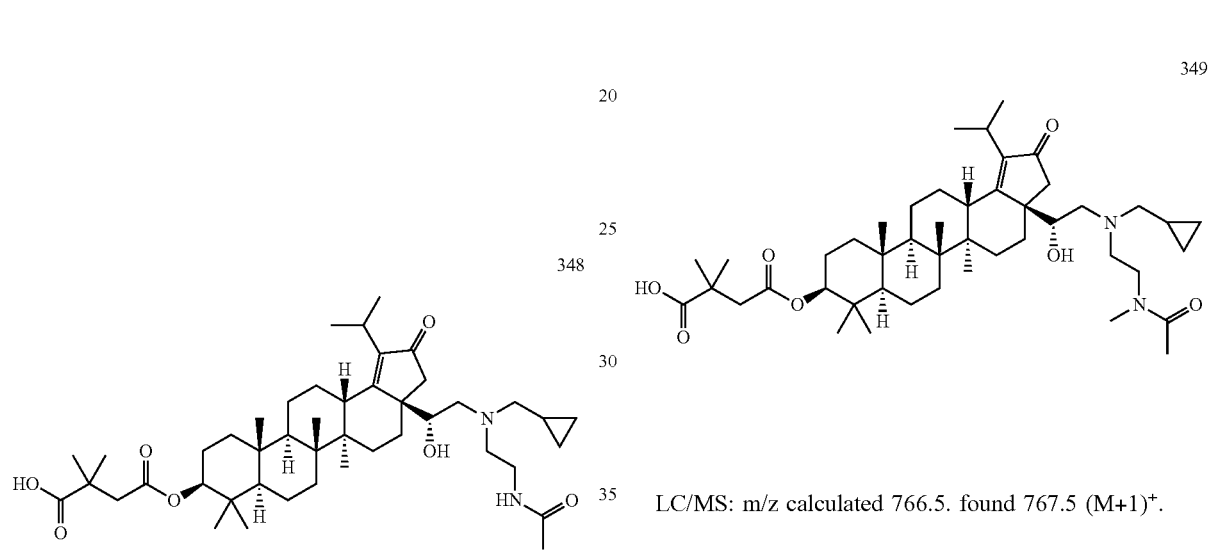

LC/MS: m/z calculated 766.5. found 767.5 $(M+1)^+$.

Example 281

Compound 350

4-(((3aR,5aR,5bR,7aR,9S,11aR,11bR,13aS)-3a-((R)-2-((2-amino-2-oxoethyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid LC/MS: m/z calculated 752.5. found 753.5 $(M+1)^+$.

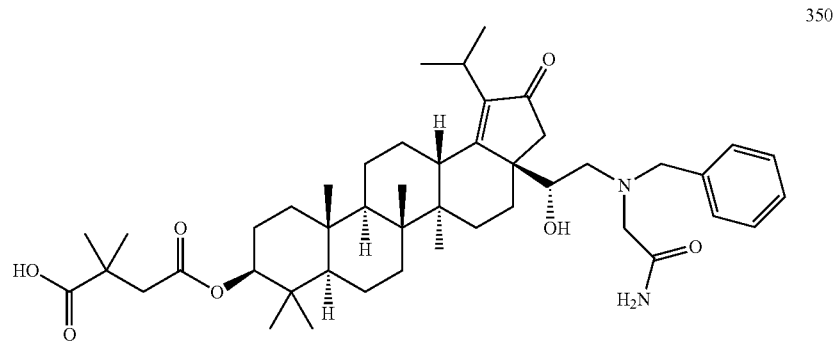

LC/MS: m/z calculated 760.5. found 761.5 $(M+1)^+$.

Example 282

Compound 351

4-(((3aR,5aR,5bR,7aR,9S,11aR,11bR,13aS)-3a-((R)-2-(benzyl(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

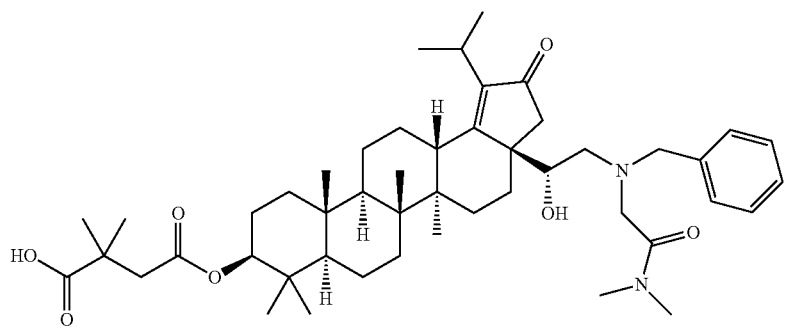

351

LC/MS: m/z calculated 788.5. found 789.5 $(M+1)^+$.

Example 283

Compound 352

4-(((3aR,5aR,5bR,7aR,9S,11aR,11bR,13aS)-3a-((S)-1-hydroxy-2-(isobutylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

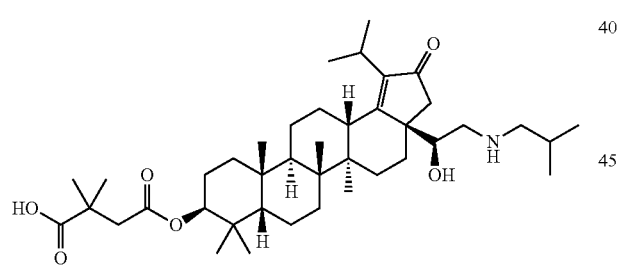

352

LC/MS: m/z calculated 669.5. found 670.5 $(M+1)^+$.

Example 284

Compound 353

4-(((3aR,5aR,5bR,7aR,9S,11aR,11bR,13aS)-3a-((R)-2-(2-amino-N-(pyridin-3-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

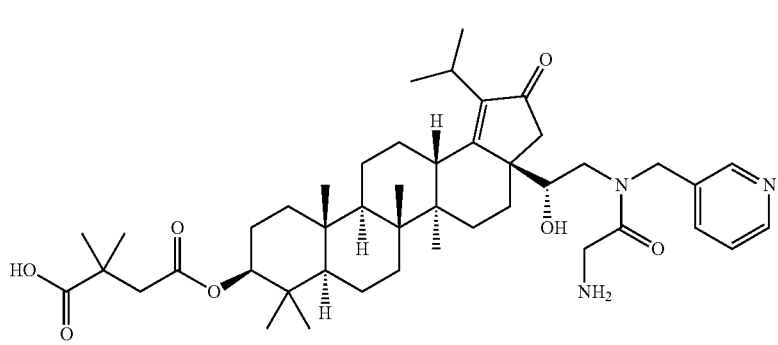

353

LC/MS: m/z calculated 761.5. found 762.5 $(M+1)^+$.

Example 285

Compound 354

4-(((3aR,5aR,5bR,7aR,9S,11aR,11bR,13aS)-3a-((R)-2-(2-(dimethylamino)-N-(pyridin-3-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

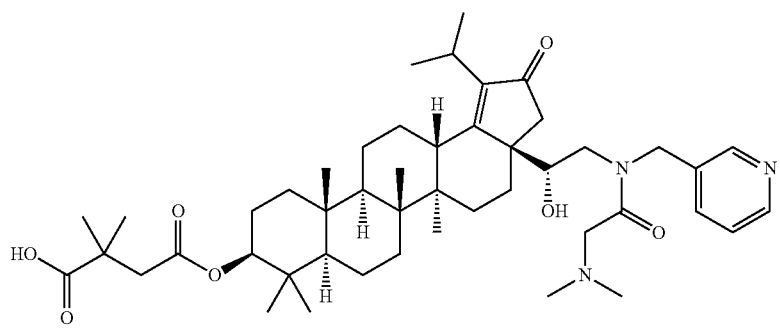

354

LC/MS: m/z calculated 789.5. found 790.5 (M+1)$^+$.

Example 286

Compound 355

4-(((3aR,5aR,5bR,7aR,9S,11aR,11bR,13aS)-3a-((R)-1-hydroxy-2-(2-(methylamino)-N-(pyridin-3-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

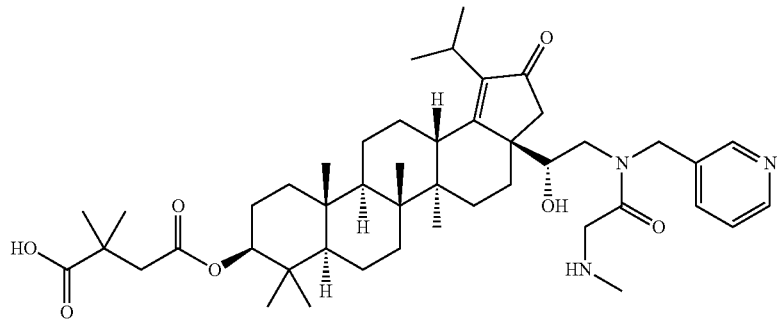

355

LC/MS: m/z calculated 775.5. found 776.5 (M+1)$^+$.

Example 287

Compound 356

4-(((3aR,5aR,5bR,7aR,9S,11aR,11bR,13aS)-3a-((R)-1-hydroxy-2-((3-(trifluoromethyl)benzyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

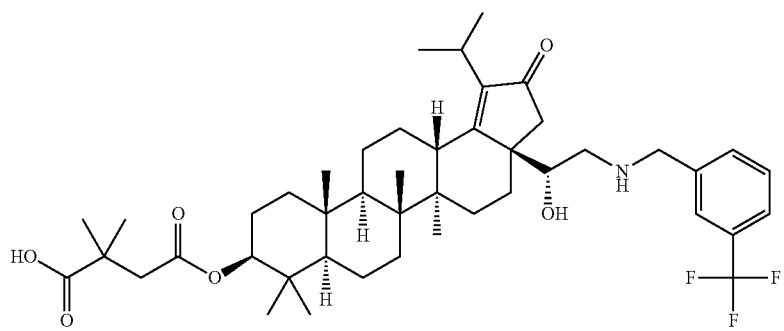

356

LC/MS: m/z calculated 771.5. found 772.4 (M+1)$^+$.

Example 288

Compound 357

4-(((3aR,5aR,5bR,7aR,9S,11aR,11bR,13aS)-3a-((R)-1-hydroxy-2-((pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

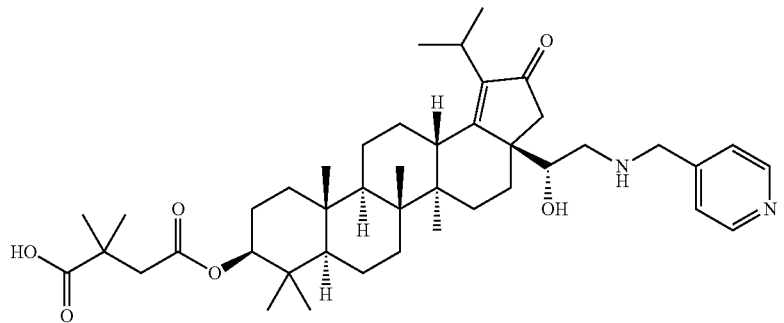

357

LC/MS: m/z calculated 704.5. found 705.5 (M+1)$^+$.

Example 289

Compound 358

4-(((3aR,5aR,5bR,7aR,9S,11aR,11bR,13aS)-3a-((1R)-1-hydroxy-2-(((tetrahydrofuran-2-yl)methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

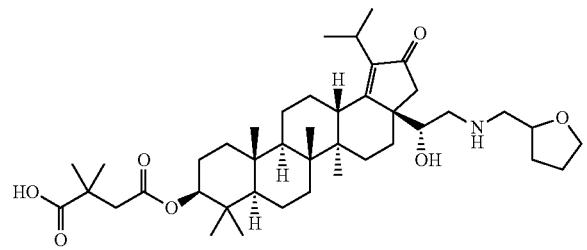

358

LC/MS: m/z calculated 697.5. found 698.5 (M+1)⁺.

Example 290

Compound 359

4-(((3aR,5aR,5bR,7aR,9S,11aR,11bR,13aS)-3a-((R)-2-(cyclohexyl(methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

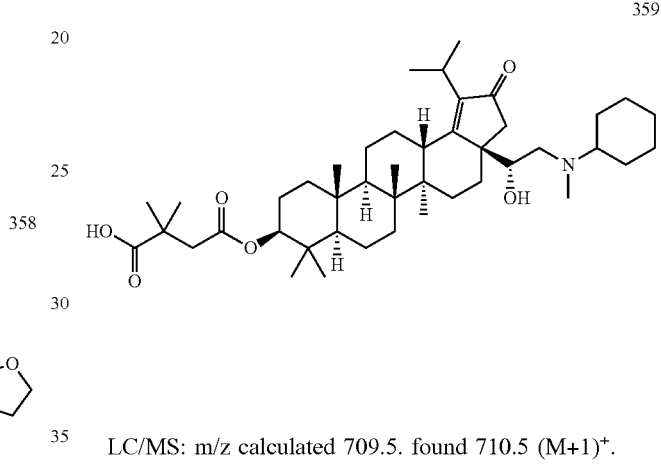

359

LC/MS: m/z calculated 709.5. found 710.5 (M+1)⁺.

Example 291

Compound 360

4-(((3aR,5aR,5bR,7aR,9S,11aR,11bR,13aS)-3a-((R)-1-hydroxy-2-(((S)-1-hydroxy-4-methylpentan-2-yl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

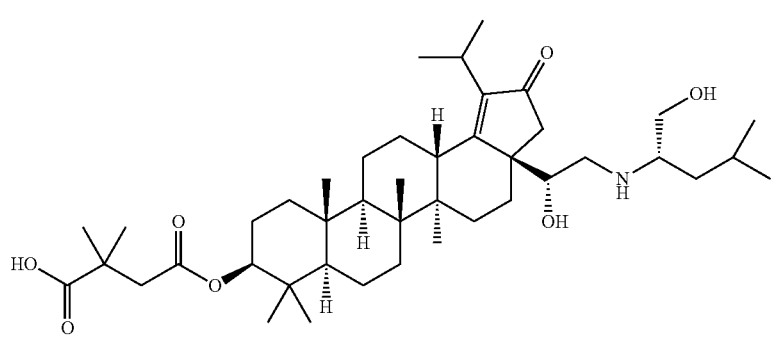

360

LC/MS: m/z calculated 713.5. found 714.5 (M+1)⁺.

Example 292

Compound 361

4-(((3aR,5aR,5bR,7aR,9S,11aR,11bR,13aS)-3a-((R)-1-hydroxy-2-((1-methylpiperidin-4-yl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

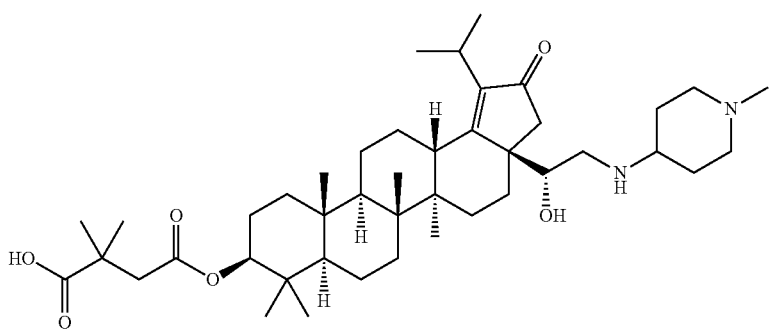

361

LC/MS: m/z calculated 710.5. found 711.5 (M+1)$^+$.

Example 293

Compound 362

4-(((3aR,5aR,5bR,7aR,9S,11aR,11bR,13aS)-3a-((R)-2-(N-benzyl-1-carboxyformamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

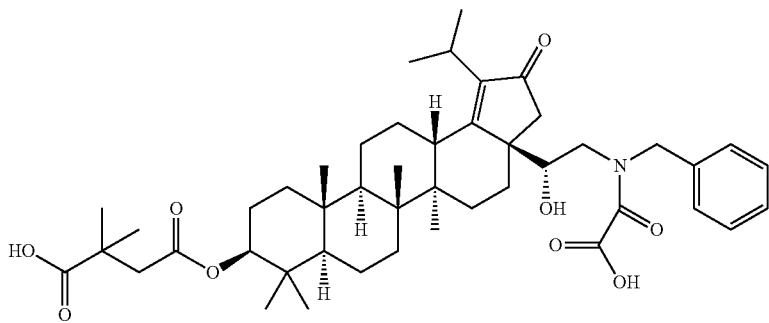

362

LC/MS: m/z calculated 775.5. found 776.5 (M+1)$^+$.

Example 294

Compound 363

4-(((3aR,5aR,5bR,7aR,9S,11aR,11bR,13aS)-3a-((R)-2-(2-amino-N-benzyl-2-oxoacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

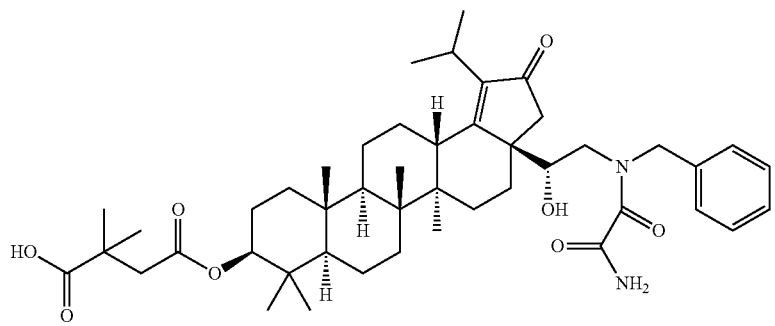

363

LC/MS: m/z calculated 774.5. found 775.5 (M+1)$^+$.

Example 295

Compound 364

4-(((3aR,5aR,5bR,7aR,9S,11aR,11bR,13aS)-3a-((R)-1-hydroxy-2-(isobutylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

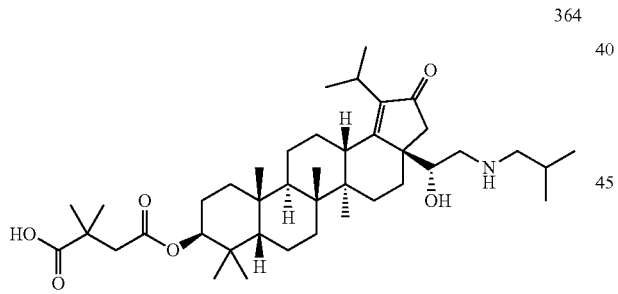

364

LC/MS: m/z calculated 669.5. found 670.5 (M+1)$^+$.

Example 296

Compound 365

4-(((3aR,5aR,5bR,7aR,9S,11aR,11bR,13aS)-3a-((R)-1-hydroxy-2-(phenethylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

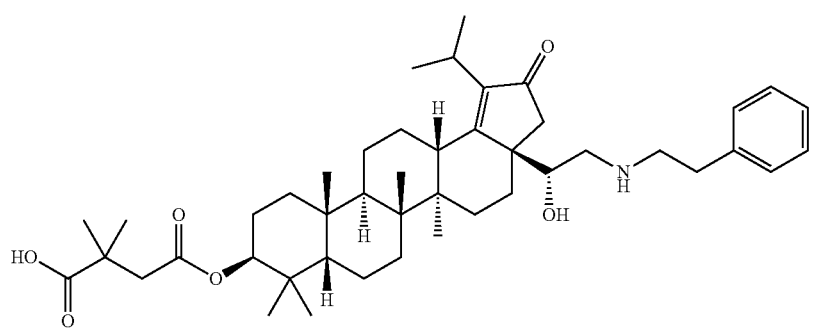

365

LC/MS: m/z calculated 717.5. found 718.5 (M+1)$^+$.

Example 297

Compound 366

4-(((3aR,5aR,5bR,7aR,9S,11aR,11bR,13aS)-3a-((R)-2-((2-(dimethylamino)ethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

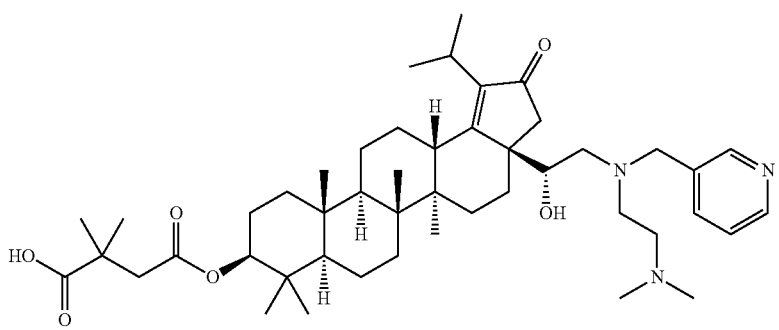

366

LC/MS: m/z calculated 775.5. found 776.5 (M+1)$^+$.

Example 298

Compound 367

4-(((3aR,5aR,5bR,7aR,9S,11aR,11bR,13aS)-3a-((R)-2-((2-aminoethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

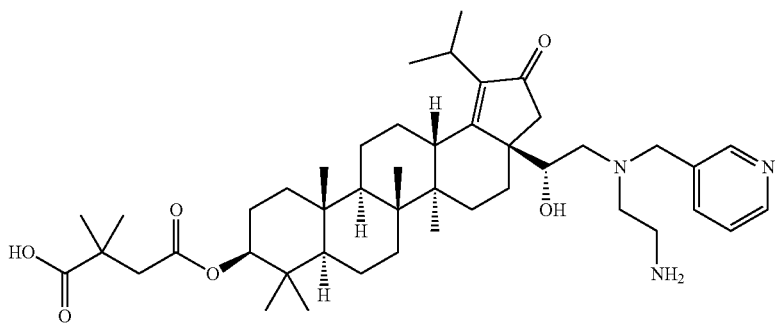

367

LC/MS: m/z calculated 747.5. found 748.5 (M+1)$^+$.

Example 299

Compound 368

4-(((3aR,5aR,5bR,7aR,9S,11aR,11bR,13aS)-3a-((R)-2-((1-(5-chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

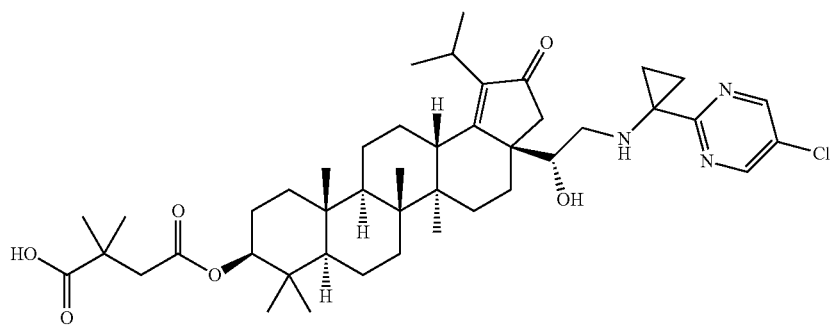

368

LC/MS: m/z calculated 765.5. found 766.5 (M+1)⁺.

Example 300

Compound 369

4-(((3aR,5aR,5bR,7aR,9S,11aR,11bR,13aS)-3a-((R)-2-(2-amino-N-(pyridin-4-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

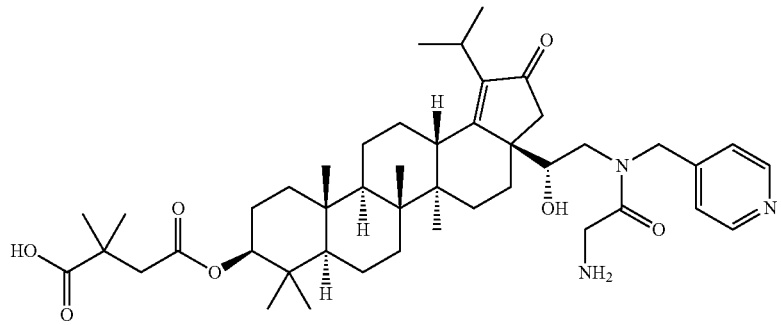

369

LC/MS: m/z calculated 761.5. found 762.5 (M+1)⁺.

Example 301

Compound 370

4-(((3aR,5aR,5bR,7aR,9S,11aR,11bR,13aS)-3a-((R)-1-hydroxy-2-(2-(methylamino)-N-(pyridin-4-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

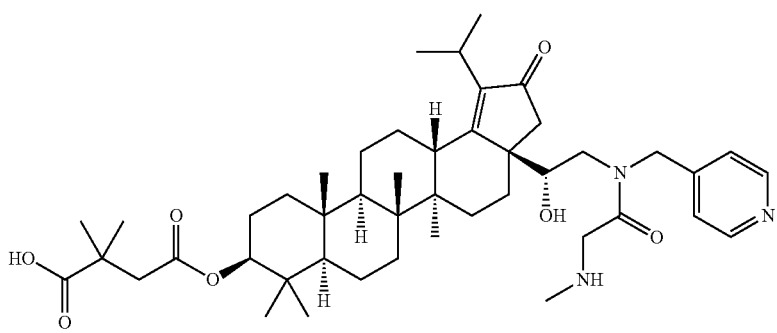

370

LC/MS: m/z calculated 775.5. found 776.5 (M+1)$^+$.

Example 302

Compound 371

4-(((3aR,5aR,5bR,7aR,9S,11aR,11bR,13aS)-3a-((R)-2-(2-(dimethylamino)-N-(pyridin-4-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

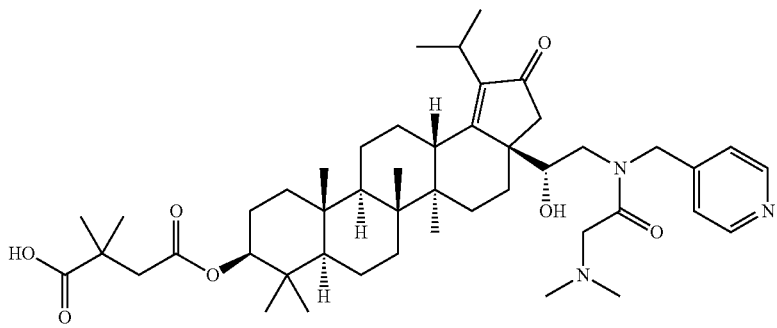

371

LC/MS: m/z calculated 789.5. found 790.5 (M+1)$^+$.

Example 303

Compound 372

4-(((3aR,5aR,5bR,7aR,9S,11aR,11bR,13aS)-3a-((R)-2-((2-(dimethylamino)ethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

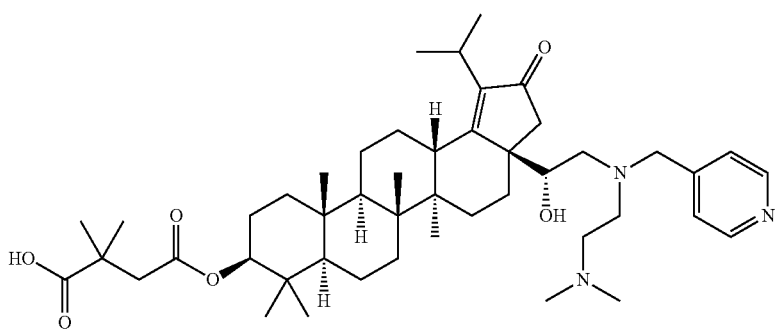

372

LC/MS: m/z calculated 775.5. found 776.5 (M+1)$^+$.

Example 304

Compound 373

4-(((3aR,5aR,5bR,7aR,9S,11aR,11bR,13aS)-3a-((R)-1-hydroxy-2-((2-(methylamino)ethyl)(pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

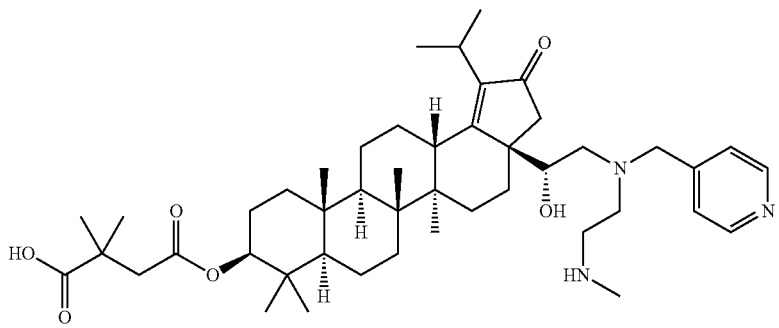

373

LC/MS: m/z calculated 761.5. found 762.5 (M+1)$^+$.

Example 305

Compound 374

4-(((3aR,5aR,5bR,7aR,9S,11aR,11bR,13aS)-3a-(2-(cyclohexanecarboxamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

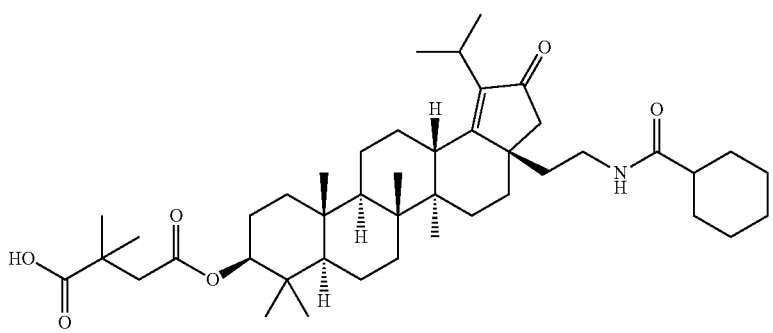

374

LC/MS: m/z calculated 707.5. found 708.5 $(M+1)^+$.

Example 306

Compound 375

4-(((3aR,5aR,5bR,7aR,9S,11aR,11bR,13aS)-3a-((R)-2-((2-aminoethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

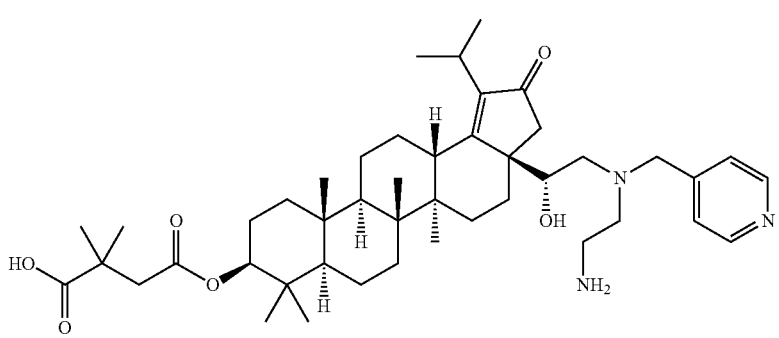

375

LC/MS: m/z calculated 747.5. found 748.5 $(M+1)^+$.

Example 307

Compound 376

4-(((3aR,5aR,5bR,7aR,9S,11aR,11bR,13aS)-3a-((R)-2-((2-aminoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

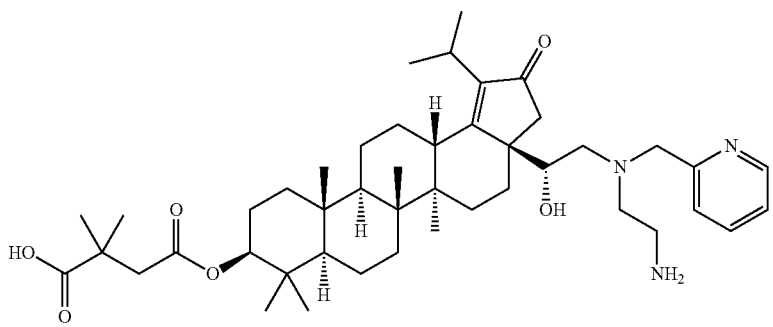

376

LC/MS: m/z calculated 747.5. found 748.5 (M+1)$^+$.

Example 308

Compound 377

4-(((3aR,5aR,5bR,7aR,9S,11aR,11bR,13aS)-3a-((R)-1-hydroxy-2-((2-(N-methylacetamido)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

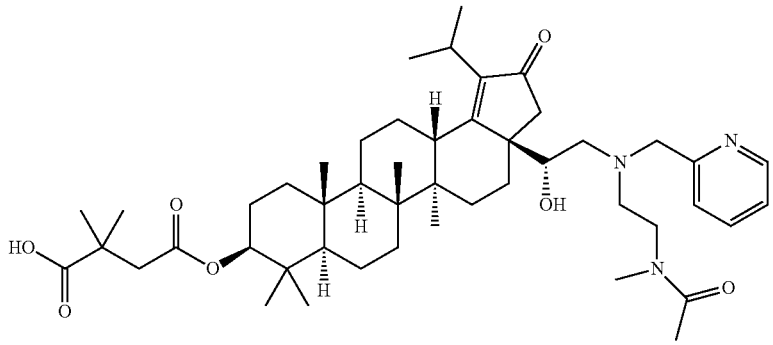

377

LC/MS: m/z calculated 803.5. found 804.5 (M+1)$^+$.

Example 309

Compound 378

4-(((3aR,5aR,5bR,7aR,9S,11aR,11bR,13aS)-3a-((R)-2-((1-(5-chloropyrimidin-2-yl)cyclopropyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

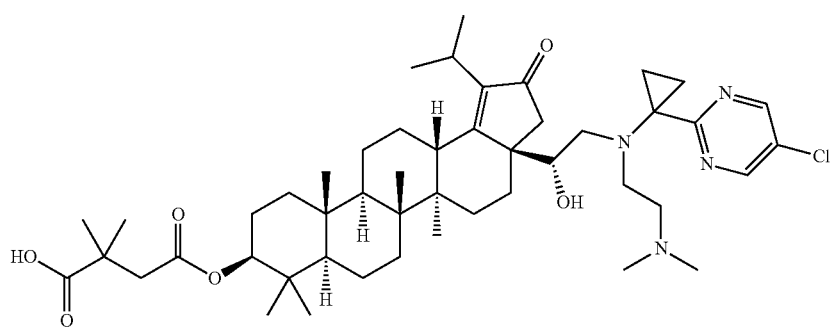

378

LC/MS: m/z calculated 836.5. found 837.5 (M+1)$^+$.

Example 310

Compound 379

4-(((3aR,5aR,5bR,7aR,9S,11aR,11bR,13aS)-3a-((R)-2-(benzyl(2-(methylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

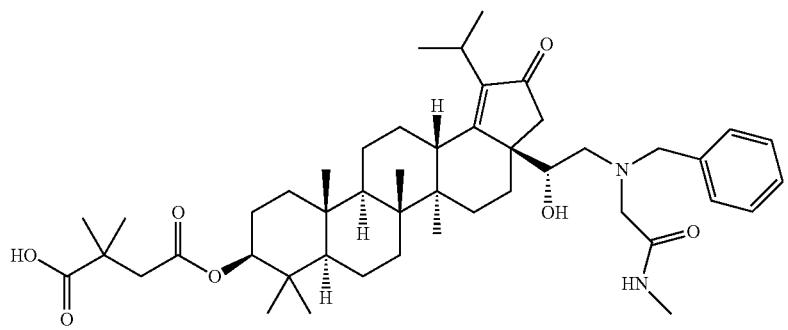

379

LC/MS: m/z calculated 774.5. found 775.5 (M+1)$^+$.

Example 311

Compound 380

4-(((3aR,5aR,5bR,7aR,9S,11aR,11bR,13aS)-3a-((R)-2-((2-(dimethylamino)-2-oxoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

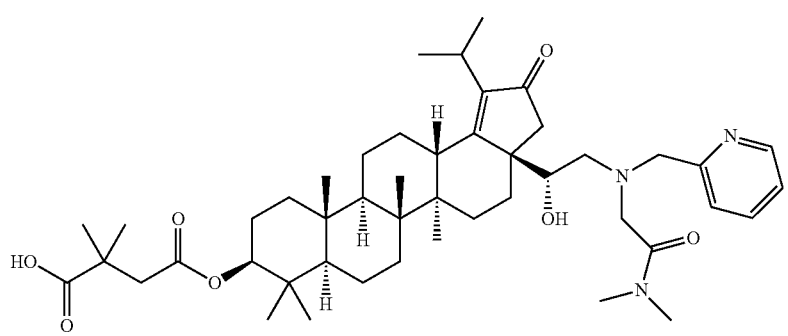

380

LC/MS: m/z calculated 789.5. found 790.5 (M+1)$^+$.

Example 312

Compound 381

4-(((3aR,5aR,5bR,7aR,9S,11aR,11bR,13aS)-3a-((R)-2-(benzyl(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

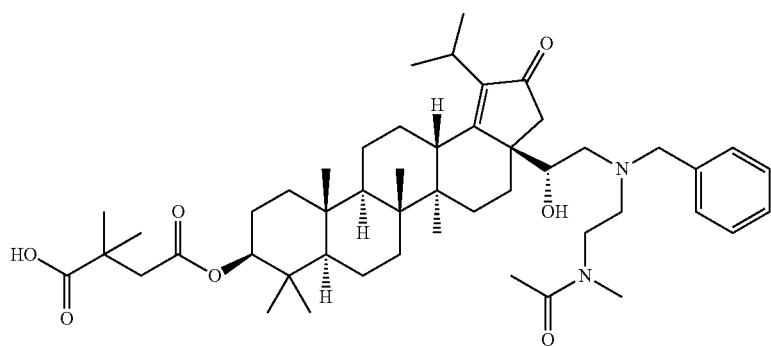

381

LC/MS: m/z calculated 802.5. found 803.5 (M+1)$^+$.

Example 313

Compound 382

4-(((3aR,5aR,5bR,7aR,9S,11aR,11bR,13aS)-3a-((R)-2-(benzyl(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

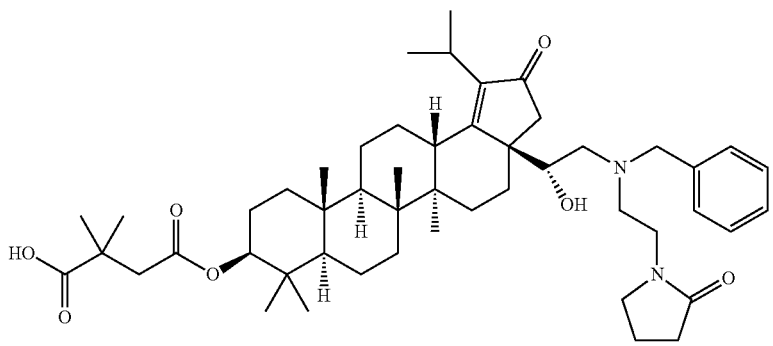

382

LC/MS: m/z calculated 814.5. found 815.5 (M+1)$^+$.

Example 314

Compound 383

4-(((3aR,5aR,5bR,7aR,9S,11aR,11bR,13aS)-3a-((R)-2-(((1H-benzo[d]imidazol-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

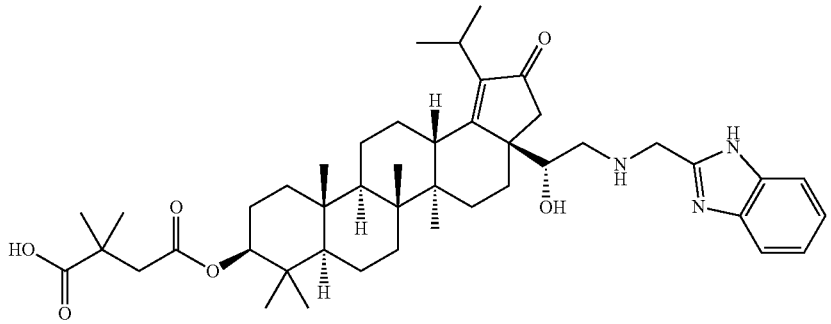

383

LC/MS: m/z calculated 743.5. found 744.5 (M+1)$^+$.

Example 315

Compound 384

4-(((3aR,5aR,5bR,7aR,9S,11aR,11bR,13aS)-3a-((R)-2-(2-(aminomethyl)-1H-benzo[d]imidazol-1-yl)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

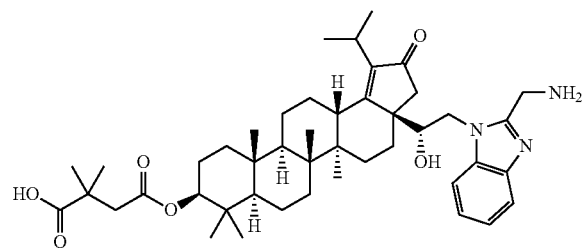

384

LC/MS: m/z calculated 743.5. found 744.5 (M+1)$^+$.

Example 316

Compound 385

4-(((3aR,5aR,5bR,7aR,9S,11aR,11bR,13aS)-3a-((S)-2-((1-(4-chlorophenyl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

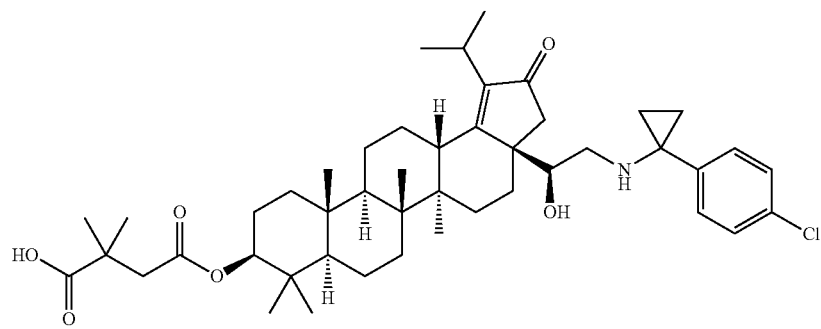

385

LC/MS: m/z calculated 763.5. found 764.5 (M+1)$^+$.

Example 317

Compound 386

4-(((3aR,5aR,5bR,7aR,9S,11aR,11bR,13aS)-3a-((R)-2-((1-(4-chlorophenyl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

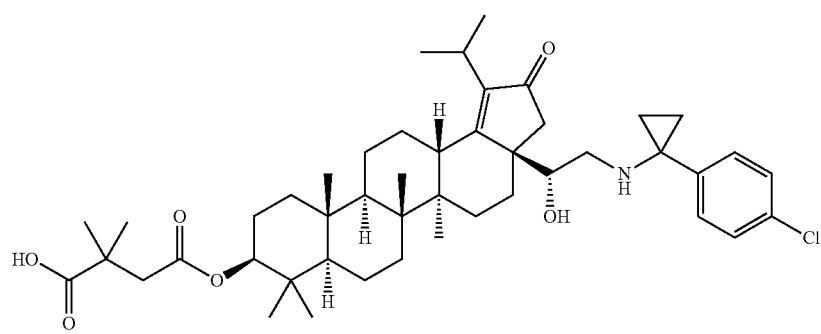

386

LC/MS: m/z calculated 763.5. found 764.5 (M+1)$^+$.

Example 318

Compound 387

4-(((3aR,5aR,5bR,7aR,9S,11aR,11bR,13aS)-3a-((R)-1-hydroxy-2-((2-morpholinoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

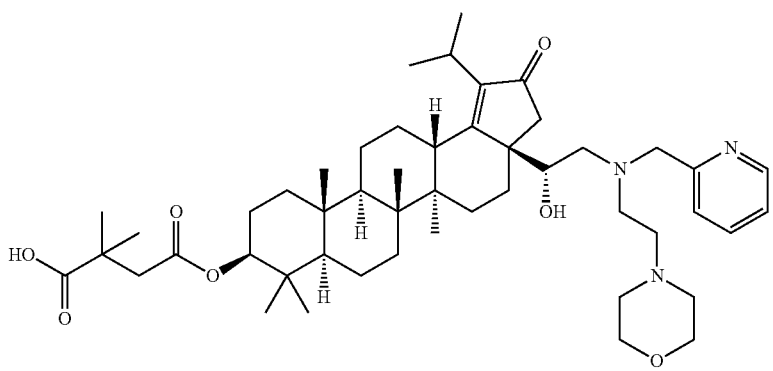

387

LC/MS: m/z calculated 817.6. found 818.5 (M+1)$^+$.

Example 319

Compound 388

4-(((3aR,5aR,5bR,7aR,9S,11aR,11bR,13aS)-3a-((R)-1-hydroxy-2-((2-(2-oxopyrrolidin-1-yl)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

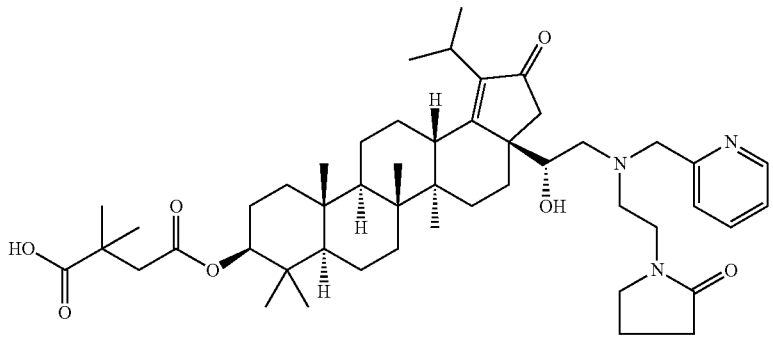

388

LC/MS: m/z calculated 815.5. found 816.5 (M+1)$^+$.

Example 320

Compound 389

4-(((3aR,5aR,5bR,7aR,9S,11aR,11bR,13aS)-3a-((S)-1-hydroxy-2-(phenethylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

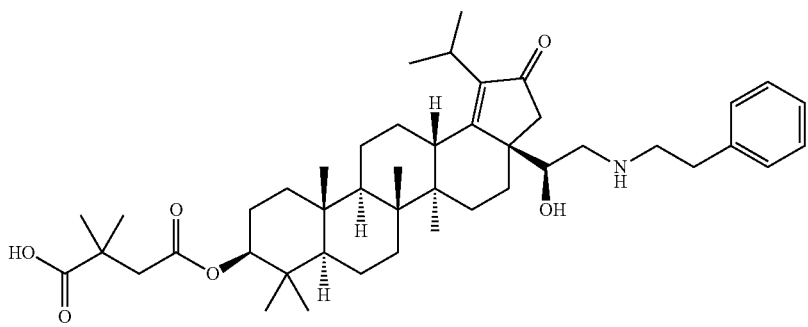

389

LC/MS: m/z calculated 717.5. found 718.5 (M+1)+.

Example 321

Compound 390

4-(((3aR,5aR,5bR,7aR,9S,11aR,11bR,13aS)-3a-((R)-1-hydroxy-2-((thiazol-5-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

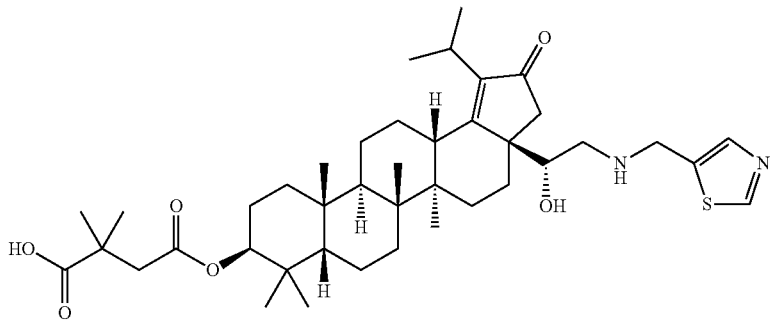

390

LC/MS: m/z calculated 710.4. found 711.4 (M+1)+.

Example 322

Compound 391

4-(((3aR,5aR,5bR,7aR,9S,11aR,11bR,13aS)-3a-(2-(cyclopentylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

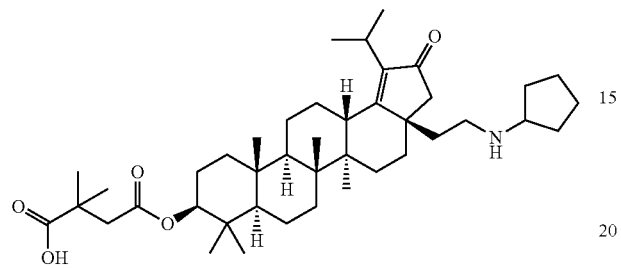

LC/MS: m/z calculated 665.5. found 666.5 (M+1)$^+$.

Example 323

Compound 392

4-(((3aR,5aR,5bR,7aR,9S,11aR,11bR,13aS)-3a-((R)-2-((2-(dimethylamino)-2-oxoethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

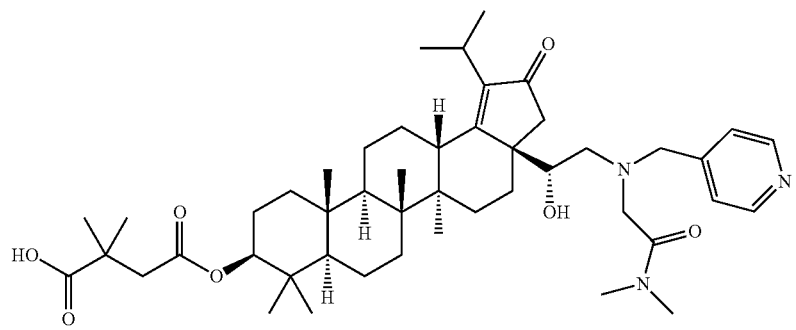

LC/MS: m/z calculated 789.5. found 790.5 (M+1)$^+$.

Example 324

Compound 393

4-(((3aR,5aR,5bR,7aR,9S,11aR,11bR,13aS)-3a-((R)-2-((2-amino-2-oxoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

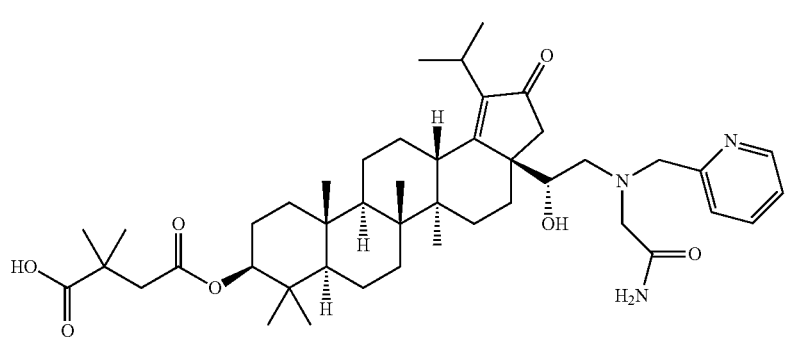

LC/MS: m/z calculated 761.5. found 762.5 (M+1)$^+$.

Example 325

Compound 394

4-(((3aR,5aR,5bR,7aR,9S,11aR,11bR,13aS)-3a-((R)-1-hydroxy-2-((2-((2-hydroxyethyl)amino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

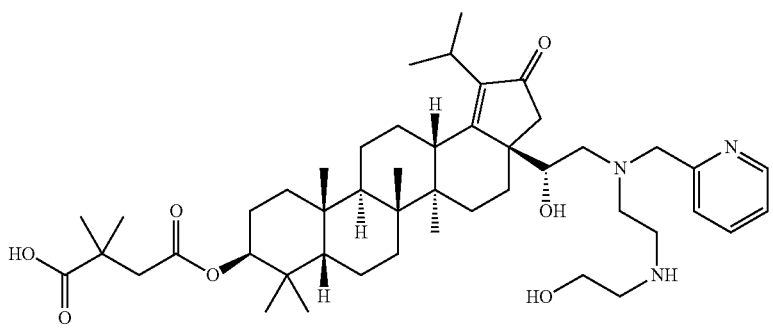

394

LC/MS: m/z calculated 791.5. found 792.5 $(M+1)^+$.

Example 326

Compound 395

4-(((3aR,5aR,5bR,7aR,9S,11aR,11bR,13aS)-3a-((R)-1-hydroxy-2-((2-((2-methoxyethyl)amino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

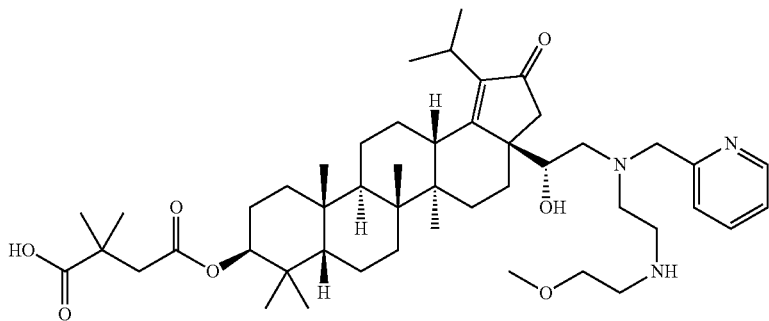

395

LC/MS: m/z calculated 805.6. found 806.5 $(M+1)^+$.

Example 327

Compound 396

4-(((3aR,5aR,5bR,7aR,9S,11aR,11bR,13aS)-3a-((R)-2-((2-((tert-butoxycarbonyl)amino)ethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

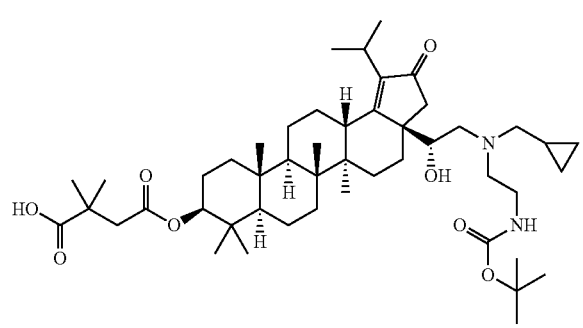

LC/MS: m/z calculated 810.6. found 811.5 (M+1)$^+$.

Example 328

Compound 397

4-(((3aR,5aR,5bR,7aR,9S,11aR,11bR,13aS)-3a-((R)-2-((2-((tert-butoxycarbonyl)(methyl)amino)ethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid LC/MS: m/z calculated 824.6. found 825.5 (M+1)$^+$.

Example 329

Compound 398

4-(((3aR,5aR,5bR,7aR,9S,11aR,11bR,13aS)-3a-(2-(N-benzyl-1-carboxyformamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid LC/MS: m/z calculated 759.5. found 760.5 (M+1)$^+$.

Example 330

Compound 399

4-(((3aR,5aR,5bR,7aR,9S,11aR,11bR,13aS)-3a-((R)-2-((2-aminoethyl)(cyclopropylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

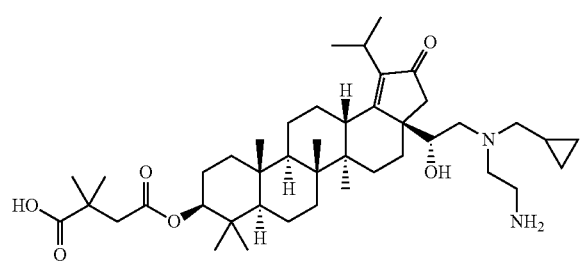

399

LC/MS: m/z calculated 710.5. found 711.5 (M+1)$^+$.

Example 331

Compound 400

4-(((3aR,5aR,5bR,7aR,9S,11aR,11bR,13aS)-3a-((R)-2-((2-acetamidoethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

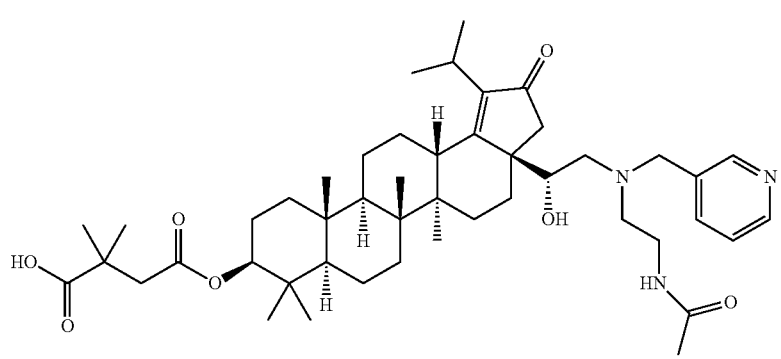

400

LC/MS: m/z calculated 789.5. found 790.5 (M+1)$^+$.

Example 332

Compound 401

4-(((3aR,5aR,5bR,7aR,9S,11aR,11bR,13aS)-3a-((R)-1-hydroxy-2-((thiazol-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

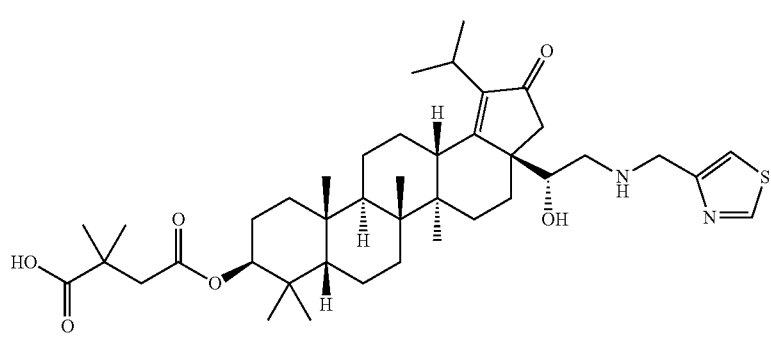

401

LC/MS: m/z calculated 710.4. found 711.4 (M+1)$^+$.

Example 333

Compound 402

4-(((3aR,5aR,5bR,7aR,9S,11aR,11bR,13aS)-3a-((R)-1-hydroxy-2-((thiazol-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

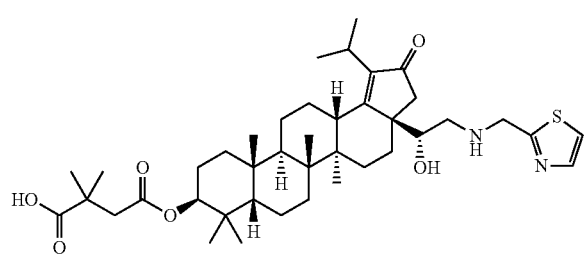

402

LC/MS: m/z calculated 710.4. found 711.4 (M+1)$^+$.

Example 334

Compound 403

4-(((3aR,5aR,5bR,7aR,9S,11aR,11bR,13aS)-3a-((R)-2-((2-(dimethylamino)ethyl)(thiazol-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

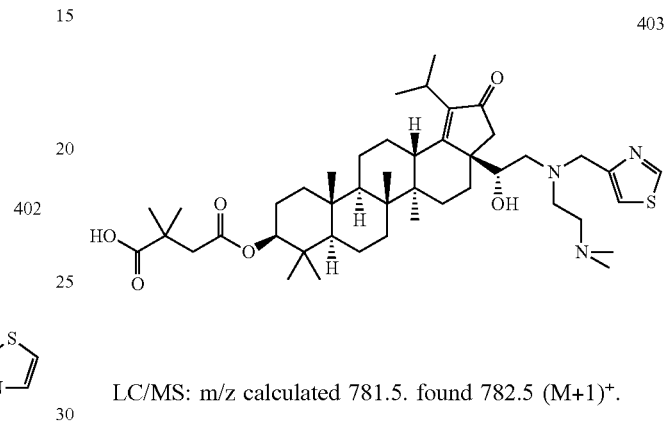

403

LC/MS: m/z calculated 781.5. found 782.5 (M+1)$^+$.

Example 335

Compound 404

4-(((3aR,5aR,5bR,7aR,9S,11aR,11bR,13aS)-3a-(2-(benzyl(carboxymethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

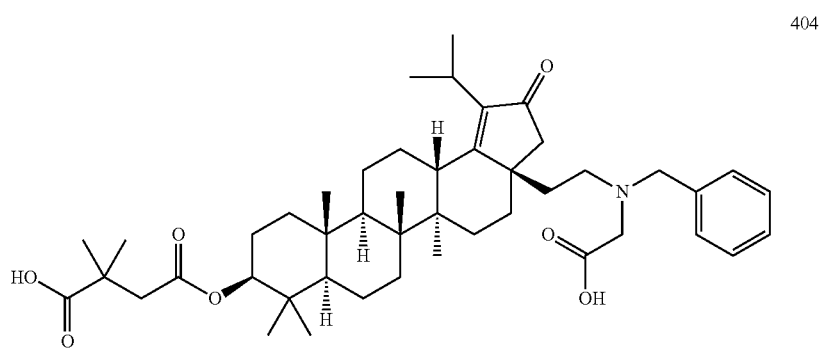

404

LC/MS: m/z calculated 745.5. found 746.5 (M+1)$^+$.

Example 336

Compound 405

4-(((3aR,5aR,5bR,7aR,9S,11aR,11bR,13aS)-1-isopropyl-5a,5b,8,8,11a-pentamethyl-3a-(2-(N-methylbenzamido)ethyl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

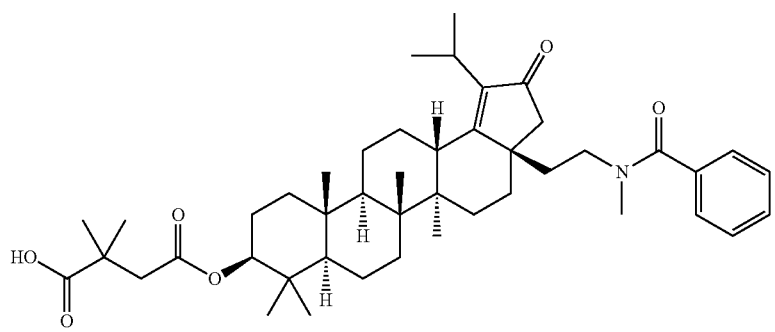

405

LC/MS: m/z calculated 715.5. found 716.5 (M+1)$^+$.

Example 337

Compound 406

4-(((3aR,5aR,5bR,7aR,9S,11aR,11bR,13aS)-3a-(2-(N-benzyl-2-(dimethylamino)-2-oxoacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

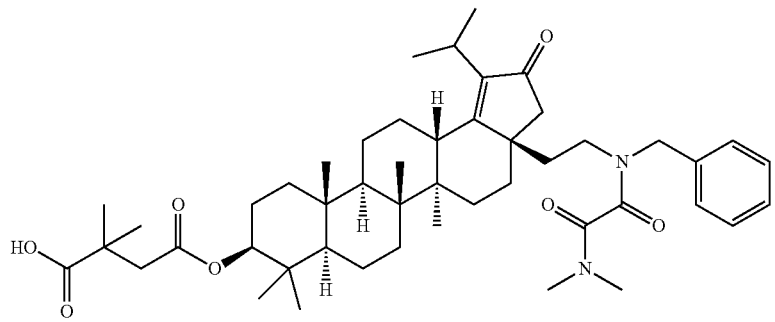

406

LC/MS: m/z calculated 786.5. found 787.5 (M+1)$^+$.

Example 338

Compound 407

4-(((3aR,5aR,5bR,7aR,9S,11aR,11bR,13aS)-3a-((R)-2-((2-acetamidoethyl)(benzyl)amino)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

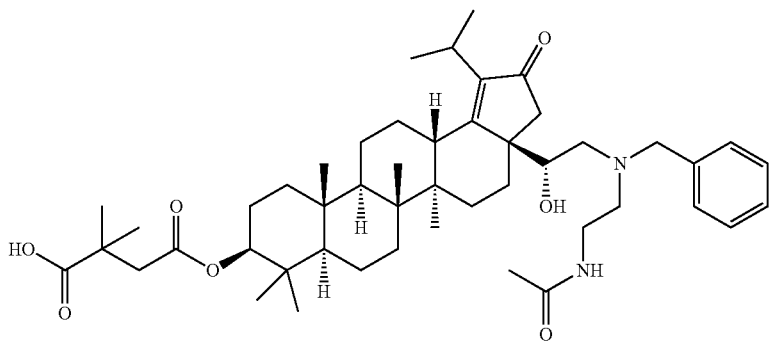

407

LC/MS: m/z calculated 788.5. found 789.5 (M+1)$^+$.

Example 339

Compound 408

4-(((3aR,5aR,5bR,7aR,9S,11aR,11bR,13aS)-3a-(2-(2-amino-N-benzyl-2-oxoacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

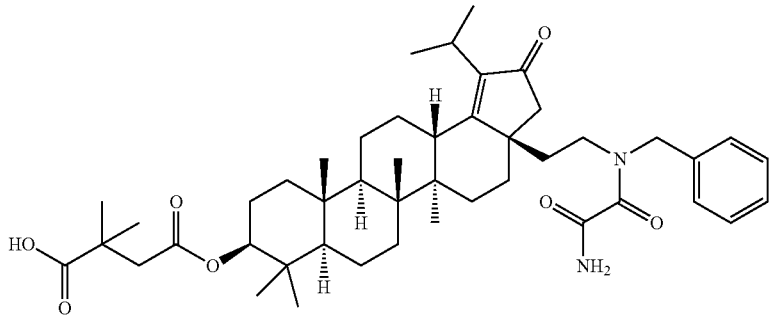

408

LC/MS: m/z calculated 758.5. found 759.5 (M+1)$^+$.

Example 340

Compound 409

4-(((3aR,5aR,5bR,7aR,9S,11aR,11bR,13aS)-3a-((R)-2-((2-acetamidoethyl)(pyridin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

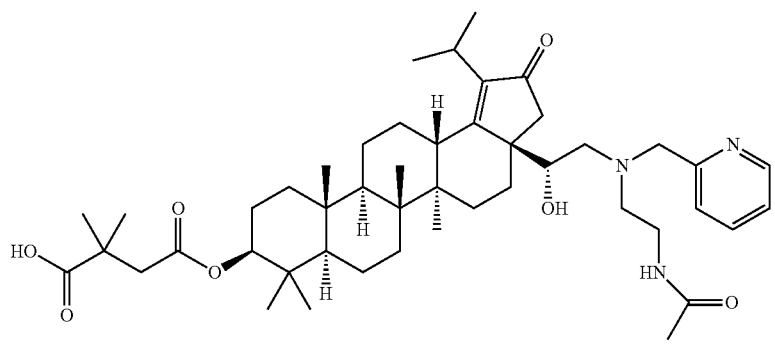

409

LC/MS: m/z calculated 789.5. found 790.5 (M+1)$^+$.

Example 341

Compound 410

4-(((3aR,5aR,5bR,7aR,9S,11aR,11bR,13aS)-3a-((R)-2-((2-(dimethylamino)ethyl)(thiazol-5-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

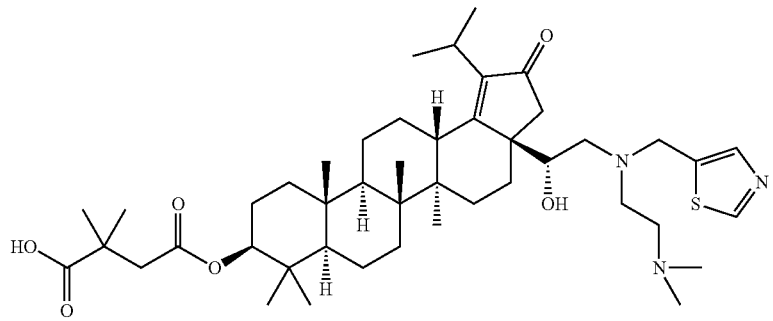

410

LC/MS: m/z calculated 781.5. found 782.5 (M+1)$^+$.

Example 342

Compound 411

4-(((3aR,5aR,5bR,7aR,9S,11aR,11bR,13aS)-3a-((R)-2-((2-(dimethylamino)ethyl)(thiazol-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

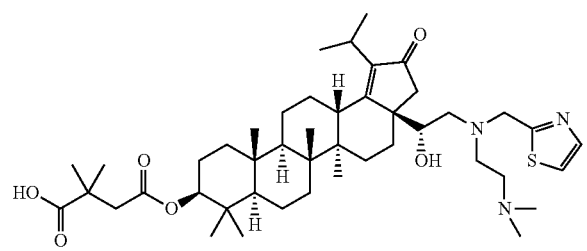

411

LC/MS: m/z calculated 781.5. found 782.5 (M+1)⁺.

Example 343

Compound 412

4-(((3aR,5aR,5bR,7aR,9S,11aR,11bR,13aS)-3a-((R)-2-((cyclopropylmethyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

412

LC/MS: m/z calculated 724.5. found 725.5 (M+1)⁺.

Example 344

Compound 413

4-(((3aR,5aR,5bR,7aR,9S,11aR,11bR,13aS)-3a-((R)-2-((2-acetamidoethyl)(pyridin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

413

LC/MS: m/z calculated 789.5. found 790.5 (M+1)⁺

Example 345

Compound 414

4-(((3aR,5aR,5bR,7aR,9S,11aR,11bR,13aS)-3a-((R)-2-((2-acetamidoethyl)(cyclopropylmethyl)amino)-1-acetoxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

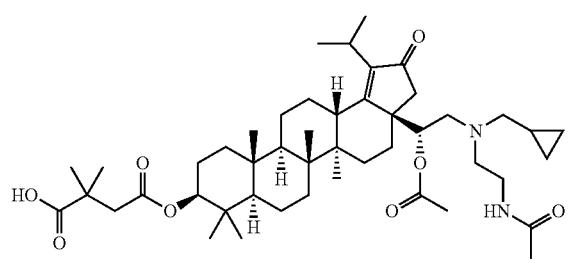

414

LC/MS: m/z calculated 794.5. found 795.5 (M+1)⁺.

Example 346

Compound 415

4-(((3aR,5aR,5bR,7aR,9S,11aR,11bR,13aS)-3a-((R)-1-acetoxy-2-((cyclopropylmethyl)(2-(N-methylacetamido)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

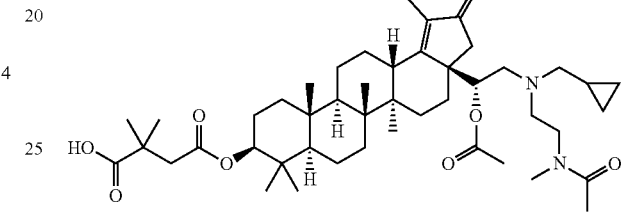

415

LC/MS: m/z calculated 808.6. found 809.5 (M+1)⁺.

Example 347

Compound 416

4-(((3aR,5aR,5bR,7aR,9S,11aR,11bR,13aS)-3a-((R)-2-(((5-chloropyrimidin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

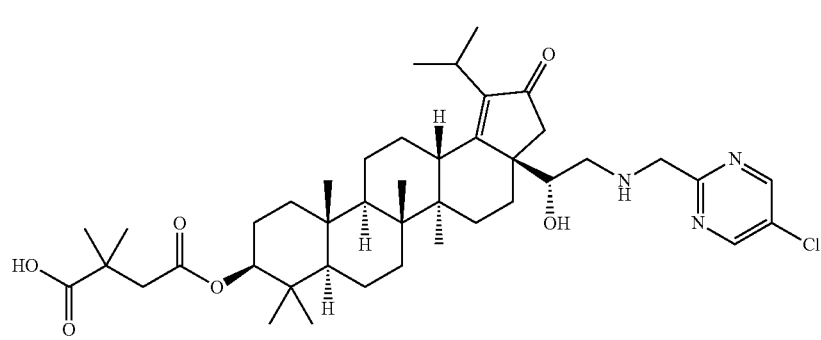

416

LC/MS: m/z calculated 739.4. found 740.4 (M+1)⁺.

Example 348

Compound 417

4-(((3aR,5aR,5bR,7aR,9S,11aR,11bR,13aS)-3a-((R)-2-((2-(dimethylamino)ethyl)(pyrimidin-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

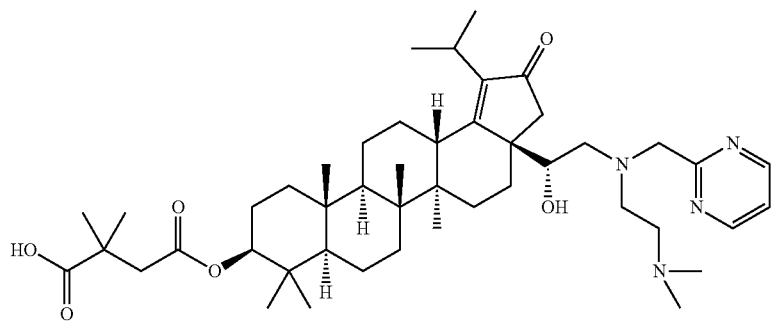

LC/MS: m/z calculated 776.5. found 777.5 (M+1)⁺.

Example 349

Compound 418

4-(((3aR,5aR,5bR,7aR,9S,11aR,11bR,13aS)-3a-((S)-2-(((5-chloropyrimidin-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

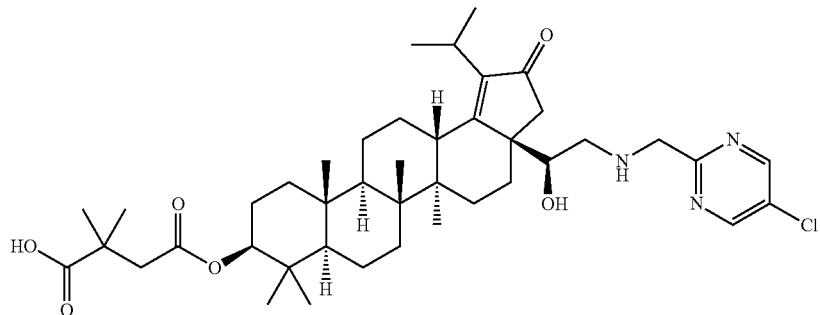

LC/MS: m/z calculated 739.4. found 740.4 (M+1)⁺.

Example 350

Compound 419

4-(((3aR,5aR,5bR,7aR,9S,11aR,11bR,13aS)-3a-((R)-1-hydroxy-2-((2-(methylamino)ethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

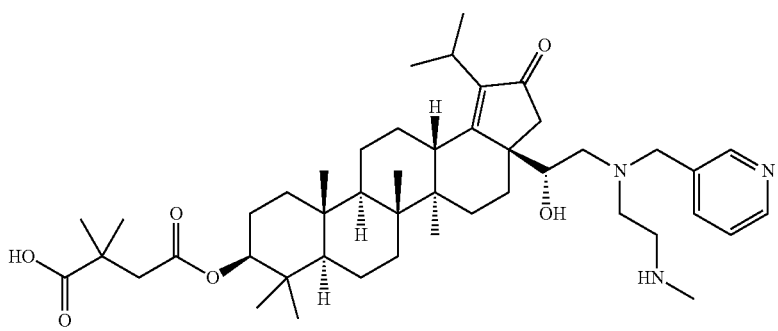

LC/MS: m/z calculated 761.5. found 762.5 (M+1)⁺.

Example 351

Compound 420

4-(((3aR,5aR,5bR,7aR,9S,11aR,11bR,13aS)-1-isopropyl-5a,5b,8,8,11a-pentamethyl-2-oxo-3a-((R)-2-oxo-3-(pyridin-2-ylmethyl)oxazolidin-5-yl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

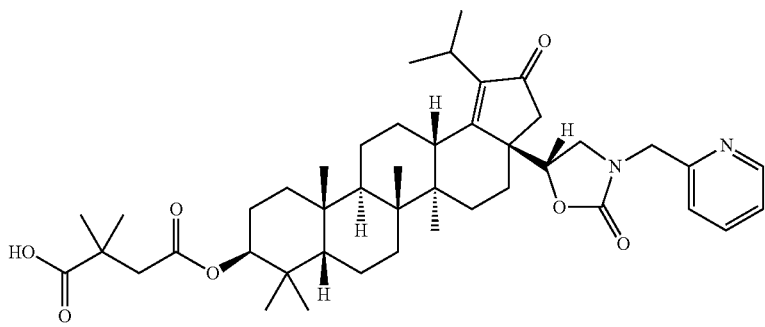

LC/MS: m/z calculated 730.5. found 731.4 (M+1)⁺.

Example 352

Compound 421

4-(((3aR,5aR,5bR,7aR,9S,11aR,11bR,13aS)-3a-((S)-2-((1-(5-chloropyrimidin-2-yl)cyclopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

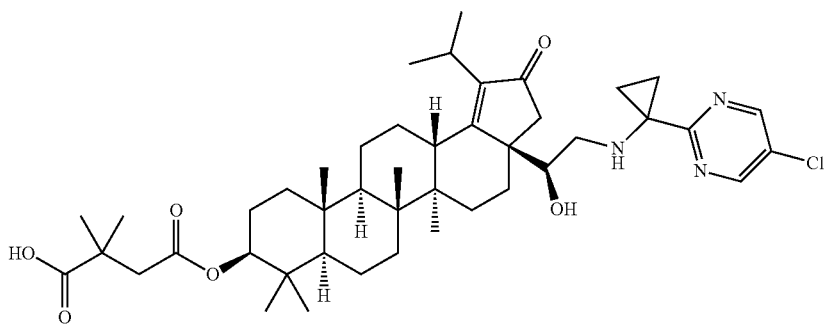

421

LC/MS: m/z calculated 765.4. found 766.4 (M+1)$^+$.

Example 353

Compound 422

4-(((3aR,5aR,5bR,7aR,9S,11aR,11bR,13aS)-3a-((R)-2,11-dimethyl-3,10-dioxo-5-(pyridin-3-ylmethyl)-8-oxa-2,5,11-triazadodecan-7-yl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

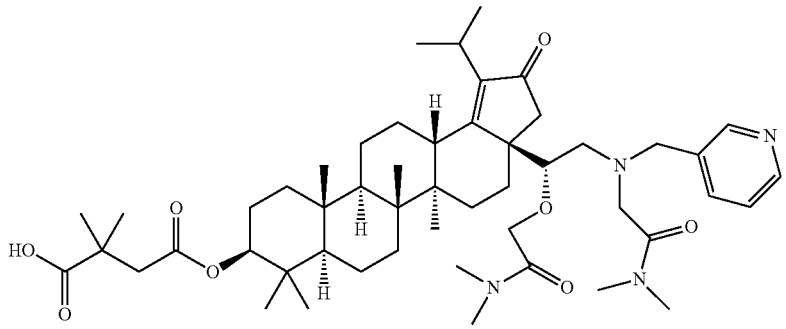

422

LC/MS: m/z calculated 874.6. found 875.6 (M+1)$^+$.

Example 354

Compound 423

4-(((3aR,5aR,5bR,7aR,9S,11aR,11bR,13aS)-3a-((R)-1-hydroxy-2-((2-(methylamino)-2-oxoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

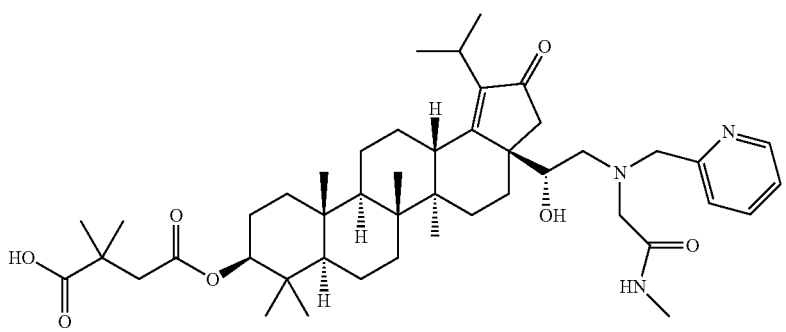

423

LC/MS: m/z calculated 775.5. found 776.5 $(M+1)^+$.

Example 355

Compound 424

4-(((3aR,5aR,5bR,7aR,9S,11aR,11bR,13aS)-3a-((R)-2-((2-(dimethylamino)-2-oxoethyl)(pyridin-3-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

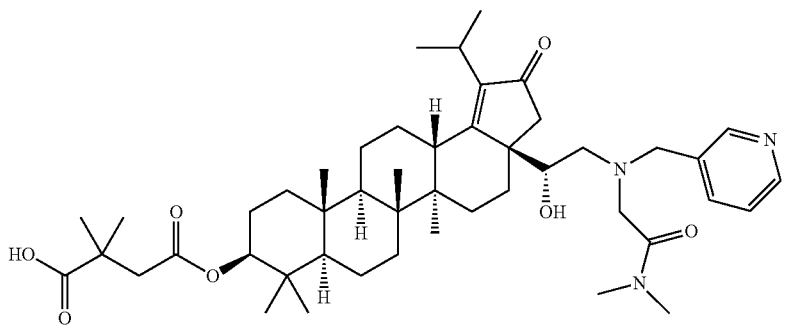

424

LC/MS: m/z calculated 789.5. found 790.5 $(M+1)^+$.

Example 356

Compound 425

4-(((3aR,5aR,5bR,7aR,9S,11aR,11bR,13aS)-3a-((R)-2-(2-(dimethylamino)-N-(pyrimidin-2-ylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

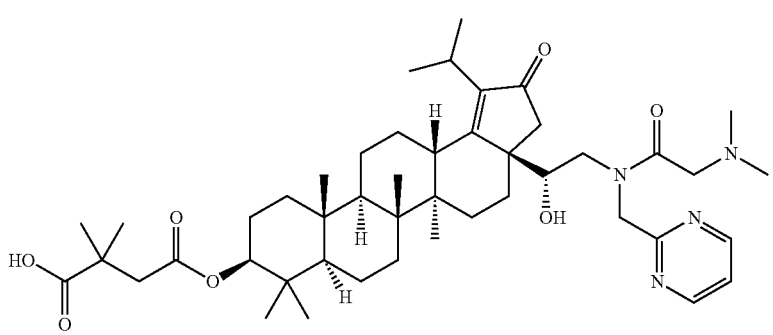

425

LC/MS: m/z calculated 790.5. found 791.5 (M+1)$^+$.

Example 357

Compound 426

4-(((3aR,5aR,5bR,7aR,9S,11aR,11bR,13aS)-1-isopropyl-5a,5b,8,8,11a-pentamethyl-2-oxo-3a-(2-(picolinamido)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

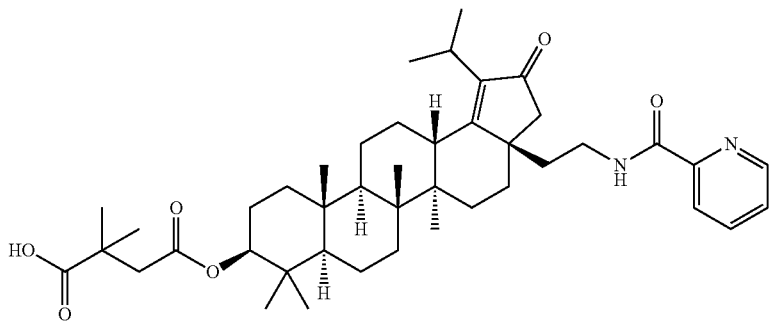

426

LC/MS: m/z calculated 702.5. found 703.4 (M+1)$^+$.

Example 358

Compound 427

4-(((3aR,5aR,5bR,7aR,9S,11aR,11bR,13aS)-3a-((R)-2-((2-(1H-imidazol-1-yl)ethyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

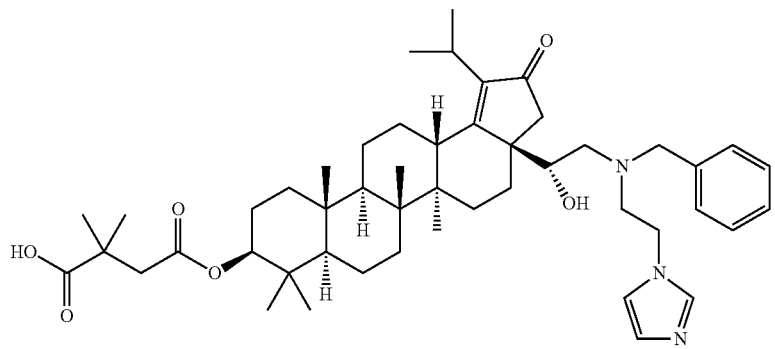

427

LC/MS: m/z calculated 797.5. found 798.5 (M+1)$^+$.

Example 359

Compound 428

4-(((3aR,5aR,5bR,7aR,9S,11aR,11bR,13aS)-3a-((R)-2-((3-(1H-imidazol-1-yl)propyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

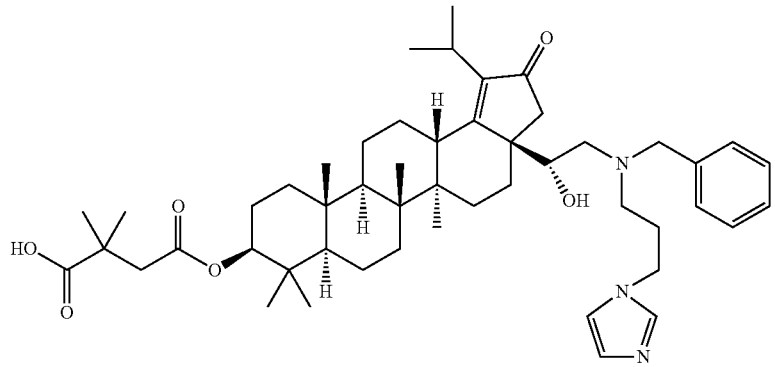

428

LC/MS: m/z calculated 811.5. found 812.5 (M+1)$^+$.

Example 360

Compound 429

4-(((3aR,5aR,5bR,7aR,9S,11aR,11bR,13aS)-3a-((S)-2-((3-(1H-imidazol-1-yl)propyl)(benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

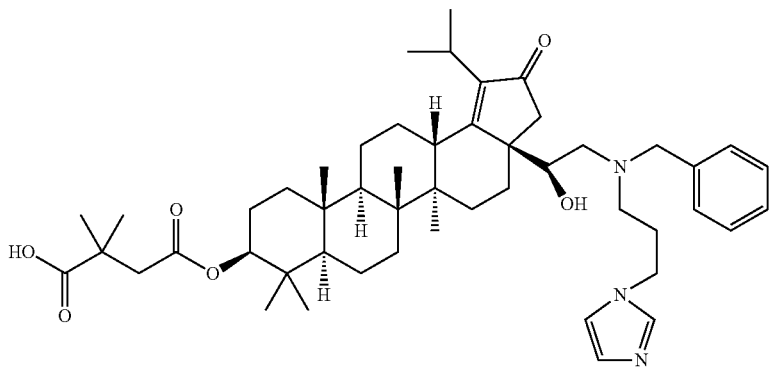

429

LC/MS: m/z calculated 811.5. found 812.5 (M+1)$^+$.

Example 361

Compound 430

4-(((3aR,5aR,5bR,7aR,9S,11aR,11bR,13aS)-3a-(2-(N-benzyl-2-(dimethylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

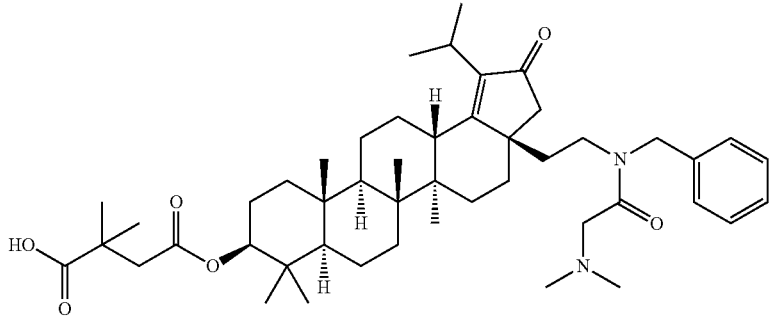

430

LC/MS: m/z calculated 772.5. found 773.5 (M+1)$^+$.

Example 362

Compound 431

4-(((3aR,5aR,5bR,7aR,9S,11aR,11bR,13aS)-3a-((R)-2-(2-(dimethylamino)-N-isopropylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

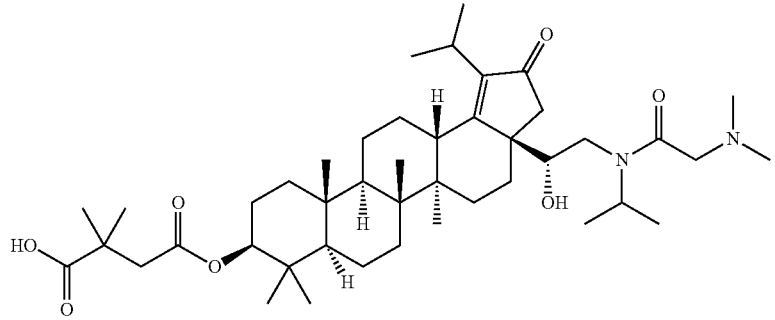

LC/MS: m/z calculated 740.5. found 741.5 (M+1)$^+$.

Example 363

Compound 432

4-(((3aR,5aR,5bR,7aR,9S,11aR,11bR,13aS)-3a-((R)-1-hydroxy-2-(N-isopropyl-2-(methylamino)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

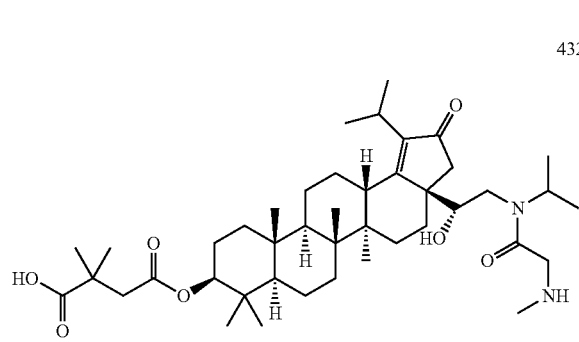

LC/MS: m/z calculated 726.5. found 727.5 (M+1)$^+$.

Example 364

Compound 433

4-(((3aR,5aR,5bR,7aR,9S,11aR,11bR,13aS)-3a-((R)-2-(2-amino-N-isopropylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

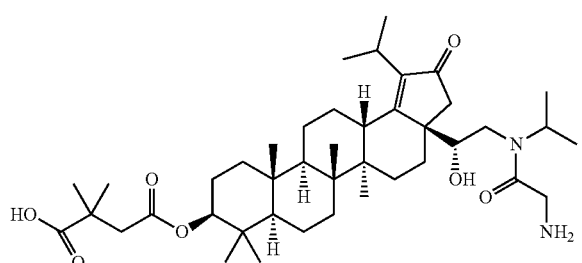

LC/MS: m/z calculated 712.5. found 713.5 (M+1)$^+$.

Example 365

Compound 434

4-(((3aR,5aR,5bR,7aR,9S,11aR,11bR,13aS)-3a-((R)-2-((2-(dimethylamino)ethyl)(3-(trifluoromethoxy)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

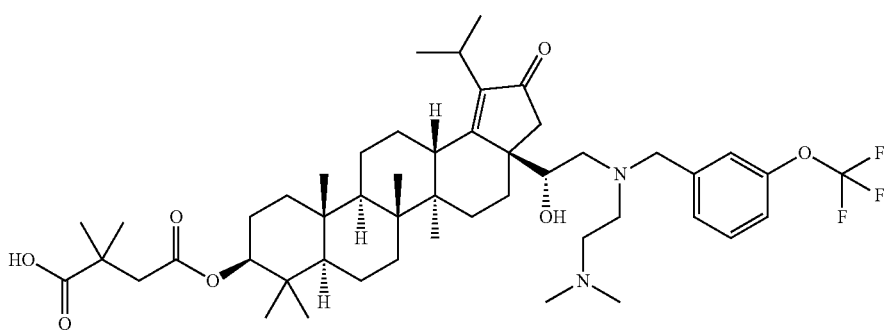

434

LC/MS: m/z calculated 858.5. found 859.5 (M+1)$^+$.

Example 366

Compound 435

4-(((3aR,5aR,5bR,7aR,9S,11aR,11bR,13aS)-3a-((R)-2-((2-(dimethylamino)ethyl)(4-(trifluoromethoxy)benzyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

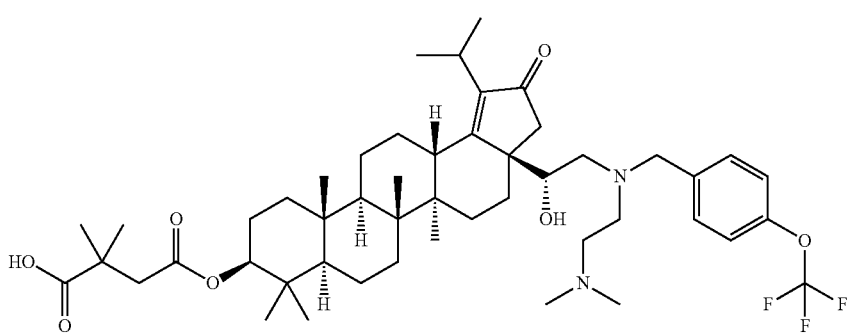

435

LC/MS: m/z calculated 858.5. found 859.5 (M+1)$^+$.

Example 367

Compound 436

4-(((3aR,5aR,5bR,7aR,9S,11aR,11bR,13aS)-3a-(2-(2-(dimethylamino)-N-(pyridin-2-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

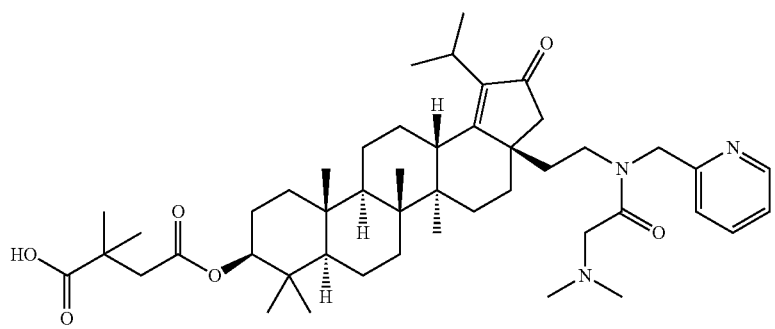

436

LC/MS: m/z calculated 773.5. found 774.5 $(M+1)^+$.

Example 368

Compound 437

4-(((3aR,5aR,5bR,7aR,9S,11aR,11bR,13aS)-3a-((R)-2-((2-aminoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 369

Compound 438

4-(((3aR,5aR,5bR,7aR,9S,11aR,11bR,13aS)-3a-((R)-2-((2-acetamidoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

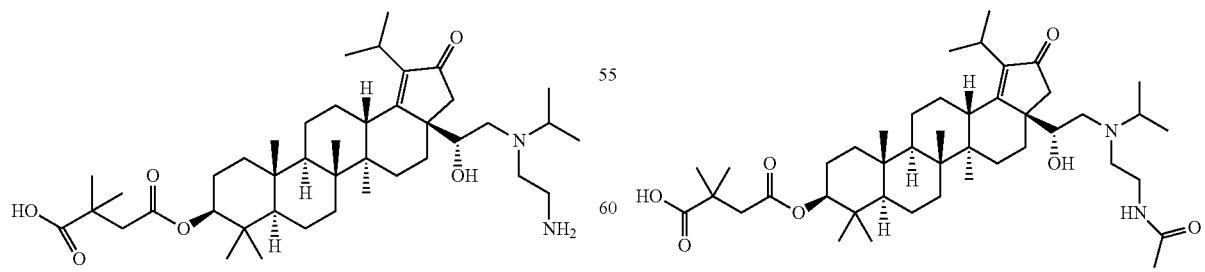

LC/MS: m/z calculated 698.5. found 699.5 $(M+1)^+$.

LC/MS: m/z calculated 740.5. found 741.5 $(M+1)^+$.

Example 370

Compound 439

4-(((3aR,5aR,5bR,7aR,9S,11aR,11bR,13aS)-3a-((R)-2-((2-(dimethylamino)-2-oxoethyl)(thiazol-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

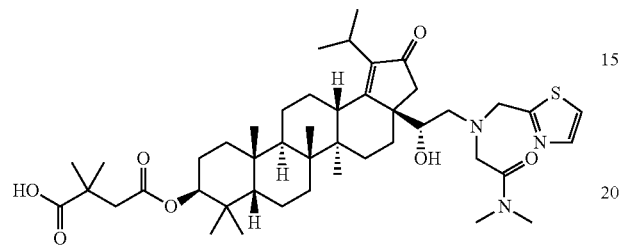

LC/MS: m/z calculated 795.5. found 796.4 (M+1)$^+$.

Example 371

Compound 440

4-(((3aR,5aR,5bR,7aR,9S,11aR,11bR,13aS)-1-isopropyl-5a,5b,8,8,11a-pentamethyl-3a-((R)-2-methyl-5-(pyridin-2-ylmethyl)-8,11-dioxa-2,5-diazadodecan-7-yl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

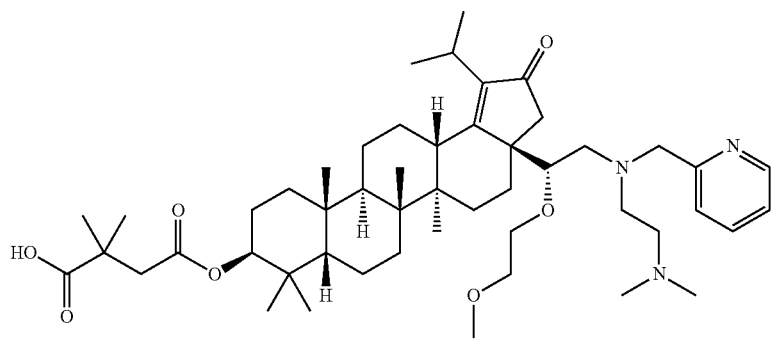

LC/MS: m/z calculated 833.6. found 834.5 (M+1)$^+$.

Example 372

Compound 441

4-(((3aR,5aR,5bR,7aR,9S,11aR,11bR,13aS)-3a-((R)-2-((S)—N-benzyl-3,4-dihydroxybutanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

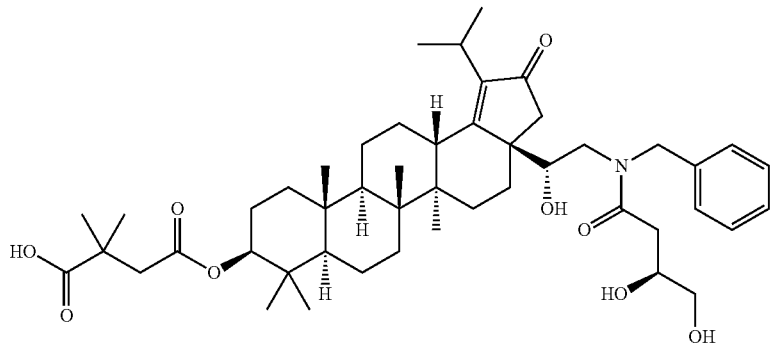

LC/MS: m/z calculated 805.5. found 806.5 (M+1)$^+$.

323

Example 373

Compound 442

4-(((3aR,5aR,5bR,7aR,9S,11aR,11bR,13aS)-3a-((R)-2-((2-amino-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

442

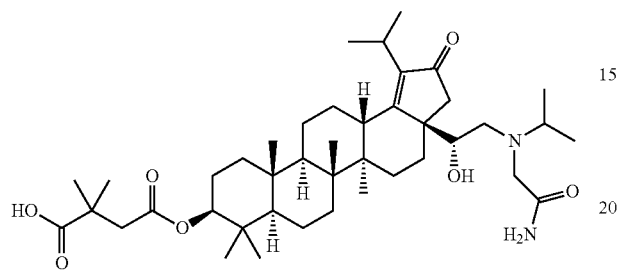

LC/MS: m/z calculated 712.5. found 713.5 (M+1)$^+$.

Example 374

Compound 443

4-(((3aR,5aR,5bR,7aR,9S,11aR,11bR,13aS)-3a-((R)-2-((2-(dimethylamino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

443

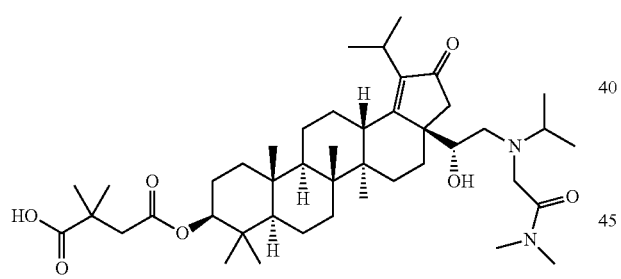

LC/MS: m/z calculated 740.5. found 741.5 (M+1)$^+$.

324

Example 375

Compound 444

4-(((3aR,5aR,5bR,7aR,9S,11aR,11bR,13aS)-3a-((R)-1-hydroxy-2-(isopropyl(2-((methylamino)-2-oxoethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

444

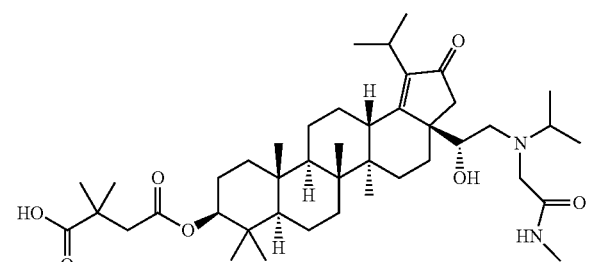

LC/MS: m/z calculated 726.5. found 727.5 (M+1)$^+$.

Example 376

Compound 445

4-(((3aR,5aR,5bR,7aR,9S,11aR,11bR,13aS)-3a-((R)-2-((S)-3,4-dihydroxy-N-(pyridin-2-ylmethyl)butanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

445

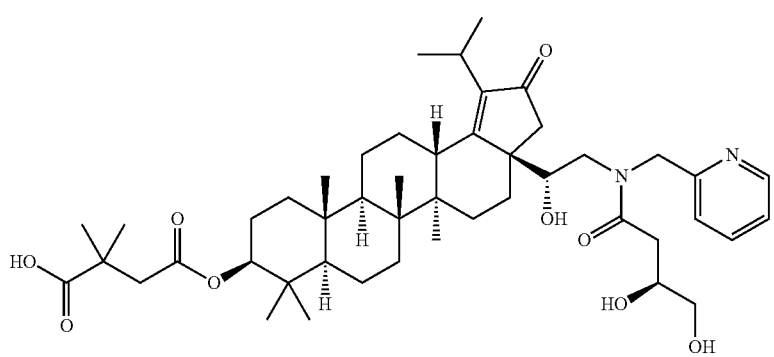

LC/MS: m/z calculated 806.5. found 807.5 (M+1)$^+$.

Example 377

Compound 446

4-(((3aR,5aR,5bR,7aR,9S,11aR,11bR,13aS)-3a-((R)-2-((2-(ethylamino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

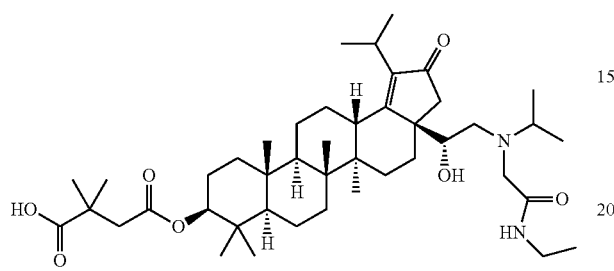

446

LC/MS: m/z calculated 740.5. found 741.5 $(M+1)^+$.

Example 378

Compound 447

4-(((3aR,5aR,5bR,7aR,9S,11aR,11bR,13aS)-3a-((R)-2-((carboxymethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

447

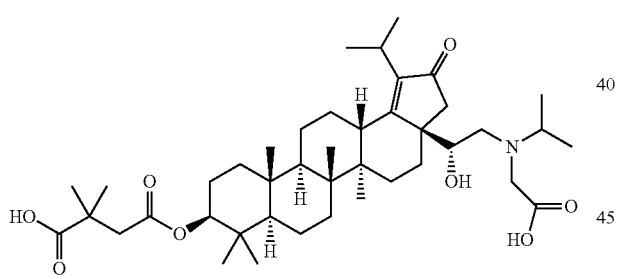

LC/MS: m/z calculated 713.5. found 714.5 $(M+1)^+$.

Example 379

Compound 448

4-(((3aR,5aR,5bR,7aR,9S,11aR,11bR,13aS)-3a-((R)-2-((2-(cyclopropylamino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

448

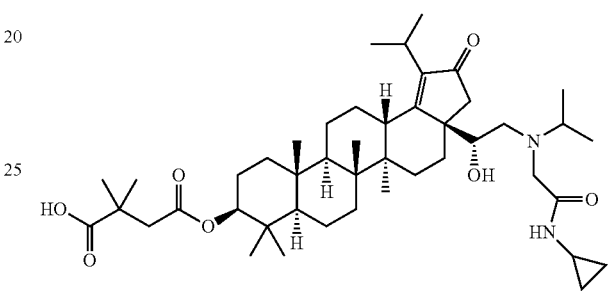

LC/MS: m/z calculated 752.5. found 753.5 $(M+1)^+$.

Example 380

Compound 449

4-(((3aR,5aR,5bR,7aR,9S,11aR,11bR,13aS)-3a-((R)-2-(((5-chloropyrimidin-2-yl)methyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

449

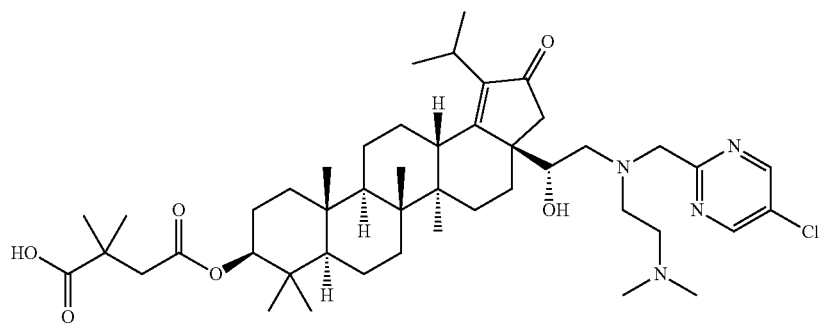

LC/MS: m/z calculated 810.5. found 811.5 $(M+1)^+$.

327

Example 381

Compound 450

4-(((3aR,5aR,5bR,7aR,9S,11aR,11bR,13aS)-3a-((R)-2-(N-(cyclopropylmethyl)acetamido)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

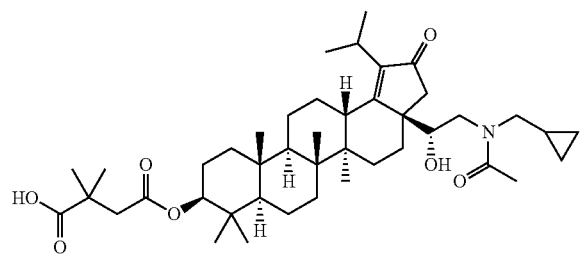

450

LC/MS: m/z calculated 709.5. found 710.5 (M+1)$^+$.

328

Example 382

Compound 451

4-(((3aR,5aR,5bR,7aR,9S,11aR,11bR,13aS)-1-isopropyl-5a,5b,8,8,11a-pentamethyl-2-oxo-3a-(2-((pyridin-2-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

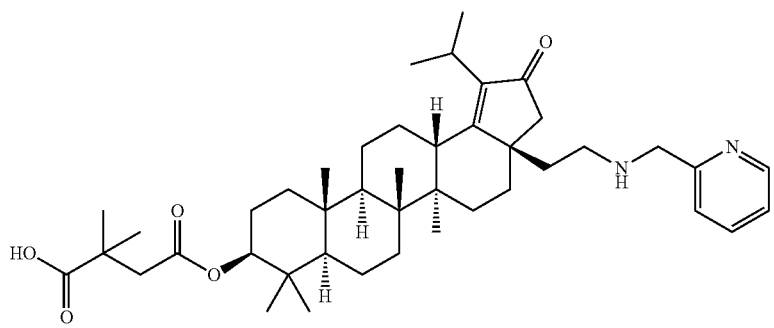

451

LC/MS: m/z calculated 688.5. found 689.5 (M+1)$^+$.

Example 383

Compound 452

4-(((3aR,5aR,5bR,7aR,9S,11aR,11bR,13aS)-3a-((R)-2-((cyclopropylmethyl)(methyl)amino)-1-hydroxy-ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

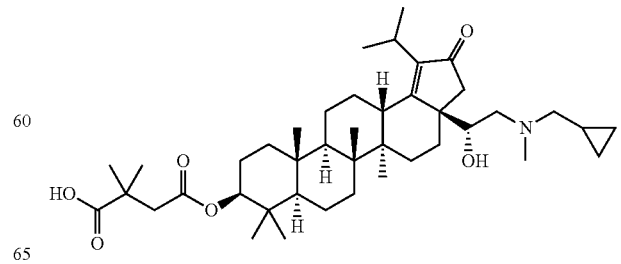

452

LC/MS: m/z calculated 681.5. found 682.5 (M+1)$^+$.

Example 384

Compound 453

4-(((3aR,5aR,5bR,7aR,9S,11aR,11bR,13aS)-3a-((R)-2-(N-(cyclopropylmethyl)-2-(methylamino)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

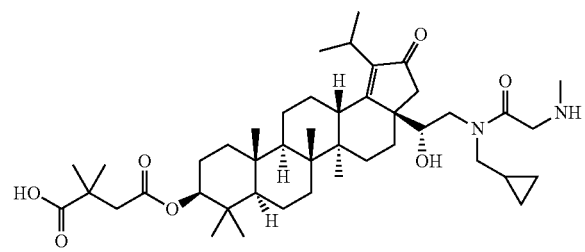

LC/MS: m/z calculated 738.5. found 739.5 (M+1)$^+$.

Example 385

Compound 454

4-(((3aR,5aR,5bR,7aR,9S,11aR,11bR,13aS)-3a-((R)-2-(N-benzylisobutyramido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

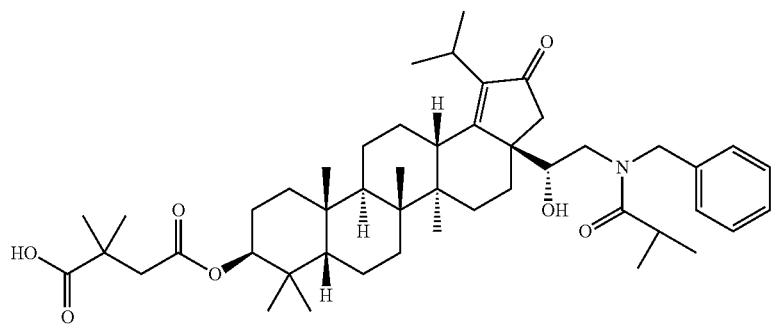

LC/MS: m/z calculated 773.5. found 774.5 (M+1)$^+$.

Example 386

Compound 455

4-(((3aR,5aR,5bR,7aR,9S,11aR,11bR,13aS)-3a-((R)-2-(N-benzyl-3-methylbutanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

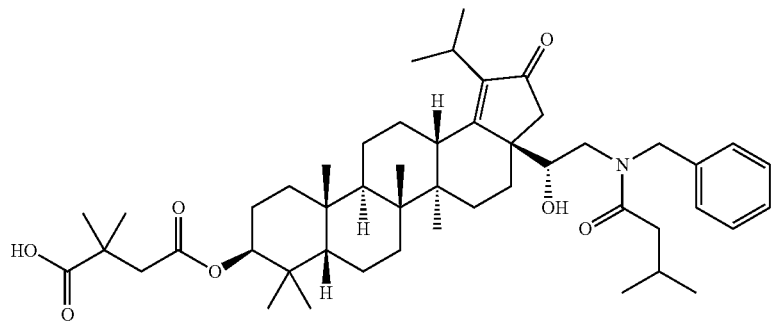

LC/MS: m/z calculated 787.5. found 788.5 (M+1)$^+$.

Example 387

Compound 456

4-(((3aR,5aR,5bR,7aR,9S,11aR,11bR,13aS)-3a-((R)-2-(N-benzylpropionamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

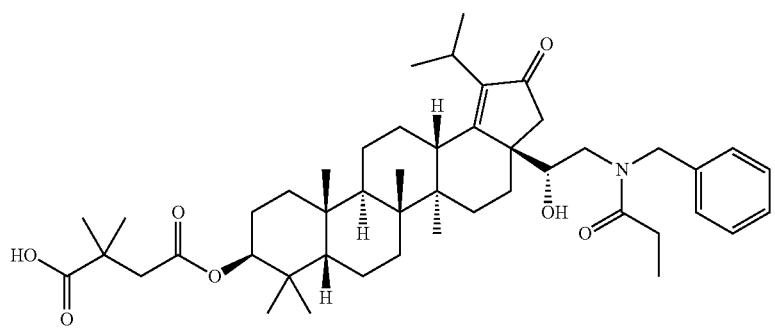

456

LC/MS: m/z calculated 759.5. found 760.5 (M+1)$^+$.

Example 388

Compound 457

4-(((3aR,5aR,5bR,7aR,9S,11aR,11bR,13aS)-1-isopropyl-5a,5b,8,8,11a-pentamethyl-2-oxo-3a-(2-((pyridin-3-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

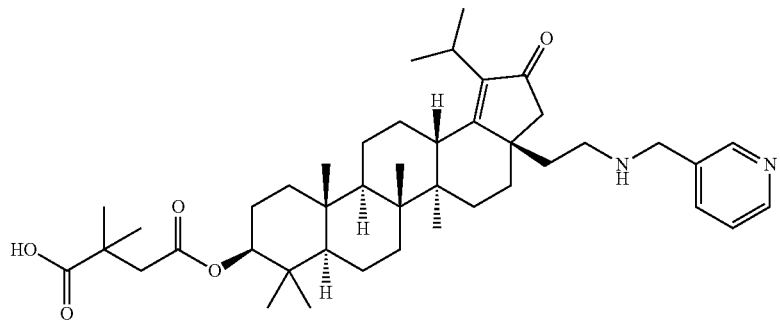

457

LC/MS: m/z calculated 688.5. found 689.5 (M+1)$^+$.

Example 389

Compound 458

4-(((3aR,5aR,5bR,7aR,9S,11aR,11bR,13aS)-1-isopropyl-5a,5b,8,8,11a-pentamethyl-2-oxo-3a-(2-((pyridin-4-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

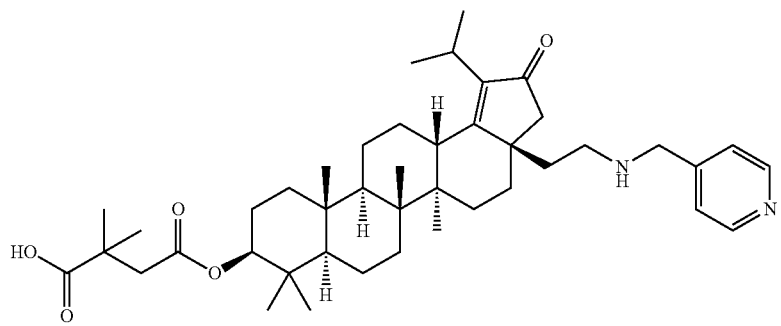

458

LC/MS: m/z calculated 688.5. found 689.5 $(M+1)^+$.

Example 390

Compound 459

4-(((3aR,5aR,5bR,7aR,9S,11aR,11bR,13aS)-3a-((R)-2-((cyclopropylmethyl)(2-(pyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

459

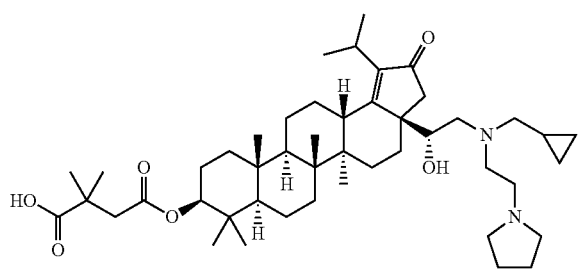

LC/MS: m/z calculated 764.6. found 765.5 $(M+1)^+$.

Example 391

Compound 460

4-(((3aR,5aR,5bR,7aR,9S,11aR,11bR,13aS)-3a-((R)-2-(N-benzylacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

460

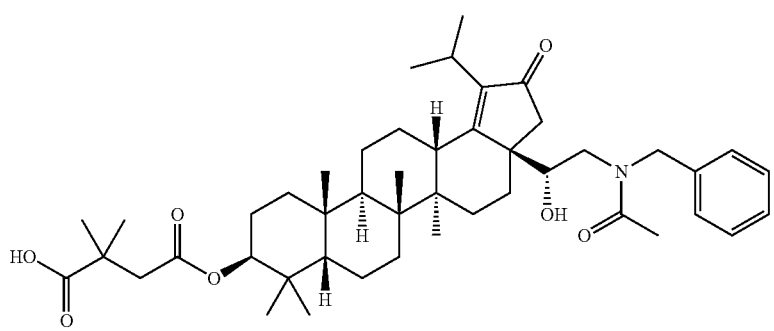

LC/MS: m/z calculated 745.5. found 746.5 $(M+1)^+$.

Example 392

Compound 461

4-(((3aR,5aR,5bR,7aR,9S,11aR,11bR,13aS)-3a-((R)-2-(benzyl(2-morpholinoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

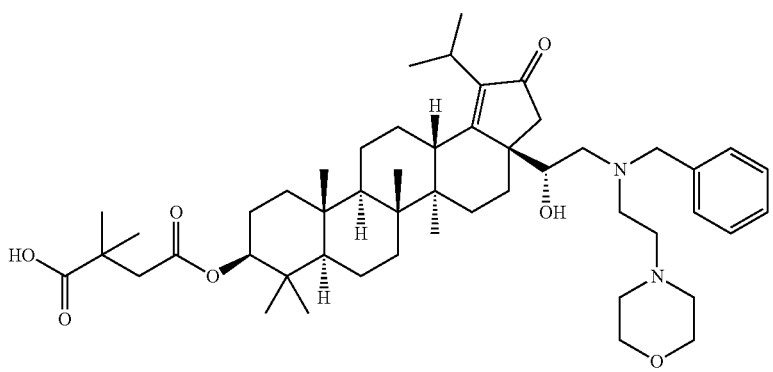

461

LC/MS: m/z calculated 816.6. found 817.5 (M+1)$^+$.

Example 393

Compound 462

4-(((3aR,5aR,5bR,7aR,9S,11aR,11bR,13aS)-3a-((R)-2-(N,3-dimethylbutanamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

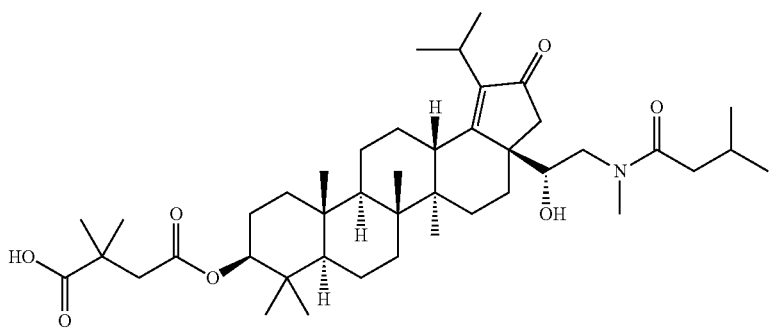

462

LC/MS: m/z calculated 711.5. found 712.5 (M+1)$^+$.

Example 394

Compound 463

4-(((3aR,5aR,5bR,7aR,9S,11aR,11bR,13aS)-3a-((R)-2-(N-(cyclopropylmethyl)-2-(2-oxopyrrolidin-1-yl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

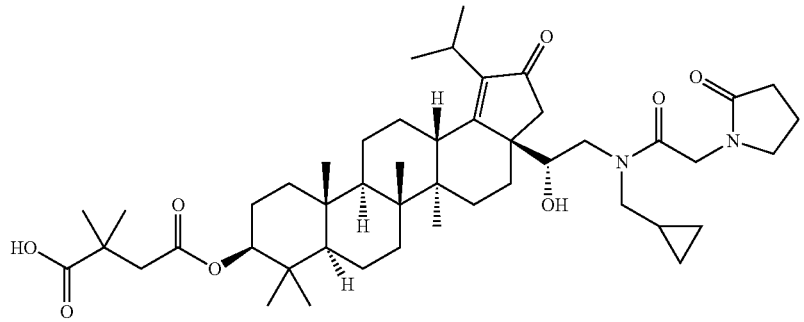

463

LC/MS: m/z calculated 792.5. found 793.5 (M+1)$^+$.

Example 395

Compound 464

4-(((3aR,5aR,5bR,7aR,9S,11aR,11bR,13aS)-3a-((R)-1-(isobutyryloxy)-2-(methylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

Example 396

Compound 465

4-(((3aR,5aR,5bR,7aR,9S,11aR,11bR,13aS)-3a-(2-((cyclobutylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

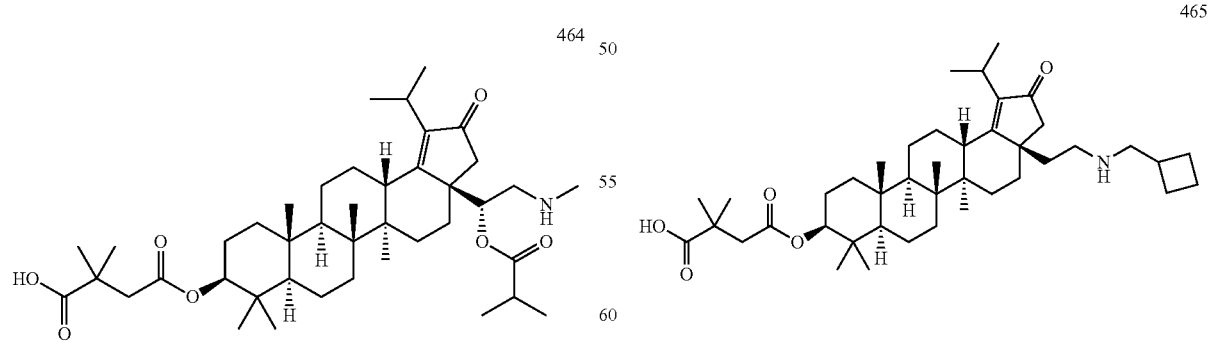

LC/MS: m/z calculated 697.5. found 698.5 (M+1)$^+$.

LC/MS: m/z calculated 665.5. found 666.5 (M+1)$^+$.

Example 397

Compound 466

4-(((3aR,5aR,5bR,7aR,9S,11aR,11bR,13aS)-3a-(2-((cyclopropylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

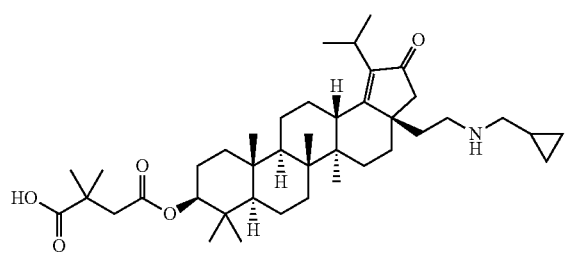

LC/MS: m/z calculated 651.5. found 652.5 (M+1)$^+$.

Example 398

Compound 467

4-(((3aR,5aR,5bR,7aR,9S,11aR,11bR,13aS)-3a-((R)-2-(N-(cyclobutylmethyl)-2-(dimethylamino)acet-amido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

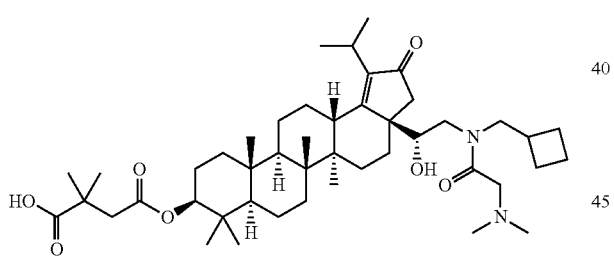

LC/MS: m/z calculated 766.5. found 767.5 (M+1)$^+$.

Example 399

Compound 468

4-(((3aR,5aR,5bR,7aR,9S,11aR,11bR,13aS)-3a-(2-((cyclobutylmethyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

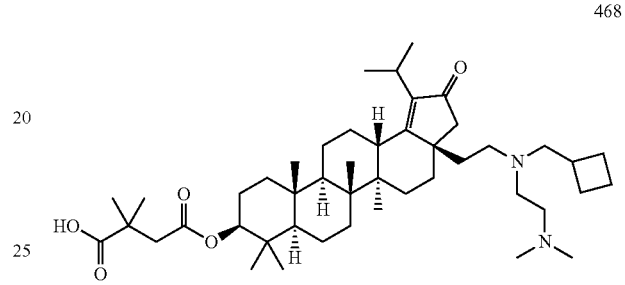

LC/MS: m/z calculated 736.6. found 737.5 (M+1)$^+$.

Example 400

Compound 469

4-(((3aR,5aR,5bR,7aR,9S,11aR,11bR,13aS)-3a-((R)-1-hydroxy-2-((pyrimidin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

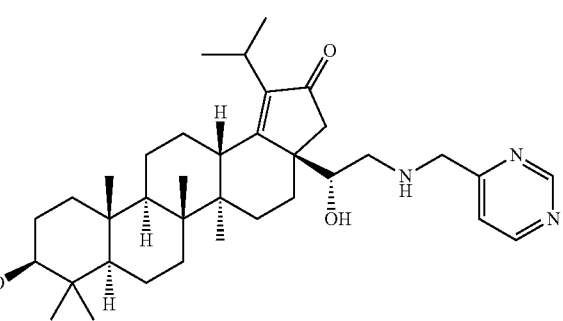

LC/MS: m/z calculated 705.5. found 706.5

Example 401

Compound 470

4-(((3aR,5aR,5bR,7aR,9S,11aR,11bR,13aS)-3a-((R)-2-(N-(cyclobutylmethyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

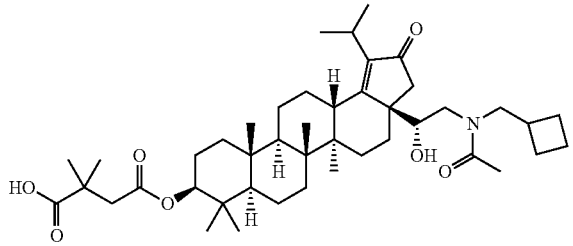

LC/MS: m/z calculated 723.5. found 724.5 (M+1)$^+$.

Example 402

Compound 471

4-(((3aR,5aR,5bR,7aR,9S,11aR,11bR,13aS)-3a-((R)-1-((4-chlorobenzoyl)oxy)-2-(methylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

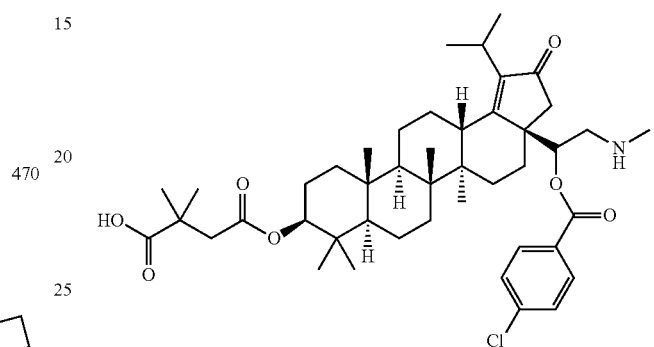

LC/MS: m/z calculated 765.4. found 766.4 (M+1)$^+$.

Example 403

Compound 472

4-(((3aR,5aR,5bR,7aR,9S,11aR,11bR,13aS)-3a-((R)-1-(benzoyloxy)-2-((2-hydroxyethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

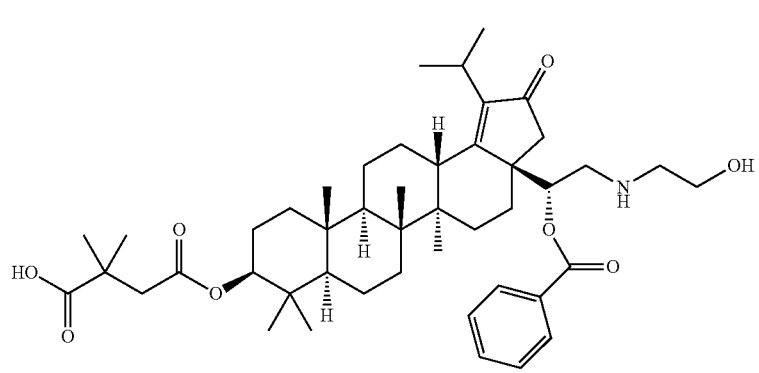

LC/MS: m/z calculated 761.5. found 762.4 (M+1)$^+$.

Example 404

Compound 473

4-(((3aR,5aR,5bR,7aR,9S,11aR,11bR,13aS)-1-isopropyl-5a,5b,8,8,11a-pentamethyl-3a-((R)-2-(methylamino)-1-(2-phenylacetoxy)ethyl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

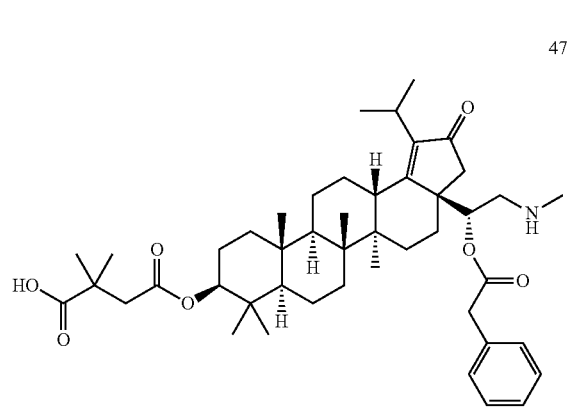

LC/MS: m/z calculated 745.5. found 746.5 (M+1)⁺.

Example 405

Compound 474

4-(((3aR,5aR,5bR,7aR,9S,11aR,11bR,13aS)-3a-((R)-1-hydroxy-2-(N-methylacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

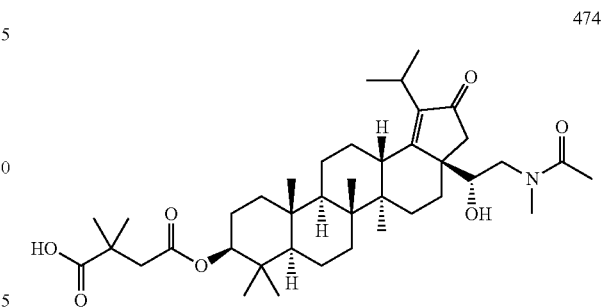

LC/MS: m/z calculated 669.5. found 670.4 (M+1)⁺.

Example 406

Compound 475

4-(((3aR,5aR,5bR,7aR,9S,11aR,11bR,13aS)-3a-((R)-2-(4-chloro-N-methylbenzamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

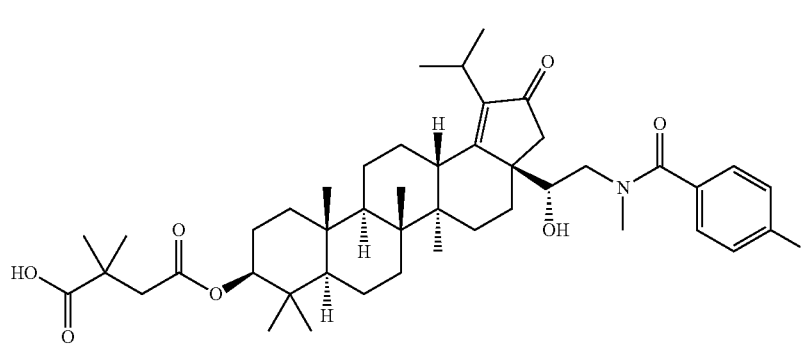

LC/MS: m/z calculated 765.4. found 766.4 (M+1)⁺.

Example 407

Compound 476

4-(((3aR,5aR,5bR,7aR,9S,11aR,11bR,13aS)-3a-((R)-1-hydroxy-2-(N-methyl-2-phenylacetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

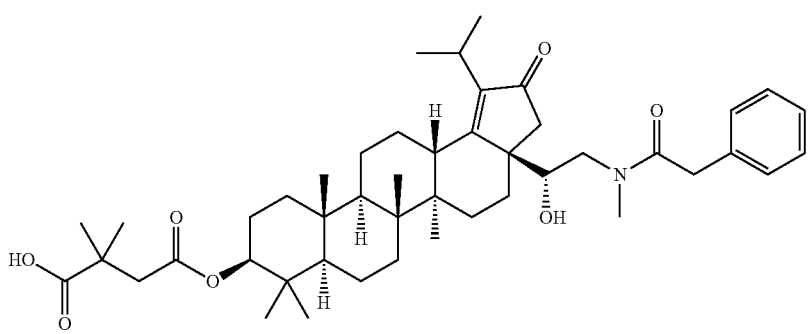

476

LC/MS: m/z calculated 745.5. found 746.5 (M+1)$^+$.

Example 408

Compound 477

4-(((3aR,5aR,5bR,7aR,9S,11aR,11bR,13aS)-3a-((R)-1-hydroxy-2-(N-(2-hydroxyethyl)benzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

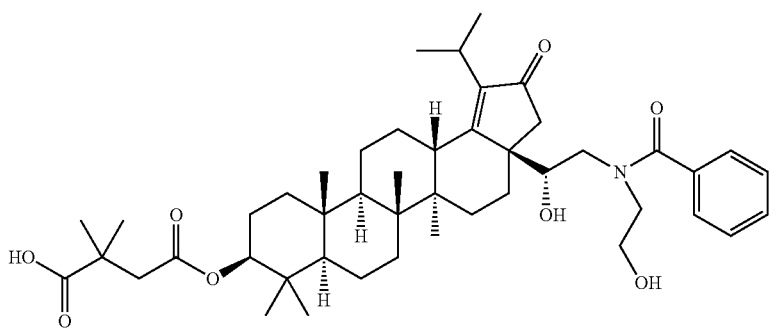

477

LC/MS: m/z calculated 761.5. found 762.4 (M+1)$^+$.

Example 409

Compound 478

4-(((3aR,5aR,5bR,7aR,9S,11aR,11bR,13aS)-3a-((R)-1-hydroxy-2-((pyrimidin-5-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

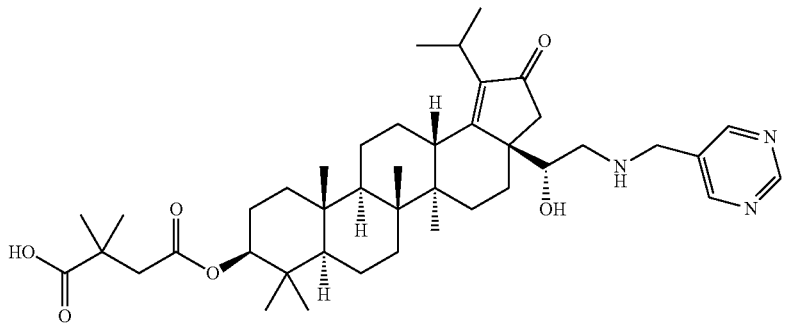

LC/MS: m/z calculated 705.5. found 706.5 (M+1)$^+$.

Example 410

Compound 479

4-(((3aR,5aR,5bR,7aR,9S,11aR,11bR,13aS)-3a-((R)-2-((2-((cyclobutylmethyl)amino)-2-oxoethyl)(isopropyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

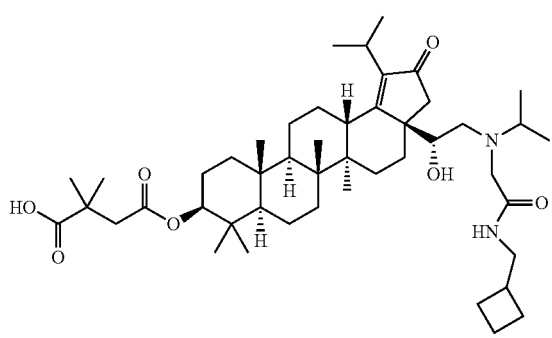

LC/MS: m/z calculated 780.6. found 781.6 (M+1)$^+$.

Example 411

Compound 480

4-(((3aR,5aR,5bR,7aR,9S,11aR,11bR,13aS)-3a-((R)-1-hydroxy-2-(N-methylisobutyramido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

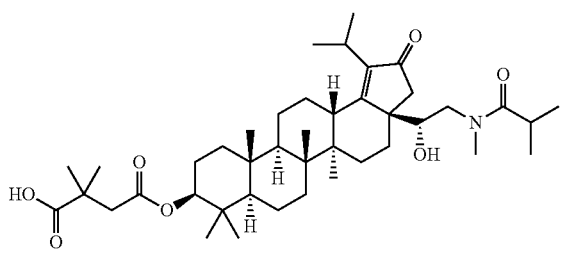

LC/MS: m/z calculated 697.5. found 698.5 (M+1)$^+$.

Example 412

Compound 481

4-(((3aR,5aR,5bR,7aR,9S,11aR,11bR,13aS)-3a-((R)-1-hydroxy-2-(N-methylcyclopentanecarboxamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

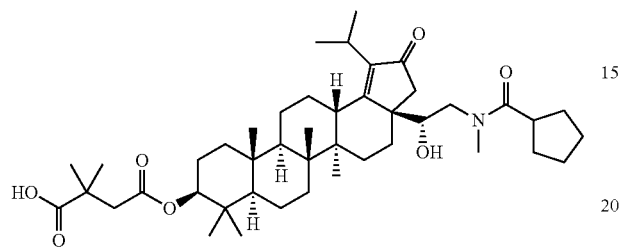

LC/MS: m/z calculated 723.5. found 724.5 $(M+1)^+$.

Example 413

Compound 482

4-(((3aR,5aR,5bR,7aR,9S,11aR,11bR,13aS)-3a-((R)-1-hydroxy-2-(N-methylcyclohexanecarboxamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

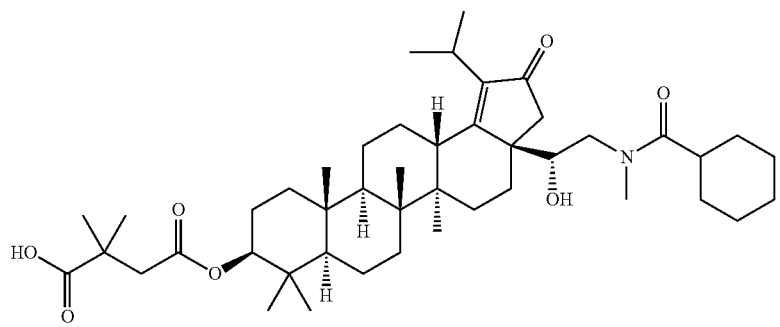

LC/MS: m/z calculated 737.5. found 738.5 $(M+1)^+$.

Example 414

Compound 483

4-(((3aR,5aR,5bR,7aR,9S,11aR,11bR,13aS)-3a-(2-((cyclopropylmethyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

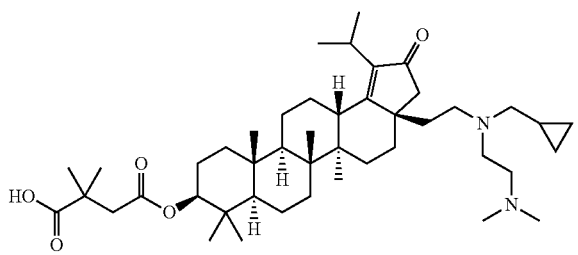

LC/MS: m/z calculated 722.6. found 723.6 $(M+1)^+$.

Example 415

Compound 484

4-(((3aR,5aR,5bR,7aR,9S,11aR,11bR,13aS)-3a-(2-(cyclopentyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

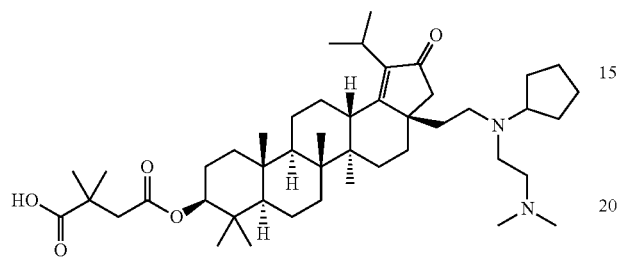

484

LC/MS: m/z calculated 736.6. found 737.5 (M+1)$^+$.

Example 416

Compound 485

4-(((3aR,5aR,5bR,7aR,9S,11aR,11bR,13aS)-3a-((R)-2-((2-(dimethylamino)ethyl)(pyrimidin-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

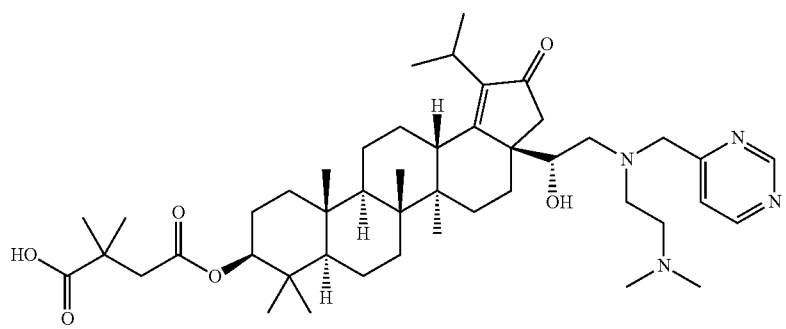

485

LC/MS: m/z calculated 776.5. found 777.5 (M+1)$^+$.

Example 417

Compound 486

4-(((3aR,5aR,5bR,7aR,9S,11aR,11bR,13aS)-3a-((S)-2-(benzyl(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

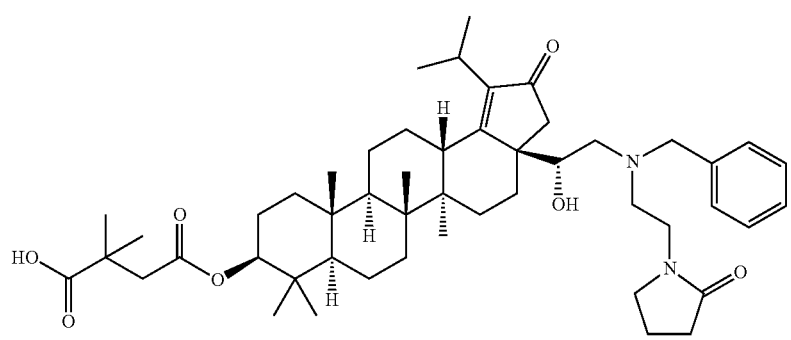

486

LC/MS: m/z calculated 814.5. found 815.5 (M+1)$^+$.

Example 418

Compound 487

4-(((3aR,5aR,5bR,7aR,9S,11aR,11bR,13aS)-3a-((R)-1-hydroxy-2-(N-methylpicolinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

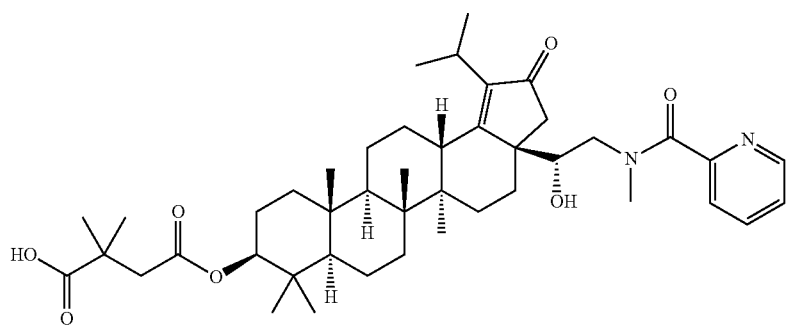

487

LC/MS: m/z calculated 732.5. found 733.5 (M+1)$^+$.

Example 419

Compound 488

4-(((3aR,5aR,5bR,7aR,9S,11aR,11bR,13aS)-3a-((R)-2-(N-(4-chlorobenzyl)-2-hydroxyacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

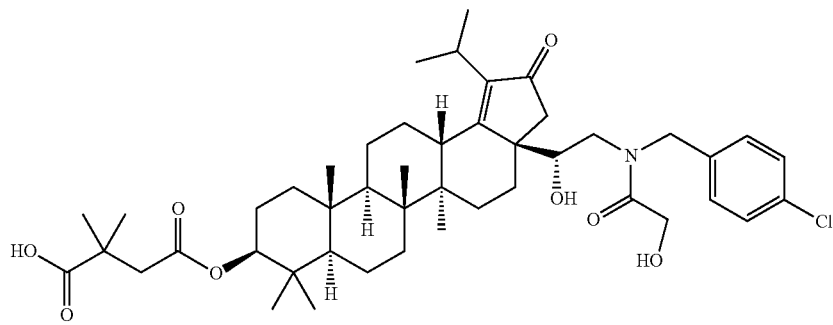

488

LC/MS: m/z calculated 795.4. found 796.3 (M+1)$^+$.

Example 420

Compound 489

4-(((3aR,5aR,5bR,7aR,9S,11aR,11bR,13aS)-3a-((R)-1-hydroxy-2-(N-methylisonicotinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

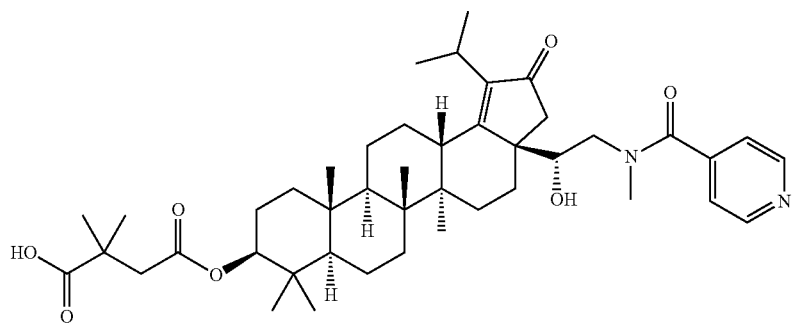

489

LC/MS: m/z calculated 732.5. found 733.5 (M+1)$^+$.

Example 421

Compound 490

4-(((3aR,5aR,5bR,7aR,9S,11aR,11bR,13aS)-3a-((R)-1-hydroxy-2-(N-methylnicotinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

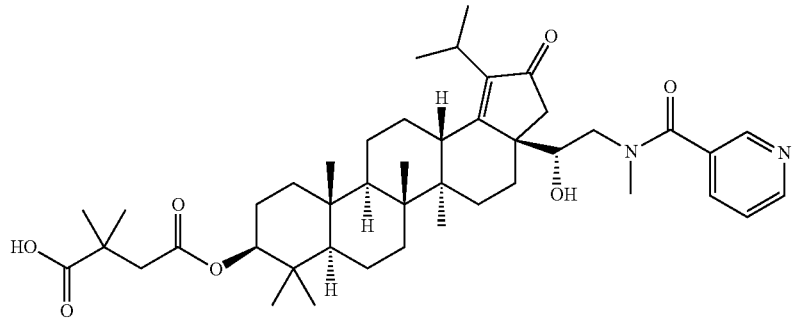

490

LC/MS: m/z calculated 732.5. found 733.4 (M+1)$^+$.

Example 422

Compound 491

4-(((3aR,5aR,5bR,7aR,9S,11aR,11bR,13aS)-3a-((R)-2-(N-(4-chlorobenzyl)-2-methoxyacetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

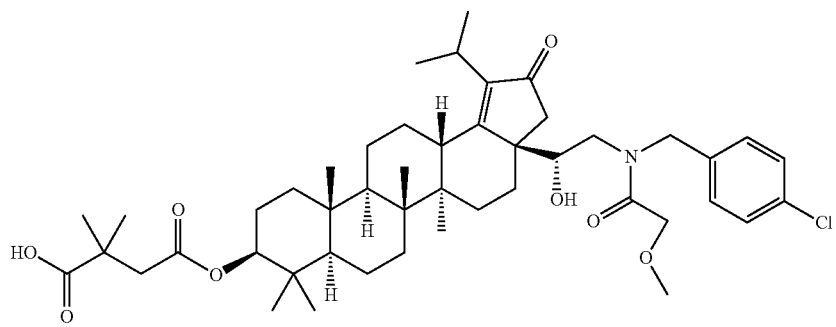

491

LC/MS: m/z calculated 809.5. found 810.3 $(M+1)^+$.

Example 423

Compound 492

4-(((3aR,5aR,5bR,7aR,9S,11aR,11bR,13aS)-3a-((R)-2-(N-(4-chlorobenzyl)isobutyramido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

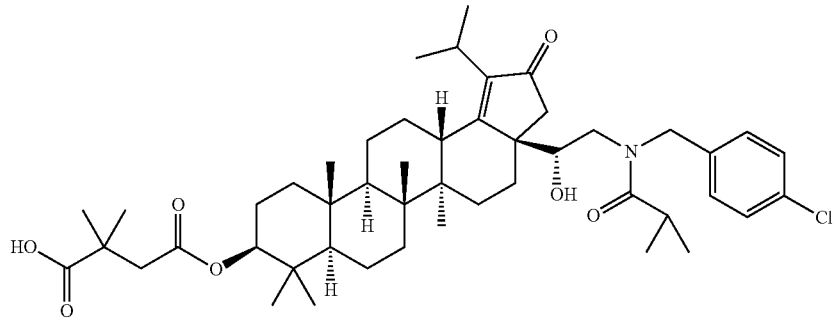

492

LC/MS: m/z calculated 807.5. found 808.5 $(M+1)^+$.

Example 424

Compound 493

4-(((3aR,5aR,5bR,7aR,9S,11aR,11bR,13aS)-3a-((R)-2-(N-(2-(dimethylamino)ethyl)-5-methyl-1,3,4-oxadiazole-2-carboxamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

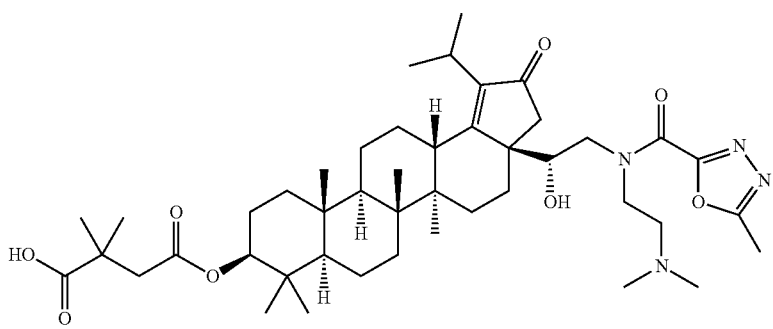

493

LC/MS: m/z calculated 794.5. found 795.5 (M+1)$^+$.

Example 425

Compound 494

4-(((3aR,5aR,5bR,7aR,9S,11aR,11bR,13aS)-1-isopropyl-5a,5b,8,8,11a-pentamethyl-2-oxo-3a-(2-((pyrimidin-2-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

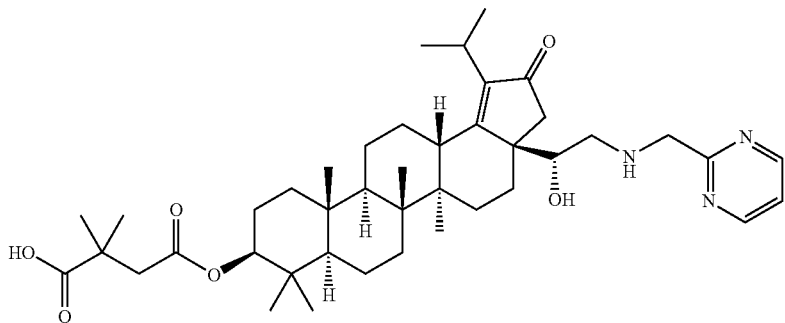

494

LC/MS: m/z calculated 689.5. found 690.4 (M+1)$^+$.

Example 427

Compound 496

4-(((3aR,5aR,5bR,7aR,9S,11aR,11bR,13aS)-3a-((R)-2-((4-chlorobenzyl)amino)-1-sulfoethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

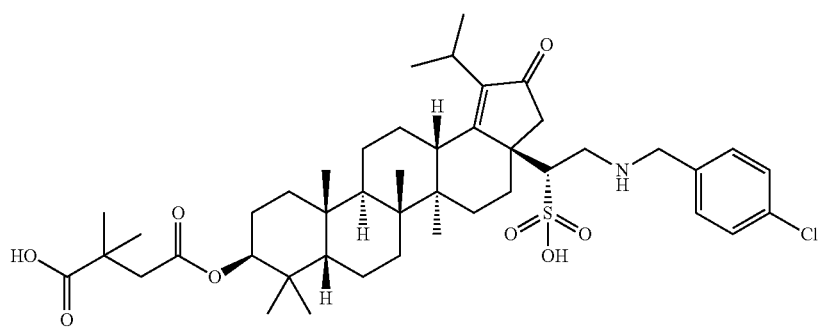

LC/MS: m/z calculated 801.4. found 802.2 (M+1)$^+$.

Example 428

Compound 497

4-(((3aR,5aR,5bR,7aR,9S,11aR,11bR,13aS)-1-isopropyl-5a,5b,8,8,11a-pentamethyl-2-oxo-3a-(2-((pyrimidin-4-ylmethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

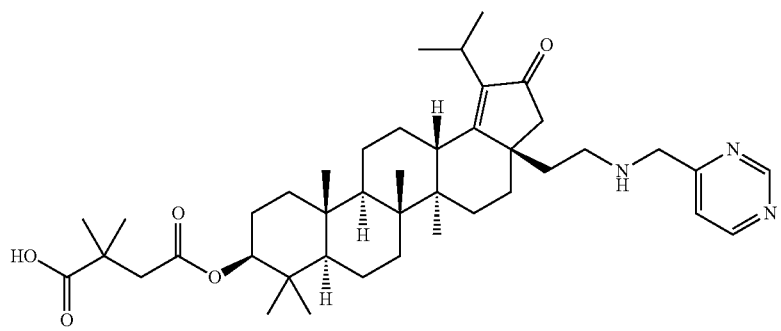

LC/MS: m/z calculated 689.5. found 690.4 (M+1)$^+$.

Example 429

Compound 498

4-(((3aR,5aR,5bR,7aR,9S,11aR,11bR,13aS)-3a-(2-((2-(dimethylamino)-2-oxoethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

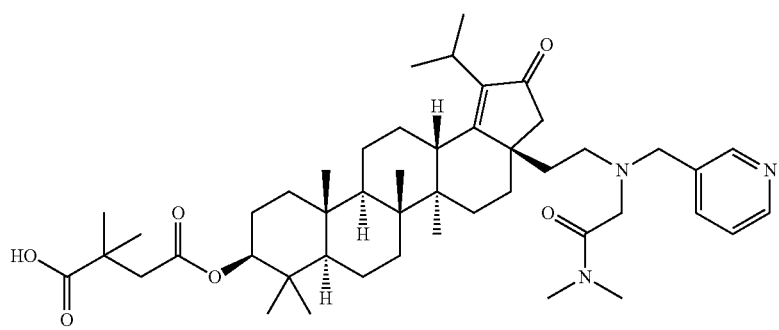

498

LC/MS: m/z calculated 773.5. found 774.5 (M+1)$^+$.

Example 430

Compound 499

4-(((3aR,5aR,5bR,7aR,9S,11aR,11bR,13aS)-3a-(2-((2-(dimethylamino)-2-oxoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

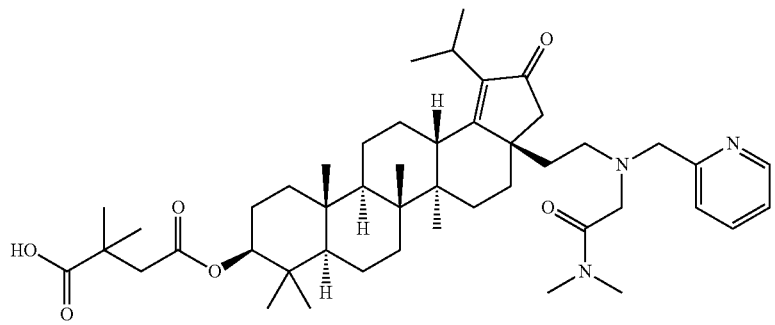

499

LC/MS: m/z calculated 773.5. found 774.5 (M+1)$^+$.

Example 431

Compound 500

4-(((3aR,5aR,5bR,7aR,9S,11aR,11bR,13aS)-3a-((R)-2-((2-(dimethylamino)ethyl)(pyrimidin-5-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

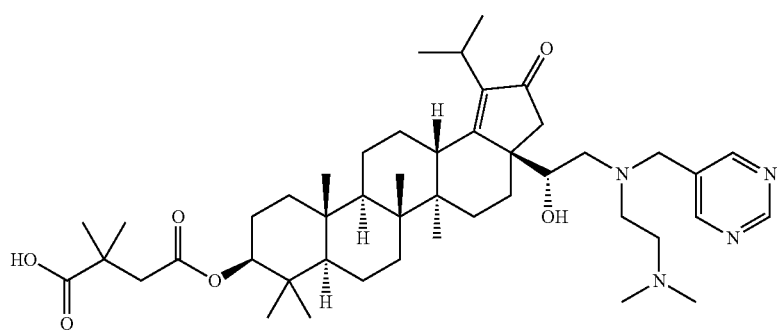

LC/MS: m/z calculated 776.5. found 777.4 (M+1)$^+$.

Example 433

Compound 502

4-(((3aR,5aR,5bR,7aR,9S,11aR,11bR,13aS)-1-isopropyl-5a,5b,8,8,11a-pentamethyl-2-oxo-3a-(2-(((R)-1-(pyridin-2-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

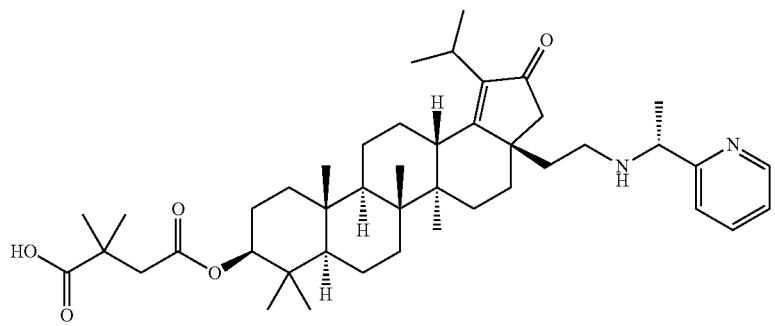

LC/MS: m/z calculated 702.5. found 703.3 (M+1)$^+$.

Example 434

Compound 503

4-(((3aR,5aR,5bR,7aR,9S,11aR,11bR,13aS)-3a-((R)-2-(N-(cyclobutylmethyl)-2-(2-oxopyrrolidin-1-yl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

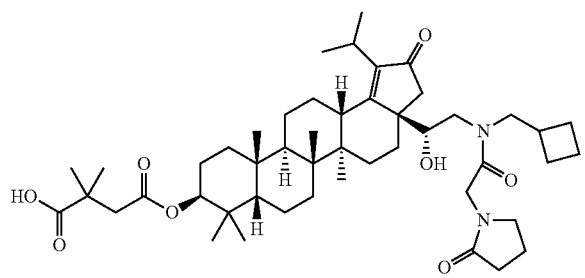

503

LC/MS: m/z calculated 806.5. found 806.9 (M+1)$^+$.

Example 435

Compound 504

4-(((3aR,5aR,5bR,7aR,9S,11aR,11bR,13aS)-3a-((R)-2-((cyclobutylmethyl)(2-(methylamino)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

504

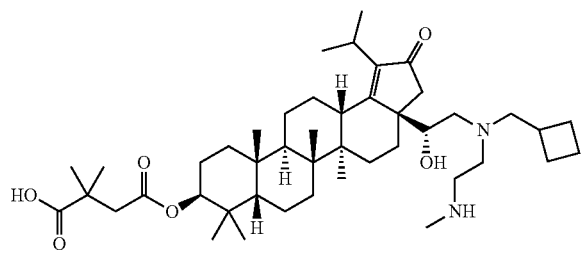

LC/MS: m/z calculated 738.5. found 739.5 (M+1)$^+$.

Example 436

Compound 505

4-(((3aR,5aR,5bR,7aR,9S,11aR,11bR,13aS)-3a-((R)-2-((2-(dimethylamino)ethyl)(oxazol-2-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

505

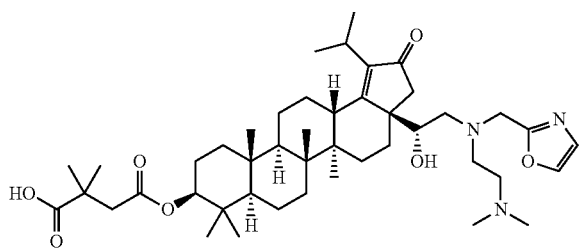

LC/MS: m/z calculated 765.5. found 765.9 (M+1)$^+$.

Example 437

Compound 506

4-(((3aR,5aR,5bR,7aR,9S,11aR,11bR,13aS)-3a-((R)-1-hydroxy-2-(1-oxoisoindolin-2-yl)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

506

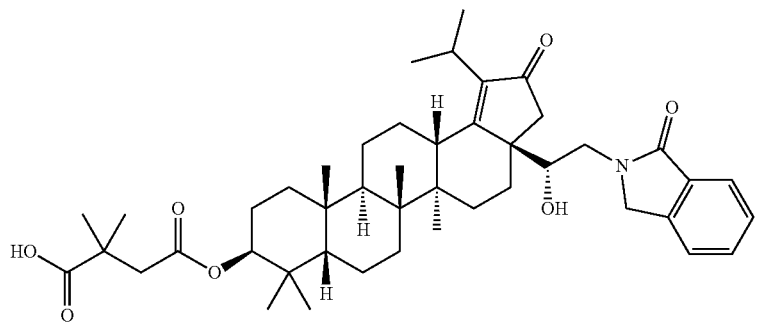

LC/MS: m/z calculated 729.5. found 729.9 (M+1)$^+$.

Example 438

Compound 507

4-(((3aR,5aR,5bR,7aR,9S,11aR,11bR,13aS)-3a-(2-(cyclobutylamino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

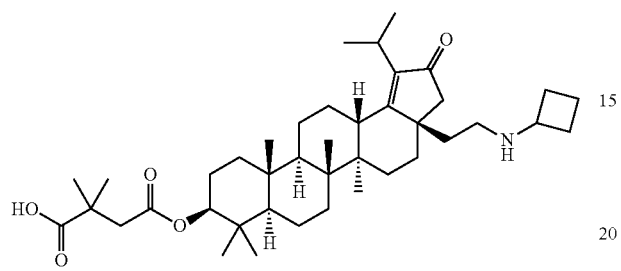

507

LC/MS: m/z calculated 651.5. found 652.0 (M+1)$^+$.

Example 439

Compound 508

4-(((3aR,5aR,5bR,7aR,9S,11aR,11bR,13aS)-3a-(2-(cyclobutyl(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

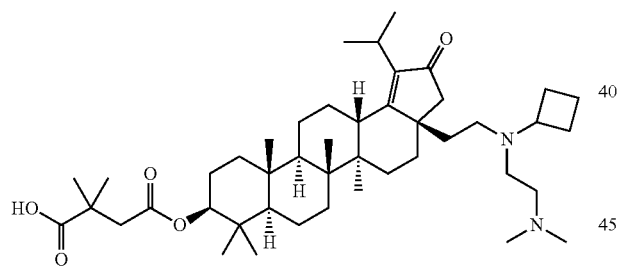

508

LC/MS: m/z calculated 722.6. found 723.0 (M+1)$^+$.

Example 440

Compound 509

4-(((3aR,5aR,5bR,7aR,9S,11aR,11bR,13aS)-3a-((R)-2-((2-acetamidoethyl)(cyclobutylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

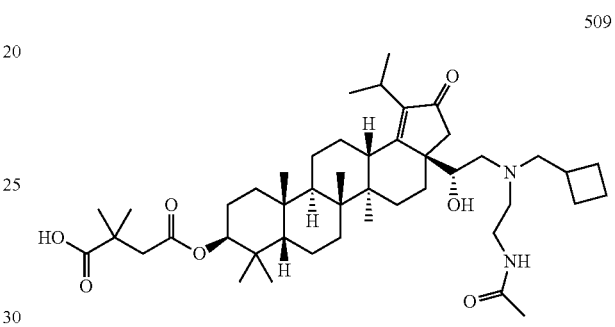

509

LC/MS: m/z calculated 766.5. found 766.9 (M+1)$^+$.

Example 441

Compound 510

4-(((3aR,5aR,5bR,7aR,9S,11aR,11bR,13aS)-3a-(2-(2-(dimethylamino)-N-(pyridin-3-ylmethyl)acetamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

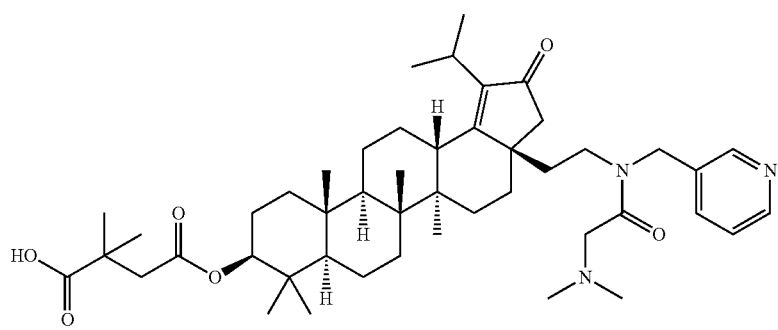

510

LC/MS: m/z calculated 773.5. found 774.5 (M+1)$^+$.

Example 442

Compound 511

4-(((3aR,5aR,5bR,7aR,9S,11aR,11bR,13aS)-3a-(2-((2-(dimethylamino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

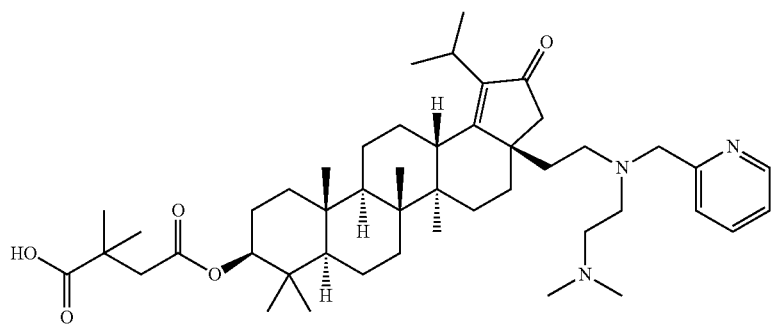

511

LC/MS: m/z calculated 759.6. found 760.5 (M+1)+.

Example 443

Compound 512

4-(((3aR,5aR,5bR,7aR,9S,11aR,11bR,13aS)-3a-((R)-2-((cyclobutylmethyl)(2-(dimethylamino)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

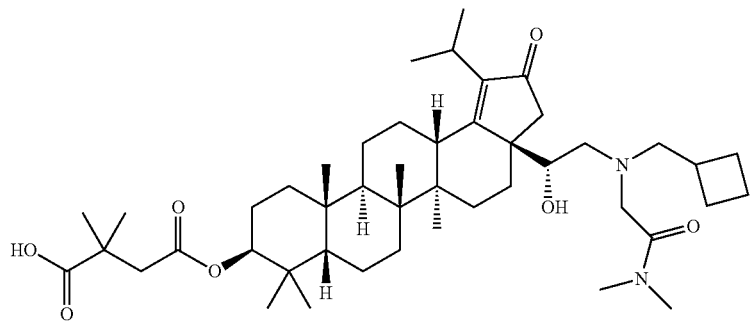

512

LC/MS: m/z calculated 766.5. found 767.5 (M+1)+.

Example 444

Compound 513

4-(((3aR,5aR,5bR,7aR,9S,11aR,11bR,13aS)-3a-(2-((2-(dimethylamino)ethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

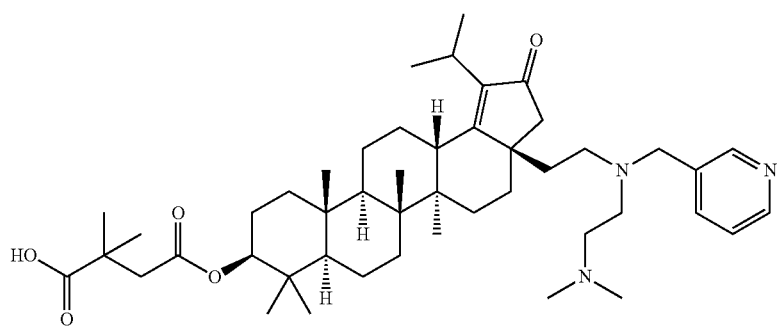

513

LC/MS: m/z calculated 759.6. found 760.5 (M+1)$^+$.

Example 445

Compound 514

4-(((3aR,5aR,5bR,7aR,9S,11aR,11bR,13aS)-3a-(2-((2-(dimethylamino)ethyl)(pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

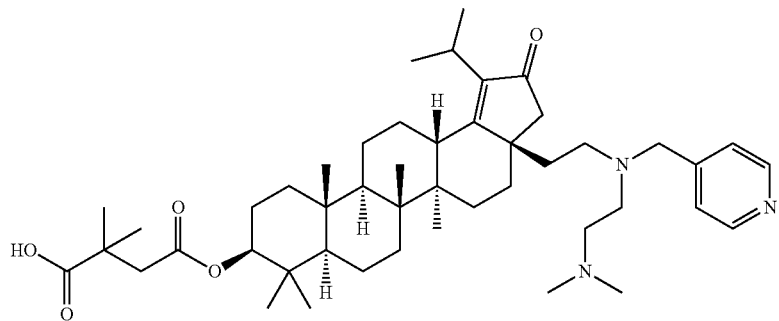

514

LC/MS: m/z calculated 759.6. found 760.5 (M+1)$^+$.

Example 446

Compound 515

4-(((3aR,5aR,5bR,7aR,9S,11aR,11bR,13aS)-3a-(2-(2-(dimethylamino)-N-(pyridin-4-ylmethyl)acet-amido)ethyl)-1-isopropyl-5a,5b,8,8,11a-pentam-ethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

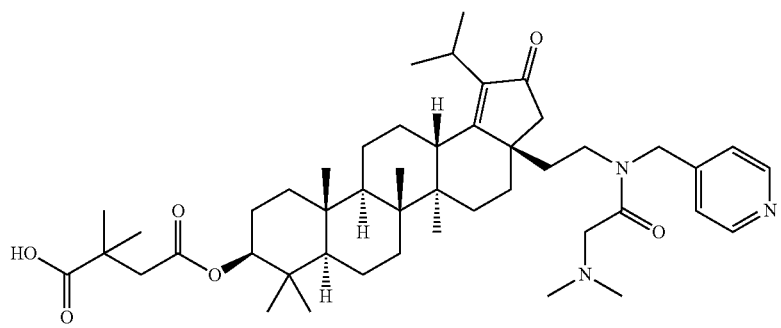

515

LC/MS: m/z calculated 773.5. found 774.5 (M+1)⁺.

Example 447

Compound 516

4-(((3aR,5aR,5bR,7aR,9S,11aR,11bR,13aS)-3a-((R)-2-((cyclobutylmethyl)(2-(N-methylacetamido)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

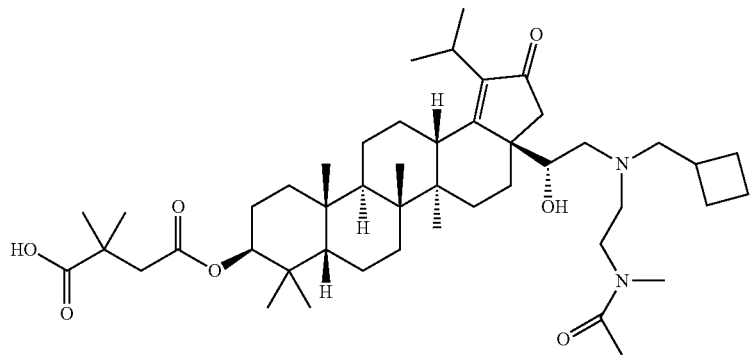

516

LC/MS: m/z calculated 780.6. found 781.4 (M+1)⁺.

Example 448

Compound 517

4-(((3aR,5aR,5bR,7aR,9S,11aR,11bR,13aS)-3a-((R)-1-hydroxy-2-(((R)-1-(pyrimidin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

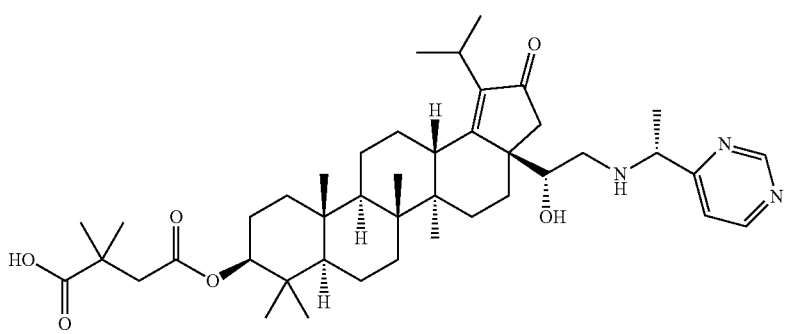

517

LC/MS: m/z calculated 719.5. found 720.4 (M+1)$^+$.

Example 449

Compound 518

4-(((3aR,5aR,5bR,7aR,9S,11aR,11bR,13aS)-3a-(2-((azetidin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

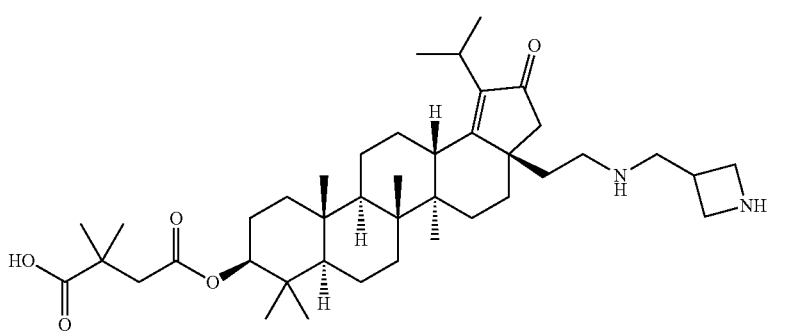

518

LC/MS: m/z calculated 666.5. found 667.4 (M+1)$^+$.

Example 450

Compound 519

4-(((3aR,5aR,5bR,7aR,9S,11aR,11bR,13aS)-3a-((R)-2-(N-(cyclopropylmethyl)-2-(pyrrolidin-1-yl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

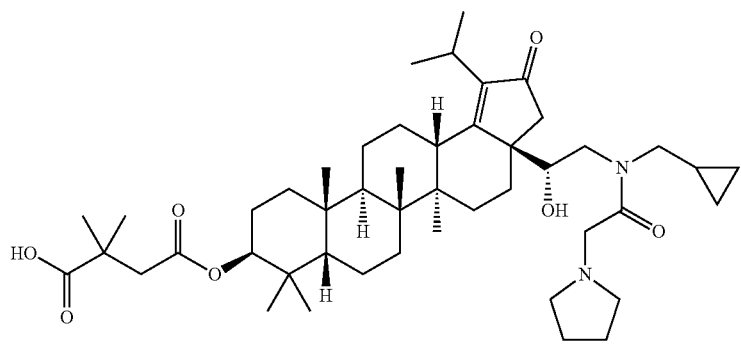

519

LC/MS: m/z calculated 778.5. found 779.5 $(M+1)^+$.

Example 451

Compound 520

4-(((3aR,5aR,5bR,7aR,9S,11aR,11bR,13aS)-1-isopropyl-5a,5b,8,8,11a-pentamethyl-2-oxo-3a-(2-(((R)-1-(pyridin-4-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

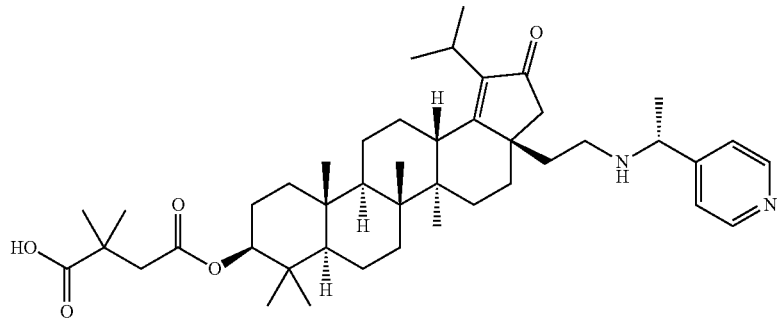

520

LC/MS: m/z calculated 702.5. found 703.5 $(M+1)^+$.

Example 452

Compound 521

4-(((3aR,5aR,5bR,7aR,9S,11aR,11bR,13aS)-3a-(2-((azetidin-3-ylmethyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

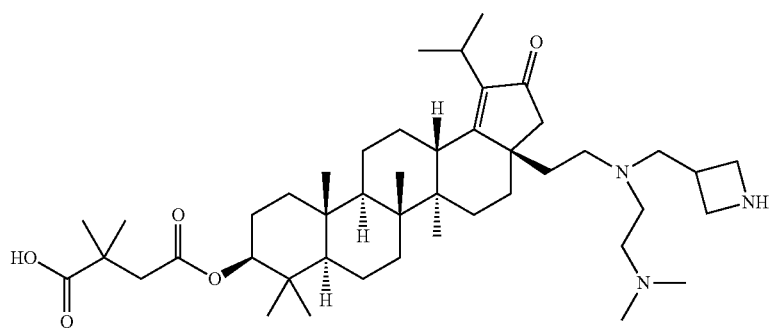

521

LC/MS: m/z calculated 737.6. found 738.7 (M+1)$^+$.

Example 454

Compound 523

4-(((3aR,5aR,5bR,7aR,9S,11aR,11bR,13aS)-3a-((R)-1-hydroxy-2-((2-morpholinoethyl)(pyridin-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

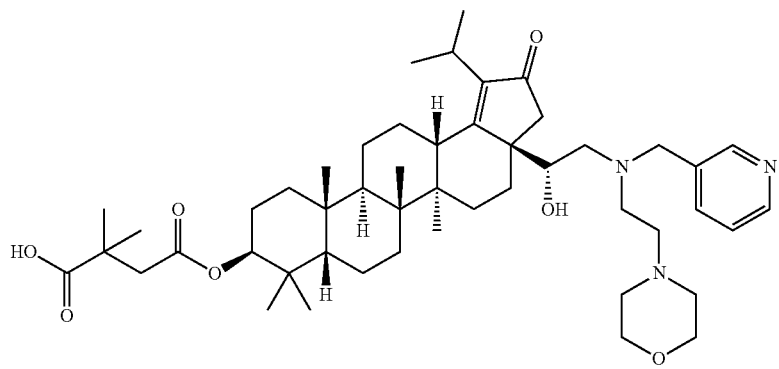

523

LC/MS: m/z calculated 817.6. found 818.5 (M+1)$^+$.

Example 455

Compound 524

4-(((3aR,5aR,5bR,7aR,9S,11aR,11bR,13aS)-3a-(2-((2-(dimethylamino)ethyl)((R)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

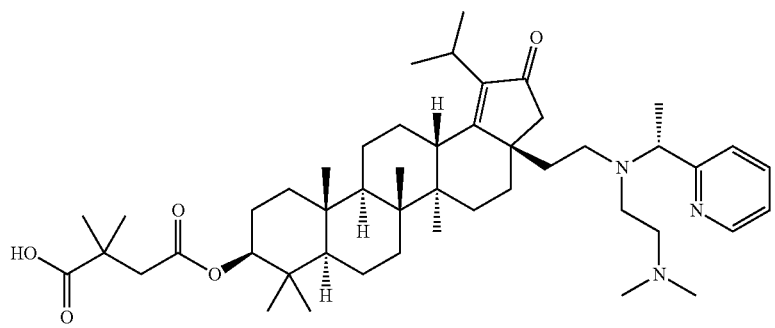

524

LC/MS: m/z calculated 773.6. found 774.5 $(M+1)^+$.

Example 456

Compound 525

4-(((3aR,5aR,5bR,7aR,9S,11aR,11bR,13aS)-3a-((R)-2-((2-(dimethylamino)ethyl)((5-methyl-1,3,4-oxadiazol-2-yl)methyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

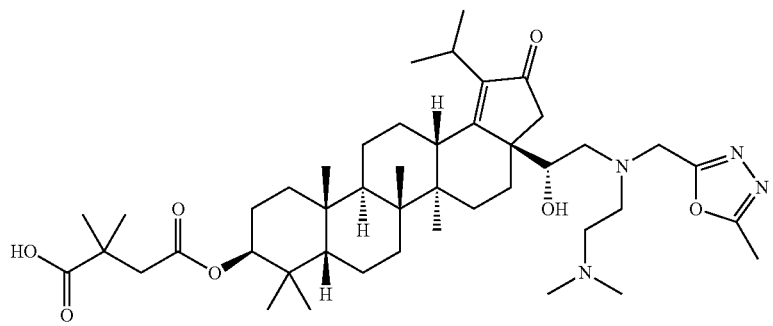

LC/MS: m/z calculated 780.6. found 781.5 $(M+1)^+$.

Example 457

Compound 526

4-(((3aR,5aR,5bR,7aR,9S,11aR,11bR,13aS)-1-isopropyl-5a,5b,8,8,11a-pentamethyl-2-oxo-3a-(2-(((R)-1-(pyridin-3-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

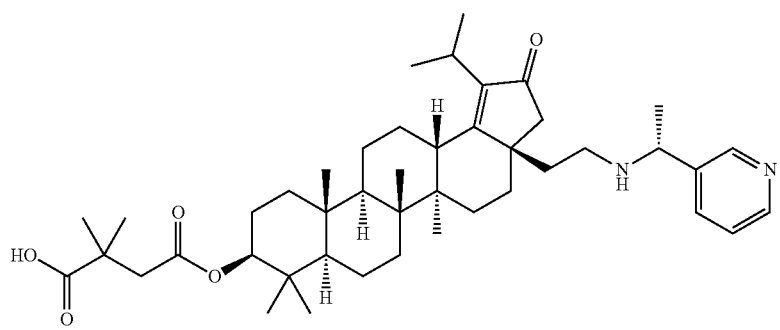

526

LC/MS: m/z calculated 702.5. found 703.5 (M+1)$^+$.

Example 458

Compound 527

4-(((3aR,5aR,5bR,7aR,9S,11aR,11bR,13aS)-3a-(2-(((1-acetylazetidin-3-yl)methyl)(2-(dimethylamino)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

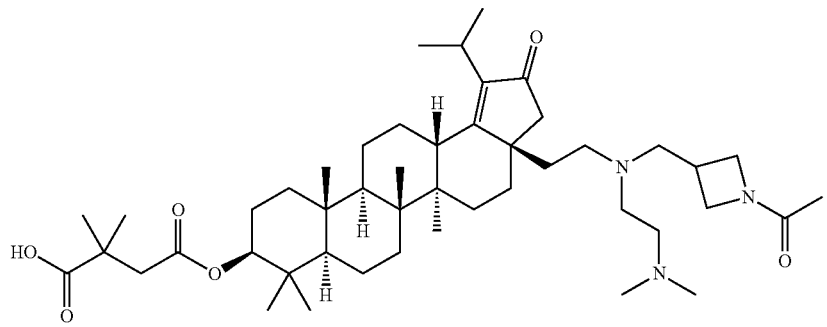

527

LC/MS: m/z calculated 779.6. found 780.7 (M+1)$^+$.

Example 459

Compound 528

4-(((3aR,5aR,5bR,7aR,9S,11aR,11bR,13aS)-3a-(2-((2-(dimethylamino)ethyl)(pyrimidin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

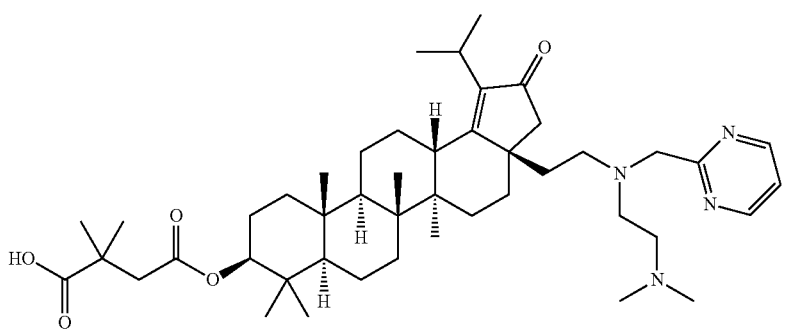

528

LC/MS: m/z calculated 760.5. found 761.7 $(M+1)^+$.

Example 460

Compound 529

4-(((3aR,5aR,5bR,7aR,9S,11aR,11bR,13aS)-3a-((R)-1-hydroxy-2-(((S)-1-(pyrimidin-5-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

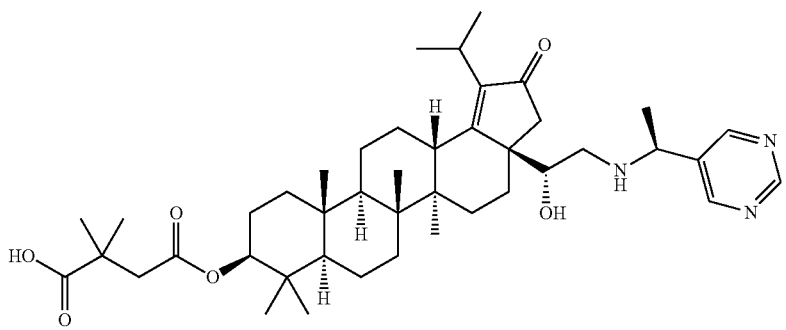

529

LC/MS: m/z calculated 719.5. found 720.5 $(M+1)^+$.

Example 461

Compound 530

4-(((3aR,5aR,5bR,7aR,9S,11aR,11bR,13aS)-3a-((R)-1-hydroxy-2-((2-morpholino-2-oxoethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

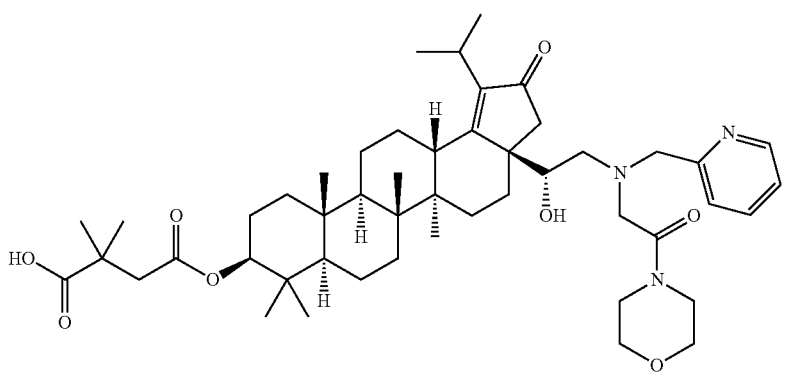

530

LC/MS: m/z calculated 831.5. found 832.7 (M+1)+.

Example 462

Compound 531

4-(((3aR,5aR,5bR,7aR,9S,11aR,11bR,13aS)-3a-(2-((2-(dimethylamino)ethyl)((R)-1-(pyridin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

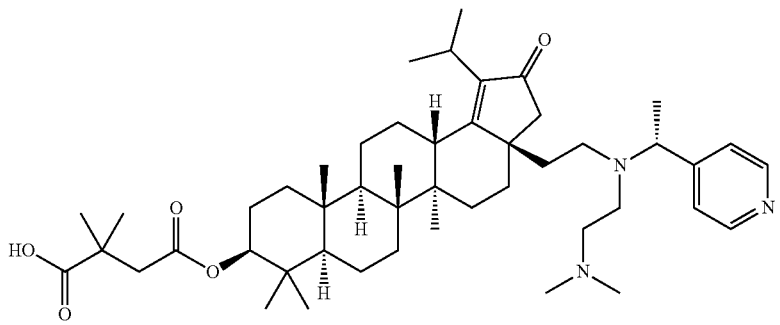

531

LC/MS: m/z calculated 773.6. found 774.7 (M+1)+.

Example 463

Compound 532

4-(((3aR,5aR,5bR,7aR,9S,11aR,11bR,13aS)-3a-((R)-2-(benzyl(2-morpholino-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

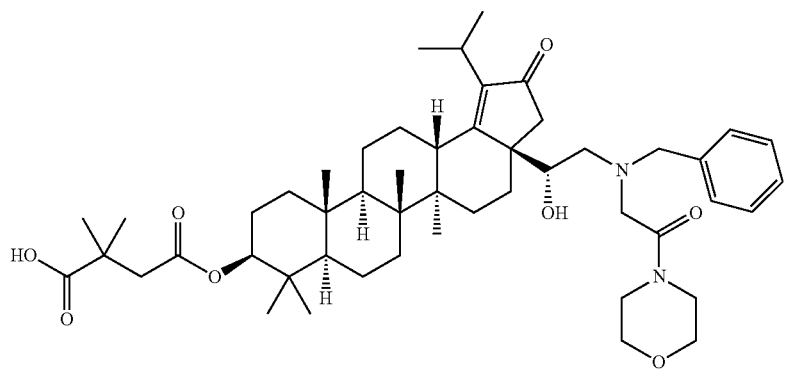

532

LC/MS: m/z calculated 830.5. found 831.5 (M+1)$^+$.

Example 464

Compound 533

4-(((3aR,5aR,5bR,7aR,9S,11aR,11bR,13aS)-3a-(2-((cyclopentylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

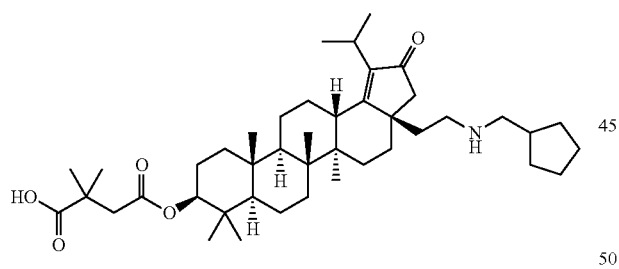

533

LC/MS: m/z calculated 679.5. found 680.7 (M+1)$^+$.

Example 465

Compound 534

4-(((3aR,5aR,5bR,7aR,9S,11aR,11bR,13aS)-3a-(2-(((1-acetylazetidin-3-yl)methyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

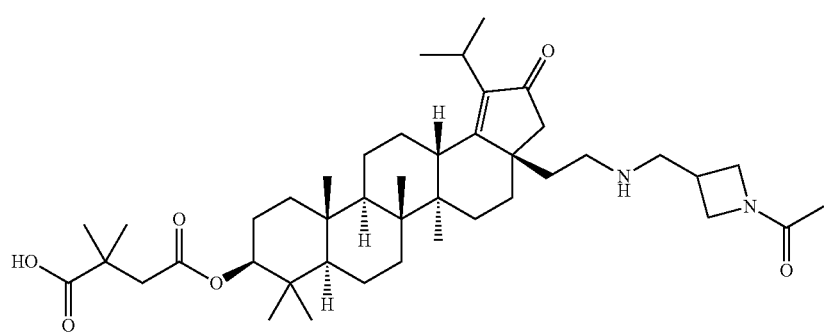

534

LC/MS: m/z calculated 708.5. found 709.7 (M+1)$^+$.

Example 466

Compound 535

4-(((3aR,5aR,5bR,7aR,9S,11aR,11bR,13aS)-3a-((R)-1-hydroxy-2-((2-((2-methoxyethyl)(methyl)amino)ethyl)(pyridin-2-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

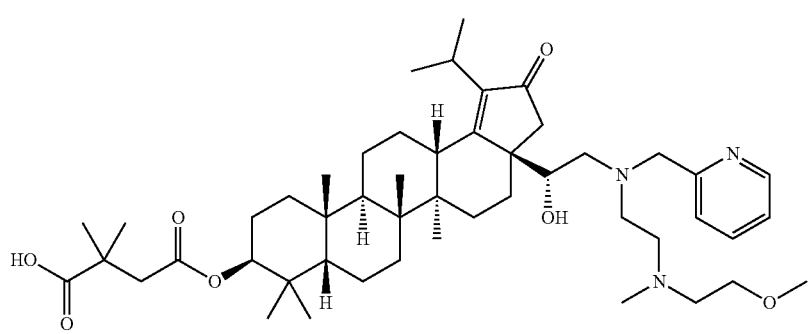

535

LC/MS: m/z calculated 819.6. found 820.5 (M+1)$^+$.

Example 467

Compound 536

4-(((3aR,5aR,5bR,7aR,9S,11aR,11bR,13aS)-3a-(2-(N-(2-(dimethylamino)ethyl)benzamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

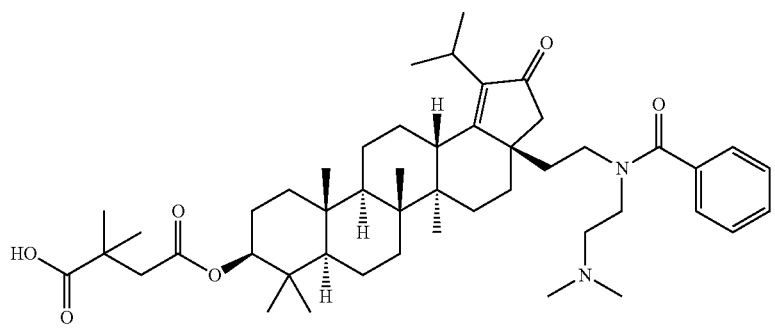

536

LC/MS: m/z calculated 772.5. found 773.5 (M+1)$^+$.

Example 468

Compound 537

4-(((3aR,5aR,5bR,7aR,9S,11aR,11bR,13aS)-3a-((R)-1-hydroxy-2-(((S)-1-(pyrimidin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

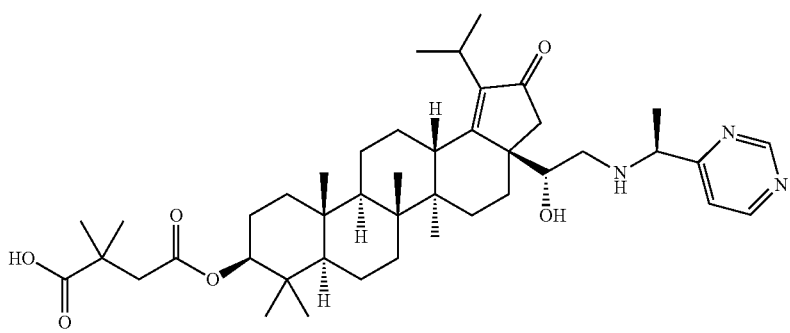

LC/MS: m/z calculated 719.5. found 720.5 $(M+1)^+$.

Example 469

Compound 538

4-(((3aR,5aR,5bR,7aR,9S,11aR,11bR,13aS)-1-isopropyl-5a,5b,8,8,11a-pentamethyl-2-oxo-3a-(2-((1-(pyridin-2-yl)cyclopropyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

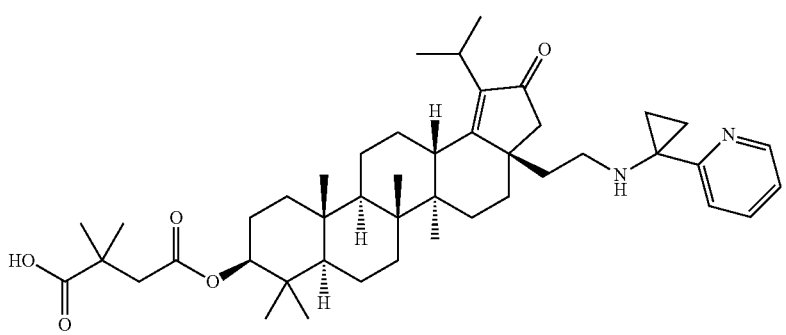

LC/MS: m/z calculated 714.5. found 715.5 $(M+1)^+$.

Example 471

Compound 540

4-(((3aR,5aR,5bR,7aR,9S,11aR,11bR,13aS)-1-isopropyl-5a,5b,8,8,11a-pentamethyl-2-oxo-3a-(2-(piperidin-1-yl)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

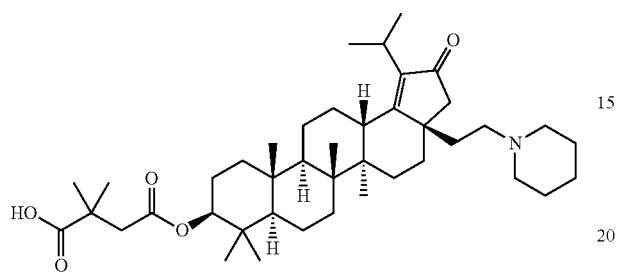

540

LC/MS: m/z calculated 665.5. found 666.5 (M+1)$^+$.

Example 472

Compound 541

4-(((3aR,5aR,5bR,7aR,9S,11aR,11bR,13aS)-1-isopropyl-5a,5b,8,8,11a-pentamethyl-2-oxo-3a-(2-(((S)-1-(pyridin-3-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

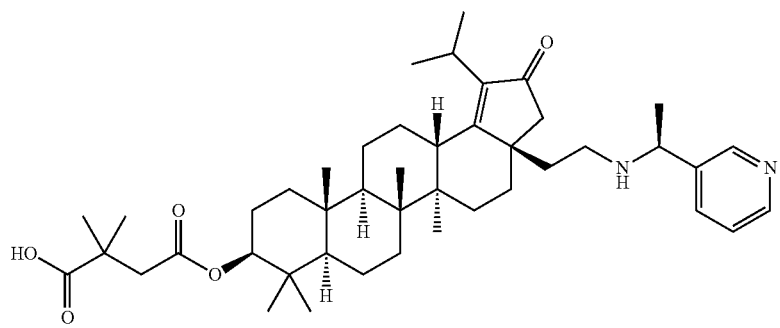

541

LC/MS: m/z calculated 702.5. found 703.4 (M+1)$^+$.

Example 473

Compound 542

4-(((3aR,5aR,5bR,7aR,9S,11aR,11bR,13aS)-3a-(2-((2-(dimethylamino)ethyl)((S)-1-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

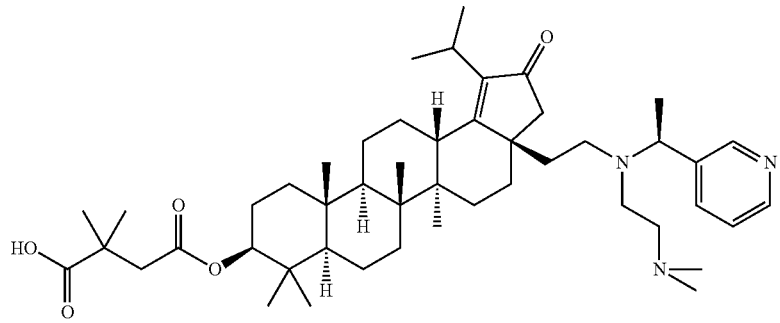

542

LC/MS: m/z calculated 773.6. found 774.7 (M+1)$^+$.

Example 474

Compound 543

4-(((3aR,5aR,5bR,7aR,9S,11aR,11bR,13aS)-3a-(2-((2-(dimethylamino)ethyl)((R)-1-(pyridin-3-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

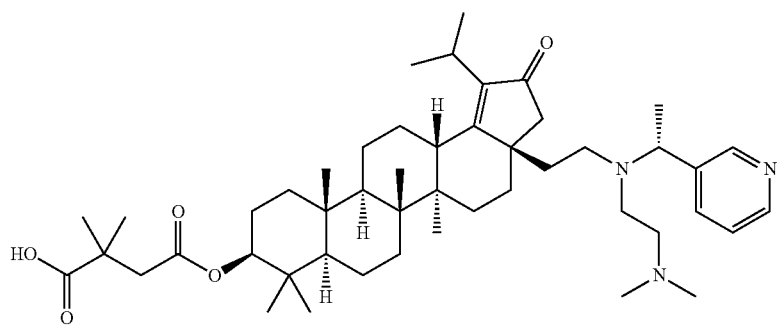

543

LC/MS: m/z calculated 773.6. found 774.7 (M+1)$^+$.

Example 475

Compound 544

4-(((3aR,5aR,5bR,7aR,9S,11aR,11bR,13aS)-3a-((R)-1-hydroxy-2-(((R)-1-(pyrimidin-5-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

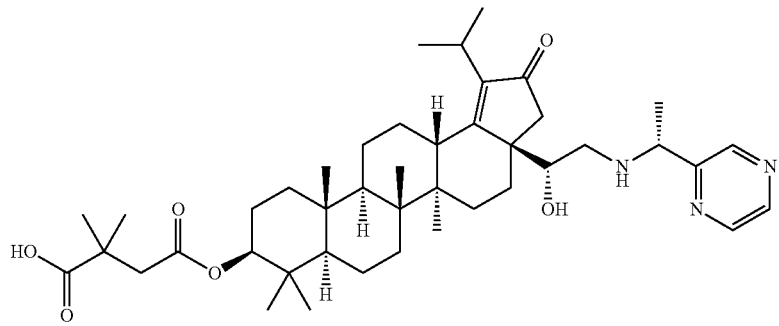

544

LC/MS: m/z calculated 719.5. found 719.8 (M+1)$^+$.

Example 476

Compound 545

4-(((3aR,5aR,5bR,7aR,9S,11aR,11bR,13aS)-3a-((R)-2-(N-(2-chlorobenzyl)acetamido)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

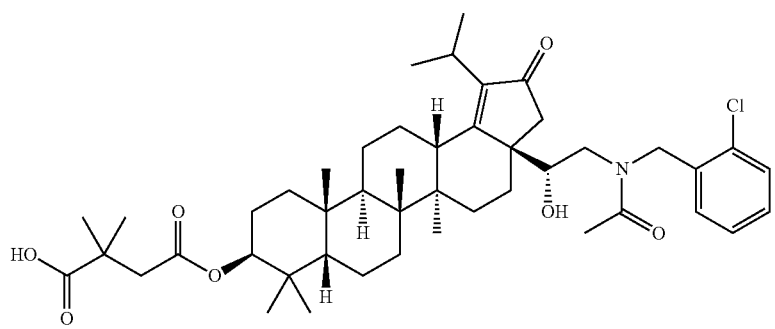

545

LC/MS: m/z calculated 779.4. found 780.3 $(M+1)^+$.

Example 477

Compound 546

4-(((3aR,5aR,5bR,7aR,9S,11aR,11bR,13aS)-3a-((R)-2-((4-chlorobenzyl)(2-(2-oxopyrrolidin-1-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

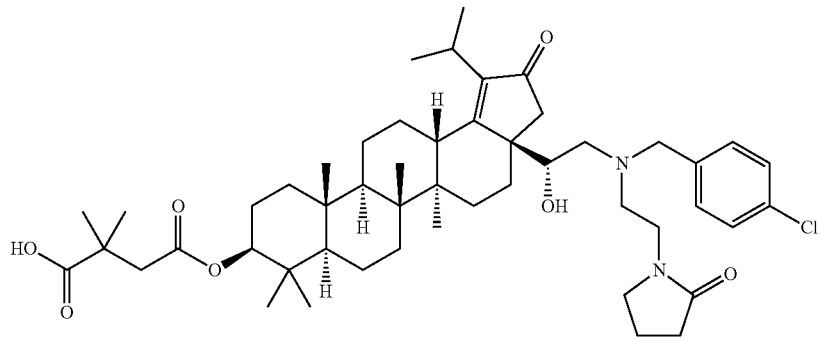

546

LC/MS: m/z calculated 848.5. found 849.5 $(M+1)^+$.

Example 478

Compound 547

4-(((3aR,5aR,5bR,7aR,9S,11aR,11bR,13aS)-1-iso-propyl-5a,5b,8,8,11a-pentamethyl-3a-(2-((oxetan-3-ylmethyl)amino)ethyl)-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

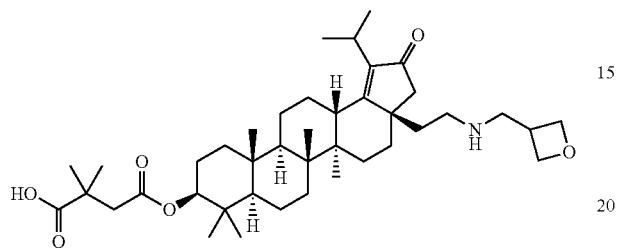

547

LC/MS: m/z calculated 667.5. found 668.4 (M+1)$^+$.

Example 479

Compound 548

4-(((3aR,5aR,5bR,7aR,9S,11aR,11bR,13aS)-1-iso-propyl-5a,5b,8,8,11a-pentamethyl-2-oxo-3a-(2-(((S)-1-(pyridin-2-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

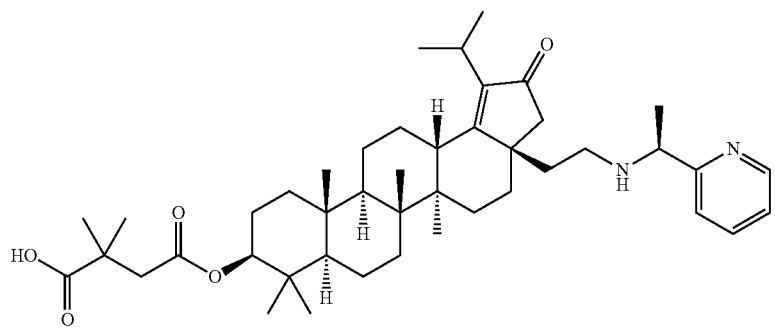

548

LC/MS: m/z calculated 702.5. found 703.5 (M+1)$^+$.

Example 480

Compound 549

4-(((3aR,5aR,5bR,7aR,9S,11aR,11bR,13aS)-1-iso-propyl-5a,5b,8,8,11a-pentamethyl-2-oxo-3a-(2-(((S)-1-(pyridin-4-yl)ethyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

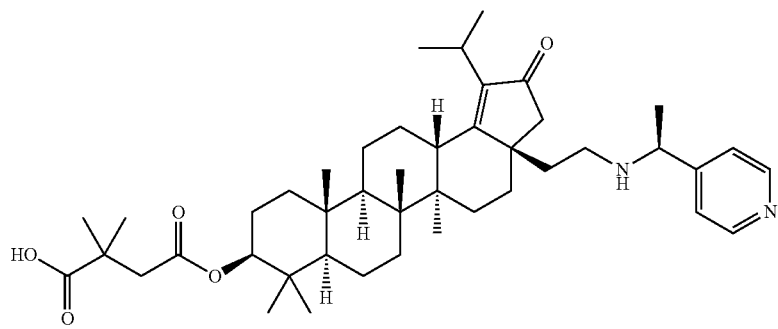

549

LC/MS: m/z calculated 702.5. found 703.4 (M+1)$^+$.

Example 481

Compound 550

4-(((3aR,5aR,5bR,7aR,9S,11aR,11bR,13aS)-3a-((R)-2-((2-(dimethylamino)ethyl)((R)-1-(pyrimidin-4-yl)ethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

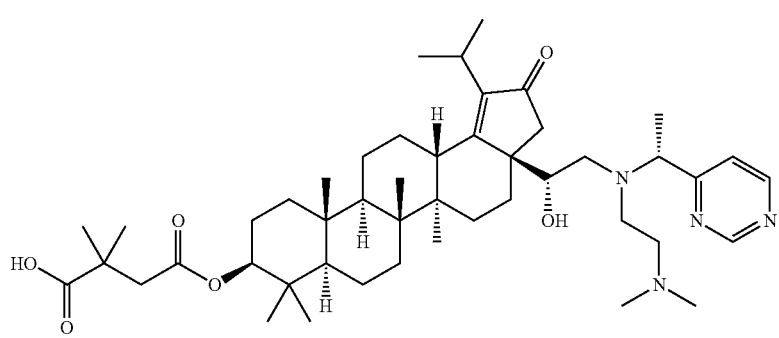

550

LC/MS: m/z calculated 790.6. found 791.5 (M+1)$^+$.

Example 482

Compound 551

4-(((3aR,5aR,5bR,7aR,9S,11aR,11bR,13aS)-3a-(2-((2-(dimethylamino)ethyl)(1-(pyridin-2-yl)cyclopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

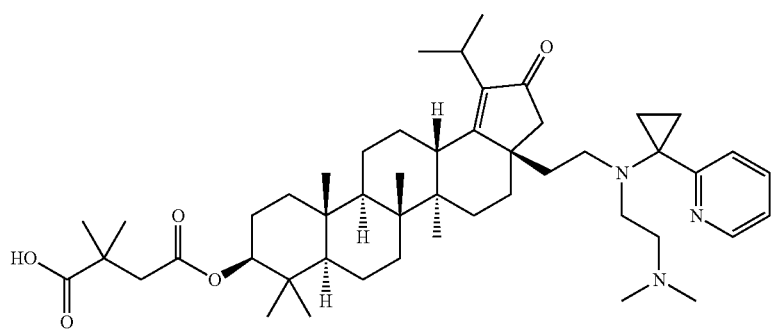

551

LC/MS: m/z calculated 785.6. found 786.5 (M+1)$^+$.

Example 483

Compound 552

4-(((3aR,5aR,5bR,7aR,9S,11aR,11bR,13aS)-1-isopropyl-5a,5b,8,8,11a-pentamethyl-2-oxo-3a-(2-((2-(pyridin-2-yl)propan-2-yl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

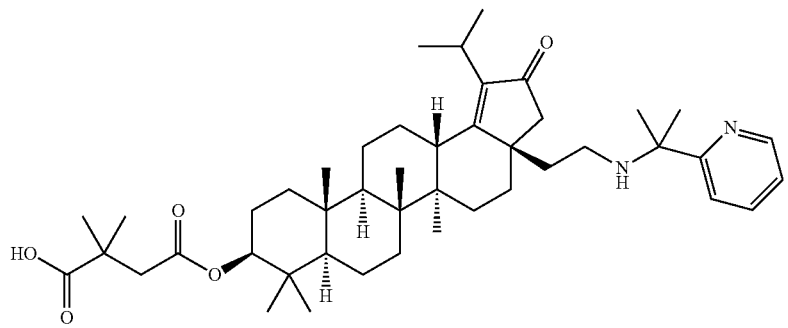

552

LC/MS: m/z calculated 716.5. found 717.5 (M+1)+.

Example 484

Compound 553

4-(((3aR,5aR,5bR,7aR,9S,11aR,11bR,13aS)-3a-(2-((2-(dimethylamino)ethyl)(oxetan-3-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

553

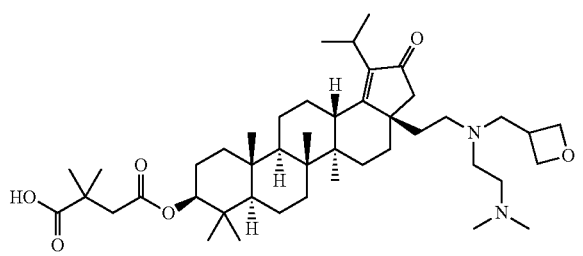

LC/MS: m/z calculated 738.5. found 739.5 (M+1)+.

Example 485

Compound 554

4-(((3aR,5aR,5bR,7aR,9S,11aR,11bR,13aS)-3a-(2-((2-(dimethylamino)ethyl)((S)-1-(pyridin-2-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

554

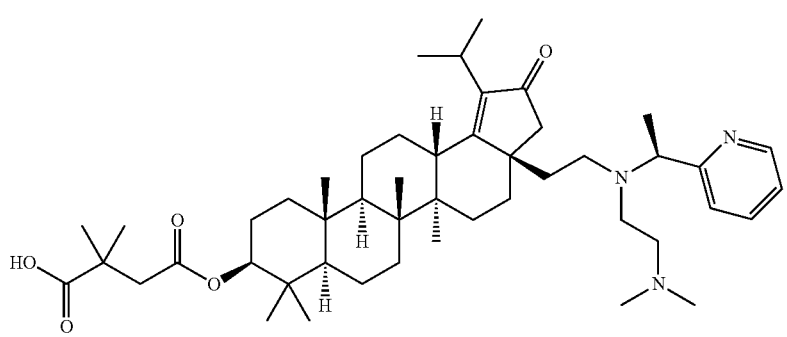

LC/MS: m/z calculated 773.6. found 774.5 (M+1)+.

Example 486

Compound 555

4-(((3aR,5aR,5bR,7aR,9S,11aR,11bR,13aS)-3a-(2-((2-(dimethylamino)ethyl)((S)-1-(pyridin-4-yl)ethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

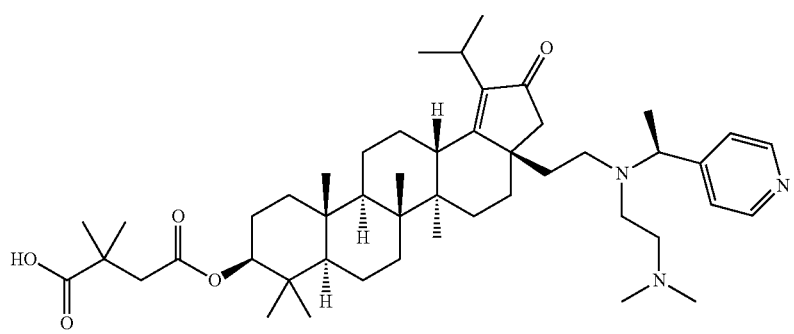

555

LC/MS: m/z calculated 773.6. found 774.5 $(M+1)^+$.

Example 487

Compound 556

4-(((3aR,5aR,5bR,7aR,9S,11aR,11bR,13aS)-1-isopropyl-5a,5b,8,8,11a-pentamethyl-2-oxo-3a-(2-((1-(pyrimidin-2-yl)cyclopropyl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

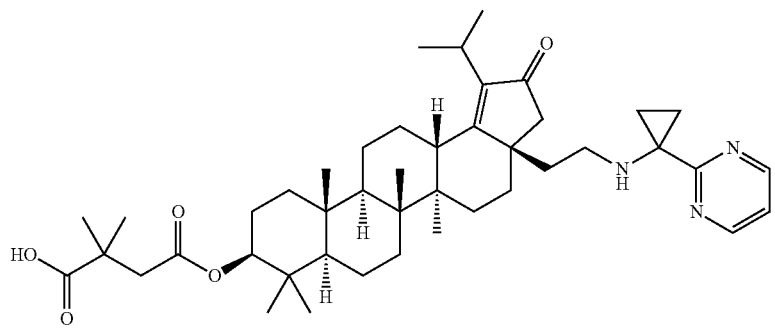

556

LC/MS: m/z calculated 715.5. found 716.5 $(M+1)^+$.

Example 488

Compound 557

4-(((3aR,5aR,5bR,7aR,9S,11aR,11bR,13aS)-3a-(2-((2-(dimethylamino)ethyl)(1-(pyrimidin-2-yl)cyclopropyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

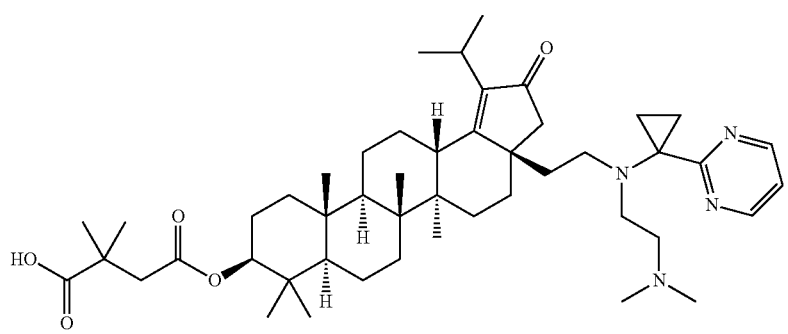

557

LC/MS: m/z calculated 786.6. found 787.5 (M+1)$^+$.

Example 489

Compound 558

4-(((3aR,5aR,5bR,7aR,9S,11aR,11bR,13aS)-3a-(2-(N-(2-(dimethylamino)ethyl)picolinamido)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

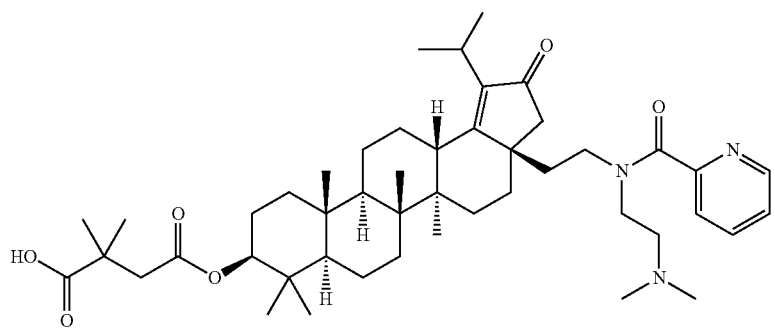

558

LC/MS: m/z calculated 773.5. found 774.5 (M+1)$^+$.

Example 490

Compound 559

4-(((3aR,5aR,5bR,7aR,9S,11aR,11bR,13aS)-1-isopropyl-5a,5b,8,8,11a-pentamethyl-2-oxo-3a-(2-((2-(pyridin-3-yl)propan-2-yl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

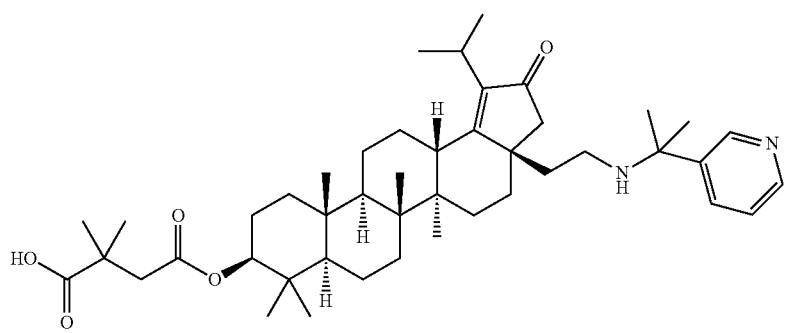

LC/MS: m/z calculated 716.5. found 717.5 (M+1)$^+$.

Example 491

Compound 560

4-(((3aR,5aR,5bR,7aR,9S,11aR,11bR,13aS)-1-isopropyl-5a,5b,8,8,11a-pentamethyl-2-oxo-3a-(2-((2-(pyridin-4-yl)propan-2-yl)amino)ethyl)-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

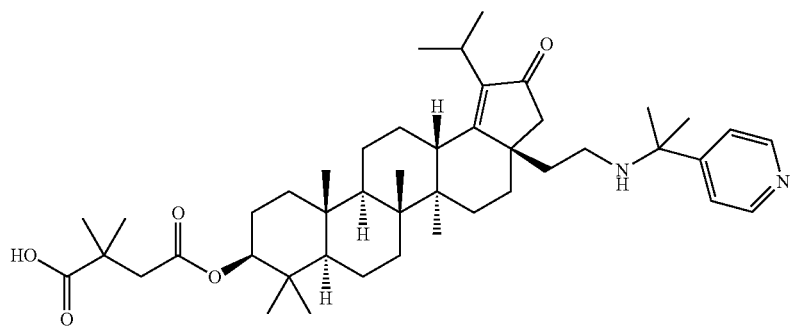

LC/MS: m/z calculated 716.5. found 717.5 (M+1)$^+$.

Example 492

Compound 561

4-(((3aR,5aR,5bR,7aR,9S,11aR,11bR,13aS)-3a-((R)-2-(benzyl(2-(4-methylpiperazin-1-yl)-2-oxoethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

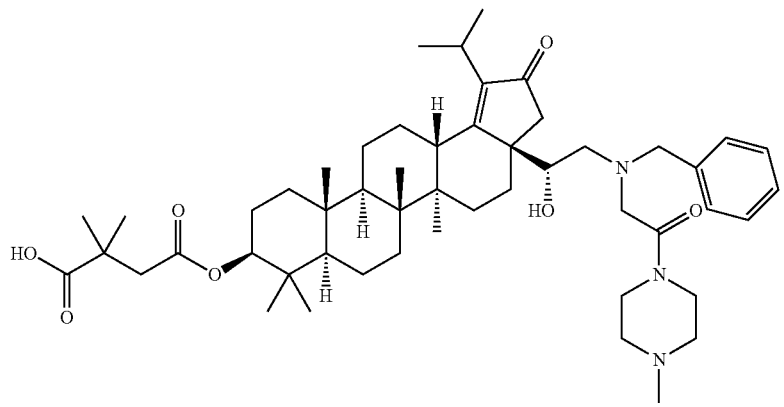

561

LC/MS: m/z calculated 843.6. found 844.5 (M+1)$^+$.

Example 493

Compound 562

4-(((3aR,5aR,5bR,7aR,9S,11aR,11bR,13aS)-3a-((R)-2-((2-(dimethylamino)ethyl)(oxazol-4-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

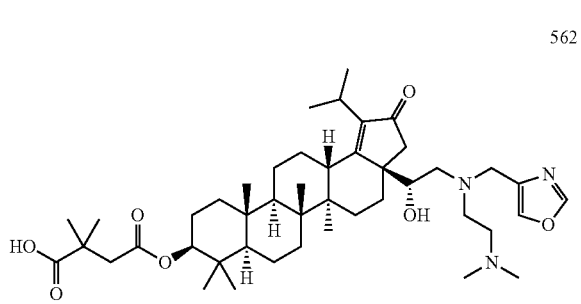

562

LC/MS: m/z calculated 765.5. found 766.5 (M+1)$^+$.

Example 494

Compound 563

4-(((3aR,5aR,5bR,7aR,9S,11aR,11bR,13aS)-3a-(2-((2-(dimethylamino)ethyl)(2-(pyridin-2-yl)propan-2-yl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

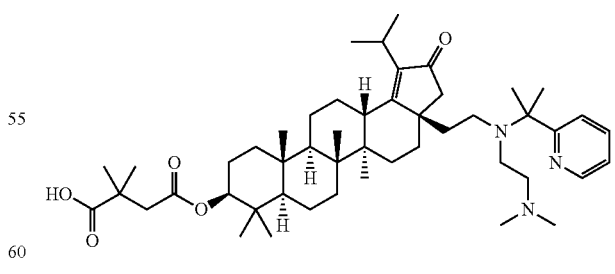

563

LC/MS: m/z calculated 787.6. found 788.5 (M+1)$^+$.

Example 495

Compound 564

4-(((3aR,5aR,5bR,7aR,9S,11aR,11bR,13aS)-3a-(2-((2-(dimethylamino)-2-oxoethyl)(pyridin-4-ylmethyl)amino)ethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

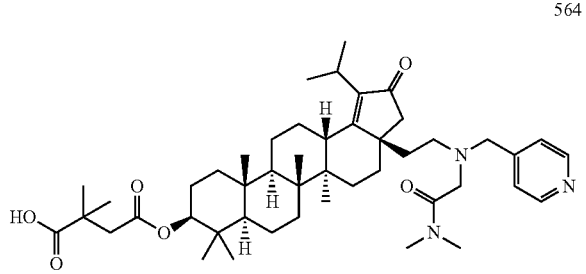

564

LC/MS: m/z calculated 773.6. found 774.5 (M+1)$^+$.

Example 496

Compound 565

4-(((3aR,5aR,5bR,7aR,9S,11aR,11bR,13aS)-3a-((R)-2-((2-(dimethylamino)ethyl)(oxazol-5-ylmethyl)amino)-1-hydroxyethyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)-2,2-dimethyl-4-oxobutanoic acid

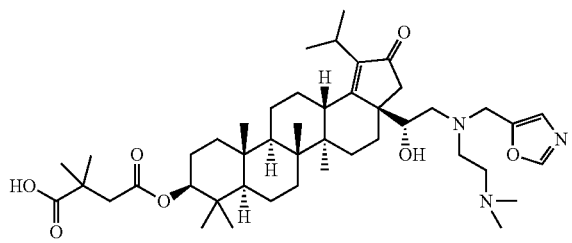

565

LC/MS: m/z calculated 765.5. found 766.5 (M+1)$^+$.

Methods for the preparation of the betulin derivatives, including the compounds of formula (I) and formula (II) are described in WO2013090664 deriving from U.S. Provisional Application 61/576,448, filed Dec. 16, 2011, which is incorporated herein by reference in its entirety.

The pharmaceutical compositions of the invention are presented as pharmaceutical compositions suitable for parenteral administration. The compositions may also include a safe and effective amount of other active ingredients, such as antimicrobial agents, antiviral agents, or preservatives.

It will be appreciated by those skilled in the art that the amount of active ingredients required for use in treatment will vary according to a variety of factors, including the nature of the condition being treated and the age and condition of the patient, and will ultimately be at the discretion of the attending physician, veterinarian or health care practitioner.

Compositions of the present invention enable patients greater freedom from multiple dosage regimens and ease the needed diligence required in remembering complex daily dosing times and schedules. The compositions of the present invention are particularly suitable for administration as a single dose monthly, bi-monthly or tri-monthly, or at any interval between 30 and 365 days, including every six or twelve months.

Advantageously, the compositions of the present invention may be administered once per month.

The compositions of the present invention may be used in combination with other pharmaceutical formulations as a component of a multiple drug treatment regimen. Such combinations could be administered to a subject in one dosage unit, such as a fixed dose combination or it could be administered in separate dosage units.

Compositions of the present invention may also be packaged as articles of manufacture comprising a therapeutically effective amount of a compound of formula (I), or a pharmaceutically acceptable salt thereof; and therapeutically effective amount of one or more of the following: nucleoside reverse transcriptase inhibitor, non-nucleoside reverse transcriptase inhibitor, protease inhibitor, and integrase inhibitor.

In one embodiment, the compositions of the present invention could be administered to a subject in combination with one or more of the following HIV treatment compounds: dolutegravir, rilpivirine, and/or a compound having the following structure:

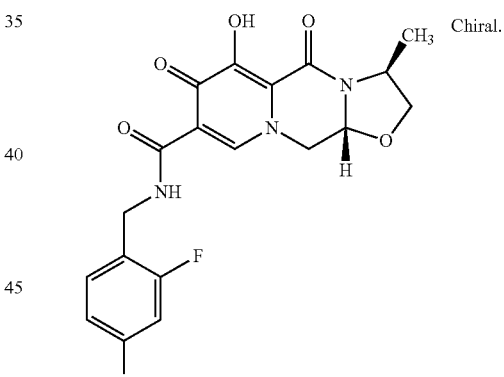

The packaging material may also have labelling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with a pharmaceutical article of manufacture. The package insert and any article of manufacture labelling provides information relating to the pharmaceutical composition. The information and labelling provides various forms of information utilized by health-care professionals and patients, describing the composition, its dosage and various other parameters required by regulatory agencies such as the United States Food and Drug Agencies.

The present invention further provides the following embodiments:

(a) A parenteral pharmaceutical composition comprising an effective amount of compound of formula (I) or a pharmaceutically acceptable salt thereof, for the long term treatment of HIV infection, or prevention of HIV infection in an individual at risk of being infected by HIV, wherein the composition is administered intermittently at a time interval of at least one week.
(b) The composition according to (a) wherein the composition is administered once every two weeks.
(c) The composition according to (a) wherein the composition is administered once every month.
(d) The composition according to any one of (a) to (c) wherein the effective amount of compound of formula (I) or a pharmaceutically acceptable salt thereof is selected such that the blood plasma concentration of compound of formula (I) in a subject is kept during a prolonged period of time at a level between a maximum blood plasma level which is the blood plasma level that causes significant side effects and the minimum blood plasma level that is the lowest blood plasma level that causes a compound of formula (I) to provide effective treatment or prevention of HIV infection.
(e) The composition according to (d) wherein the blood plasma level of a subject is kept at a level equal to or above about 150 ng/ml, in particular equal to or above about 600 ng/ml.
(f) The composition according to any one of (a) to (e), wherein the composition is administered subcutaneously or intramuscularly.
(g) The composition according to any one of (a) to (f), which comprises the aforementioned surfactant system comprising polysorbate and/or polyvinylpyrrolidone.
(h) A method for the treatment or prevention of an HIV infection in a human comprising a pharmaceutical composition according to any of the above (a) to (g).

The dose of a compound of formula (I) administered, which is the amount of compound (I) in the parenteral composition for use in the invention, may be selected such that the blood plasma concentration of compound (I) in a subject is kept during a prolonged period of time above a minimum blood plasma level. The term "minimum blood plasma level" (or $C_{min}$) in this context refers to the lowest efficacious blood plasma level, that is, the blood plasma level of compound (I) that provides effective prevention or treatment HIV infection. In the case of transmission of HIV from an individual infected by HIV to an individual not infected by HIV, this is the lowest blood plasma level that is effective in inhibiting said transmission.

The blood plasma level of compound (I) in a subject may be kept at a level above a minimum blood plasma level of about 170 ng/ml, about 700 ng/ml, or about 1000 ng/ml. The blood plasma levels of compound (I) in a subject may be kept above these minimum blood plasma levels because at lower levels the drug may no longer be effective, thereby increasing the risk of transmission of HIV infection, and may be suboptimal for treatment of HIV infected subjects. Plasma levels of compound (I) may be kept at higher levels to avoid the development of HIV mutations, while maintaining a safety margin.

An advantage of the mode of administration of compound (I) is that high $C_{min}$ levels can be achieved without a commensurate high $C_{max}$, which could mitigate potential side effects associated with $C_{max}$.

The effective amount of compound (I) to be administered may be selected such that the blood plasma concentrations in a subject are kept during a prolonged period of time at a level between a maximum plasma level (or $C_{max}$) and the minimum blood plasma level (or $C_{min}$).

In some embodiments the blood plasma level of compound (I) in a subject may be kept between the minimum blood plasma level (or $C_{min}$ as specified above) and the lower maximum plasma level of compound (I) (or $C_{max}$) which is defined as the level that corresponds to the lowest blood plasma level where compound (I) acts therapeutically. The lowest level where compound (I) acts therapeutically is the lowest blood plasma level that is effective in inhibiting replication of HIV in individuals infected by HIV so that the viral load of HIV is relatively low, for example where the viral load (represented as the number of copies of viral RNA in a specified volume of serum) is below about 200 copies/ml, in particular below about 100 copies/ml, more particularly below 50 copies/ml, specifically below the detection limit of the assay for HIV.

As mentioned above, the blood plasma levels of compound (I) depend on the amount of active ingredient in each parenteral dosage administered. However, it also depends on the frequency of the administrations (i.e. the time interval between each administration). Both parameters can be used to direct the blood plasma levels to the desired values. The dose may be higher where administrations are less frequent.

Although the plasma levels of compound (I) should remain below a maximum or above a minimum value, they may surpass the maximal value or drop below the minimal value during relatively short periods of time, which may be as short as possible. The maximum and minimum plasma levels therefore can be expressed as mean plasma levels during a certain period of time.

In some instances there may be a small initial plasma concentration peak shortly after administration, after which the plasma levels achieve a steady-state.

The compositions of the present invention conveniently allow administration of the compound of Formula I (or any compound in table 1) in unit dosage form containing, for example, from about 1 mg to about 1000 mg, from about 20 mg to about 100 mg, from about 20 mg to about 300 mg, from about 25 mg to about 800 mg, from about 25 mg to about 100 mg, from about 100 mg to about 200 mg, from about 200 mg to about 400 mg, from about 100 mg to about 800 mg, from about 100 mg to about 600 mg, from about 100 mg to about 400 mg per unit dosage form, or from about 400 mg to about 800 mg. In one embodiment, the unit dose is from about 100 mg to about 200 mg, which is administered to the subject once every month. In some embodiments, there could be an initially loading dose that is substantially higher than the later maintenance dose. Therefore, in one embodiment, the compound of Formula I is administered initially to the subject as a loading dose in amount that ranges from 400 mg to 800 mg and then is administered as a maintenance dose thereafter in an amount that ranges from about 20 mg to about 300 mg. In another embodiment, the subject could be dosed initially with 800 mg, then dosed at 100 mg thereafter.

The unit dose concentration of the compound of Formula I (or any compound in table 1) in the formulation may be selected from any of the following ranges: 0.05-0.5 µM, 0.5 to 1 µM, 1-5 µM, 5-25 µM, 25-50 µM, or 50-150 µM.

The dose to be administered may be calculated on a basis of about 1 mg/day to about 50 mg/day, preferably 3 mg/day to about 30 mg/day. This corresponds to a weekly dose of about 7 mg to about 350 mg, preferably about 20 mg to about 200 mg, or to a monthly dose of about 30 mg to about 1500 mg, preferably about 90 mg to about 900 mg. Doses for other dosing regimens can readily be calculated by multiplying the daily dose with the number of days between each administration.

The dose to be administered may be calculated on a basis of about 0.001 mg/kg/day to about 1 mg/kg/day, preferably 0.05 mg/kg/day to about 0.5 mg/kg/day. This corresponds to a weekly dose of about 0.5 mg to about 500 mg, preferably about 20 mg to about 200 mg, or to a monthly dose of about 30 mg to about 1500 mg, preferably about 90 mg to about 900 mg. Doses for other dosing regimens can readily be calculated by multiplying the daily dose with the number of days between each administration.

Once administered, the blood plasma levels of compound (I) in a subject may be more or less stable. After initial rise of the blood plasma levels, a steady state mode may be achieved during a prolonged period of time. By "steady state" is meant the condition in which the amount of drug present in the blood plasma of a subject stays at more or less the same level over a prolonged period of time. The plasma levels of compound (I) may then gradually decrease over time, and when the minimum plasma level is reached, then the next dose of compound (I) may be administered. The term "stays at more or less the same level" does not exclude that there can be small fluctuations of the plasma concentrations within an acceptable range, for example, within about 30%, about 20%, or about 10%.

The parenteral compositions of compound (I) may be administered by intravenous injection or, preferably by subcutaneous or intramuscular administration.

The present invention is based on the use of parenteral compositions of the active ingredient compound (I) and therefore the nature of the carrier is selected for suitability for parenteral administration. The carrier in most cases will comprise sterile water, in although other ingredients, for example, to aid solubility, may be included. Injectable solutions or suspensions, for example, may be prepared in which the carrier comprises saline solution, glucose solution or a mixture of saline and glucose solution. Further, the carrier may contain the surfactant system mentioned above such as polysorbate and polyethyleneglycol.

The parenteral pharmaceutical composition comprising compound (I) of the present invention is long-acting. Accordingly, the composition is useful for the treatment or prevention of HIV infection with administration at long time intervals, compared with conventional compositions or with other compounds similar to compound (I) in chemical structure. The compositions of the present invention can be intermittently administered to a patient, e.g., once per week, once per month, once per every 2 months, or one per every 3 months. In one embodiment, the compositions of the present invention could be administered at higher dosages (e.g., 800 mg) as a "loading dose" for the first one to three months, while after the first one to months the dosage could be lowered.

Therefore, the compositions of the present invention and an administration by subcutaneous (SC) or intramuscular (IM) injection using the same can lead to a remarkable reduction in medication (pill) burden or difficulty in patient compliance. Further, such intermittent administration of a composition of the present invention can contribute to maintaining therapy at appropriate compliance which leads to prevention of emergence of drug resistant HIV and maintaining the efficacy of therapy for an extended period of time.

In embodiment, the compound of Formula I formulation is a liquid suspension form for a bolus intramuscular or subcutaneous administration at a concentration ranges from 10 mg/ml to 250 mg/ml and having an injection volume of up to 4 ml (e.g., 2 injections, each 2 ml).

EXAMPLES

The following examples further describe and exemplify particular embodiments within the scope of the present Invention. The examples are given solely for illustration and are not to be construed as limitations as many variations are possible without departing from spirit and scope of the Invention.

The compound of Formula I, may be synthesized by one of skill in the art by following the teachings of PCT Published Application No. WO WO2013090664 deriving from U.S. Provisional Application 61/576,448, filed Dec. 16, 2011 which disclose a class of compounds useful in the treatment of HIV infection and AIDS.

A Thermo Orion 9110DJWP microelectrode and a Metrohmn 827 pH Meter were used for pH measurements. An Advanced Micro-Osmometer 3320 was used for osmolarity measurements. A Retsch PM400 planetary mill was used for wet bead milling.

Example 1

Preparation of LAP Vehicle 1.0 g of Polysorbate 80 was added to a 0.5 L volumetric flask. About 100 mL of Water for Injection (WFI) was added to the flask to dissolve. 8.5 g of Plasdone K29/32 was added to the flask with an additional 300 mL of WFI. The contents were stirred with a stir bar to dissolve. Phosphate buffer: 0.11039 g $NaH_2PO_4$; 0.27598 g $NaH_2PO_4:H_2O$; and 0.22572 g $Na_2HPO_4$ along with 4.16389 g NaCl as isotonicity agent was added. The mixture was again stirred to dissolve and then was q.s. to 500 mL. The solution was filtered through a 0.22 micrometer Corning filter. The resultant LAP vehicle was 1.7% w/v Plasdone K29/32 and 0.2% w/v Polysorbate 80 in phosphate buffer: 0.004M $NaH_2Po_4$ and 0.006M $Na_2HPO_4$.

Example 2

Homogenized Suspension Compositions (a) 2.5 mg/ml Homogenized Solution of the Compound of Formula I in LAP Vehicle for Subcutaneous Injection (SQ)

17.5 mg of the compound of Formula (I) was added to a clear 10 ml sterile vial with a crimp cap. The LAP Vehicle (as prepared in Example 1) was added to a weight of 7 grams. The solution was homogenized using a handheld Polytron PT1200F homogenizer for 1-2 minutes with a speed increasing from low to near max. The solution was then stirred at ambient room temperature. The resulting title solution had an osmolarity of 299 mOsm/kg and pH of 6.92. The solution was utilized for 5 mg/kg SQ injections.

(b) 10.0 mg/ml Homogenized Solution of the Compound of Formula I in LAP Vehicle for SC and IM (Intra-Muscular) Injection 80 mg of the compound of Formula (I) was added to a clear 10 ml sterile vial with a crimp cap. The LAP Vehicle (as prepared in Example 1) was added to a weight of 8 grams. The solution was homogenized using a handheld Polytron PT1200F homogenizer for 1-2 minutes with a speed increasing from low to near max. The solution was then stirred at ambient room temperature. The resulting title solution had an osmolarity of 300 mOsm/kg and pH of 7.25. The solution was utilized for 5 mg/kg IM injections and 20 mg/kg SQ injections.

(c) 25.0 mg/ml Homogenized Solution of the Compound of Formula I in LAP Vehicle for SC and IM (Intra-Muscular) Injection 250 mg of the compound of Formula (I) was added to a clear 20 ml sterile vial with a crimp cap. The LAP Vehicle (as prepared in Example 1) was added to a weight of 10 grams. The solution was homogenized using a handheld Polytron PT1200F homogenizer for 1-2 minutes with a speed increasing from low to near max. The solution was then stirred at ambient room temperature. The resulting title solution had an osmolarity of 323 mOsm/kg and pH of 7.68. The solution was utilized for 2.5 mg/kg IM injections and 2.5 mg/kg SQ injections.

(d) 40.0 mg/ml Homogenized Solution of the Compound of Formula I in LAP Vehicle for IM Injection 160 mg of the compound of Formula (I) was added to a clear 5 ml sterile vial with a crimp cap. The LAP Vehicle (as prepared in Example 1) was added to a weight of 4 grams. The solution was homogenized using a handheld Polytron PT1200F homogenizer for 1-2 minutes with a speed increasing from low to near max. The solution was then stirred at ambient room temperature. The resulting title solution had an osmolarity of 329 mOsm/kg and pH of 7.87. The solution was used for 20 mg/kg IM injections.

Example 3

Wet Bead Milling Formulations

(a) Preparation of Wet Bead Milled Stock Suspension of the Compound of Formula I in LAP Vehicle 500 mg of the compound of Formula I is weighed into a 50 mL milling vessel. compound of Formula I was added to a clear 10 ml sterile vial with a crimp cap. The LAP Vehicle (as prepared in Example 1) was added to a weight of 10 grams thereby yielding a 100 mg/ml suspension. Beads were added at 4× suspension volume and the milling vessel was sealed with security tape. Milling was started at 250 rμm for 3 hours using a planetary mill PM400 with a 15 minute interval. After 3 hours the milling vessel was left in the planetary mill overnight at ambient room temperature. The beads were filtered using a 25 mm Easy pressure Syringe Filter Holder (screen size:149 micrometers). A milky suspension was collected and stirred with a stir bar to defoam. The resulting wet bead milled (WBM) suspension had an osmolarity of 303 mOsm/kg and pH of 7.2. The solution was utilized for preparing the WBM suspensions following.

(b) 10.0 mg/ml WBM Suspension of the Compound of Formula I in LAP Vehicle for IM Injection 0.426 g of WBM suspension of Example 3(a) was added to a clear 5 ml sterile vial with a crimp cap. The LAP Vehicle (as prepared in Example 1) was added to a weight of 2 grams. The contents were swirled to mix. The resulting title solution had a pH of 6.87. The solution was utilized for 5 mg/kg IM injections.

(c) 2.5 mg/ml WBM Suspension of the Compound of Formula I in LAP Vehicle for SQ Injection 0.266 g of WBM suspension of Example 3(a) was added to a clear 10 ml sterile vial with a crimp cap. The LAP Vehicle (as prepared in Example 1) was added to a weight of 5 grams. The contents were swirled to mix. The resulting title solution had a pH of 6.78. The solution was utilized for 5 mg/kg SQ injections.

Injections were made in Sprague-Dawley rats SQ and IM at 5 and 20 mg/kg doses with $T_{1/2}$, $C_{max}$, $T_{max}$, and AUC being measured. Results are shown in Table 2 and FIG. 1, In FIG. 1 the human protein adjusted $IC_{90}$=4.31 ng/mL; the y-axis was a LAP concentration mean (n=3 per IM/SQ route); $T_{1/2}$ IV=3.4 hours; and $AUC_{0-24}$ IV=2.96 hr*microgram/mL.

TABLE 2

| Route of Administration | Dose | $T_{1/2}$ (days) | $C_{max}$ (ng/ml) | $T_{max}$ (h) | $AUC_{0-t}$ (h * μg/ml) |
|---|---|---|---|---|---|
| SQ | 5 | 5.0 ± 2.2 | 170.3 ± 9.2 | 6.7 ± 2.3 | $^a$8.0 ± 0.5 |
|  | 20 | 19.3 ± 9.5 | 284.7 ± 48.4 | 6.7 ± 2.3 | $^b$23.9 ± 7.2 |
| IM | 5 | 6.2 ± 2.5 | 100.3 ± 7.8 | 5.3 ± 2.3 | $^c$7.7 ± 1.0 |
|  | 20 | 12.4 ± 5.1 | 177.7 ± 56.9 | 8.0 ± 4.0 | $^d$24.9 ± 9.5 |

$^a$= 24 days;
$^b$= 57 days;
$^c$= days; and
$^d$= 42 days

Figure 2:
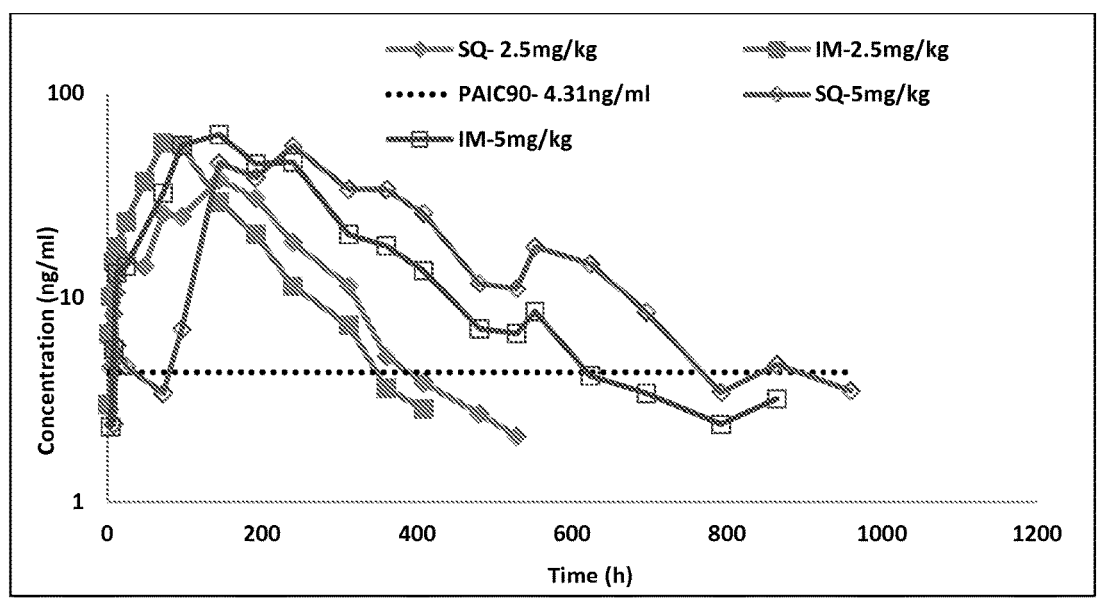
FIG. 2 depicts a plot of LAP Mean Concentration of a compound of Formula I versus time in hours of a LAP Dog PK study at 2.5 mg/kg and 5 mg/kg doses.

Injections were also made in Beagle dogs SQ and IM at 5 and 20 mg/kg doses with $T_{1/2}$, $C_{max}$, $T_{max}$, and AUC measured. Results are shown in Table 3 and FIG. 2. In FIG. 2 the human protein adjusted $IC_{90}$=4.31 ng/mL; the y-axis was a LAP concentration mean (n=3 per IM/SQ route); $T_{1/2}$ IV=6.9 hours; and $AUC_{0-24}$ IV=4.15 hr*microgram/mL.

TABLE 3

| Route of administration | Dose mg/kg | $T_{1/2}$ (days) | $C_{max}$ (ng/ml) | $T_{max}$ (h) | $AUC_{0-t}$ (h * μg/ml) |
|---|---|---|---|---|---|
| SQ | 2.5 | 4 ± 3 | 38.0 ± 11.0 | 144 ± 0 | $^a$7.9 ± 1.9 |
|  | 5 | 5.3 ± 2.3 | 59.0 ± 14.5 | 208 ± 55.4 | $^b$17.4 ± 1.4 |
| IM | 2.5 | 3 ± 3 | 59.3 ± 23.2 | 80.0 ± 13.9 | $^c$8.6 ± 2.0 |
|  | 5 | 4.9 ± 1.1 | 69.7 ± 7.2 | 128.0 ± 27.7 | $^d$16.2 ± 1.9 |

$^a$= 22 days;
$^b$= 40 days;
$^c$= 17 days; and
$^d$= 36 days

Example 4

Experimental Procedure for Rat LAP Study

For one formulation, if a particle size ($D_{50}$) of >1 μm is desired, the drug (compound of Formula I) is either directly suspended into the aqueous buffer solution, or firstly milled by air milling into a more desirable particle size then followed by the suspension. In such cases, the suspension was prepared by weighing the drug and the buffer solution components into a suitable container followed by adding water for injection. The mixture was then vortexed until a uniform suspension was formed without visible agglomerates. Additional water for injection was then added to the target volume. Alternatively, if a particle size ($D_{50}$) of <1 μm is desired, the drug is firstly suspended into the buffer solution as stated above, then subjected to bead milling or microfluidization process in order to reduce the particle size to the submicron range. The prepared suspension is then subjected to a terminal sterilization by γ-irradiation at a minimum dose of 25 kGy.

For a second formulation, the drug (compound of Formula I) and selected encapsulating polymer were co-dissolved in a suitable organic solvent, wherein the organic solvent met the following criteria: a) had a good solubility for the compound of Formula I and the selected polymer, b) was not miscible with water; c) had a low boiling point, thus a good volatility. Suitable organic solvents are; for example, methylene chloride (used in this Example), chloroform, ethyl acetate, ethyl formate, etc. The solution was then mixed at a volume ratio 1:2 to 1:100 with water containing 0.1-10% (w/v) surfactant selected from polyvinyl alcohol (PVA 1% PVA used in this Example), polyvinyl pyrrolidone (PVP), poloxamers, polysorbates, polyethoxylated castor oil, tocopheryl polyethylene glycol succinate, etc, to form a uniform emulsion. The emulsion was then subjected to vacuum evaporation to completely remove the volatile organic solvent, for example, in a rotorvap. The uniform suspension was then centrifuged and the resulting pellet was washed with water for injection 3 times to remove the surfactant. The washed pellet was then resuspended by water for injection in a suitable container followed by freeze drying into powdery microparticles encapsulating the compound of Formula I. The microparticles were then finally subjected to a terminal sterilization by γ-irradiation on dry ice at a minimum dose of 25 kGy.

Microparticle A: (Drug:Resomer 752S 1:1)
Microparticle B: (Drug:Resomer 752S 1:2)

Figure 3:
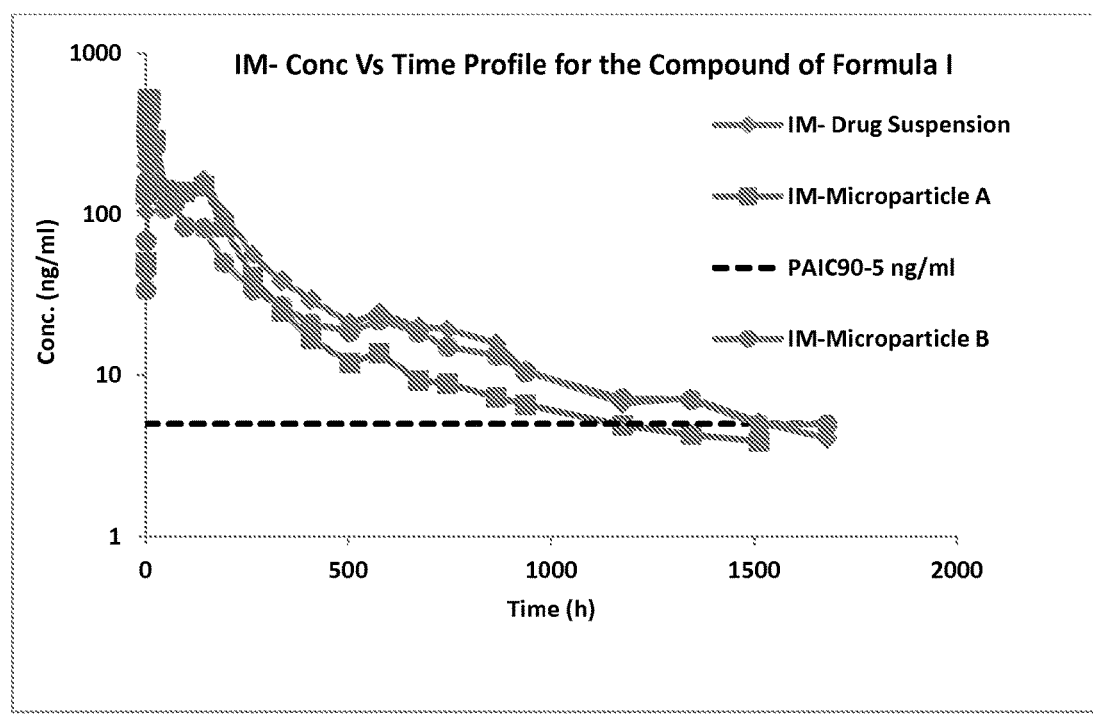
FIG. 3 depicts a plot of LAP Mean Concentration of a compound of Formula I versus time in hours of a LAP Rat (IM) PK study for different drug microparticle formulations

On the day of the study, the microparticle A (compound of Formula I:Resomer 752S 1:1) and B (Compound of Formula I:Resomer 752S 1:2) were mixed with 0.912 and 0.945 ml of vehicle, respectively, by vortexing until a visually uniform suspension was obtained with no large agglomerates. The drug suspension was already formulated as a uniform 1 ml suspension and was re-suspended by vortexing until a visually uniform suspension was obtained with no large agglomerates. Three male Crl:CD rats per formulation were dosed and sampled for the intramuscular route of administration of the compound of Formula I. The intramuscular dose of the compound of Formula I was administered as a single dose of 20 mg/kg and at a dose volume of 0.5 ml/kg. Blood samples were collected at 0.5, 1, 2, 4, 6, 8, 12, and 24 hours and up to 1680 hours post dose administration. For each time point after dosing, approximately 0.1 ml blood samples were collected through tail-snip method, and immediately frozen and stored at −70° C. until analysis. Rat blood samples were then analyzed for the concentrations of the compound of Formula I using a method based on protein precipitation followed by LC-MS/MS analysis. The results of this Example are shown in Table 4 and graphed in FIG. 3.

TABLE 4

| Route (Dose) | Formulation | $T_{1/2}$ (days) | $C_{max}$ (ng/ml) | $T_{max}$ (hr) | $AUC_{0-1680\ h/70\ days}$ (h * mg/ml) |
|---|---|---|---|---|---|
| IM 5 mg/kg | Drug Suspension | 16 ± 0.6 | 284.0 ± 129.8 | 5.3 ± 2.3 | 56.5 ± 18.7 |
| IM 5 mg/kg | Microparticle A | 11 ± 5.7 | 612.7 ± 143.4 | 8.7 ± 3.1 | 49.5 ± 7.8 |
| IM 5 mg/ig | Microparticle B | 10.0 ± 3.5 | 424.7 ± 82.4 | 10.0 ± 3.5 | 46.2 ± 5.3 |

The invention claimed is:

1. A long acting parenteral pharmaceutical composition, comprising: a compound of Table 1 or a pharmaceutically acceptable salt thereof.

2. A long acting parenteral pharmaceutical composition, comprising: the compound of Formula I

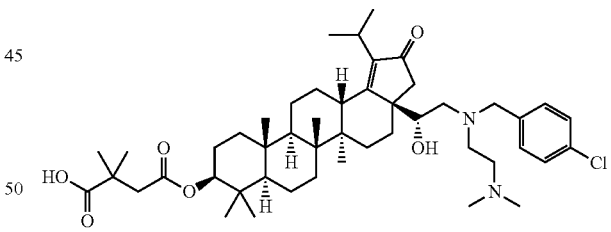

or a pharmaceutically acceptable salt thereof.

3. A method for the treatment of an HIV infection in a human having an HIV infection, comprising: administering to the human a long acting parenteral pharmaceutical composition according to either claim 1 or 2.

4. A method for the treatment of an HIV infection in a human having an HIV infection, comprising: administering to the human a long acting parenteral pharmaceutical composition including the compound of Formula I

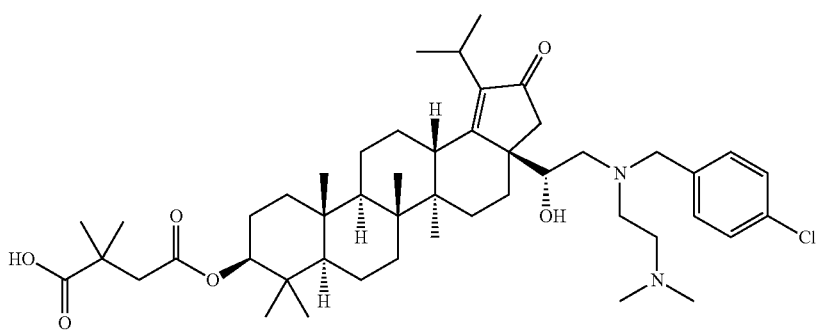

I or a pharmaceutically acceptable salt thereof.

5. The pharmaceutical composition according to claim 2, further comprising a surfactant system.

6. The pharmaceutical composition according to claim 5, wherein the surfactant system comprises a surfactant in an amount ranging from about 0.1% (w/v) to about 3% (w/v) surfactant.

7. The pharmaceutical composition according to claim 5, wherein the surfactant system comprises a surfactant in an amount ranging from about 0.2% (w/v) to about 0.4% (w/v) surfactant.

8. The pharmaceutical composition according to claim 5, wherein the surfactant system comprises about 0.4% (w/v) surfactant.

9. The pharmaceutical composition according to claim 5, wherein the surfactant system comprises a surfactant selected from the group consisting of polyoxyethylene sorbitan fatty acid esters, poloxamers, sorbitan esters of fatty acids (SPAN), polyethoxylated castor oil, tocopheryl polyethylene glycol succinate, and polyvinyl alcohols.

10. The pharmaceutical composition according to claim 9, wherein the surfactant system comprises a surfactant that is polysorbate 80.

11. The pharmaceutical composition according to claim 5, wherein the surfactant system comprises a stabilizer that is selected from the group consisting of polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyarluronic acid, polyvinyl alcohol (PVA) and polyvinylpyrrolidone (PVP).

12. The pharmaceutical composition according to claim 11, wherein the surfactant system comprises a stabilizer that is polyethylene glycol.

13. The pharmaceutical composition according to claim 12, wherein the surfactant system comprises a stabilizer that is PEG-3350.

14. The pharmaceutical composition according to claim 11, wherein the surfactant system comprises a stabilizer in an amount that ranges from about 1% (w/v) to about 5% (w/v) stabilizer.

15. The pharmaceutical composition according to claim 14, wherein the surfactant system comprises about 2% (w/v) stabilizer.

16. The pharmaceutical composition according to claim 5, wherein the surfactant system comprises a buffer salt.

17. The pharmaceutical composition according to claim 16, wherein the surfactant system comprises a buffer salt that is phosphate buffered saline.

18. The pharmaceutical composition according to claim 16, wherein the surfactant system comprises a buffer salt at a concentration of about 10 mM.

19. The pharmaceutical composition according to claim 2, wherein the compound of Formula I is in a crystalline form prior to encapsulating into a microparticle and combining with a surfactant system.

20. The pharmaceutical composition according to claim 2, wherein the compound of Formula I is in an amorphous microparticle form.

21. The pharmaceutical composition according to claim 2, wherein the compound of Formula I is in a microparticle form, wherein the microparticles of the compound of Formula I range in size from about 0.05 µm to about 100 µm.

22. The pharmaceutical composition according to claim 2, wherein the compound of Formula I is in a microparticle form, wherein the microparticles of the compound of Formula I range in size from about 0.1 µm to about 5 µm.

23. The pharmaceutical composition according to claim 2, wherein the compound of Formula I is encapsulated in a polymer.

24. The pharmaceutical composition according to claim 22, wherein the compound of Formula I is encapsulated in a polymer that comprises poly (lactic-co-glycolic) acid.

25. The method according to claim 4, wherein the human is administered the long acting parenteral pharmaceutical composition including the compound of Formula I, on a dosing regimen ranging from about every week to about every three months.

26. The method according to claim 25, wherein the human is administered the long acting parenteral pharmaceutical composition including the compound of Formula I, on a dosing regimen ranging from about every week to about every two months.

27. The method according to claim 25, wherein the human is administered the long acting parenteral pharmaceutical composition including the compound of Formula I, on a dosing regimen that is monthly.

28. A long acting parenteral pharmaceutical composition, comprising: the compound of Formula I

I

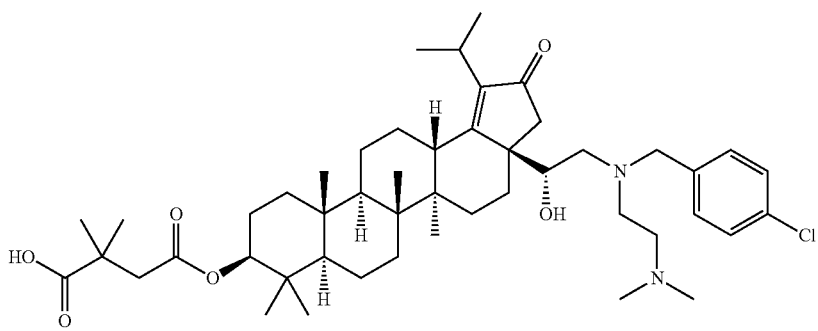

or a pharmaceutically acceptable salt thereof,
in combination with one or more additional compounds selected from the group consisting of dolutegravir, ritonavir, rilpivirine, and a compound having the following structure:

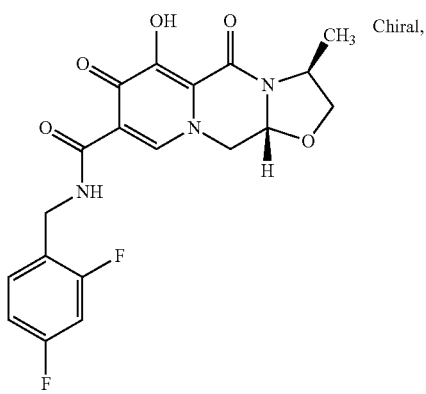 [SMILES: C[C@H]1CO[C@@H]2Cn3cc(C(=O)NCc4ccc(F)cc4F)c(=O)c(O)c3C(=O)N12]

or a pharmaceutically salt thereof.

29. A method for the treatment of an HIV infection in a human having an HIV infection, comprising: administering to the human a long acting parenteral pharmaceutical composition including the compound of Formula I in combination with one or more additional compounds selected from the group consisting of dolutegravir, ritonavir, rilpivirine, and a compound having the following structure:

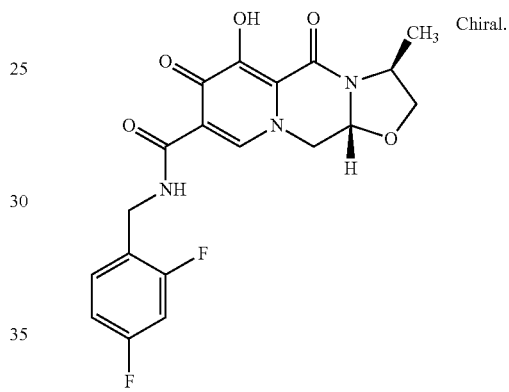

30. The pharmaceutical composition according to claim 2, wherein the compound of Formula I is in a microparticle form, wherein the microparticles of the compound of Formula I range in size from about 0.05 µm to about 100 µm, wherein said microparticles comprise substantially the same size.

31. The pharmaceutical composition according to claim 2, wherein the compound of Formula I is in a microparticle form, wherein the microparticles of the compound of Formula I range in size from about 0.05 µm to about 100 µm, wherein said microparticles comprise two or more substan-

I

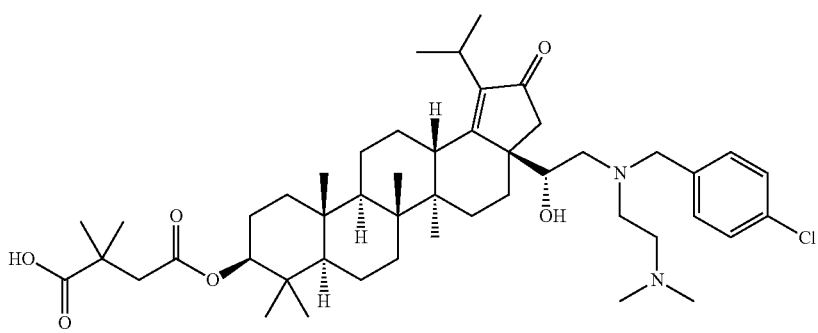

or a pharmaceutically acceptable salt thereof, tially different particle sizes that provide for earlier and later release after administration to a subject and result in varying absorption kinetics therein.

32. The pharmaceutical composition according to claim 2, wherein the compound of Formula I is in a microparticle form, wherein the microparticles of the compound of Formula I range in size from about 0.05 µm to about 0.5 µm.

33. The pharmaceutical composition according to claim 2, wherein the compound of Formula I is in a microparticle form, wherein the microparticles of the compound of Formula I range in size from about 0.5 µm to about 5 µm.

34. The pharmaceutical composition according to claim 2, wherein the compound of Formula I is in a microparticle form, wherein the microparticles of the compound of Formula I range in size from about 5 µm to about 25 µm.

35. The pharmaceutical composition according to claim 2, wherein the compound of Formula I is in a microparticle form, wherein the microparticles of the compound of Formula I range in size from about 25 µm to about 100 µm.

36. The pharmaceutical composition according to claim 2, wherein the compound of Formula I is present in an amount ranging from about 20 mg to about 100 mg.

37. The pharmaceutical composition according to claim 2, wherein the compound of Formula I is present in an amount ranging from about 100 mg to about 200 mg.

38. The pharmaceutical composition according to claim 2, wherein the compound of Formula I is present in an amount ranging from about 200 mg to about 400 mg.

39. The pharmaceutical composition according to claim 2, wherein the compound of Formula I is present in an amount ranging from about 400 mg to about 800 mg.

40. The method according to claim 4, wherein the compound of Formula I is administered initially to the subject as a loading dose in amount that ranges from 400 mg to 800 mg and then is administered as a maintenance dose thereafter in an amount that ranges from about 20 mg to about 300 mg.

41. The method according to claim 4, wherein the long acting parenteral composition comprising the compound of Formula I is administered to the subject only after the subject has been administered treatment comprising a generally accepted anti-retroviral regimen.

* * * * *